United States Patent
Dinges et al.

(10) Patent No.: US 10,556,914 B2
(45) Date of Patent: Feb. 11, 2020

(54) SUBSTITUTED ISOXAZOLOPYRIDAZINONES AND ISOTHIAZOLOPYRIDAZINONES AND METHODS OF USE

(71) Applicants: AbbVie Inc., North Chicago, IL (US); AbbVie Deutschland GmbH & Co. KG, Wiesbaden (DE)

(72) Inventors: Jürgen Dinges, North Chicago, IL (US); Achim Moeller, Ludwigshafen (DE); Michael Ochse, Ludwigshafen (DE); Martin Schmidt, Ludwigshafen (DE); Michael Schulz, Ludwigshafen (DE); Sean Turner, Ludwigshafen (DE); Elizabeth Louise Van Der Kam, Ludwigshafen (DE); Anil Vasudevan, North Chicago, IL (US)

(73) Assignees: ABBVIE INC., North Chicago, IL (US); ABBVIE DEUTSCHLAND GMBH & CO. KG, Wiesbaden (DE)

( * ) Notice: Subject to any disclaimer, the term of this patent is extended or adjusted under 35 U.S.C. 154(b) by 0 days.

(21) Appl. No.: 16/409,323

(22) Filed: May 10, 2019

(65) Prior Publication Data

US 2019/0367531 A1 Dec. 5, 2019

Related U.S. Application Data

(63) Continuation of application No. 15/266,473, filed on Sep. 15, 2016, now abandoned.

(30) Foreign Application Priority Data

Sep. 15, 2015 (WO) ................ PCT/CN2015/089614
Nov. 10, 2015 (EP) ...................................... 15193907

(51) Int. Cl.
*C07D 498/04* (2006.01)
*C07D 513/04* (2006.01)
*A61K 31/4985* (2006.01)

(52) U.S. Cl.
CPC ........ *C07D 498/04* (2013.01); *A61K 31/4985* (2013.01); *C07D 513/04* (2013.01)

(58) Field of Classification Search
CPC . C07D 498/04; C07D 513/04; A61K 31/4985
USPC .......................................... 544/236; 514/248
See application file for complete search history.

(56) References Cited

FOREIGN PATENT DOCUMENTS

| WO | WO-9611680 A2 | 4/1996 |
|----|---------------|--------|
| WO | WO-2008130314 A1 | 10/2008 |
| WO | WO-2011113904 A1 | 9/2011 |

OTHER PUBLICATIONS

Anghinah R., et al., "Effect of Baclofen on Pain in Diabetic Neuropathy," Muscle & Nerve, 1994, vol. 17 (8), pp. 958-959.
Bettler B., et al., "Molecular Structure and Physiological Functions of GABA(B) Receptors," Physiological Reviews, 2004, vol. 84 (3), pp. 835-867.
Boeckxstaens G.E., et al., "Reflux Inhibitors: A New Approach for Gerd?," Current Opinion in Pharmacology, 2008, vol. 8 (6), pp. 685-689.
Bolser D.C., et al., "Antitussive Effects of GABAB Agonists in the Cat and Guinea-pig," British Journal of Pharmacology, 1993, vol. 110 (1), pp. 491-495.
Bowery N.G., et al., "GABAB Receptor: A Site of Therapeutic Benefit," Current Opinion in Pharmacology, 2006, vol. 6 (1), pp. 37-43.
Bowery N.G., et al., "Historical Perspective and Emergence of the GABAB Receptor," Advances in Pharmacology, 2010, vol. 58, pp. 1-18.
Bowery N.G., et al., "International Union of Pharmacology. XXXIII. Mammalian Gamma-aminobutyric Acid(B) Receptors: Structure and Function," Pharmacological Reviews, 2002, vol. 54 (2), pp. 247-264.
Bredenoord A.J, "Lesogaberan, a GABA(B) Agonist for the Potential Treatment of Gastroesophageal Reflux Disease," ldrugs, Sep. 2009, vol. 12 (9), pp. 576-584.
Brennan J.L., et al., "Clinical Effectiveness of Baclofen for the Treatment of Alcohol Dependence: A Review," Clinical Pharmacology, Jul. 3, 2013, vol. 5, pp. 99-107.
Brusberg M., et al., "The GABA(B) Receptor Agonist, Baclofen, and the Positive Allosteric Modulator, CGP7930, Inhibit Visceral Pain-related Responses to Colorectal Distension in Rats," Neuropharmacology, 2009, vol. 56 (2), pp. 362-367.
Cao Y.Q., et al., "Effects of Familial Hemiplegic Migraine Type 1 Mutations on Neuronal P/Q-type Ca2+ Channel Activity and Inhibitory Synaptic Transmission," Proceedings of the National Academy of Sciences, Feb. 15, 2005, vol. 102 (7), pp. 2590-2595.
Cesari N., et al., "Arylpiperazinylalkylpyridazinones and Analogues as Potent and Orally Active Antinociceptive Agents: Synthesis and Studies on Mechanism of Action," Medicinal Chemistry, 2006, vol. 49 (26), pp. 7826-7835.

(Continued)

*Primary Examiner* — Deepak R Rao
(74) *Attorney, Agent, or Firm* — Neal, Gerber & Eisenberg LLP

(57) ABSTRACT

Compounds of formula (I)

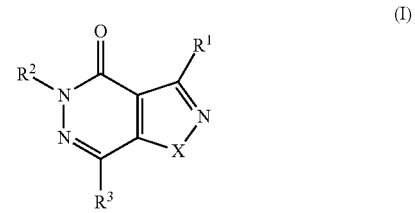

and pharmaceutically acceptable salts thereof, wherein $R^1$, $R^2$ and $R^3$ are as defined in the specification, are useful in treating conditions or disorders prevented by or ameliorated by positive allosteric modulation of the γ-aminobutyric acid B (GABA-B) receptor. Methods for making the compounds are described. Also described are pharmaceutical compositions of compounds of formula (I), and methods for using such compounds and compositions.

16 Claims, No Drawings

(56) References Cited

OTHER PUBLICATIONS

Chantegrel., et al., "Synthesis of Lsoxazolo[4,5-d]Pyridazin-4(5H)-Ones and 4-Acyl-5-Hydroxy-3(2H)-Pyridazinones," Journal of Heterocyclic Chemistry, 1990, vol. 27 (4), pp. 927-934.
Cryan J.F., et al., "Behavioral Characterization of the Novel GABAB Receptor-positive Modulator Gs39783 (N,n'-dicyclopentyl-2-methylsulfanyl-5-nitro-pyrimidine-4,6-diamine): Anxiolytic-like Activity Without Side Effects Associated With Baclofen or Benzodiazepines," Journal of Pharmacology and Experimental Therapeutics, 2004, vol. 310 (3), pp. 952-963.
Dal P.V., et al., "Heterocyclic-Fused 3(2H)-Pyridazinones as Potent and Selective POE IV Inhibitors: Further structure Activity Relationships and Molecular Modelling Studies," European Journal of Medicinal Chemistry, 1998, vol. 33 (10), pp. 789-797.
Dal P.V., et al., "Isoxazolo[3,4-d]Pyridazinones and Analogues as Leishmania Mexicana PDE Inhibitors," Farmaco, 2002, vol. 57 (2), pp. 89-96.
Faidallah H.M., et al., "Synthesis and Biological Evaluation of Some Novel Urea and Thiourea Derivatives of Isoxazolo[4,5-D]Pyridazine and Structurally Related Thiazolo[4,5-D]Pyridazine as Antimicrobial Agents," Archives of Pharmacal Research , 2013, vol. 36 (11), pp. 1354-1368.
Filip M., et al., "GABAB Receptors as a Therapeutic Strategy in Substance Use Disorders: Focus on Positive Allosteric Modulators," Neuropharmacology, 2015, vol. 88, pp. 36-47.
Fritschy J.M., et al., "GABAB-receptor Splice Variants Gb1a and Gb1b in Rat Brain: Developmental Regulation, Cellular Distribution and Extrasynaptic Localization," European Journal of Neuroscience, 1999, vol. 11 (3), pp. 761-768.
Froestl W., et al., "Novel GABA(B) Receptor Positive Modulators: A Patent Survey," Expert Opinion on Therapeutic Patents, 2010, vol. 20 (8), pp. 1007-1017.
Fromm G.H., et al., "Baclofen in the Treatment of Trigeminal Neuralgia: Double-blind Study and Long-term Follow-up," Annals of Neurology, 1984, vol. 15 (3), pp. 240-244.
Gablofen, Prescribing Information, 2010, 18 pages.
Gjoni T., et al., "Receptor Activation Involving Positive Allosteric Modulation, Unlike Full Agonism, Does Not Result in GABAB Receptor Desensitization," Neuropharmacology, 2008, vol. 55 (8), pp. 1293-1299.
Hampson D.R., et al., "The Neurochemical Basis for the Treatment of Autism Spectrum Disorders and Fragile X Syndrome," Biochemical Pharmacology, May 2011, vol. 81 (9), pp. 1078-1086.
Hering-Hanit R., et al., "Baclofen for Prevention of Migraine," Cephalalgia : An International Journal of Headache, 1999, vol. 19 (6), pp. 589-591.
Hering-Hanit R., et al., "Baclofen in Cluster Headache," Headache, 2000, vol. 40 (1), pp. 48-51.
Hirano A.A., et al., "Cellular Distribution and Subcellular Localization of Molecular Components of Vesicular Transmitter Release in Horizontal Cells of Rabbit Retina," Journal of Comparative Neurology, 2005, vol. 488 (1), pp. 70-81.
Hulikal, Deuterium Labeled Compounds in Drug Discovery Process, Abstract, 2010.
International Search Report and Written Opinion for Application No. mailed on PCT/EP2016/071619, dated Nov. 15, 2016, 9 pages.
Kalinichev M., et al., "ADX71441, A Novel, Potent and Selective Positive Allosteric Modulator of the GABA(B) Receptor, Shows Efficacy in Rodent Models of Overactive Bladder," British Journal of Pharmacology, Feb. 2014, vol. 171 (4), pp. 995-1006.
Kleschevnikov A.M., et al., "Deficits in Cognition and Synaptic Plasticity in a Mouse Model of Down Syndrome Ameliorated by GABAB Receptor Antagonists," The Journal of Neuroscience, 2012, vol. 32 (27), pp. 9217-9227.
Koek W., et al., "GABAB Receptor-positive Modulators: Enhancement of GABAB Receptor Agonist Effects in Vivo," The Journal of Pharmacology and Experimental Therapeutics, 2010, vol. 335 (1), pp. 163-171.
Krupitsky E.M., et al., "Baclofen Administration for the Treatment of Affective Disorders in Alcoholic Patients," Drug and Alcohol Dependence, 1993, vol. 33 (2), pp. 157-163.
Kumar K., et al., "Therapeutic Potential of GABA(B) Receptor Ligands in Drug Addiction, Anxiety, Depression and Other CNS Disorders.," Pharmacology, biochemistry, and behavior, Sep. 2013, vol. 110, pp. 174-184.
Lacy B.E., et al., "Lesogaberan: GABAB Receptor Agonist Treatment of Gastroesophageal Reflux Disease," Drugs of the Future, 2010, vol. 35 (12), pp. 987-992.
Lehmann A., et al., "GABAB Receptor Agonism as a Novel Therapeutic Modality in the Treatment of Gastroesophageal Reflux Disease," Advances in Pharmacology, 2010, vol. 58, pp. 287-313.
Lozano R., et al., "Modulation of the Gabaergic Pathway for the Treatment of Fragile X Syndrome," Neuropsychiatric Disease and Treatment, 2014, vol. 10, pp. 1769-1779.
Magnaghi V., et al., "Nerve Regenerative Effects of GABA-B Ligands in a Model of Neuropathic Pain," BioMed Research International, 2014, vol. 2014, p. 368678.
Malcangio M., et al., "GABAB Receptors and Pain," Neuropharmacology, May 11, 2017, pp. S0028-3908(17)30218-6.
Mombereau C., et al., "Genetic and Pharmacological Evidence of a Role for GABA(B) Receptors in the Modulation of Anxiety- and Antidepressant-like Behavior," Neuropsychopharmacology, 2004, vol. 29 (6), pp. 1050-1062.
Nowak P., et al., "Antinociceptive Effects of H3 (R-methylhistamine) and GABA(B) (baclofen)-Receptor Ligands in an Orofacial Model of Pain in Rats," Neurotoxicity Research, Aug. 2013, vol. 24 (2), pp. 258-264.
Oblak A.L., et al., "Decreased GABA(B) Receptors in the Cingulate Cortex and Fusiform Gyrus in Autism," Journal of Neurochemistry, 2010, vol. 114 (5), pp. 1414-1413.
Oliveira F.G., et al., "Molecular Docking Study and Development of an Empirical Binding Free Energy Model for Phosphodiesterase 4 Inhibitors," Bioorganic & Medicinal Chemistry, 2006, vol. 14 (17), pp. 6001-6011.
Ong J., et al., "Clinical Potential of GABAB Receptor Modulators," CNS Drug Reviews, 2005, vol. 11 (3), pp. 317-334.
Ozadali K., et al., "Synthesis and Biological Evaluation of Isoxazolo[4,5-D]Pyridazin-4-(5h)-One Analogues as Potent Anti-Inflammatory Agents," Bioorganic & Medicinal Chemistry , 2012, vol. 20 (9), pp. 2912-2922.
Phillips T.J., et al., "Targeting GABAB Receptors for Anti-Abuse Drug Discovery," Expert Opinion on Brug Discovery, Nov. 2014, vol. 9 (11), pp. 1307-1317.
Pimlott S.L., et al., "Radiotracer Development in Psychiatry," Nuclear Medicine Communications, 2005, vol. 26 (3), pp. 183-188.
Pin J.P., et al., "Activation Mechanism of the Heterodimeric GABA(B) Receptor," Biochemical Pharmacology, 2004, vol. 68 (8), pp. 1565-1572.
Pin J.P., et al., "Allosteric Modulators of GABA(B) Receptors: Mechanism of Action and Therapeutic Perspective," Current Neuropharmacology, 2007, vol. 5 (3), pp. 195-201.
Ross J.C., et al., "Acute Intrathecal Baclofen Withdrawal: A Brief Review of Treatment Options," Neurocritical Care, 2011, vol. 14 (1), pp. 103-108.
Sands S.A., et al., "Differential Regulation of GABA B Receptor Subunit Expression and Function," The Journal of Pharmacology and Experimental Therapeutics, 2003, vol. 305 (1), pp. 191-196.
Sanger G.J., et al., "Treatment of Nausea and Vomiting: Gaps in Our Knowledge," Autonomic Neuroscience : Basic & Clinical, 2006, vol. 129 (1-2), pp. 3-16.
Schuler V., et al., "Epilepsy, Hyperalgesia, Impaired Memory, and Loss of Pre- and Postsynaptic GABA(B) Responses in Mice Lacking GABA(B(1))," Neuron, 2001, vol. 31 (1), pp. 47-58.
Slonimski M., et al., "Intrathecal Baclofen in Pain Management," Regional Anesthesia and Pain Medicine, 2004, vol. 29 (3), pp. 269-276.
Smith P.F., et al., "Revisiting Baclofen for the Treatment of Severe Chronic Tinnitus," Frontiers in Neurology, 2012, vol. 3, pp. 34.
Spano M.S., et al., "The GABAB Receptor Agonist Baclofen Prevents Heroin-induced Reinstatement of Heroin-seeking Behavior in Rats," Neuropharmacology, 2007, vol. 52 (7), pp. 1555-1562.

(56) References Cited

OTHER PUBLICATIONS

Strange P.G, "Use of the Gtp?s ([35s]GTP?S and Eu-GTP?S) Binding Assay for Analysis of Ligand Potency and Efficacy at G Protein-coupled Receptors," British Journal of Pharmacology, 2010, vol. 161 (6), pp. 1238-1249.

Taylor M.C., et al., "A Double-blind Crossover Trial of Baclofen—a New Treatment for the Unstable Bladder Syndrome," British Journal of Urology, 1979, vol. 51 (6), pp. 504-505.

Vlachou S., et al., "Repeated Administration of the GABAB Receptor Positive Modulator Bhf177 Decreased Nicotine Self-administration, and Acute Administration Decreased Cue-induced Reinstatement of Nicotine Seeking in Rats," Psychopharmacology, 2011, vol. 215 (1), pp. 117-128.

Wang L., et al., "Allosteric Modulators of G Protein-coupled Receptors: Future Therapeutics for Complex Physiological Disorders," Journal of Pharmacology and Experimental Therapeutics, 2009, vol. 331 (2), pp. 340-348.

SUBSTITUTED ISOXAZOLOPYRIDAZINONES AND ISOTHIAZOLOPYRIDAZINONES AND METHODS OF USE

CROSS-REFERENCE TO RELATED PATENT APPLICATIONS

This patent application is a continuation of U.S. patent application Ser. No. 15/266,473, filed on Sep. 15, 2016, which claims priority to International Patent Application No. PCT/CN2015/089614, filed on Sep. 15, 2015, and European Patent Application No. 15193907.1, filed Nov. 10, 2015. The entire contents of these applications are incorporated by reference into this patent application.

BACKGROUND OF THE INVENTION

Technical Field

The invention relates to substituted pyrazolopyrimidines that are positive allosteric modulators of the γ-aminobutyric acid receptor (e.g., GABA-B PAM), useful in treating diseases and conditions mediated and modulated by the γ-aminobutyric acid receptor B. Additionally, the invention relates to compositions containing compounds of the invention and processes of their preparation.

Description of Related Technology

The inhibitory neurotransmitter, γ-aminobutyric acid (GABA) exerts its actions through three distinct receptors—the ionotropic GABA-A and GABA-C receptors, and the metabotropic GABA-B receptor. The GABA-B receptor is a member of the class C family of GPCRs. The GABA-B receptor is an obligate heterodimer composed of a GABA-B1 and a GABA-B2 subunit (Bettler, B., et al. *Physiol Rev* 2004; 84: 835-867). Notably, heterodimerization of the B1 and B2 subunits is required for proper GABA-B receptor expression and function (Pin, J. P., et al. *Biochem Pharmacol* 2004; 68: 1565-1572). Agonist binding to the B1 subunit of the GABA-B heterodimer results in transactivation of the B2 subunit and subsequent stimulation of $G_{i/o}$ proteins. This, in turn, activates $K^+$ currents, inhibits $Ca^{2+}$ currents, and decreases cAMP via negative regulation of adenylyl cyclase.

GABA-B receptor subunits are found both pre- and post-synaptically throughout the CNS and the periphery, with highest expression in the thalamus, cortex, cerebellum and dorsal horn (Fritschy, J. M., et al. *Eur J Neurosci* 1999; 11: 761-768). Functional receptor expression appears to be limited by the presence of the GABA-B2 subunit, which is often detected at lower levels than the B1 subunits (Bowery, N. G. *Adv Pharmacol* 2010; 58: 1-182). Therapeutically, the beneficial effects of GABA-B receptor stimulation include muscle relaxation, substance abuse treatment (especially in alcohol dependence), antinociception, spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus. The in vivo consequence of GABA-B activation has been confirmed experimentally with knockout mouse models, which are hyperalgesic, and clinically with the GABA-B orthosteric agonist, baclofen (Slonimski, M., et al. *Reg Anesth Pain Med* 2004; 29: 269-276. Bowery, N. G., et al. *Pharmacol Rev* 2002; 54: 247-264). Unfortunately, the utility of baclofen is limited by drug tolerance and severe side effects, including hypothermia, seizures, sedation and cognitive deficits. Baclofen has poor brain penetrance and requires high doses for engagement of CNS GABA-B receptors, resulting in elevated plasma concentrations. Peripheral GABA-B receptors on smooth and skeletal muscle are activated by these high plasma concentrations and appear to mediate a subset of baclofen side effects, including hypothermia and seizures that are hypothesized to arise from erratic muscle contractions. Drug tolerance requiring dose escalation has been reported three to seven days after initiation of baclofen and most likely arises from receptor desensitization (Sands, S. A., et al. *J Pharmacol Exp Ther* 2003; 305: 191-196). This reduction in GABA-B receptor signaling mimics the genotype of GABA-B knockout mice, which also exhibit severe cognitive and learning deficits (Schuler, V., et al. *Neuron* 2001; 31: 47-58). Tolerance and receptor desensitization following repeated baclofen administration may therefore underlie the cognitive deficits and learning impairments associated with baclofen treatment. Finally, abrupt discontinuation of intrathecal baclofen results in severe withdrawal symptoms, including seizures (Ross, J. C., et al. *Neurocrit Care* 2011; 14: 103-108). This indicates an underlying change in the physiological balance of GABA neurotransmitter and GABA-B receptor after continued exogenous agonist stimulation. Similarly, the GABA-B knockout mouse exhibits epileptiform seizures, further underscoring the importance of maintaining the normal, physiological GABA-B tone within the CNS. While the GABA-B receptor remains a valid drug target, the side effects and tolerance associated with baclofen has led to the development of alternatives to classic orthosteric activation of the receptor.

To exploit the beneficial aspects of GABA-B stimulation, the disclosure describes positive allosteric receptor ligands for modulation of the GABA-B receptor. Positive allosteric modulators alter the receptor conformation and enhance the activity of the endogenous orthosteric agonist, either by increasing the affinity or the efficacy of the orthosteric ligand at the receptor (Wang, L., et al. *J Pharmacol Exp Ther* 2009; 331: 340-348). Because allosteric modulators rely on local levels of endogenous ligand and have little or no activity of their own, they are thought to represent a safer and more subtle means of receptor regulation. The hypothesis is that GABA-B receptor allosteric modulators, and possibly allosteric agonists, will be effective therapeutic agents while minimizing the side effects caused by agonist activation of the orthosteric GABA-B site. In addition to pain indications (Anghinah, R., et al. *Muscle Nerve* 1994; 17(8): 958-959. Fromm G. H., et al. *Ann. Neuro.* 1984; 15: 240-244), GABA-B modulators could also be used in the treatment of depression, spasticity (Bowery, N. G. *Curr Opin Pharmacol* 2006; 6; 37-433. Froestl, W. *Expert Opin Ther Pat* 2010; 20: 1007-1017. Ong, J., et al. *CNS Drug Rev* 2005; 11: 317-334)), fragile X syndrome (Lozano, R., et al. *Neuropsychiatric Disease and Treatment* 2014; 10: 1769-1779), Down's syndrome (Kleschevnikov, A. M., et al. *Journal of Neuroscience* 2012; 32(27): 9217-9227), autism (Oblak, A. L., et al. *Journal of Neurochemistry* 2010; 114(5): 1414-23), retinal ganglion cell degeneration (Hirano, A. A., et al. *Journal of Comparative Neurology* 2005; 488(1): 70-81), gastro-esophageal reflux disease (GERD) (Lacy, B. E., et al. *Drugs of the Future* 2010; 35(12): 987-992. Boeckxstaens, C. E. et al. *Current Opinion in Pharmacology* 2008; 8(6): 685-689. Lehmann, A., et al. *Advances in Pharmacology* 2010; 58: 287-313) smoking cessation (Vlachou, S., et al. *Psychopharmacology* 2011; 215(1): 117-128), addiction of narcotic agents (Spano, M. S., et al. *Neuropharmacology* 2007;

52(7): 1555-62), emesis (Sanger, G. J., et al. *Autonomic Neuroscience* 2006; 129(1-2): 3-16), cough (Bolser, D. C., et al. *British Journal of Pharmacology* 1993; 110(1): 491-495), overactive bladder (Taylor, M. C., et al. *British J. Urology* 1979; 51: 504-505), anxiety (Krupitsky, E. M., et al. *Drug and Alcohol Dependence* 1993; 33: 157-163. Cryan, J. F., et al. *JPharmacolExp Ther* 2004; 310: 952-963. Mombereau, C., et al. *Neuropsychopharmacology* 2004; 29: 1050-1062), migraine (Hering-Hanit, R., Cephalalgia 1999; 19(6): 589-91. Hering-Hanit, R., et al. *Headache* 2000; 40(1): 48-51), and tinnitus (Smith, P. F., et al. *Frontiers in Neurology* 2012; 3: 34). Positive allosteric modulators (PAMs) bind to functionally and topographically distinct allosteric sites on the receptor and act at a distance from the orthosteric site to enhance the efficacy of the endogenous ligand. A single receptor may possess multiple, discrete allosteric sites, each with a unique subset of ligands. Pure PAMs are devoid of activity on their own—they will only enhance the potency and/or efficacy of the endogenous agonist—thus their pharmacological profile is spatially and temporally controlled by the normal physiological interaction between the endogenous ligand and its receptor. This highlights a critical difference between PAMs and orthosteric agonists—PAMs avoid the maximum on/off at all receptors that occurs with classic orthosteric agonist stimulation. Because PAMs rely on endogenous agonist concentrations for activity, they promote fine-tuning of the GABA signal in a physiologically-relevant manner. Importantly, GABA-B PAMs do not cause receptor desensitization (Gjoni, T., et al. *Neuropharmacology* 2008; 55: 1293-1299), so the clinical tolerance and side effects related to receptor desensitization that are observed with baclofen are unlikely to occur. Finally, the majority of GABA-B PAMs tested in the literature (Brusberg, M., et al. *Neuropharmacology* 2009; 56: 362-367. Froestl, W. *Expert Opin Ther Pat* 2010; 20: 1007-1017. Koek, W., et al. *J Pharmacol Exp Ther* 2010; 335: 163-17. Pin, J. P., et al. *Curr Neuropharmacol* 2007; 5, 195-201) show greatly enhanced brain penetrance as compared to baclofen and excellent efficacies in preliminary studies with minimum or no side effects. K. Ozadal et al., *Bioorg. Med. Chem.* (2012), 20(9), 2912-2922 describe the ethyl esters of 3-methyl-4-oxo-7-(phenylmethyl)-isoxazolo[4,5-d]pyridazine-5(4H)-acetic acid, of 3-methyl-4-oxo-7-((4-methoxyphenyl)methyl)-isoxazolo[4,5-d]pyridazine-5(4H)-acetic acid and of 3-methyl-4-oxo-7-((4-nitrophenyl)methyl)-isoxazolo[4,5-d]pyridazine-5(4H)-acetic acid as intermediates in the preparation of anti-inflammatory isoxazolo[4,5-d]pyridazine-4(5H)-one compounds bearing either an amino-substituted 1,3,4-thiadiazole moiety or a 1,2,4-triazole-5-thione moiety.

N. Cesari et al., *J. Med. Chem.* (2006), 49 (26), 7826-7835, describe 3-methyl-4-oxo-7-phenyl-isoxazolo[4,5-d]pyridazine-5(4H)-propionic acid as an intermediate in the preparation of arlypiperazinlylalkyl-substituted isoxazolo[4,5-d]pyridazine-4(5H)-ones, which are rally active antinociceptive agents.

V. Dal Piaz et al, *Farmaco* (2002), 57(2), 89-96 and Europ. *J. Med. Chem.* 1998, 33(10), 789-797 describe, inter alia, 3-methyl-7-phenyl-5-(phenylmethyl)-isoxazolo[4,5-d]pyridazin-4(5H)-one, 3-methyl-7-phenyl-5-(prop-2-ynyl)-isoxazolo[4,5-d]pyridazin-4(5H)-one, 3,5-dimethyl-7-phenyl-isoxazolo[4,5-d]pyridazin-4(5H)-one, 5-ethyl-3-methyl-7-phenyl-isoxazolo[4,5-d]pyridazin-4(5H)-one and 5-butyl-3-methyl-7-phenyl-isoxazolo[4,5-d]pyridazin-4(5H)-one as inhibitors of PDE III and PDE IV.

B. Chantegrel et al., *J. Heterocycl. Chem.*, (1990), 27(4), 927-934 describe the preparation of certain isocazolo[4,5-d]pyridzin-4(5H)ones, namely 3-methyl-7-phenyl-5-(phenylmethyl)-isoxazolo[4,5-d]pyridazin-4(5H)-one and 3,7-dimethyl-5-(phenylmethyl)-isoxazolo[4,5-d]pyridazin-4(5H)-one.

H. M. Faidallah, Archives of *Pharmaceutical Research* (2013), 36(11), 1354-1368, describe 3,7-dimethyl-5-(2,2,2-trifluoroacetyl)-isoxazolo[4,5-d]pyridazoin-4(5H)-one as an intermediate in the preparation of urea, thiourea or sulfonylurea derivatives of isoxazolo[4,5-d]pyridazin-4(5H)-ones having antibacterial properties.

Apart from that, the ethyl ester of 3-methyl-4-oxo-7-phenyl-isoxazolo[4,5-d]pyridazine-5(4H)-propionic acid [CAS 1027087-89-3] and 3,5,7-trimethyl-isoxazolo[4,5-d]pyridazin-4(5H)-one [CAS 685542-42-1] can be found in databases.

These collective data emphasize the need for alternative therapeutics at the GABA-B receptor, and highlight the unique ability of PAMs to stimulate the receptor without baclofen-like side effects.

SUMMARY

The invention is directed to substituted isoxazolopyridazinones and isothiazolopyridazinones having a structure of formula (I)

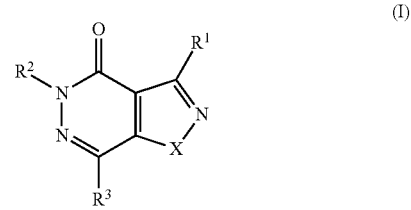

or a pharmaceutically acceptable salt or isotopically labelled form thereof, wherein:

X is O or S;

$R^1$ is selected from the group consisting of $C_1$-$C_6$alkyl, $C_2$-$C_6$alkenyl, $C_2$-$C_6$alkynyl, $C_3$-$C_6$cycloalkyl, and phenyl; wherein,
  $C_1$-$C_6$alkyl, $C_2$-$C_6$alkenyl, and $C_2$-$C_6$alkynyl are unsubstituted, partly or completely fluorinated and/or are substituted with one or more, e.g. 1 or 2 substituents independently selected from the group consisting of $C_1$-$C_6$alkoxy, fluoro$C_1$-$C_6$alkoxy, hydroxy, and oxo;
  $C_3$-$C_6$cycloalkyl is optionally substituted with one or more substituents, e.g. from 1 to 6 substituents, which are independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo;
  phenyl is optionally substituted with one or more, e.g. 1, 2, 3, 4 or 5 substituents, selected from $C_1$-$C_6$alkyl, $C_1$-$C_6$alkoxy, fluoro$C_1$-$C_6$alkyl, fluoro$C_1$-$C_6$alkoxy, and halo; $R^2$ is selected from the group consisting of $C_1$-$C_6$alkyl, $C_2$-$C_6$alkenyl, $C_2$-$C_6$alkynyl, and —$(CR^aR^b)_n$-$G^1$; wherein,
  $C_1$-$C_6$alkyl, $C_2$-$C_6$alkenyl, and $C_2$-$C_6$alkynyl are unsubstituted, partly or completely fluorinated and/or substituted with one or more, e.g. 1 or 2, substituents independently selected from the group consisting of $C_1$-$C_6$alkoxy, fluoro$C_1$-$C_6$alkoxy, hydroxy, and oxo;

$R^a$ and $R^b$ are independently selected at each occurrence from the group consisting of hydrogen, $C_1$-$C_6$alkyl, fluoro$C_1$-$C_6$alkyl, fluoro$C_1$-$C_6$alkoxy, and phenyl; wherein
  phenyl is optionally substituted with one or more, e.g. 1, 2, 3, 4 or 5 substituents selected from $C_1$-$C_6$alkyl, $C_1$-$C_6$alkoxy, fluoro$C_1$-$C_6$alkyl, fluoro$C_1$-$C_6$alkoxy, and halo;
n is 1, 2 or 3;
$G^1$ is selected from the group consisting of phenyl, bicyclic aryl, monocyclic heteroaryl, and bicyclic heteroaryl; wherein the phenyl, the bicyclic aryl, the monocyclic heteroaryl, and the bicyclic heteroaryl are optionally substituted with 1, 2, 3 or 4 substituents independently selected from the group consisting of $C_1$-$C_6$alkyl, $C_1$-$C_6$alkoxy, cyano, fluoro$C_1$-$C_6$alkyl, fluoro$C_1$-$C_6$alkoxy, halo, and hydroxy;
$R^3$ is selected from the group consisting of $C_1$-$C_6$alkyl, $C_3$-$C_6$cycloalkyl, phenyl, phenyl$C_1$-$C_6$alkyl, bicyclic aryl, bicyclic aryl$C_1$-$C_6$alkyl, monocyclic heteroaryl$C_1$-$C_6$alkyl, monocyclic heteroaryl, and bicyclic heteroaryl; wherein
  $C_1$-$C_6$alkyl is unsubstituted, partly or completely fluorinated and/or substituted with one or more, e.g. 1 or 2, substituents independently selected from the group consisting of $C_1$-$C_6$alkoxy, fluoro$C_1$-$C_6$alkoxy, fluorine, hydroxy, and oxo;
  $C_3$-$C_6$cycloalkyl is optionally substituted with one or more substituents, e.g. with 1, 2, 3, 4, 5 or 6 substituents, independently selected from the group consisting of $C_1$-$C_6$alkyl, fluoro$C_1$-$C_6$alkyl, $C_1$-$C_6$alkoxy, fluoro$C_1$-$C_6$alkoxy, fluorine, hydroxy, and oxo; and
  phenyl, phenyl of phenyl$C_1$-$C_6$alkyl, bicyclic aryl, bicyclic aryl of bicyclic aryl$C_1$-$C_6$alkyl, monocyclic heteroaryl of monocyclic heteroaryl$C_1$-$C_6$alkyl, monocyclic heteroaryl and bicyclic heteroaryl are optionally substituted with 1, 2, 3 or 4 substituents $R^{Ar}$, which are independently selected from the group consisting of $C_1$-$C_6$alkyl, $C_2$-$C_6$alkenyl, $C_2$-$C_6$alkynyl, halogen, cyano, —$OR^{1a}$, —$OC(O)R^{1a}$, —$OC(O)N(R^d)(R^{3a})$, —$SR^{1a}$, —$S(O)_2R^{2a}$, —$S(O)_2N(R^d)(R^{3a})$, —$C(O)R^{1a}$, —$C(O)OR^{1a}$, $C(O)N(R^d)(R^{3a})$, $N(R^d)(R^{3a})$, —$N(R^c)C(O)R^{1a}$, —$N(R)S(O)_2R^{2a}$, —$N(R^c)C(O)O(R^{1a})$, —$N(R^c)C(O)N(R^d)(R^{3a})$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^d)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^d)(R^d)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^d)(R^d)(R^{3a})$, —$(CR^{4a}R^{5a})_m$—$N(R^d)(R^{3a})$, —$(CR^{4a}R_{5a})_m N(R^c)C(O)R^{1a}$, —$(CR^{4a}R^{5a})_m$—$N(R^c)S(O)_2R^{2a}$—$(CR^{4a}R^{5a})_m$—$N(R)C(O)O(R^{1a})$, —$(CR^{4a}R^{5a})_m$—$N(R)C(O)N(R^d)(R^{3a})$, cyano$C_1$-$C_6$-alkyl and fluoro$C_1$-$C_6$-alkyl;
m is 1, 2, 3, or 4;
$R^c$ and $R^d$, at each occurrence, are each independently hydrogen, $C_1$-$C_6$alkyl, or fluoro$C_1$-$C_6$-alkyl;
$R^{1a}$ and $R^{3a}$, at each occurrence, are each independently hydrogen, $C_1$-$C_6$alkyl, or fluoro$C_1$-$C_6$-alkyl;
$R^d$ and $R^{3a}$, if present as a group $N(R^d)(R^{3a})$, such as in substituents —$C(O)N(R^d)(R^{3a})$, —$(CR^{4a}R^{5a})_m$—$C(O)N(R^d)(R^{3a})$, —$S(O)_2N(R^d)(R^{3a})$, —$N(R^c)C(O)N(R^d)(R^{3a})$, —$(CR^{4a}R^{5a})_m$—$S(O)_2N(R^d)(R^{3a})$, —$(CR^{4a}R^{5a})_m$—$N(R)C(O)N(R^d)(R^{3a})$, —$(CR^{4a}R^{5a})_m$—$N(R)(R^{3a})$, or —$N(R^d)(R^{3a})$, may together with the nitrogen atom of $N(R^d)(R^{3a})$ also form an N-bound saturated, 3 to 8 membered heterocycle, which in addition to the nitrogen atom may have 1 or 2 further heteroatoms as ring members, which are selected from O, S and N;
$R^c$ and $R^{1a}$, if present as a group —$N(R^c)C(O)R^{1a}$, may together with the atoms of said moiety form an N-bound saturated 3 to 8 membered heterocycle, which has an oxo group in 2-position and which in addition to the nitrogen atom may have 1 or 2 further heteroatoms as ring members, which are selected from O, S and N; and
$R^{2a}$, at each occurrence, is independently $C_1$-$C_6$alkyl, or fluoro$C_1$-$C_6$-alkyl; and
$R^{4a}$ and $R^{5a}$, at each occurrence, are each independently hydrogen, fluorine, $C_1$-$C_6$alkyl, or fluoro$C_1$-$C_6$-alkyl.

The following groups of compounds of the formula (I) are not part of the invention:
  Compounds of formula (I), where X is O, $R^1$ is methyl, $R^2$ is methyl, ethyl, n-butyl, unsubstituted benzyl, prop-2-ynyl, 2-(ethoxycarbonyl)ethyl or 2-carboxyethyl and $R^3$ is unsubstituted phenyl;
  Compounds of formula (I), where X is O, $R^1$ is methyl, $R^2$ is methyl, 2,2,2-trifluoroacetyl or unsubstituted benzyl, and $R^3$ is methyl;
  Compounds of formula (I), where X is O, $R^1$ is methyl, $R^2$ is ethoxycarbonylmethyl and $R^3$ is unsubstituted benzyl, or 4-methoxybenzyl.

Another aspect of the invention relates to pharmaceutical compositions comprising at least one compound of the invention, i.e. a compound of the formula (I), a pharmaceutically acceptable salt or isotopically labelled form thereof. In particular, the invention relates to a pharmaceutically composition comprising a therapeutically effective amount of a compound of the invention, i.e. a compound of the formula (I), a pharmaceutically acceptable salt or isotopically labelled form thereof in combination with a pharmaceutically acceptable carrier, diluent or excipient. Such compositions can be administered in accordance with a method or use of the invention, typically as part of a therapeutic regimen for treatment or prevention of conditions and disorders related to γ-aminobutyric acid receptor B (GABA-B) activity.

Yet another aspect of the invention relates to a method of enhancing the activity of the endogenous orthosteric agonist by altering the GABA-B receptor conformation by treatment at an allosteric binding site with a positive allosteric modulator.

The invention also relates to the compounds of the invention, a pharmaceutically acceptable salt or isotopically labelled form thereof for use in therapy, in particular for use in the treatment of a condition or disorder modulated by the γ-aminobutyric acid B (GABA-B) receptor in a mammal.

The invention also relates to the use of a compound of the invention, a pharmaceutically acceptable salt or isotopically labelled form thereof for the preparation of a medicament, in particular for the preparation of a medicament for the treatment of a condition or disorder modulated by the γ-aminobutyric acid B (GABA-B) receptor in a mammal.

Conditions and disorders related to γ-aminobutyric acid receptor B (GABA-B) activity include but are not limited to pain, substance abuse (especially in alcohol dependence), spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine and tinnitus, preferably in mammals. Accordingly, the compounds and compositions of the invention are useful as a medicament for treating or preventing γ-aminobutyric acid receptor B modulated diseases.

The compounds, compositions comprising the compounds, methods for making the compounds, and methods for treating or preventing conditions and disorders by administering the compounds are further described herein.

In a particular aspect, the compounds of the invention are provided for use in the treatment of pain, substance abuse (especially in alcohol dependence), and spasticity.

In an alternative embodiment, certain of the compounds of the invention have a positive allosteric modulator activity.

These and other objects of the invention are described in the following paragraphs. These objects should not be deemed to narrow the scope of the invention.

DETAILED DESCRIPTION OF THE INVENTION

Described herein are compounds of formula (I)

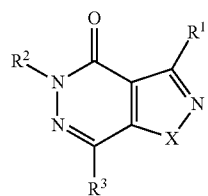

(I)

wherein $R^1$, $R^2$, $R^3$, and X are defined above in the Summary and below in the Detailed Description. Further, compositions comprising such compounds and methods for treating conditions and disorders using such compounds and compositions are also described.

Compounds described herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions of Terms

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

Certain terms as used in the specification are intended to refer to the following definitions, as detailed below.

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH2CH2-, and —CH=C(CH3)CH2-.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, and likewise the term "alkyl" in alkylcarbonyl, alkylcarbonylamino, alkylsulfonyl and alkylsulfonylamino, means a straight or branched, saturated hydrocarbon chain containing from 1 to 10 carbon atoms. The term "lower alkyl" or "$C_1$-$C_6$alkyl" means a straight or branched chain hydrocarbon containing from 1 to 6 carbon atoms. The term "$C_1$-$C_3$alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon containing from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

In the context of alkyl, alkenyl and alkynyl the term "partly or completely fluorinated" means that at least one, e.g. 1, 2, 3, 4, 5, 6, 7, 8 or 9 or all of the hydrogen atoms of alkyl, alkenyl or alkynyl has been replaced by fluorine atoms.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "alkoxyalkyl" as used herein, means an alkoxy group, as defined herein, appended to the parent molecular moiety through an alkylene group, as defined herein. Representative examples of alkoxyalkyl include, but are not limited to, methoxymethyl, ethoxymethyl, 2-methoxyethyl, 2-ethoxyethyl, 2-methoxypropyl, 2-ethoxypropyl, 3-methoxypropyl and 3-ethoxypropyl.

The term "arylalkyl" as used herein, means an aryl group, as defined herein, appended to the parent molecular moiety through an alkylene group, as defined herein. Representative examples of arylalkyl include, but are not limited to, benzyl, 1-phenylethyl, 2-phenylethyl, 3-phenylpropyl, and 2-naphth-2-ylethyl.

The term "carbonyl" as used herein means a —C(=O)— group.

The term "carboxy" as used herein means a —CO$_2$H group.

The term "cyano" as used herein, means a —CN group.

The terms "amido" and "carbamoyl", as used herein means a —C(O)NH2 group.

The term "amino" as used herein means an —NH$_2$ group.

The term "cycloalkyl" or "cycloalkane" as used herein, means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The spirocyclic cycloalkyl groups of the present invention can be appended to the parent molecular moiety through any substitutable carbon atom of the groups.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, fluoromethyl, 2-fluoroethyl, 2,2-difluoroethyl, 2,2,2-trifluoroethyl, trifluoromethyl, difluoromethyl, pentafluoroethyl, 1,1,2-trifluoroisopropyl, and trifluoropropyl such as 3,3,3-trifluoropropyl.

The term "halo" or "halogen" as used herein, means Cl, Br, I, or F.

The term "haloalkyl" as used herein, means an alkyl group, as defined herein, in which one, two, three, four, five, six, seven or eight hydrogen atoms are replaced by halogen, in particular by fluorine. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a heterocyclic aromatic radical and includes monocyclic heteroaryl and bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl", as used herein, refers to refers to a heteroaryl group attached to the parent molecular moiety through an alkyl group.

The term "heterocycle" or "heterocyclic" as used herein, means a non-aromatic heterocyclic radical and includes a monocyclic heterocycle, a bicyclic heterocycle, a tricyclic heterocycle, or a spirocyclic heterocycle. If not stated otherwise, the heterocyclic radical is saturated or has one or two non-conjugated endocyclic double bonds, e.g. a C=N or C=C double bond. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and octahydro-1H-4,7-epiminoisoindole. The spirocyclic heterocycles are exemplified by a monocyclic heterocycle as defined herein wherein one carbon atom of the monocyclic heterocycle is bridged by two ends of an alkylene chain. In the spirocyclic heterocycle, one or more carbon atoms in the bridging alkylene chain may be replaced with a heteroatom. Examples of spirocyclic heterocycles include, but are not limited to, 4,7-diazaspiro[2.5]octane, 2-oxa-6-azaspiro[3.3]heptane, 2,6-diazaspiro[3.3]heptane, 2-oxa-5,8-diazaspiro[3.5]nonane, 2,7-diazaspiro[3.5]nonane, 1,4-dioxa-8-azaspiro[4.5]decane, 1,6-diazaspiro[3.3]heptane, 1-azaspiro[4.4]nonane, 7-azaspiro[3.5]nonane, 1,4-dioxa-7-azaspiro[4.4]nonane, 5,8-diazaspiro[3.5]nonane, 5,8-dioxa-2-azaspiro[3.4]octane, 2-oxa-6-azaspiro[3.4]octane, 6-oxa-1-azaspiro[3.3]heptane, 6-oxa-2-azaspiro[3.4]octane, 6-oxa-2-azaspiro[3.5]nonane, and 7-oxa-2-azaspiro[3.5]nonane. The monocyclic, bicyclic, tricyclic, and spirocyclic heterocycles are connected to the parent molecular moiety through any carbon atom or any nitrogen atom contained within the rings, and can be unsubstituted or substituted.

The term "heterocycloalkyl", as used herein, refers to refers to a heterocycle group attached to the parent molecular moiety through an alkyl group.

The term "heterocyclecarbonyl" refers to a heterocycle, as defined herein, appended to the parent molecular moiety through a carbonyl group, as defined herein. Representative examples of heterocyclocarbonyl include, but are not limited to, piperidine-1-carbonyl, morpholine-4-carbonyl, and pyrrolidine-1-carbonyl.

The term "heteroatom" as used herein, means a nitrogen, oxygen, or sulfur atom.

The term "hydroxyl" or "hydroxy" as used herein, means an —OH group.

The term "oxo" as used herein means (=O).

If, for example, alkyl, alkenyl or alkynyl are substituted with both hydroxy and oxo, hydroxy and oxo may be bound to the same carbon atom thus forming a carboxy group.

If, for example, alkyl, alkenyl or alkynyl are substituted with both alkoxy and oxo, alkoxy and oxo may be bound to the same carbon atom thus forming an alkoxycarbonyl group.

In some instances, the number of carbon atoms in a hydrocarbyl substituent (e.g., alkyl, alkenyl, alkynyl, cycloalkyl, haloalkyl, alkoxy, and haloalkoxy, etc.) is indicated by the prefix "$C_x$-$C_y$", wherein x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms.

As used herein, the term "radiolabel" or "isotopically labeled form" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In preferred embodiments, the subject is a human.

Compounds of the Invention

Compounds of the invention can have the formula (I) as described in the Summary.

Particular values of variable groups in compounds of formula (I) are as follows. Such values can be used where appropriate with any of the other values, definitions, claims or embodiments defined hereinbefore or hereinafter.

Irrespective of its occurrence, $R^1$ is as defined above or selected from the group consisting of $C_1$-$C_6$alkyl, $C_2$-$C_6$alkenyl, $C_2$-$C_6$alkynyl and $C_3$-$C_6$cycloalkyl; wherein:

$C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo and where $C_1$-$C_6$alkyl, $C_2$-$C_6$alkenyl, and $C_2$-$C_6$alkynyl are in particular unsubstituted, partly or completely fluorinated and/or substituted with one of $C_1$-$C_6$alkoxy; and $C_3$-$C_6$cycloalkyl is unsubstituted or substituted with 1, 2, 3, 4 or 5 substituents, in particular with 1 or 2 substituents, which are independently selected from the group consisting of $C_1$-$C_6$alkyl, $C_1$-$C_6$alkoxy, fluorine, fluoroC$_1$-$C_6$alkyl, fluoroC$_1$-$C_6$alkoxy, hydroxy, and oxo and especially from the group consisting of $C_1$-$C_3$alkyl, $C_1$-$C_3$alkoxy and fluorine.

Irrespective of its occurrence, $R^1$ may also be selected from the group consisting of $C_1$-$C_6$alkyl, fluoroC$_1$-$C_6$alkyl, $C_1$-$C_4$-alkoxy-$C_1$-$C_4$-alkyl and cyclopropyl, wherein cyclopropyl is unsubstituted or substituted with 1 or 2 substituents independently selected from the group consisting of $C_1$-$C_3$alkyl, fluorine, and fluoroC$_1$-$C_3$alkyl.

Irrespective of its occurrence, $R^1$ may also be selected from the group consisting of $C_1$-$C_4$alkyl, $C_1$-$C_2$-alkoxy-$C_1$-$C_2$-alkyl and cyclopropyl, wherein cyclopropyl is unsubstituted or substituted with 1 or 2 substituents independently selected from the group consisting of methyl, ethyl, fluorine, and fluoroC$_1$-$C_2$alkyl.

Irrespective of its occurrence, $R^1$ may also be phenyl, which is unsubstituted or substituted with 1, 2, 3 or 4 substituents or with 1 or 2 substituents, where the substituents are selected from the group consisting of $C_1$-$C_6$alkyl, $C_1$-$C_6$alkoxy, fluoroC$_1$-$C_6$alkyl, fluoroC$_1$-$C_6$alkoxy, and halo, and where the substituents are in particular selected from the group consisting of $C_1$-$C_3$alkyl, $C_1$-$C_3$alkoxy, fluoroC$_1$-$C_2$alkyl, fluoroC$_1$-$C_2$alkoxy, fluorine or chlorine.

Examples of $R^1$ include methyl, ethyl, isopropyl, n-propyl, cyclopropyl, methoxymethyl, phenyl which is unsubstituted or substituted by halo.

According to a first group of embodiments, $R^2$ is selected from the group consisting of $C_1$-$C_6$alkyl, $C_2$-$C_6$alkenyl, and $C_2$-$C_6$alkynyl; wherein $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo or where $C_1$-$C_6$alkyl, $C_2$-$C_6$alkenyl, and $C_2$-$C_6$alkynyl are in particular unsubstituted or partly or completely fluorinated.

According to a subgroup of the first group of embodiments, $R^2$ is $C_1$-$C_6$alkyl, which is unsubstituted, partly or completely fluorinated and/or substituted with one or two substituents independently selected from the group consisting of $C_1$-$C_6$alkoxy, hydroxy, and oxo or where $C_1$-$C_6$alkyl is in particular unsubstituted or partly or completely fluorinated.

According to a further subgroup of the first group of embodiments, $R^2$ is $C_1$-$C_6$alkyl or fluoroC$_1$-$C_6$alkyl.

Examples of such radicals $R^2$ of this first group of embodiments include but are not limited to methyl, ethyl, n-propyl, n-butyl, isobutyl, 2-methylbutyl and 3-methylbutyl.

In the first group and in the subgroups of the first group of embodiments, $R^1$ is as defined above or selected from the group consisting of $C_1$-$C_6$alkyl, $C_2$-$C_6$alkenyl, $C_2$-$C_6$alkynyl and $C_3$-$C_6$cycloalkyl; wherein $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo and where $C_1$-$C_6$alkyl, $C_2$-$C_6$alkenyl, and $C_2$-$C_6$alkynyl are in particular unsubstituted, partly or completely fluorinated and/or substituted with one of $C_1$-$C_6$alkoxy; and $C_3$-$C_6$cycloalkyl is unsubstituted or substituted with 1, 2, 3, 4 or 5 substituents, in particular with 1 or 2 substituents, which are independently selected from the group consisting of $C_1$-$C_6$alkyl, $C_1$-$C_6$alkoxy, fluorine, fluoroC$_1$-$C_6$alkyl, fluoroC$_1$-$C_6$alkoxy, hydroxy, and oxo and especially from the group consisting of $C_1$-$C_3$alkyl, $C_1$-$C_3$alkoxy and fluorine.

In the first group and in the subgroups of the first group of embodiments, $R^1$ may also be selected from the group consisting of $C_1$-$C_6$alkyl, fluoroC$_1$-$C_6$alkyl, $C_1$-$C_4$-alkoxy-$C_1$-$C_4$-alkyl and cyclopropyl, wherein cyclopropyl is unsubstituted or substituted with 1 or 2 substituents independently selected from the group consisting of $C_1$-$C_3$alkyl, fluorine, and fluoroC$_1$-$C_3$alkyl.

In the first group and in the subgroups of the first group of embodiments, $R^1$ may also be selected from the group consisting of $C_1$-$C_4$alkyl, $C_1$-$C_2$-alkoxy-$C_1$-$C_2$-alkyl and cyclopropyl, wherein cyclopropyl is unsubstituted or substituted with 1 or 2 substituents independently selected from the group consisting of methyl, ethyl, fluorine, and fluoroC$_1$-$C_2$alkyl.

In the first group and in the subgroups of the first group of embodiments, $R^1$ may also be phenyl, which is unsubstituted or substituted with 1, 2, 3 or 4 substituents or with 1 or 2 substituents, where the substituents are selected from the group consisting of $C_1$-$C_6$alkyl, $C_1$-$C_6$alkoxy, fluoroC$_1$-$C_6$alkyl, fluoroC$_1$-$C_6$alkoxy, and halo, and where the substituents are in particular selected from the group consisting of $C_1$-$C_3$alkyl, $C_1$-$C_3$alkoxy, fluoroC$_1$-$C_2$alkyl, fluoroC$_1$-$C_2$alkoxy, fluorine or chlorine.

According to a second group of embodiments, $R^2$ is —(CR$^a$R$^b$)$_n$-G$^1$, wherein n, R$^a$, R$^b$ and G$^1$ are as defined above, or wherein n is 1 or 2 or wherein n is 1.

If G$^1$ is a phenyl radical, phenyl is in particular substituted with 1, 2, 3 or 4 substituents as defined above.

A skilled person will readily appreciate that for n being 2 or 3 the moieties CR$^a$R$^b$ can be identical or different.

According to a first subgroup of the second group of embodiments, $R^2$ is —(CR$^a$R$^b$)$_n$-G$^1$, wherein n, R$^a$ and R$^b$ are as defined above and wherein G$^1$ is selected from the group consisting of phenyl and monocyclic heteroaryl, in particular phenyl and 6 membered monocyclic hetaryl, such as 2, 3 or 4 pyridyl;

wherein the phenyl and the monocyclic heteroaryl of G$^1$ are unsubstituted or substituted with 1, 2, 3 or 4 substituents, in particular with 1 or 2 substituents, which are independently selected from the group consisting of $C_1$-$C_6$alkyl, $C_1$-$C_6$alkoxy, cyano, fluoro$C_1$-$C_6$alkyl, fluoro$C_1$-$C_6$alkoxy, halo, and hydroxy.

According to a second subgroup of the second group of embodiments, $R^2$ is —$(CR^aR^b)_n$-$G^1$, wherein n, $R^a$ and $R^b$ are as defined above and wherein $G^1$ is phenyl, which is unsubstituted or in particular substituted with 1, 2, 3 or 4 substituents, where the substituents are independently selected from the group consisting of $C_1$-$C_6$alkyl, $C_1$-$C_6$alkoxy, fluoro$C_1$-$C_6$alkyl, fluoro$C_1$-$C_6$alkoxy, halo, and hydroxyl and in particular from the group consisting of $C_1$-$C_3$alkyl, $C_1$-$C_3$alkoxy, fluoro$C_1$-$C_3$alkyl, fluorine and chlorine.

According to a third subgroup of the second group of embodiments, $R^2$ is —$(CR^aR^b)_n$-$G^1$, wherein n, $R^a$ and $R^b$ are as defined above and wherein $G^1$ is phenyl, which is substituted with 1 or 2 substituents as defined above, where the substituents are independently selected from the group consisting of $C_1$-$C_6$alkyl, $C_1$-$C_6$alkoxy, fluoro$C_1$-$C_6$alkyl, fluoro$C_1$-$C_6$alkoxy, halo, and hydroxyl and in particular from the group consisting of $C_1$-$C_3$alkyl, $C_1$-$C_3$alkoxy, fluoro$C_1$-$C_3$alkyl, fluorine and chlorine.

In the second group of embodiments and in the first, second and third subgroup of embodiments, $R^a$ and $R^b$ are as defined above,
- or $R^a$ and $R^b$ are independently selected at each occurrence from the group consisting of hydrogen, $C_1$-$C_6$alkyl and phenyl, wherein phenyl is unsubstituted or substituted with 1, 2 or 3 substituents selected from the group consisting of $C_1$-$C_6$alkyl, $C_1$-$C_6$alkoxy, fluoro$C_1$-$C_6$alkyl, fluoro$C_1$-$C_6$alkoxy, and halo;
- or $R^a$ and $R^b$ are independently selected at each occurrence from the group consisting of hydrogen, $C_1$-$C_3$alkyl and phenyl, wherein phenyl is unsubstituted or substituted with 1, 2 or 3 substituents selected from the group consisting of $C_1$-$C_3$alkyl, fluoro$C_1$-$C_3$alkyl, $C_1$-$C_3$alkoxy, fluorine and chlorine.
- or $R^a$ and $R^b$ are independently selected at each occurrence from the group consisting of hydrogen, methyl and phenyl, wherein phenyl is unsubstituted or substituted with 1or 2 substituents selected from the group consisting of methyl, trifluoromethyl, methoxy, fluorine and chlorine.

In particular, either one or both of the radicals $R^a$ and $R^b$ of each group $CR^aR^b$ is/are hydrogen.

In a fourth subgroup of the second group of embodiments, the moiety —$(CR^aR^b)_n$— is $CH_2$, $CH_2CH_2$, $CH(CH_3)$ or CH(phenyl), where phenyl is unsubstituted or carries 1 substituent as defined above or a substituent selected from the group consisting of $C_1$-$C_3$alkyl, $C_1$-$C_3$alkoxy, fluorine and chlorine. In this particular subgroup of the second embodiments, and G1 is as above.

In fifth subgroup of the second group of embodiments, the moiety —$(CR^aR^b)_n$— is $CH_2$, $CH_2CH_2$, $CH(CH_3)$ or CH(phenyl), where phenyl is unsubstituted or carries 1 substituent as defined above or a substituent selected from the group consisting of $C_1$-$C_3$alkyl, $C_1$-$C_3$alkoxy, fluorine and chlorine and G1 is as defined in the first, second or third subgroup of the second group of embodiments.

In a sixth subgroup of the second group of embodiments the moiety —$(CR^aR^b)_n$— is $CH(CH_3)$.

In a seventh subgroup of the second group of embodiments the moiety —$(CR^aR^b)_n$— is $CH(CH_3)$, which has predominately R-configuration. Predominately R-configuration means that the molar ratio of the R-enantiomer to the S-enantiomer is >1:1, in particular >3:1, more particularly >4:1 and especially >9:1.

In an eighth subgroup of the second group of embodiments the moiety —$(CR^aR^b)_n$— is $CH(CH_3)$, which has predominately R-configuration and G1 is as defined in the first, second or third subgroup of embodiments.

Examples of such radicals $R^2$ of this second group of embodiments include but are not limited to 4-chlorphenylmethyl, 3-(trifluoromethyl)phenylmethyl, 4-(trifluoromethyl)phenylmethyl, 4-methoxy-3-(trifluoromethyl)phenylmethyl, 2-fluoro-5-(trifluoromethyl)phenylmethyl, 5-chloro-2-fluorophenylmethyl, 4-chloro-2-fluorophenylmethyl, 4-chlorophenylphenylmethyl, 2,4-difluorophenylmethyl, 4-fluoro-3-(trifluoromethyl)phenylmethyl, 4-chloro-3-(trifluoromethyl)phenylmethyl, 2-fluorophenylmethyl, 4-fluorophenylmethyl, (1RS)-1-(4-chlorphenyl)ethyl, (1R)-1-(4-chlorphenyl)ethyl, (1S)-1-(4-chlorphenyl)ethyl, 2-(4-chlorphenyl)ethyl, (1RS)-1-(4-(trifluoromethyl)phenyl)ethyl, (1R)-1-(4-(trifluoromethyl)phenyl)ethyl, (1S)-1-(4-(trifluoromethyl)phenyl)ethyl, and 4-pyridylmethyl.

In the second group of embodiments and also in the first, second, third, fourth, fifth, sixth, seventh and eighth subgroups of the second group of embodiments, $R^1$ is as defined above or selected from the group consisting of $C_1$-$C_6$alkyl, $C_2$-$C_6$alkenyl, $C_2$-$C_6$alkynyl and $C_3$-$C_6$cycloalkyl; wherein
- $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo and where $C_1$-$C_6$alkyl, $C_2$-$C_6$alkenyl, and $C_2$-$C_6$alkynyl are in particular unsubstituted, partly or completely fluorinated and/or substituted with one of $C_1$-$C_6$alkoxy; and
- $C_3$-$C_6$cycloalkyl is unsubstituted or substituted with 1, 2, 3, 4 or 5 substituents, in particular with 1 or 2 substituents, which are independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo and especially from the group consisting of $C_1$-$C_3$alkyl, $C_1$-$C_3$alkoxy and fluorine.

In the second group of embodiments and also in the first, second, third, fourth, fifth, sixth, seventh and eighth subgroups of the second group of embodiments, $R^1$ may also be selected from the group consisting of $C_1$-$C_6$alkyl, fluoro$C_1$-$C_6$alkyl, $C_1$-$C_4$-alkoxy-$C_1$-$C_4$-alkyl and cyclopropyl, wherein cyclopropyl is unsubstituted or substituted with 1 or 2 substituents independently selected from the group consisting of $C_1$-$C_3$alkyl, fluorine, and fluoro$C_1$-$C_3$alkyl.

In the second group of embodiments and also in the first, second, third, fourth, fifth, sixth, seventh and eighth subgroups of the second group of embodiments, $R^1$ may also be selected from the group consisting of $C_1$-$C_4$alkyl, $C_1$-$C_2$-alkoxy-$C_1$-$C_2$-alkyl and cyclopropyl, wherein cyclopropyl is unsubstituted or substituted with 1 or 2 substituents independently selected from the group consisting of methyl, ethyl, fluorine, and fluoro$C_1$-$C_2$alkyl.

In the second group of embodiments and also in the first, second, third, fourth, fifth, sixth, seventh and eighth subgroups of the second group of embodiments, $R^1$ may also be phenyl, which is unsubstituted or substituted with 1, 2, 3 or 4 substituents or with 1 or 2 substituents, where the substituents are selected from the group consisting of $C_1$-$C_6$alkyl, $C_1$-$C_6$alkoxy, fluoro$C_1$-$C_6$alkyl, fluoro$C_1$-$C_6$alkoxy, and halo, and where the substituents are in particular selected from the group consisting of $C_1$-$C_3$alkyl, $C_1$-$C_3$alkoxy, fluoro$C_1$-$C_2$alkyl, fluoro$C_1$-$C_2$alkoxy, fluorine or chlorine.

Irrespective of its occurrence, $R^3$ is as defined above.

According to a third group of embodiments $R^3$ is selected from the group consisting of $C_1$-$C_6$alkyl and $C_3$-$C_6$cycloalkyl; wherein
- $C_1$-$C_6$alkyl is unsubstituted, partly or completely fluorinated and/or substituted with one or two substituents independently selected from the group consisting of $C_1$-$C_6$alkoxy, hydroxy, and oxo; and
- $C_3$-$C_6$cycloalkyl is unsubstituted or substituted with 1, 2, 3, 4 or 5 substituents independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo.

In a subgroup of the third embodiment $R^3$ is $C_1$-$C_6$alkyl or fluoro$C_1$-$C_6$alkyl.

According to a forth group of embodiments $R^3$ is selected from the group consisting of phenyl, phenyl$C_1$-$C_6$alkyl, bicyclic aryl, bicyclic aryl$C_1$-$C_6$alkyl, monocyclic heteroaryl$C_1$-$C_6$alkyl, monocyclic heteroaryl, and bicyclic heteroaryl; wherein the phenyl, the phenyl of phenyl$C_1$-$C_6$alkyl, the bicyclic aryl, the bicyclic aryl of bicyclic aryl$C_1$-$C_6$alkyl, the monocyclic heteroaryl of monocyclic heteroaryl$C_1$-$C_6$alkyl, the monocyclic heteroaryl and the bicyclic heteroaryl are optionally substituted with 1, 2, 3 or 4 substituents $R^{Ar}$.

In a subgroup of the fourth embodiment $R^3$ is selected from the group consisting of phenyl and monocyclic heteroaryl, such as pyridyl, pyrimidinyl or thienyl; wherein phenyl is substituted with 1, 2, 3 or 4 substituents $R^{Ar}$ and where the monocyclic heteroaryl is unsubstituted or substituted with 1, 2, 3 or 4 substituents $R^{Ar}$.

In a further subgroup of the fourth embodiment $R^3$ is phenyl which is substituted with 1, 2, 3 or 4 substituents $R^{Ar}$ and where the monocyclic heteroaryl is unsubstituted or substituted with 1, 2, 3 or 4 substituents $R^{Ar}$.

Irrespective of its occurrence and also in the fourth embodiment and in the subgroups of the forth embodiment the substituents $R^{Ar}$ are as defined above or, independently of its occurrence, selected from the group consisting of $C_1$-$C_6$alkyl, halogen, —$OR^{1a}$, —$S(O)_2N(R^d)(R^{3a})$, —$C(O)R^{1a}$, —$C(O)OR^{1a}$, —$C(O)N(R^d)(R^{3a})$, —$N(R^d)(R^{3a})$, —$N(R^c)C(O)R^{1a}$, —$N(R)S(O)_2R^{2a}$ and fluoro$C_1$-$C_6$-alkyl; wherein $R^{1a}$, $R^{2a}$, $R^{3a}$, $R^c$ and $R^d$ are as defined above or
- $R^c$ and $R^d$, at each occurrence, are each independently hydrogen, $C_1$-$C_6$alkyl, or fluoro$C_1$-$C_6$-alkyl;
- $R^{1a}$ and $R^{3a}$, at each occurrence, are each independently hydrogen, $C_1$-$C_6$alkyl, or fluoro$C_1$-$C_6$-alkyl;
- $R^d$ and $R^{3a}$, if present as a group $N(R^d)(R^{3a})$, such as in substituents —$C(O)N(R^d)(R^{3a})$ or —$N(R^d)(R^{3a})$, may together with the atoms of said moiety form a pyrrolidin-1-yl, piperidin-1-yl or azepan-1-yl radical; and
- $R^{2a}$, at each occurrence, is independently $C_1$-$C_6$alkyl, or fluoro$C_1$-$C_6$-alkyl.

Examples of such radicals $R^{Ar}$ include but are not limited to fluoro, chloro, amino, hydroxyl, methyl, methoxy, carbamoyl, carboxy, acetylamino, methylsulfonylamino, N-methylaminocarbonyl, N,N-dimethylaminocarbonyl, N-ethylaminocarbonyl, 1-pyrrolidin-2-onyl.

Examples of such radicals $R^3$ include but are not limited to methyl, ethyl, phenyl, 3-fluorophenyl, 4-fluorophenyl, 2-aminophenyl, 3-aminophenyl, 2-hydroxyphenyl, 2-methylphenyl, 2-methoxyphenyl, 4-methoxyphenyl, 3-carbamoylphenyl, 3-(acetylamino)phenyl, 3-(methylsulfonylamino)phenyl, 3-(aminosulfonyl)phenyl, 3,4-difluorophenyl, 3,5-difluorophenyl, 2,4-bis(methoxy)phenyl, 3,4-bis(methoxy)phenyl, 2,5-bis(methoxy)phenyl, 2-methoxy-5-fluorophenyl, 2-amino-5-fluorophenyl, 2-methoxy-5-carboxyphenyl, 2-methoxy-5-(trifluoromethyl)phenyl, 2-methoxy-5-(acetylamino)phenyl, 2-methoxy-3-(acetylamino)phenyl, 2-(trifluoromethoxy)-5-(acetylamino)phenyl, 2-methoxy-5-(methylsulfonyl-amino)phenyl, 4-fluoro-3-(acetylamino)phenyl, 2-methyl-5-(acetylamino)phenyl, 2-methyl-5-hydroxyphenyl, 2-methoxy-5-(aminocarbonyl)phenyl, 3-amino-2-(aminocarbonyl)phenyl, 2-methoxy-5-(N-methylaminocarbonyl)phenyl, 2-methoxy-5-(N-ethylaminocarbonyl)phenyl, 2-methoxy-5-(N,N-dimethylamino-carbonyl)phenyl, 2-methoxy-5-(pyrrolidin-1-ylcarbonyl)phenyl, 2-methoxy-5-(pyrrolidin-2on-1-yl)phenyl, 3-methoxy-5-(N,N-dimethylaminocarbonyl)phenyl, 2-amino-5-chlorophenyl, 2-amino-5-(trifluoromethyl)phenyl, 2-amino-3,5-difluorophenyl, 2-methyl-3-(acetylamino)-4-fluorophenyl, 3-pyridyl, 5-pyrimidinyl, 2-fluoro-3-pyridyl, 2-amino-4-pyridyl, 5-fluoro-3-pyridyl, 2-chloro-3-pyridyl, indol-5-yl, 2,6-difluoropyridin-4-yl, 2-thienyl, 1-ethylpyrazol-5-yl, and 1H-pyrrolo[2,3-b]pyridine-6-yl.

Irrespective of its occurrence, X is in particular O.

In the first group of embodiments and in the subgroups of the first group of embodiments, X is as defined above or X is O.

In the second group of embodiments and in the subgroups of the second group of embodiments, X is as defined above or X is O.

In the third group of embodiments and in the subgroups of the third group of embodiments, X is as defined above or X is O.

In the fourth group of embodiments and in the subgroups of the forth group of embodiments, X is as defined above or X is O.

In the third group of embodiments, in the fourth group of embodiments and also in the subgroups of the third and fourth groups of embodiments, $R^1$ is as defined above or selected from the group consisting of $C_1$-$C_6$alkyl, $C_2$-$C_6$alkenyl, $C_2$-$C_6$alkynyl and $C_3$-$C_6$cycloalkyl; wherein
- $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo and where $C_1$-$C_6$alkyl, $C_2$-$C_6$alkenyl, and $C_2$-$C_6$alkynyl are in particular unsubstituted, partly or completely fluorinated and/or substituted with one of $C_1$-$C_6$alkoxy; and
- $C_3$-$C_6$cycloalkyl is unsubstituted or substituted with 1, 2, 3, 4 or 5 substituents, in particular with 1 or 2 substituents, which are independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo and especially from the group consisting of $C_1$-$C_3$alkyl, $C_1$-$C_3$alkoxy and fluorine.

In the third group of embodiments, in the fourth group of embodiments and also in the subgroups of the third and fourth groups of embodiments, $R^1$ may also be selected from the group consisting of $C_1$-$C_6$alkyl, fluoro$C_1$-$C_6$alkyl, $C_1$-$C_4$-alkoxy-$C_1$-$C_4$-alkyl and cyclopropyl, wherein cyclopropyl is unsubstituted or substituted with 1 or 2 substituents independently selected from the group consisting of $C_1$-$C_3$alkyl, fluorine, and fluoro$C_1$-$C_3$alkyl.

In the third group of embodiments, in the fourth group of embodiments and also in the subgroups of the third and fourth groups of embodiments, $R^1$ may also be selected from the group consisting of $C_1$-$C_4$alkyl, $C_1$-$C_2$-alkoxy-$C_1$-$C_2$-alkyl and cyclopropyl, wherein cyclopropyl is unsubstituted or substituted with 1 or 2 substituents independently selected from the group consisting of methyl, ethyl, fluorine, and fluoro$C_1$-$C_2$alkyl.

In the third group of embodiments, in the fourth group of embodiments and also in the subgroups of the third and fourth groups of embodiments, $R^1$ may also be phenyl, which is unsubstituted or substituted with 1, 2, 3 or 4 substituents or with 1 or 2 substituents, where the substituents are selected from the group consisting of $C_1$-$C_6$alkyl, $C_1$-$C_6$alkoxy, fluoro$C_1$-$C_6$alkyl, fluoro$C_1$-$C_6$alkoxy, and halo, and where the substituents are in particular selected from the group consisting of $C_1$-$C_3$alkyl, $C_1$-$C_3$alkoxy, fluoro$C_1$-$C_2$alkyl, fluoro$C_1$-$C_2$alkoxy, fluorine or chlorine.

A fifth group of embodiments relates to compounds of the formula (I) or to their pharmaceutically acceptable salts or isotopically labeled forms, wherein $R^1$ is selected from the group consisting of $C_1$-$C_6$alkyl, $C_2$-$C_6$alkenyl, $C_2$-$C_6$alkynyl and $C_3$-$C_6$cycloalkyl; wherein $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo and where $C_1$-$C_6$alkyl, $C_2$-$C_6$alkenyl, and $C_2$-$C_6$alkynyl are in particular unsubstituted, partly or completely fluorinated and/or substituted with one of $C_1$-$C_6$alkoxy; and $C_3$-$C_6$cycloalkyl is unsubstituted or substituted with 1, 2, 3, 4 or 5 substituents, in particular with 1 or 2 substituents, which are independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo and especially from the group consisting of $C_1$-$C_3$alkyl, $C_1$-$C_3$alkoxy and fluorine;

$R^2$ is as defined for the first group of embodiments or as defined for the subgroups of the first group of embodiments;

$R^3$ is as defined for the third group of embodiments or as defined for the subgroup of the third group of embodiments, and X is as defined above or X is O.

A sixth group of embodiments relates to compounds of the formula (I) and to their pharmaceutically acceptable salts or isotopically labeled forms, wherein $R^1$ is selected from the group consisting of $C_1$-$C_6$alkyl, $C_2$-$C_6$alkenyl, $C_2$-$C_6$alkynyl and $C_3$-$C_6$cycloalkyl; wherein $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo and where $C_1$-$C_6$alkyl, $C_2$-$C_6$alkenyl, and $C_2$-$C_6$alkynyl are in particular unsubstituted, partly or completely fluorinated and/or substituted with one of $C_1$-$C_6$alkoxy; and $C_3$-$C_6$cycloalkyl is unsubstituted or substituted with 1, 2, 3, 4 or 5 substituents, in particular with 1 or 2 substituents, which are independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo and especially from the group consisting of $C_1$-$C_3$alkyl, $C_1$-$C_3$alkoxy and fluorine;

$R^2$ is as defined for the second group of embodiments or as defined for the first, second, third, fourth, fifth, sixth or seventh subgroups of the second group of embodiments;

$R^3$ is as defined for the third group of embodiments or as defined for the subgroup of the third group of embodiments; and X is as defined above or X is O.

A seventh group of embodiments relates to compounds of the formula (I) and to their pharmaceutically acceptable salts or isotopically labeled forms, wherein $R^1$ is selected from the group consisting of $C_1$-$C_6$alkyl, $C_2$-$C_6$alkenyl, $C_2$-$C_6$alkynyl and $C_3$-$C_6$cycloalkyl; wherein $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo and where $C_1$-$C_6$alkyl, $C_2$-$C_6$alkenyl, and $C_2$-$C_6$alkynyl are in particular unsubstituted, partly or completely fluorinated and/or substituted with one of $C_1$-$C_6$alkoxy; and $C_3$-$C_6$cycloalkyl is unsubstituted or substituted with 1, 2, 3, 4 or 5 substituents, in particular with 1 or 2 substituents, which are independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo and especially from the group consisting of $C_1$-$C_3$alkyl, $C_1$-$C_3$alkoxy and fluorine;

$R^2$ is as defined for the first group of embodiments or as defined for the subgroups of the first group of embodiments;

$R^3$ is as defined for the third group of embodiments or as defined for the subgroup of the fourth group of embodiments; and X is as defined above or X is O.

An eighth group of embodiments relates to compounds of the formula (I) and to their pharmaceutically acceptable salts or isotopically labeled forms, wherein $R^1$ is selected from the group consisting of $C_1$-$C_6$alkyl, $C_2$-$C_6$alkenyl, $C_2$-$C_6$alkynyl and $C_3$-$C_6$cycloalkyl; wherein $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo and where $C_1$-$C_6$alkyl, $C_2$-$C_6$alkenyl, and $C_2$-$C_6$alkynyl are in particular unsubstituted, partly or completely fluorinated and/or substituted with one of $C_1$-$C_6$alkoxy; and $C_3$-$C_6$cycloalkyl is unsubstituted or substituted with 1, 2, 3, 4 or 5 substituents, in particular with 1 or 2 substituents, which are independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo and especially from the group consisting of $C_1$-$C_3$alkyl, $C_1$-$C_3$alkoxy and fluorine;

$R^2$ is as defined for the second group of embodiments or as defined for the first, second, third, fourth, fifth, sixth or seventh subgroups of the second group of embodiments;

$R^3$ is as defined for the fourth group of embodiments or as defined for the subgroup of the fourth group of embodiments; and X is as defined above or X is O.

A $9^{th}$ group of embodiments relates to compounds of the formula (I) and to their pharmaceutically acceptable salts or isotopically labeled forms, wherein $R^1$ is selected from the group consisting of $C_1$-$C_6$alkyl, fluoro$C_1$-$C_6$alkyl, $C_1$-$C_4$-alkoxy-$C_1$-$C_4$-alkyl and cyclopropyl, wherein cyclopropyl is unsubstituted or substituted with 1 or 2 substituents independently selected from the group consisting of $C_1$-$C_3$alkyl, fluorine, and fluoro$C_1$-$C_3$alkyl, and where $R^1$ is in particular selected from the group consisting of $C_1$-$C_4$alkyl, $C_1$-$C_2$-alkoxy-$C_1$-$C_2$-alkyl and cyclopropyl, wherein cyclopropyl is unsubstituted or substituted with 1 or 2 substituents independently selected from the group consisting of methyl, ethyl, fluorine, and fluoroC$_1$-C$_2$alkyl;

R$^2$ is as defined for the first group of embodiments or as defined for the subgroups of the first group of embodiments, and R$^3$ is as defined for the third group of embodiments or as defined for the subgroup of the third group of embodiments.

In the 9$^{th}$ group of embodiments, X is as defined above or X is O.

A 10$^{th}$ group of embodiments relates to compounds of the formula (I) and to their pharmaceutically acceptable salts or isotopically labeled forms, wherein R$^1$ is selected from the group consisting of C$_1$-C$_6$alkyl, fluoroC$_1$-C$_6$alkyl, C$_1$-C$_4$-alkoxy-C$_1$-C$_4$-alkyl and cyclopropyl, wherein cyclopropyl is unsubstituted or substituted with 1 or 2 substituents independently selected from the group consisting of C$_1$-C$_3$alkyl, fluorine, and fluoroC$_1$-C$_3$alkyl, and where R$^1$ is in particular selected from the group consisting of C$_1$-C$_4$alkyl, C$_1$-C$_2$-alkoxy-C$_1$-C$_2$-alkyl and cyclopropyl, wherein cyclopropyl is unsubstituted or substituted with 1 or 2 substituents independently selected from the group consisting of methyl, ethyl, fluorine, and fluoroC$_1$-C$_2$alkyl;

R$^2$ is as defined for the second group of embodiments or as defined for the first, second, third, fourth, fifth, sixth or seventh subgroups of the second group of embodiments, and R$^3$ is as defined for the third group of embodiments or as defined for the subgroup of the third group of embodiments.

In the 10$^{th}$ group of embodiments, X is as defined above or X is O.

An 11$^{th}$ group of embodiments relates to compounds of the formula (I) and to their pharmaceutically acceptable salts or isotopically labeled forms, wherein R$^1$ is selected from the group consisting of C$_1$-C$_6$alkyl, fluoroC$_1$-C$_6$alkyl, C$_1$-C$_4$-alkoxy-C$_1$-C$_4$-alkyl and cyclopropyl, wherein cyclopropyl is unsubstituted or substituted with 1 or 2 substituents independently selected from the group consisting of C$_1$-C$_3$alkyl, fluorine, and fluoroC$_1$-C$_3$alkyl, and where R$^1$ is in particular selected from the group consisting of C$_1$-C$_4$alkyl, C$_1$-C$_2$-alkoxy-C$_1$-C$_2$-alkyl and cyclopropyl, wherein cyclopropyl is unsubstituted or substituted with 1 or 2 substituents independently selected from the group consisting of methyl, ethyl, fluorine, and fluoroC$_1$-C$_2$alkyl;

R$^2$ is as defined for the first group of embodiments or as defined for the subgroups of the first group of embodiments, and R$^3$ is as defined for the third group of embodiments or as defined for the subgroup of the fourth group of embodiments.

In the 11$^{th}$ group of embodiments, X is as defined above or X is O.

A 12$^{th}$ group of embodiments relates to compounds of the formula (I) and to their pharmaceutically acceptable salts or isotopically labeled forms, wherein R$^1$ is selected from the group consisting of C$_1$-C$_6$alkyl, fluoroC$_1$-C$_6$alkyl, C$_1$-C$_4$-alkoxy-C$_1$-C$_4$-alkyl and cyclopropyl, wherein cyclopropyl is unsubstituted or substituted with 1 or 2 substituents independently selected from the group consisting of C$_1$-C$_3$alkyl, fluorine, and fluoroC$_1$-C$_3$alkyl, and where R$^1$ is in particular selected from the group consisting of C$_1$-C$_4$alkyl, C$_1$-C$_2$-alkoxy-C$_1$-C$_2$-alkyl and cyclopropyl, wherein cyclopropyl is unsubstituted or substituted with 1 or 2 substituents independently selected from the group consisting of methyl, ethyl, fluorine, and fluoroC$_1$-C$_2$alkyl;

R$^2$ is as defined for the second group of embodiments or as defined for the first, second, third, fourth, fifth, sixth or seventh subgroups of the second group of embodiments, and R$^3$ is as defined for the fourth group of embodiments or as defined for the subgroup of the fourth group of embodiments.

In the 11$^{th}$ group of embodiments, X is as defined above or X is O.

A special group of embodiments relates to compounds, wherein

R$^1$ is selected from the group consisting of methyl, ethyl, isopropyl, n-propyl, cyclopropyl, methoxymethyl and phenyl which is unsubstituted or substituted by halo.

R$^2$ is selected from the group consisting of 4-chlorphenylmethyl, 3-(trifluoromethyl)phenylmethyl, 4-(trifluoromethyl)phenylmethyl, 4-methoxy-3-(trifluoromethyl)phenylmethyl, 2-fluoro-5-(trifluoromethyl)phenylmethyl, 5-chloro-2-fluorophenylmethyl, 4-chloro-2-fluorophenylmethyl, 4-chlorophenylphenylmethyl, 2,4-difluorophenylmethyl, 4-fluoro-3-(trifluoromethyl)phenylmethyl, 4-chloro-3-(trifluoromethyl)phenylmethyl, 2-fluorophenylmethyl, 4-fluorophenylmethyl, (1RS)-1-(4-chlorphenyl)ethyl, (1R)-1-(4-chlorphenyl)ethyl, (1S)-1-(4-chlorphenyl)ethyl, 2-(4-chlorphenyl)ethyl, (1RS)-1-(4-(trifluoromethyl)phenyl)ethyl, (1R)-1-(4-(trifluoromethyl)phenyl)ethyl, (1S)-1-(4-(trifluoromethyl)phenyl)ethyl, and 4-pyridylmethyl;

R$^3$ is selected from the group consisting of methyl, ethyl, phenyl, 3-fluorophenyl, 4-fluorophenyl, 2-aminophenyl, 3-aminophenyl, 2-hydroxyphenyl, 2-methylphenyl, 2-methoxyphenyl, 4-methoxyphenyl, 3-carbamoylphenyl, 3-(acetylamino)phenyl, 3-(methylsulfonylamino)phenyl, 3-(aminosulfonyl)phenyl, 3,4-difluorophenyl, 3,5-difluorophenyl, 2,4-bis(methoxy)phenyl, 3,4-bis(methoxy)phenyl, 2,5-bis(methoxy)phenyl, 2-methoxy-5-fluorophenyl, 2-amino-5-fluorophenyl, 2-methoxy-5-carboxyphenyl, 2-methoxy-5-(trifluoromethyl)phenyl, 2-methoxy-5-(acetylamino)phenyl, 2-methoxy-3-(acetylamino)phenyl, 2-(trifluoromethoxy)-5-(acetylamino)phenyl, 2-methoxy-5-(methylsulfonylamino)phenyl, 4-fluoro-3-(acetylamino)phenyl, 2-methyl-5-(acetylamino)phenyl, 2-methyl-5-hydroxyphenyl, 2-methoxy-5-(aminocarbonyl)phenyl, 3-amino-2-(aminocarbonyl)phenyl, 2-methoxy-5-(N-methylaminocarbonyl)phenyl, 2-methoxy-5-(N-ethylaminocarbonyl)phenyl, 2-methoxy-5-(N,N-dimethylaminocarbonyl)phenyl, 2-methoxy-5-(pyrrolidin-1-ylcarbonyl)phenyl, 2-methoxy-5-(pyrrolidin-2-on-1-yl)phenyl, 3-methoxy-5-(N,N-dimethylaminocarbonyl)phenyl, 2-amino-5-chlorophenyl, 2-amino-5-(trifluoromethyl)phenyl, 2-amino-3,5-difluorophenyl, 2-methyl-3-(acetylamino)-4-fluorophenyl, 3-pyridyl, 5-pyrimidinyl, 2-fluoro-3-pyridyl, 2-amino-4-pyridyl, 5-fluoro-3-pyridyl, 2-chloro-3-pyridyl, indol-5-yl, 2,6-difluoropyridin-4-yl, 2-thienyl, 1-ethylpyrazol-5-yl, and 1H-pyrrolo[2,3-b]pyridine-6-yl; and X is O.

Specific embodiments contemplated as part of the invention also include, but are not limited to, compounds or pharmaceutically acceptable salts or isotopically labeled forms thereof, as defined, for example:

N-(3-{5-[(1S)-1-(4-chlorophenyl)ethyl]-3-cyclopropyl-4-oxo-4,5-dihydro[1,2]oxazolo[4,5-d]pyridazin-7-yl}-4-methoxyphenyl)acetamide;

5-(4-chlorobenzyl)-7-(4-methoxyphenyl)-3-methyl[1,2]oxazolo[4,5-d]pyridazin-4(5H)-one;

N-(3-{5-[(1R)-1-(4-chlorophenyl)ethyl]-3-cyclopropyl-4-oxo-4,5-dihydro[1,2]oxazolo[4,5-d]pyridazin-7-yl}-4-methoxyphenyl)acetamide;

5-[1-(4-chlorophenyl)ethyl]-7-(2,6-difluoropyridin-4-yl)-3-methyl[1,2]oxazolo[4,5-d]pyridazin-4(5H)-one;

7-(2,4-dimethoxyphenyl)-3-methyl-5-(pyridin-4-ylmethyl)[1,2]oxazolo[4,5-d]pyridazin-4(5H)-one;

7-(2-amino-5-chlorophenyl)-5-[1-(4-chlorophenyl)ethyl]-3-methyl[1,2]oxazolo[4,5-d]pyridazin-4(5H)-one;

5-[1-(4-chlorophenyl)ethyl]-7-(2-chloropyridin-3-yl)-3-methyl[1,2]oxazolo[4,5-d]pyridazin-4(5H)-one;

N-{5-[5-(4-chlorobenzyl)-3-methyl-4-oxo-4,5-dihydro[1,2]oxazolo[4,5-d]pyridazin-7-yl]-2-fluorophenyl}acetamide;

7-(2,5-dimethoxyphenyl)-5-[4-methoxy-3-(trifluoromethyl)benzyl]-3-methyl[1,2]oxazolo[4,5-d]pyridazin-4(5H)-one;

5-[2-(4-chlorophenyl)ethyl]-7-(2,5-dimethoxyphenyl)-3-methyl[1,2]oxazolo[4,5-d]pyridazin-4(5H)-one;

7-[2-amino-5-(trifluoromethyl)phenyl]-5-[1-(4-chlorophenyl)ethyl]-3-methyl[1,2]oxazolo[4,5-d]pyridazin-4(5H)-one;

5-[1-(4-chlorophenyl)ethyl]-7-(1H-indol-6-yl)-3-methyl[1,2]oxazolo[4,5-d]pyridazin-4(5H)-one;

5-(4-chlorobenzyl)-7-(2,5-dimethoxyphenyl)-3-(propan-2-yl)[1,2]oxazolo[4,5-d]pyridazin-4(5H)-one;

7-(2-aminophenyl)-5-[1-(4-chlorophenyl)ethyl]-3-methyl[1,2]oxazolo[4,5-d]pyridazin-4(5H)-one;

N-(3-{5-[4-methoxy-3-(trifluoromethyl)benzyl]-3-methyl-4-oxo-4,5-dihydro[1,2]oxazolo[4,5-d]pyridazin-7-yl}phenyl)acetamide;

5-[1-(4-chlorophenyl)ethyl]-7-(5-hydroxy-2-methylphenyl)-3-methyl[1,2]oxazolo[4,5-d]pyridazin-4(5H)-one;

N-(2-fluoro-5-{5-[2-fluoro-5-(trifluoromethyl)benzyl]-3-methyl-4-oxo-4,5-dihydro[1,2]oxazolo[4,5-d]pyridazin-7-yl}phenyl)acetamide;

N-(3-{5-[1-(4-chlorophenyl)ethyl]-3-methyl-4-oxo-4,5-dihydro[1,2]oxazolo[4,5-d]pyridazin-7-yl}-4-methylphenyl)acetamide;

7-(4-fluorophenyl)-3-methyl-5-[4-(trifluoromethyl)benzyl][1,2]oxazolo[4,5-d]pyridazin-4(5H)-one;

5-(2-fluorobenzyl)-3,7-dimethyl[1,2]oxazolo[4,5-d]pyridazin-4(5H)-one;

5-[1-(4-chlorophenyl)ethyl]-7-(2,5-dimethoxyphenyl)-3-methyl[1,2]oxazolo[4,5-d]pyridazin-4(5H)-one;

5-[1-(4-chlorophenyl)ethyl]-7-(5-fluoropyridin-3-yl)-3-methyl[1,2]oxazolo[4,5-d]pyridazin-4(5H)-one;

5-(4-chlorobenzyl)-7-(3-fluorophenyl)-3-methyl[1,2]oxazolo[4,5-d]pyridazin-4(5H)-one;

N-(3-{5-[1-(4-chlorophenyl)ethyl]-3-methyl-4-oxo-4,5-dihydro[1,2]oxazolo[4,5-d]pyridazin-7-yl}phenyl)methanesulfonamide;

5-[2-fluoro-5-(trifluoromethyl)benzyl]-3,7-dimethyl[1,2]oxazolo[4,5-d]pyridazin-4(5H)-one;

7-(2-methoxyphenyl)-3-methyl-5-(pyridin-4-ylmethyl)[1,2]oxazolo[4,5-d]pyridazin-4(5H)-one;

N-{3-[5-(4-chlorobenzyl)-3-(methoxymethyl)-4-oxo-4,5-dihydro[1,2]oxazolo[4,5-d]pyridazin-7-yl]phenyl}acetamide;

5-[4-chloro-3-(trifluoromethyl)benzyl]-7-(4-fluorophenyl)-3-methyl[1,2]oxazolo[4,5-d]pyridazin-4(5H)-one;

N-(2-fluoro-5-{3-methyl-4-oxo-5-[4-(trifluoromethyl)benzyl]-4,5-dihydro[1,2]oxazolo[4,5-d]pyridazin-7-yl}phenyl)acetamide;

5-(4-fluorobenzyl)-3,7-dimethyl[1,2]oxazolo[4,5-d]pyridazin-4(5H)-one;

5-[(1S)-1-(4-chlorophenyl)ethyl]-3,7-dimethyl[1,2]oxazolo[4,5-d]pyridazin-4(5H)-one;

7-(2,4-dimethoxyphenyl)-5-[4-methoxy-3-(trifluoromethyl)benzyl]-3-methyl[1,2]oxazolo[4,5-d]pyridazin-4(5H)-one;

N-(3-{5-[1-(4-chlorophenyl)ethyl]-3-methyl-4-oxo-4,5-dihydro[1,2]oxazolo[4,5-d]pyridazin-7-yl}-2-methoxyphenyl)acetamide;

N-(3-{5-[(1R)-1-(4-chlorophenyl)ethyl]-3-methyl-4-oxo-4,5-dihydro[1,2]oxazolo[4,5-d]pyridazin-7-yl}phenyl)acetamide;

N-[4-methyl-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide;

5-(4-chlorobenzyl)-7-(2,5-dimethoxyphenyl)-3-ethyl[1,2]oxazolo[4,5-d]pyridazin-4(5H)-one;

7-(2,4-dimethoxyphenyl)-5-[4-fluoro-3-(trifluoromethyl)benzyl]-3-methyl[1,2]oxazolo[4,5-d]pyridazin-4(5H)-one;

3-{5-[1-(4-chlorophenyl)ethyl]-3-methyl-4-oxo-4,5-dihydro[1,2]oxazolo[4,5-d]pyridazin-7-yl}-4-methoxy-N,N-dimethylbenzamide;

N-(3-{5-[1-(4-chlorophenyl)ethyl]-3-methyl-4-oxo-4,5-dihydro[1,2]oxazolo[4,5-d]pyridazin-7-yl}-4-methoxyphenyl)acetamide;

N-(3-{5-[(1R)-1-(4-chlorophenyl)ethyl]-3-methyl-4-oxo-4,5-dihydro[1,2]oxazolo[4,5-d]pyridazin-7-yl}-4-methoxyphenyl)acetamide;

N-(3-{5-[4-fluoro-3-(trifluoromethyl)benzyl]-3-methyl-4-oxo-4,5-dihydro[1,2]oxazolo[4,5-d]pyridazin-7-yl}phenyl)acetamide;

5-(4-chlorobenzyl)-7-(3,4-difluorophenyl)-3-methyl[1,2]oxazolo[4,5-d]pyridazin-4(5H)-one;

5-[4-fluoro-3-(trifluoromethyl)benzyl]-3,7-dimethyl[1,2]oxazolo[4,5-d]pyridazin-4(5H)-one;

3,7-dimethyl-5-(pyridin-4-ylmethyl)[1,2]oxazolo[4,5-d]pyridazin-4(5H)-one;

N-{3-[5-(4-chlorobenzyl)-3-methyl-4-oxo-4,5-dihydro[1,2]oxazolo[4,5-d]pyridazin-7-yl]-4-methoxyphenyl}acetamide;

5-[2-fluoro-5-(trifluoromethyl)benzyl]-7-(2-methoxyphenyl)-3-methyl[1,2]oxazolo[4,5-d]pyridazin-4(5H)-one;

5-(4-chlorobenzyl)-3-cyclopropyl-7-(2,5-dimethoxyphenyl)[1,2]oxazolo[4,5-d]pyridazin-4(5H)-one;

7-(2,4-dimethoxyphenyl)-5-[2-fluoro-5-(trifluoromethyl)benzyl]-3-methyl[1,2]oxazolo[4,5-d]pyridazin-4(5H)-one;

N-[3-{5-[1-(4-chlorophenyl)ethyl]-3-methyl-4-oxo-4,5-dihydro[1,2]oxazolo[4,5-d]pyridazin-7-yl}-4-(trifluoromethoxy)phenyl]acetamide;

5-[4-methoxy-3-(trifluoromethyl)benzyl]-3,7-dimethyl[1,2]oxazolo[4,5-d]pyridazin-4(5H)-one;

N-{3-[5-(4-chlorobenzyl)-3-cyclopropyl-4-oxo-4,5-dihydro[1,2]oxazolo[4,5-d]pyridazin-7-yl]phenyl}acetamide;

5-(4-chlorobenzyl)-7-(2,5-dimethoxyphenyl)-3-propyl[1,2]oxazolo[4,5-d]pyridazin-4(5H)-one;

3-{5-[1-(4-chlorophenyl)ethyl]-3-methyl-4-oxo-4,5-dihydro[1,2]oxazolo[4,5-d]pyridazin-7-yl}benzenesulfonamide;

5-[4-fluoro-3-(trifluoromethyl)benzyl]-7-(2-methoxyphenyl)-3-methyl[1,2]oxazolo[4,5-d]pyridazin-4(5H)-one;

N-(3-{5-[1-(4-chlorophenyl)ethyl]-3-methyl-4-oxo-4,5-dihydro[1,2]oxazolo[4,5-d]pyridazin-7-yl}-4-methoxyphenyl)methanesulfonamide;

5-(4-chlorobenzyl)-3-methyl-7-(thiophen-2-yl)[1,2]oxazolo[4,5-d]pyridazin-4(5H)-one;

N-(3-{3-methyl-4-oxo-5-[4-(trifluoromethyl)benzyl]-4,5-dihydro[1,2]oxazolo[4,5-d]pyridazin-7-yl}phenyl)acetamide;

5-[(1R)-1-(4-chlorophenyl)ethyl]-3,7-dimethyl[1,2]oxazolo[4,5-d]pyridazin-4(5H)-one;

3-{5-[1-(4-chlorophenyl)ethyl]-3-methyl-4-oxo-4,5-dihydro[1,2]oxazolo[4,5-d]pyridazin-7-yl}-4-methoxybenzamide;

5-[2-(4-chlorophenyl)ethyl]-3,7-dimethyl[1,2]oxazolo[4,5-d]pyridazin-4(5H)-one;

N-(2-fluoro-5-{5-[4-fluoro-3-(trifluoromethyl)benzyl]-3-methyl-4-oxo-4,5-dihydro[1,2]oxazolo[4,5-d]pyridazin-7-yl}phenyl)acetamide;

N-(2-fluoro-5-{5-[4-methoxy-3-(trifluoromethyl)benzyl]-3-methyl-4-oxo-4,5-dihydro[1,2]oxazolo[4,5-d]pyridazin-7-yl}phenyl)acetamide;

5-[1-(4-chlorophenyl)ethyl]-7-(5-fluoro-2-methoxyphenyl)-3-methyl[1,2]oxazolo[4,5-d]pyridazin-4(5H)-one;

N-(4-methoxy-3-{3-methyl-4-oxo-5-[4-(trifluoromethyl)benzyl]-4,5-dihydro[1,2]oxazolo[4,5-d]pyridazin-7-yl}phenyl)acetamide;

2-amino-6-{5-[1-(4-chlorophenyl)ethyl]-3-methyl-4-oxo-4,5-dihydro[1,2]oxazolo[4,5-d]pyridazin-7-yl}benzamide;

7-(4-fluorophenyl)-5-[4-methoxy-3-(trifluoromethyl)benzyl]-3-methyl[1,2]oxazolo[4,5-d]pyridazin-4(5H)-one;

5-(4-chlorobenzyl)-7-(2-methoxyphenyl)-3-methyl[1,2]oxazolo[4,5-d]pyridazin-4(5H)-one;

5-[(1S)-1-(4-chlorophenyl)ethyl]-3-cyclopropyl-7-(2,5-dimethoxyphenyl)[1,2]oxazolo[4,5-d]pyridazin-4(5H)-one;

5-[4-chloro-3-(trifluoromethyl)benzyl]-3,7-dimethyl[1,2]oxazolo[4,5-d]pyridazin-4(5H)-one;

N-{3-[5-(4-chlorobenzyl)-3-methyl-4-oxo-4,5-dihydro[1,2]oxazolo[4,5-d]pyridazin-7-yl]phenyl}acetamide;

5-(4-chlorobenzyl)-7-(2,5-dimethoxyphenyl)-3-(methoxymethyl)[1,2]oxazolo[4,5-d]pyridazin-4(5H)-one;

N-(3-{5-[(1S)-1-(4-chlorophenyl)ethyl]-3-methyl-4-oxo-4,5-dihydro[1,2]oxazolo[4,5-d]pyridazin-7-yl}phenyl)acetamide;

3-{5-[1-(4-chlorophenyl)ethyl]-3-methyl-4-oxo-4,5-dihydro[1,2]oxazolo[4,5-d]pyridazin-7-yl}-4-methoxybenzoic acid;

7-(4-fluorophenyl)-3-methyl-5-(pyridin-4-ylmethyl)[1,2]oxazolo[4,5-d]pyridazin-4(5H)-one;

5-[(R)-(4-chlorophenyl)(phenyl)methyl]-3,7-diethyl[1,2]oxazolo[4,5-d]pyridazin-4(5H)-one;

5-(4-chlorobenzyl)-3-methyl-7-(2-methylphenyl)[1,2]oxazolo[4,5-d]pyridazin-4(5H)-one;

7-(2-amino-3,5-difluorophenyl)-5-[1-(4-chlorophenyl)ethyl]-3-methyl[1,2]oxazolo[4,5-d]pyridazin-4(5H)-one;

N-(3-{5-[1-(4-chlorophenyl)ethyl]-3-methyl-4-oxo-4,5-dihydro[1,2]oxazolo[4,5-d]pyridazin-7-yl}phenyl)acetamide;

5-[1-(4-chlorophenyl)ethyl]-7-[2-methoxy-5-(trifluoromethyl)phenyl]-3-methyl[1,2]oxazolo[4,5-d]pyridazin-4(5H)-one;

5-(4-chlorobenzyl)-7-(2,5-dimethoxyphenyl)-3-phenyl[1,2]oxazolo[4,5-d]pyridazin-4(5H)-one;

7-(2,5-dimethoxyphenyl)-5-[4-fluoro-3-(trifluoromethyl)benzyl]-3-methyl[1,2]oxazolo[4,5-d]pyridazin-4(5H)-one;

3-{5-[(1S)-1-(4-chlorophenyl)ethyl]-3-methyl-4-oxo-4,5-dihydro[1,2]oxazolo[4,5-d]pyridazin-7-yl}-4-methoxy-N-methylbenzamide;

5-(4-chlorobenzyl)-7-(4-fluorophenyl)-3-methyl[1,2]oxazolo[4,5-d]pyridazin-4(5H)-one;

5-(3-chloro-4-fluorobenzyl)-3,7-dimethyl[1,2]oxazolo[4,5-d]pyridazin-4(5H)-one;

N-(3-{5-[2-fluoro-5-(trifluoromethyl)benzyl]-3-methyl-4-oxo-4,5-dihydro[1,2]oxazolo[4,5-d]pyridazin-7-yl}phenyl)acetamide;

7-(2-aminopyridin-3-yl)-5-[1-(4-chlorophenyl)ethyl]-3-methyl[1,2]oxazolo[4,5-d]pyridazin-4(5H)-one;

5-(4-chlorobenzyl)-7-(2,4-dimethoxyphenyl)-3-methyl[1,2]oxazolo[4,5-d]pyridazin-4(5H)-one;

5-(5-chloro-2-fluorobenzyl)-3,7-dimethyl[1,2]oxazolo[4,5-d]pyridazin-4(5H)-one;

5-[(S)-(4-chlorophenyl)(phenyl)methyl]-3,7-diethyl[1,2]oxazolo[4,5-d]pyridazin-4(5H)-one;

5-(4-chlorobenzyl)-7-(3,5-difluorophenyl)-3-methyl[1,2]oxazolo[4,5-d]pyridazin-4(5H)-one;

N-{3-[5-(4-chlorobenzyl)-4-oxo-3-propyl-4,5-dihydro[1,2]oxazolo[4,5-d]pyridazin-7-yl]phenyl}acetamide;

5-(4-chloro-2-fluorobenzyl)-3,7-dimethyl[1,2]oxazolo[4,5-d]pyridazin-4(5H)-one;

7-(2,5-dimethoxyphenyl)-3-methyl-5-(pyridin-4-ylmethyl)[1,2]oxazolo[4,5-d]pyridazin-4(5H)-one;

N-{2-fluoro-5-[3-methyl-4-oxo-5-(pyridin-4-ylmethyl)-4,5-dihydro[1,2]oxazolo[4,5-d]pyridazin-7-yl]phenyl}acetamide;

7-(2,5-dimethoxyphenyl)-3-methyl-5-[4-(trifluoromethyl)benzyl][1,2]oxazolo[4,5-d]pyridazin-4(5H)-one;

N-{3-[5-(4-chlorobenzyl)-4-oxo-3-(propan-2-yl)-4,5-dihydro[1,2]oxazolo[4,5-d]pyridazin-7-yl]phenyl}acetamide;

7-(2-amino-5-fluorophenyl)-5-[1-(4-chlorophenyl)ethyl]-3-methyl[1,2]oxazolo[4,5-d]pyridazin-4(5H)-one;

5-[1-(4-chlorophenyl)ethyl]-7-[2-methoxy-5-(pyrrolidin-1-ylcarbonyl)phenyl]-3-methyl[1,2]oxazolo[4,5-d]pyridazin-4(5H)-one;

5-(4-chlorobenzyl)-7-(3,4-dimethoxyphenyl)-3-methyl[1,2]oxazolo[4,5-d]pyridazin-4(5H)-one;

5-[1-(4-chlorophenyl)ethyl]-7-(2-hydroxyphenyl)-3-methyl[1,2]oxazolo[4,5-d]pyridazin-4(5H)-one;

7-(2-methoxyphenyl)-5-[4-methoxy-3-(trifluoromethyl)benzyl]-3-methyl[1,2]oxazolo[4,5-d]pyridazin-4(5H)-one;

5-(4-chlorobenzyl)-7-(2,5-dimethoxyphenyl)-3-methyl[1,2]oxazolo[4,5-d]pyridazin-4(5H)-one;

N-[4-methoxy-3-(3-methyl-4-oxo-5-{(1S)-1-[4-(trifluoromethyl)phenyl]ethyl}-4,5-dihydro[1,2]oxazolo[4,5-d]pyridazin-7-yl)phenyl]acetamide;

N-{3-[5-(4-chlorobenzyl)-4-oxo-3-phenyl-4,5-dihydro[1,2]oxazolo[4,5-d]pyridazin-7-yl]phenyl}acetamide;

N-[4-methoxy-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide;

3-{5-[1-(4-chlorophenyl)ethyl]-3-methyl-4-oxo-4,5-dihydro[1,2]oxazolo[4,5-d]pyridazin-7-yl}benzamide;

N-(4-methyl-3-{3-methyl-4-oxo-5-[4-(trifluoromethyl)benzyl]-4,5-dihydro[1,2]oxazolo[4,5-d]pyridazin-7-yl}phenyl)acetamide;

3,7-dimethyl-5-(3-methylbutyl)[1,2]oxazolo[4,5-d]
pyridazin-4(5H)-one;
5-[1-(4-chlorophenyl)ethyl]-3-methyl-7-(pyridin-3-yl)[1,2]
oxazolo[4,5-d]pyridazin-4(5H)-one;
N-{3-[3-methyl-4-oxo-5-(pyridin-4-ylmethyl)-4,5-dihydro
[1,2]oxazolo[4,5-d]pyridazin-7-yl]phenyl}acetamide;
3-{5-[(1R)-1-(4-chlorophenyl)ethyl]-3-methyl-4-oxo-4,5-
dihydro[1,2]oxazolo[4,5-d]pyridazin-7-yl}-4-methoxy-
N-methylbenzamide;
N-[6-fluoro-2-methyl-3-(3-methyl-4-oxo-5-{(1R)-1-[4-(trifluoromethyl)phenyl]ethyl})-4,5-dihydro[1,2]oxazolo[4,
5-d]pyridazin-7-yl)phenyl]acetamide;
5-[1-(4-chlorophenyl)ethyl]-3-methyl-7-(pyrimidin-5-yl)[1,
2]oxazolo[4,5-d]pyridazin-4(5H)-one;
5-[1-(4-chlorophenyl)ethyl]-3,7-dimethyl[1,2]oxazolo[4,5-
d]pyridazin-4(5H)-one;
5-[1-(4-chlorophenyl)ethyl]-7-(1-ethyl-1H-pyrazol-5-yl)-3-
methyl[1,2]oxazolo[4,5-d]pyridazin-4(5H)-one;
5-[1-(4-chlorophenyl)ethyl]-3-methyl-7-(1H-pyrrolo[3,2-b]
pyridin-6-yl)[1,2]oxazolo[4,5-d]pyridazin-4(5H)-one;
N-(3-{5-[(1S)-1-(4-chlorophenyl)ethyl]-3-methyl-4-oxo-4,
5-dihydro[1,2]oxazolo[4,5-d]pyridazin-7-yl}-4-methoxyphenyl)acetamide;
7-(2-methoxyphenyl)-3-methyl-5-[4-(trifluoromethyl)benzyl][1,2]oxazolo[4,5-d]pyridazin-4(5H)-one;
3-{5-[1-(4-chlorophenyl)ethyl]-3-methyl-4-oxo-4,5-dihydro[1,2]oxazolo[4,5-d]pyridazin-7-yl}-4-methoxy-N-methylbenzamide;
5-(4-chlorobenzyl)-3-methyl-7-(pyridin-3-yl)[1,2]oxazolo
[4,5-d]pyridazin-4(5H)-one;
3,7-dimethyl-5-[3-(trifluoromethyl)benzyl][1,2]oxazolo[4,
5-d]pyridazin-4(5H)-one;
5-(4-chlorobenzyl)-3-methyl-7-phenyl[1,2]oxazolo[4,5-d]
pyridazin-4(5H)-one;
5-(2,4-difluorobenzyl)-3,7-dimethyl[1,2]oxazolo[4,5-d]
pyridazin-4(5H)-one;
3,7-dimethyl-5-[4-(trifluoromethyl)benzyl][1,2]oxazolo[4,
5-d]pyridazin-4(5H)-one;
7-(2,5-dimethoxyphenyl)-3-methyl-5-{(1R)-1-[4-(trifluoromethyl)phenyl]ethyl}[1,2]oxazolo[4,5-d]pyridazin-4
(5H)-one;
7-(3-aminophenyl)-5-[1-(4-chlorophenyl)ethyl]-3-methyl
[1,2]oxazolo[4,5-d]pyridazin-4(5H)-one;
7-(2,4-dimethoxyphenyl)-3-methyl-5-[4-(trifluoromethyl)
benzyl][1,2]oxazolo[4,5-d]pyridazin-4(5H)-one;
5-[(1R)-1-(4-chlorophenyl)ethyl]-3-cyclopropyl-7-(2,5-dimethoxyphenyl)[1,2]oxazolo[4,5-d]pyridazin-4(5H)-one;
N-{3-[5-(4-chlorobenzyl)-3-ethyl-4-oxo-4,5-dihydro[1,2]
oxazolo[4,5-d]pyridazin-7-yl]phenyl}acetamide;
7-(2,5-dimethoxyphenyl)-5-[2-fluoro-5-(trifluoromethyl)
benzyl]-3-methyl[1,2]oxazolo[4,5-d]pyridazin-4(5H)-
one; and
3-{5-[1-(4-chlorophenyl)ethyl]-3-methyl-4-oxo-4,5-dihydro[1,2]oxazolo[4,5-d]pyridazin-7-yl}-N-ethyl-4-
methoxybenzamide.

Compound names are assigned by using Name 2014 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as 13N and $^{15}$N, oxygen, such as $^{15}$O, $^{17}$O and $^{18}$O, phosphorus, such as $^{32}$P, and sulfur, such as $^{35}$S. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Present compounds may be used in the form of pharmaceutically acceptable salts. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of the invention may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The invention contemplates compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-3. In Schemes 1-3, the variables $R^1$, $R^2$ and $R^3$ are as described in the Summary.

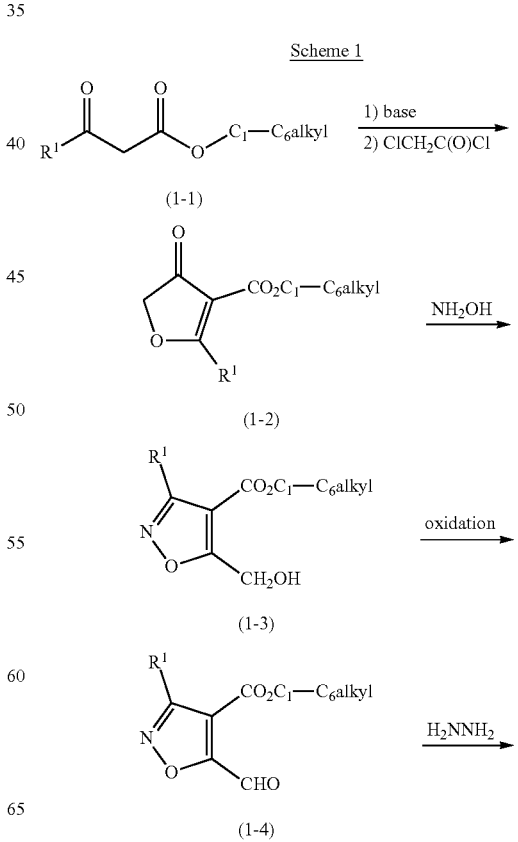

-continued

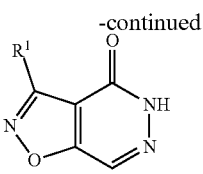

(1-5)

 Br₂ / base

(1-6)

As shown in Scheme 1, compounds of formula (1-6) can be prepared from compounds of formula (1-1). Accordingly, compounds of formula (1-1) can be treated with a base such as magnesium ethanolate at or near ambient temperature to reflux for 30 minutes to 4 hours in a solvent such as toluene. Then, a solvent such as acetonitrile can be added followed by the addition of 2-chloroacetyl chloride at about −10° C. The reaction mixture can then be allowed to warm to ambient temperature with continued stirring for 1-24 hours to give compounds of formula (1-2). Compounds of formula (1-2) can then be treated with hydroxylamine or hydroxylamine hydrochloride in the presence of a base such as sodium acetate in refluxing ethanol over 1-8 hours to give compounds of formula (1-3). The alcohols of formula (1-3) can be oxidized to the corresponding aldehydes of formula (1-4) by treatment with an appropriate oxidant such as manganese(IV) oxide in refluxing toluene over 3-10 hours or Dess-Martin periodinane in dichloromethane at ambient temperature over 4-16 hours. The aldehydes of formula (1-4) can be reacted with hydrazine or hydrazine hydrate in ethanol at 0-30° C. over 1-8 hours to give compounds of formula (1-5). Compounds of formula (1-5) can be reacted with bromine in the presence of a base such as lithium hydroxide in refluxing methanol over 6-24 hours to give compounds of formula (1-6).

Scheme 2

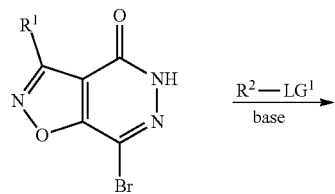

(1-6)

R²—LG¹ / base

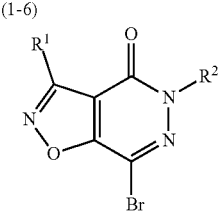

(2-1)

R³—B(OH)₂ / cross-coupling reaction conditions

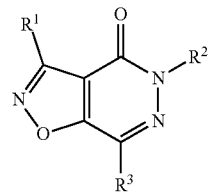

(I)

As shown in Scheme 2, compounds of formula (1-6) can be converted to compounds of formula (I). Compounds of formula (1-6) can be alkylated with R²-LG¹; wherein LG¹ is a leaving group such as chlorine, bromine, iodine or a sulfonate; in the presence of a base such as potassium carbonate in a solvent such as N,N-dimethylformamide at 20-60° C. over 1-18 hours to give compounds of formula (2-1). Compounds of formula (2-1) can be reacted with boronic acids, R³—B(OH)₂, or the corresponding boronates under Suzuki or other cross-coupling reaction conditions to give compounds of formula (I).

Scheme 3

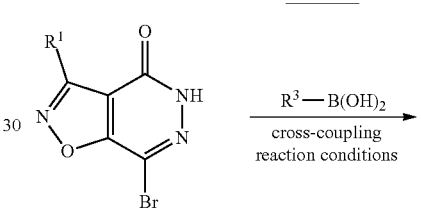

R³—B(OH)₂ / cross-coupling reaction conditions

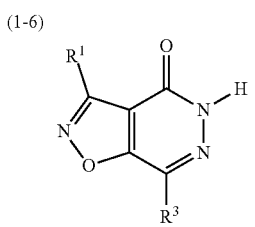

(3-1)

R²—LG¹ / base

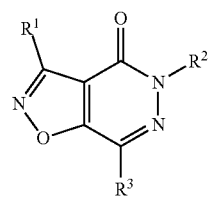

(I)

As shown in Scheme 3, compounds of formula (1-6) can be converted to compounds of formula (I) with reactions of Scheme 2 reversed in sequence. Compounds of formula (1-6) can be reacted with boronic acids, R³—B(OH)₂, or the corresponding boronates under Suzuki or other cross-coupling reaction conditions to give compounds of formula (3-1). Compounds of formula (3-1) can be alkylated with R²-LG¹; wherein LG¹ is a leaving group such as chlorine, bromine, iodine or a sulfonate; in the presence of a base such as potassium carbonate or sodium hydride in a solvent such as N,N-dimethylformamide at 20-60° C. over 1-18 hours to give compounds of formula (I).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Many of the compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Pharmaceutical Compositions

This invention also provides for pharmaceutical compositions comprising a therapeutically effective amount of a compound of formula (I), or a pharmaceutically acceptable salt or isotopically labelled form thereof together with a pharmaceutically acceptable carrier, diluent, or excipient thereof. The phrase "pharmaceutical composition" refers to a composition suitable for administration in medical or veterinary use.

The pharmaceutical compositions that comprise a compound of formula (I), alone or in combination with a second therapeutic agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula (I). In certain embodiments, the compound of formula (I) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packaged tablets, capsules, and powders in vials or ampules. Also, the unit dosage form may be a capsule, tablet, cachet, or lozenge itself, or it may be the appropriate number of any of these in packaged form. The quantity of active component in a unit dose may be varied or adjusted from 0.1 mg to 1000 mg, from 1 mg to 100 mg, from 10 mg to 50 mg, from 20 mg to 40 mg or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dosage is from about 0.005 mg/kg to about 50 mg/kg. In further embodiments, the daily dosage is from about 0.01 mg/kg to about 25 mg/kg. In yet further embodiments, the daily dosage is from about 0.05 mg/kg to about 20 mg/kg. In yet further embodiments, the daily dosage is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

Methods of Use

The compounds and compositions using any amount and any route of administration may be administered to a subject for the treatment or prevention of pain, substance abuse (especially in alcohol dependence), or spasticity.

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, via implantation, transdermally, topically, and via implantation. In certain embodiments, the compounds and compositions thereof may be delivered orally. The compounds may also be delivered rectally, bucally, intravaginally, ocularly, or by insufflation. GABA-B modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as positive allosteric modulators of GABA-B. Thus, the compounds and compositions are particularly useful for treating or lessening the severity, or progression of a disease, disorder, or a condition where the GABA-B receptor is involved. In particular, the invention provides a method for treating of pain, substance abuse, especially in alcohol dependence, or spasticity in a subject, wherein the method comprises the step of administering to said subject a therapeutically effective amount of a compound of formula (I) or a preferred embodiment thereof as set forth above, with or without a pharmaceutically acceptable carrier. Particularly, the method is for the treatment or prevention of pain.

A compound according to formula (I) or a pharmaceutically acceptable salt or isotopically labeled form thereof for use in therapy.

A compound according to formula (I) or a pharmaceutically acceptable salt or isotopically labeled form thereof for use in the treatment of a condition or disorder modulated by the γ-aminobutyric acid B (GABA-B) receptor in a mammal. Preferable, the condition or disorder is selected from the group consisting of pain, substance abuse, especially in alcohol dependence, spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine and tinnitus.

The use of a compound according to formula (I) or a pharmaceutically acceptable salt or isotopically labeled form thereof for the preparation of a medicament.

The use of a compound according to formula (I) or a pharmaceutically acceptable salt or isotopically labeled form for the preparation of a medicament for the treatment of a condition or disorder modulated by the γ-aminobutyric acid B (GABA-B) receptor in a mammal. Preferable, the consition or disorder is selected from the the group consisting of pain, substance abuse, especially in alcohol dependence, spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine and tinnitus. The medicament optionally can comprise one or more additional therapeutic agents.

The present compounds may be co-administered to a subject. The term "co-administered" means the administration of two or more different therapeutic agents that are administered to a subject by combination in the same pharmaceutical composition or separate pharmaceutical compositions. Thus co-administration involves administration at the same time of a single pharmaceutical composition comprising two or more therapeutic agents or administration of two or more different separate compositions to the same subject at the same or different times.

The compounds of the invention may be co-administered with a therapeutically effective amount of one or more agents to treat pain, where examples of the agents include, nonsteroidal anti-inflammatory drugs (NSAIDs), opioid analgesics, barbiturates, benzodiazapines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-HT$_{2A}$ receptor antagonists, cholinergic analgesics, α$_2$δ ligands (such as gabapentin or pregabalin), cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin E$_2$ subtype 4 antagonists, leukotriene B4 antagonists, 5-lipoxygenase inhibitors, sodium channel blockers, 5-HT$_3$ antagonists, N-methyl-D-aspartic acid receptor antagonists, phosphodiesterase V inhibitors, voltage-gated calcium channel blockers (e.g., N-type and T-type), and KCNQ openers (e.g., KCNQ2/3 (K$_v$7.2/3)).

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, modulate the γ-aminobutyric acid receptor, and treat a disease treatable by modulating the γ-aminobutyric acid receptor, including pain, substance abuse, especially in alcohol dependence, spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus.

This invention also is directed to a use of one or more compounds or salts or isotopically labeled forms thereof of the invention in the preparation of a medicament. The medicament optionally can comprise one or more additional therapeutic agents. In some embodiments, the medicament is useful for treating pain, substance abuse (especially in alcohol dependence), spasticity, fragile X syndrome, Down's syndrome, autism, retinal ganglion cell degeneration, gastro-esophageal reflux disease (GERD), smoking cessation, addiction of narcotic agents, emesis, cough, overactive bladder, anxiety, migraine or tinnitus.

Further benefits of Applicants' invention will be apparent to one skilled in the art from reading this patent application.

The following Examples may be used for illustrative purposes and should not be deemed to narrow the scope of the invention.

EXAMPLES

Abbreviations: d for day; h for hour; dppf for 1,1'-bis (diphenylphosphino)ferrocene, DCM for dichloromethane, DMF for N,N-dimethyl formamide, DMSO for dimethyl sulfoxide; ee for enantiomeric excess; ESI for electrospray ionization; Et for ethyl; EtOAc for ethyl acetate; HPLC for high performance liquid chromatography; MTBE for methyl-t-butyl ether, MS for mass spectrometry, LC-MS for liquid chromatography/mass spectrometry; PE for petroleum ether; psi for pounds per square inch; TFA for trifluoroacetic acid; THF for tetrahydrofurate, TLC for thin layer chromatography, and room temperature (20-25° C.); API and APCI for atmospheric pressure (chemical) ionization; SFC for supercritical fluid chromatography.

In the context of NMR spectroscopy the following appreviations are used: s for singlet; d for doublet; t for triplet; dd for doublet of doublet; m for multiplet.

Liquid Chromatography Conditions for Liquid Chromatography-Mass Spectrometry:

Method A: The gradient was 10-90% B in 1.15 minutes with a hold at 90% B for 0.40 minute, 90-10% B in 0.01 minute, and then hold at 10% B for 0.54 minute (1.0 mL/minute flow rate). Mobile phase A was 0.0375% trifluoroacetic acid in water, mobile phase B was 0.018% trifluoroacetic acid in acetonitrile. The column used for the chromatography was a 2.1×30 mm Halo® C18 column (2.7 m particles). Detection methods were diode array (DAD) and positive/negative electrospray ionization (ESI).

Method B: The gradient was 10-100% B in 3.4 minutes with a hold at 100% B for 0.45 minute, 100-10% B in 0.01 minute, and then hold at 10% B for 0.65 minute (0.8 mL/minute flow rate). Mobile phase A was 0.0375% trifluoroacetic acid in water, mobile phase B was 0.018% trifluoroacetic acid in acetonitrile. The column used for the chromatography was a 2.1×50 mm Bonna-Agela Venusil® XBP-C18 HPLC column (5 m particles). Detection methods were diode array (DAD) and evaporative light scattering (ELSD) detection as well as positive/negative electrospray ionization (ESI).

Method C: The gradient was 1-90% B in 3.4 minutes, 90-100% B for 0.45 minute, 100-1% B in 0.01 minute, and then hold at 1% B for 0.65 minute (0.8 mL/minute flow rate). Mobile phase A was 0.0375% trifluoroacetic acid in water, mobile phase B was 0.018% trifluoroacetic acid in acetonitrile. The column used for the chromatography was a 2.1×50 mm Bonna-Agela Venusil® XBP-C18 column HPLC (5 m particles). Detection methods were diode array (DAD) and evaporative light scattering (ELSD) detection as well as positive/negative electrospray ionization (ESI).

Method D: The gradient was 25-100% B in 3.4 minutes with a hold at 100% B for 0.45 minute, 100-25% B in 0.01 minute, and then held at 25% B for 0.65 minute (0.8 mL/min flow rate). Mobile phase A was 0.0375% trifluoroacetic acid in water, mobile phase B was 0.018% trifluoroacetic acid in HPLC grade acetonitrile. The column used for the chromatography was a 2.0×50 mm Phenomenex® Synergi™ Polar-RP column (4 m particles). Detection methods were diode array (DAD) and evaporative light scattering (ELSD) detection as well as positive/negative electrospray ionization (ESI).

Method E: The gradient was 40-100% B in 3.4 minutes, with a hold at 100% B for 0.45 minute, 100-40% B in 0.01 minute, and then held at 40% B for 0.65 minute (0.8 mL/min flow rate). Mobile phase A was 0.0375% trifluoroacetic acid in water, mobile phase B was 0.018% trifluoroacetic acid in acetonitrile. The column used for the chromatography was a Phenomenex® Luna® C18(2) (5 m particle size, 100 Å pore size). Detection methods are diode array (DAD) and evaporative light scattering (ELSD) detection as well as positive/negative electrospray ionization (ESI).

Method F: The gradient was 25-100% B in 3.4 minutes, 100% B for 0.45 minute, 100-25% B in 0.01 minute, and then hold at 25% B for 0.65 minute (0.8 mL/minute flow rate). Mobile phase A was 0.0375% trifluoroacetic acid in water, mobile phase B was 0.018% trifluoroacetic acid in acetonitrile. The column used for the chromatography was a 2.1×50 mm Bonna-Agela Venusil® XBP-C18 HPLC column (5 m particles). Detection methods were diode array (DAD) and evaporative light scattering (ELSD) detection as well as positive/negative electrospray ionization (ESI).

Preparative Liquid Chromatography Conditions

Method A: Phenomenex® Luna® C18 250×50 mm (10 μm) column. Mobile phase A—water with 0.09% trifluoroacetic acid, Mobile phase B—acetonitrile. Gradient—35-65% B over 20 minutes. Flow rate—80 mL/minute. Injection amount—0.7 g per injection.

Method B: Bonna-Agela C18 130×25 mm HPLC column. Mobile phase A—water with 0.075% trifluoroacetic acid, Mobile phase B—methanol. Gradient—58-88% B over 12 minutes, hold for 2 minutes, 88-100% B over 0.2 minutes, hold for 2 minutes, 100-58% B over 0.2 minutes, hold for 1.6 minutes. Flow rate—25 mL/minute. Detection at 220 and 254 nm.

Method C: Samples were purified by preparative HPLC using a Waters Sunfire™ C8(2) 5 μm column (30 mm×150 mm) at ambient temperature. A gradient of acetonitrile (A) and 0.1% trifluoroacetic acid in water (B) was used, at a flow rate of 50 mL/minute (0-1.0 minute 5% A, 0.5-8.5 minutes linear gradient % A defined in experimental, 8.7-10.7 minutes 100% A, 10.7-11 minutes linear gradient 100-5% A). Samples were injected in 1.5 mL dimethyl sulfoxide:methanol (1:1). An Agilent® 1100 Series Purification system was used, consisting of the following modules: Agilent® 1100 Series LC/MSD SL mass spectrometer with API-electrospray source; two Agilent® 1100 Series preparative pumps; Agilent 1100 Series isocratic pump; Agilent® 1100 Series diode array detector with preparative (0.3 mm) flow cell; Agilent® active-splitter; and IFC-PAL fraction collector/autosampler. The make-up pump for the mass spectrometer used 3:1 methanol:water with 0.1% formic acid at a flow rate of 1 mL/minute. Fraction collection was automatically triggered when the extracted ion chromatogram (EIC) for the target mass exceeded the threshold specified in the method. The system was controlled using Agilent® Chemstation (Rev B.10.03), Agilent® A2Prep, and Leap FractPal software, with custom Chemstation® macros for data export.

Method D: Column: Waters Xbridge™ C18, 19×150 mm, 5 m column. Eluent: Mobile phase A—water/0.05% trifluoroacetic acid; Mobile phase B—acetonitrile; flow rate—20 mL/minute; gradient—30-70% B in 10 minutes. Detection: 254 nm.

Method E: Column: Waters Xbridge™ C18, 19×150 mm, 5 m column. Eluent: Mobile phase A—water/10 mM NH$_4$CO$_3$; Mobile phase B—acetonitrile; flow rate—20 mL/minute; gradient—30-70% B in 10 minutes. Detection: 254 nm.

Method F: Samples were purified by preparative HPLC using two coupled Phenomenex® Luna® Axia™ C8, 5 μm columns (30 mm×150 mm, each) at ambient temperature. A gradient of acetonitrile (A) and 0.1% trifluoroacetic acid in water (B) was used, at a flow rate of 50 mL/minute (0-0.5 minute 5% A, 0.5-8.5 minutes linear gradient % A defined in experimental, 8.7-10.7 minutes 100% A, 10.7-11 minutes linear gradient 100-5% A). Samples were injected in 1.5 mL dimethyl sulfoxide:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter; and IFC-PAL fraction collector/autosampler. The make-up pump for the mass spectrometer used 3:1 methanol:water with 0.1% formic acid at a flow rate of 1 mL/minute. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export.

Preparative Super Critical Fluid Chromatography Conditions

Method A: Thar SFC Prep-80. Column—Daicel Chiralcel® OD-H (5 μm) 3.0×25 cm. Mobile phase A—CO$_2$, Mobile phase B—2-propanol (0.05% NH$_4$OH). Gradient A:B, 65:35. Flow rate—70 mL/minute. System back pressure—100 bar. Detection wavelength—220 nm. Sample preparation: 10 mg/mL in methanol and dichloromethane. Injection—1 mL/injection.

Method B: Thar SFC Prep-80. Column—Daicel Chiralcel® OJ-H (5 μm) 3.0×25 cm. Mobile phase A—CO$_2$, Mobile phase B—methanol (0.05% NH$_4$OH). Gradient A:B, 75:25. Flow rate—65 mL/minute. System back pressure—100 bar. Detection wavelength—220 nm. Sample preparation: 25 mg/mL in methanol. Injection—1 mL/injection.

Example 1

N-(3-{5-[(1S)-1-(4-chlorophenyl)ethyl]-3-cyclopropyl-4-oxo-4,5-dihydro[1,2]oxazolo[4,5-d]pyridazin-7-yl}-4-methoxyphenyl)acetamide

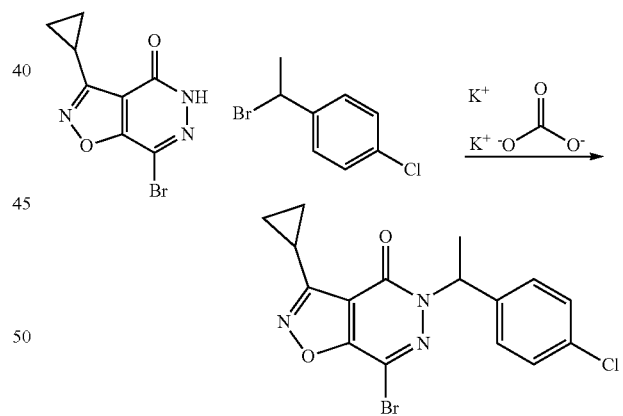

Step 1 7-bromo-5-(1-(4-chlorophenyl)ethyl)-3-cyclopropylisoxazolo[4,5-d]pyridazin-4(5H)-one To a solution of 7-bromo-3-cyclopropylisoxazolo[4,5-d]pyridazin-4(5H)-one (Example 51, 600 mg, 2.343 mmol) in N,N-dimethylformamide (10 mL) K$_2$CO$_3$ (1295 mg, 9.37 mmol) and 1-(1-bromoethyl)-4-chlorobenzene (772 mg, 3.51 mmol) were added. After stirring at 20° C. for 2 hrs, the mixture was diluted with water, extracted with EtOAc (20 ml, 3 times). The organic phase was washed with brine, concentrated under reduced pressure to get a residue, which was washed with MeOH, dried to give crude 7-bromo-5-

(1-(4-chlorophenyl)ethyl)-3-cyclopropylisoxazolo[4,5-d]pyridazin-4(5H)-one (560 mg, 1.419 mmol, 60.6% yield) as a white solid, which was used directly for next step. $^1$H NMR (400 MHz, DMSO-d6) δ ppm 7.39 (s, 4H), 7.17-7.08 (m, 2H), 6.92 (d, J=2.6 Hz, 1H), 6.30 (q, J=7.1 Hz, 1H), 3.71 (d, J=7.1 Hz, 6H), 2.46-2.39 (m, 1H), 1.71 (d, J=7.1 Hz, 3H), 1.14 (d, J=7.5 Hz, 4H).

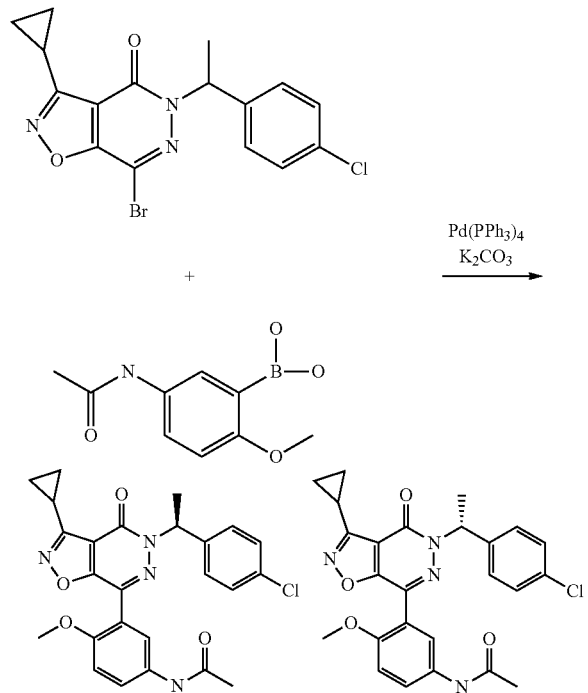

Step 2 N-(3-{5-[1-(4-chlorophenyl)ethyl]-3-cyclopropyl-4-oxo-4,5-dihydro[1,2]oxazolo[4,5-d]pyridazin-7-yl}-4-methoxyphenyl(acetamide)

To a solution of 7-bromo-5-(1-(4-chlorophenyl)ethyl)-3-cyclopropylisoxazolo-[4,5-d]pyridazin-4(5H)-one (270 mg, 0.684 mmol) in N,N-dimethylformamide (Ratio: 4.00, Volume: 2 ml) and water (Ratio: 1.000, Volume: 0.5 ml) (5-acetamido-2-methoxyphenyl)boronic acid (172 mg, 0.821 mmol), monopotassium monocarbonate (170 mg, 1.710 mmol) and Pd(Ph$_3$P)$_4$ (79 mg, 0.068 mmol) were added. After stirring at 80° C. overnight, the mixture was diluted with water, extracted with EtOAc (100 ml, 3 times). The organic phase was washed with brine, concentrated under reduced pressure. The residue was purified by preparative HPLC (Gilson 281 semi preparative HPLC system, mobile phase: A: TFA/H$_2$O=0.075% v/v, B: acetonitrile (57%→100%), column: YMC-Actus®, ODS-AQ 100*30 5 u, flow rate: 25 ml/min, monitor wavelength: 220&254 nm).

The enantiomers of N-(3-{5-[1-(4-chlorophenyl)ethyl]-3-cyclopropyl-4-oxo-4,5-dihydro[1,2]oxazolo[4,5-d]pyridazin-7-yl}-4-methoxyphenyl)acetamide were separated by supercritical fluid chromatography to give the titled compound. The mobile phase was comprised of supercritical CO$_2$ supplied by a bulk tank of 99.5% bone-dry non-certified CO$_2$ pressurized to 1200 psi (82.7 bar) with a modifier of methanol (0.1 N NH$_4$OH) at a flow rate of 60 g/minute. UV detection was set to collect at a wavelength of 220 nm, the column was heated to 35° C., and the backpressure regulator was set to maintain 100 bar. The sample was dissolved in methanol at a concentration of about 50 mg/mL, and the injection volume was 1 mL. The mobile phase was held isocratically at 35% methanol (0.1 N NH$_4$OH):CO2. The instrument was fitted with a Chiralcel® OJ-H, 5 m, 3.0 cm id×25 cm L column. $^1$H NMR (400 MHz, DMSO-d$_6$) δ ppm 9.96 (s, 1H), 7.72-7.67 (m, 2H), 7.39 (s, 4H), 7.17-7.13 (m, 1H), 6.31 (q, J=6.8 Hz, 1H), 3.72 (s, 3H), 2.45-2.39 (m, 1H), 2.02 (s, 3H), 1.71 (d, J=7.1 Hz, 3H), 1.17-1.11 (m, 4H).

Example 2

5-(4-chlorobenzyl)-7-(4-methoxyphenyl)-3-methyl[1,2]oxazolo[4,5-d]pyridazin-4(5H)-one Step 1: ethyl 2-methyl-4-oxo-4,5-dihydrofuran-3-carboxylate To an ice bath cooled solution of magnesium ethanolate (31.7 g, 277 mmol) in toluene (54 mL) was added ethyl acetoacetate (30 g, 231 mmol) dropwise. The mixture was stirred at room temperature for 1 hour. Anhydrous acetonitrile (54 mL) was added to the mixture at −10° C., followed by the slow addition of 2-chloroacetyl chloride (26.0 g, 231 mmol). The mixture was allowed to warm to room temperature and left to stir for 2 hours. A dilute solution of sulfuric acid (8 mL acid in 280 mL ice/water) was added, followed by extraction with tert-butyl methyl ether. The combined organic fractions were dried over Na$_2$SO$_4$ and filtered, and the filtrate was cooled to 0° C. A solution of triethylamine (23.33 g, 231 mmol) in tert-butyl methyl ether (50 mL) was added. The reaction mixture was left to stir at room temperature overnight. The mixture was diluted with water, and extracted with dichloromethane. The organic phase was concentrated under reduced pressure to give a residue that was purified by chromatography on silica gel and eluted with EtOAc/PE to give the titled compound (16 g, yield 40%). $^1$H NMR (400 MHz, CDCl$_3$) δ ppm 4.59 (s, 2H), 4.31 (q, J=7.06 Hz, 2H), 2.61 (s, 3H), 1.33-1.37 (m, 3H).

Step 2: ethyl 5-(hydroxymethyl)-3-methyl-1,2-oxazole-4-carboxylate

To a solution of ethyl 2-methyl-4-oxo-4,5-dihydrofuran-3-carboxylate (20 g, 118 mmol, Step 1) in anhydrous ethanol (100 mL) was added sodium acetate (9.64 g, 118 mmol) and hydroxylamine (8.17 g, 118 mmol). The mixture was heated to reflux for 1 hour. The solvent was removed under reduced pressure to give a residue that was diluted with water and extracted with ethyl acetate. The organic phase was washed with brine, dried over Na$_2$SO$_4$, and concentrated under reduced pressure to get a residue that was purified by chromatography on silica gel and eluted with EtOAc/PE to give the titled compound (12 g, yield 55%). $^1$H NMR (400 MHz, CDCl$_3$) δ ppm 4.89 (d, J=6.62 Hz, 2H), 4.38 (q, J=7.06 Hz, 2H), 3.97 (t, J=7.06 Hz, 1H), 2.46 (s, 3H), 1.41 (t, J=7.06 Hz, 3H).

Step 3: ethyl 5-formyl-3-methyl-1,2-oxazole-4-carboxylate

To a solution of ethyl 5-(hydroxymethyl)-3-methyl-1,2-oxazole-4-carboxylate (30 g, 162 mmol, Step 2) in anhydrous toluene (500 mL) was added manganese(IV) oxide (42.3 g, 486 mmol). The mixture was heated to reflux for 6 hours. The solids were removed by filtration, and the filtrate was concentrated under reduced pressure to give a residue that was purified by chromatography on silica gel and eluted with EtOAc PE to give the titled compound (13 g, yield 43%). $^1$H NMR (400 MHz, CDCl$_3$) δ ppm 10.35 (s, 1H), 4.38-4.51 (m, 2H), 2.55 (s, 3H), 1.39-1.44 (m, 3H).

Step 4: 3-methyl[1,2]oxazolo[4,5-d]pyridazin-4 (5H)-one

To a solution of ethyl 5-formyl-3-methyl-1,2-oxazole-4-carboxylate (13 g, 71.0 mmol, Step 3) in ethanol (60 mL) chilled in an ice-bath was added hydrazine hydrate (17.7 g, 355 mmol) dropwise. The resulting mixture was stirred for 2 hours. The solid was collected by filtration and dried to give the titled compound (10 g, yield 93%). $^1$H NMR (400 MHz, methol-d$_4$) δ ppm 8.48 (s, 1H), 2.62 (s, 3H).

Step 5: 7-bromo-3-methyl[1,2]oxazolo[4,5-d] pyridazin-4(5H)-one

To a solution of 3-methyl[1,2]oxazolo[4,5-d]pyridazin-4 (5H)-one (10 g, 66.2 mmol, Step 4) in CH$_3$OH (600 mL) chilled in an ice-water bath was added lithium hydroxide hydrate (22.21 g, 529 mmol) and Br$_2$ (0.387 mL, 7.51 mmol) dropwise. The mixture was heated to reflux overnight. The mixture was diluted with water and extracted with ethyl acetate. The organic phase was washed with brine, dried over Na$_2$SO$_4$, and concentrated under reduced pressure. The resultant residue was purified by chromatography on silica gel and eluted with EtOAc/PE to give the titled compound (12 g, yield 79%). $^1$H NMR (400 MHz, CDCl$_3$) δ ppm 11.37 (br, 1H), 2.63 (s, 3H).

Step 6: 7-bromo-5-(4-chlorobenzyl)-3-methyl[1,2] oxazolo[4,5-d]pyridazin-4(5H)-one To a solution of 7-bromo-3-methyl[1,2]oxazolo[4,5-d] pyridazin-4(5H)-one (8 g, 34.8 mmol, Step 5) in N,N-dimethylformamide (200 mL) was added K$_2$CO$_3$ (9.61 g, 69.6 mmol) at room temperature. 1-Chloro-4-(chloromethyl)benzene (8.4 g, 52.2 mmol) was added in one portion. The mixture was stirred at room temperature for 4 hours. The mixture was diluted with water and extracted with ethyl acetate. The organic phase was washed with brine and concentrated under reduced pressure to give a residue that was washed with CH$_3$OH to give the titled compound (12 g, yield 97%) as a solid. LCMS (ESI+) m/z 354 (M+H)$^+$, retention time 3.322 minutes; $^1$H NMR (400 MHz, CDCl$_3$) δ ppm 7.37-7.47 (m, 2H), 7.28-7.36 (m, 2H), 5.33 (s, 2H), 2.67 (s, 3H).

Step 7: 5-(4-chlorobenzyl)-7-(4-methoxyphenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Step 6) in 1,2-dimethoxyethane (4 mL) and water (1 mL) was added (4-methoxyphenyl)boronic acid (51.4 mg, 0.338 mmol), K$_2$CO$_3$ (0.097 g, 0.705 mmol) and tetrakis(triphenylphosphine)palladium(0) (0.033 g, 0.028 mmol). The resulting mixture was stirred at 80° C. overnight under N$_2$. After cooling down to room temperature, the reaction mixture was concentrated under reduced pressure to furnish a residue which was washed with a mixture of CH$_3$OH and H$_2$O to give the titled compound. LCMS (ESI+) m/z 381 (M+H)$^+$; $^1$H NMR (CDCl$_3$, 400 MHz): δ 8.09 (d, J=8.82 Hz, 2H), 7.44 (d, J=8.38 Hz, 2H), 7.30 (d, J=8.38 Hz, 2H), 7.04 (d, J=8.82 Hz, 2H), 5.41 (s, 2H), 3.89 (s, 3H), 2.70 (s, 3H).

Example 3

N-(3-{5-[(1R)-1-(4-chlorophenyl)ethyl]-3-cyclopropyl-4-oxo-4,5-dihydro[1,2]oxazolo[4,5-d]pyridazin-7-yl}-4-methoxyphenyl)acetamide The enantiomers of N-(3-{5-[1-(4-chlorophenyl)ethyl]-3-cyclopropyl-4-oxo-4,5-dihydro[1,2]oxazolo[4,5-d] pyridazin-7-yl}-4-methoxyphenyl)acetamide (see Example 1) were separated by supercritical fluid chromatography to give the titled compound. The mobile phase was comprised of supercritical CO$_2$ supplied by a bulk tank of 99.5% bone-dry non-certified CO$_2$ pressurized to 1200 psi (82.7 bar) with a modifier of methanol (0.1 N NH$_4$OH) at a flow rate of 60 g/minute. UV detection was set to collect at a wavelength of 220 nm, the column was heated to 35° C., and the backpressure regulator was set to maintain 100 bar. The sample was dissolved in methanol at a concentration of about 50 mg/mL, and the injection volume was 1 mL. The mobile phase was held isocratically at 35% methanol (0.1 N NH$_4$OH):CO2. The instrument was fitted with a Chiralcel® OJ-H, 5 m, 3.0 cm id×25 cm L column. $^1$H NMR (400 MHz, DMSO-d$_6$) δ ppm 9.96 (s, 1H), 7.72-7.67 (m, 2H), 7.39 (s, 4H), 7.17-7.13 (m, 1H), 6.31 (q, J=6.8 Hz, 1H), 3.72 (s, 3H), 2.45-2.39 (m, 1H), 2.02 (s, 3H), 1.71 (d, J=7.1 Hz, 3H), 1.17-1.11 (m, 4H).

Example 4

5-[1-(4-chlorophenyl)ethyl]-7-(2,6-difluoropyridin-4-yl)-3-methyl[1,2]oxazolo[4,5-d]pyridazin-4(5H)-one A microwave vial was charged with SiliaCat® DPP-Pd (diphenylphosphine palladium (II)) (32 mg, 0.5 mmol/g) and K$_2$CO$_3$ (34 mg). Then a solution of 7-bromo-5-[1-(4-chlorophenyl)ethyl]-3-methyl[1,2]oxazolo[4,5-d]pyridazin-4 (5H)-one (30 mg, 0.08 mmol, Example 39—Step 5) dissolved in 1,2-dimethoxyethane:water (4:1, 1.0 mL) was added, followed by (2,6-difluoropyridin-4-yl)boronic acid (25 mg, 0.16 mmol) dissolved in 1,2-dimethoxyethane:water (4:1, 0.3 mL). The resulting mixture was heated and stirred at 80° C. overnight. The reaction mixture was filtered and purified by preparative liquid chromatography (Method C, 0.5-8.5 minutes linear gradient 55-90% A) to provide the titled compound. $^1$H NMR (400 MHz, DMSO-d$_6$/D$_2$O, Temperature=90° C.) δ ppm 7.64 (s, 2H), 7.47-7.44 (m, 2H), 7.40-7.36 (m, 2H), 6.33 (q, J=6.4, 5.8 Hz, 1H), 2.62 (s, 3H), 1.84 (d, J=7.0 Hz, 3H).

Example 5

7-(2,4-dimethoxyphenyl)-3-methyl-5-(pyridin-4-ylmethyl)[1,2]oxazolo[4,5-d]pyridazin-4(5H)-one Step 1: 7-(2,4-dimethoxyphenyl)-3-methyl[1,2]oxazolo[4,5-d]pyridazin-4(5H)-one To a mixture of 7-bromo-3-methyl[1,2]oxazolo[4,5-d] pyridazin-4(5H)-one (1 g, 4.3 mmol, Example 2—Step 5) and (2,4-dimethoxyphenyl)boronic acid (1.02 g, 8.6 mmol) in 1,2-dimethoxyethane (20 mL) and H$_2$O (5 mL) was added K$_2$CO$_3$ (1.5 g, 10.9 mmol) and tetrakis(triphenylphosphine) palladium(0) (0.5 g, 0.4 mmol). The resulting mixture was stirred at 100° C. under N₂ overnight. After cooling to room temperature, the mixture was concentrated under reduced pressure. Water and methanol (20 ml, 1:1) were added to the residue, and the mixture was stirred for 10 minutes. The precipitate was collected by filtration and dried to afford the titled compound.

Step 2: 7-(2,4-dimethoxyphenyl)-3-methyl-5-(pyridin-4-ylmethyl)[1,2]oxazolo[4,5-d]pyridazin-4(5H)-one To a solution of 7-(2,4-dimethoxyphenyl)-3-methyl[1,2]oxazolo[4,5-d]pyridazin-4(5H)-one (80 mg) and $K_2CO_3$ (2.0 eq) in N,N-dimethylformamide (2 mL) was added 4-(bromomethyl)pyridine (1.1 eq), and the mixture was stirred at room temperature overnight. Water was added, and the mixture was extracted with ethyl acetate. The combined organic phase was concentrated under reduced pressure, and the residue was purified by preparative HPLC (method C) to give the titled compound.

Example 6

7-(2-amino-5-chlorophenyl)-5-[1-(4-chlorophenyl)ethyl]-3-methyl[1,2]oxazolo[4,5-d]pyridazin-4(5H)-one Step 1: methyl (4-chloro-2-(4,4,5,5-tetramethyl-1,3,2-dioxaborolan-2-yl)phenyl)carbamate To a solution of methyl 2-bromo-4-chlorophenylcarbamate (44 g, 166 mmol), 4,4,4',4',5,5,5',5'-octamethyl-2,2'-bi(1,3,2-dioxaborolane) (54.9 g, 216 mmol) and potassium acetate (40.8 g, 416 mmol) in 1,4-dioxane was added [1,1'-bis(diphenylphosphino)ferrocene]dichloropalladium(II) (6.09 g, 8.32 mmol, $Pd(dppf)Cl_2$). The mixture was stirred as 80° C. for 14 hours and then concentrated under reduced pressure. The residue was dissolved in ethyl acetate (100 mL) and extracted with brine (3×50 mL). The organic fraction was dried over sodium sulfate and concentrated under reduced pressure. The residue was purified by flash chromatography to give the titled compound.

Step 2: 7-(2-amino-5-chlorophenyl)-5-[1-(4-chlorophenyl)ethyl]-3-methyl[1,2]oxazolo[4,5-d]pyridazin-4(5H)-one 7-Bromo-5-[1-(4-chlorophenyl)ethyl]-3-methyl[1,2]oxazolo[4,5-d]pyridazin-4(5H)-one (60 mg, 0.163 mmol, Example 39—Step 5) was combined with potassium carbonate (56.2 mg, 0.407 mmol) and methyl (4-chloro-2-(4,4,5,5-tetramethyl-1,3,2-dioxaborolan-2-yl)phenyl)carbamate (50.7 mg, 0.163 mmol) in 1,2-dimethoxyethane and water (5 mL, 4:1). Then tetrakis(triphenylphosphine)palladium(0) (18.81 mg, 0.016 mmol) was added, and the mixture was heated for 4 hours at 80° C. under an argon atmosphere. The reaction mixture was partitioned between water and ethyl acetate. The organic fraction was then washed with brine, dried over $MgSO_4$, and concentrated under reduced pressure. The residue was chromatographed on silica gel eluted with 30% ethyl acetate/cyclohexane. The residue was taken into a small amount of isopropanol and treated with HCl in isopropanol. This mixture was diluted with diisopropyl ether to precipitate the hydrochloric acid salt. The solid was collected by filtration and dried in a vacuum oven to give the titled compound as a hydrochloride salt. ¹H NMR (600 MHz, DMSO-$d_6$) δ ppm 7.66 (d, J=2.4 Hz, 0H), 7.45-7.37 (m, 3H), 7.22 (dd, J=8.8, 2.5 Hz, 1H), 6.82 (d, J=8.7 Hz, 1H), 6.37 (q, J=6.9 Hz, 1H), 2.62 (s, 3H), 1.74 (d, J=7.0 Hz, 3H), 1.04 (d, J=6.0 Hz, 1H); MS (ESI+) m/z 415.0 (M+H)⁺.

Example 7

5-[1-(4-chlorophenyl)ethyl]-7-(2-chloropyridin-3-yl)-3-methyl[1,2]oxazolo[4,5-d]pyridazin-4(5H)-one 7-Bromo-5-[1-(4-chlorophenyl)ethyl]-3-methyl[1,2]oxazolo[4,5-d]pyridazin-4(5H)-one (60 mg, 0.163 mmol, Example 39—Step 5) was combined with potassium carbonate (56.2 mg, 0.407 mmol) and (2-chloropyridin-3-yl)boronic acid (30.7 mg, 0.195 mmol) in 1,2-dimethoxyethane and water (5 mL, 4:1). Then tetrakis(triphenylphosphine)palladium(0) (18.81 mg, 0.016 mmol) was added, and the mixture was heated for 4 hours at 80° C. under an argon atmosphere. The reaction mixture was partitioned between water and ethyl acetate. The organic fraction was then washed with brine, dried over $MgSO_4$, and concentrated under reduced pressure. The residue was purified by flash chromatography using a Teledyne Isco CombiFlash® Rf apparatus with a 4 g silica gel cartridge eluted with 30% ethyl acetate/cyclohexane. The product containing fractions were combined and concentrated. The residue was dried in a vacuum oven overnight to give the titled compound. ¹H NMR (600 MHz, DMSO-$d_6$) δ ppm 8.64 (dd, J=4.8, 1.9 Hz, 1H), 8.18 (dd, J=7.6, 1.9 Hz, 1H), 7.69 (dd, J=7.6, 4.8 Hz, 1H), 7.41 (s, 3H), 6.33 (q, J=7.0 Hz, 1H), 2.61 (s, 3H), 1.74 (d, J=7.0 Hz, 3H), 1.40 (s, 5H); MS (ESI+) m/z 401.0 (M+H)⁺.

Example 8

N-{5-[5-(4-chlorobenzyl)-3-methyl-4-oxo-4,5-dihydro[1,2]oxazolo[4,5-d]pyridazin-7-yl]-2-fluorophenyl)}acetamide Step 1: N-[2-fluoro-5-(4,4,5,5-tetramethyl-1,3,2-dioxaborolan-2-yl)phenyl]acetamide To a solution of N-(5-bromo-2-fluorophenyl)acetamide (6 g, 25.9 mmol) in 1,4-dioxane (100 mL) was added $K_2CO_3$ (7.61 g, 78 mmol), bis(pinacolato)diboron (7.88 g, 31 mmol) and [1,1'-bis(diphenylphosphino)ferrocene]dichloropalladium(II) (0.946 g, 1.29 mmol, $Pd(dppf)Cl_2$). The resulting mixture was heated to reflux under N₂ overnight. The reaction was diluted with water and extracted with ethyl acetate. The organic phase was washed with brine, concentrated under reduced pressure to give a residue that was purified by column chromatography on silica gel and eluted with EtOAc/PE to give the titled compound (6 g, yield 83%). ¹H NMR (400 MHz, CDCl₃) δ ppm 8.62 (d, J=7.94 Hz, 1H), 7.53 (t, J=6.62 Hz, 1H), 7.28 (s, 1H), 7.09 (dd, J=11.03 Hz, 8.38 Hz, 1H), 2.23 (s, 3H), 1.34 (s, 12H).

Step 2: N-{5-[5-(4-chlorobenzyl)-3-methyl-4-oxo-4,5-dihydro[1,2]oxazolo[4,5-d]pyridazin-7-yl]-2-fluorophenyl}acetamide To a solution of 7-bromo-5-(4-chlorobenzyl)-3-methyl[1,2]oxazolo[4,5-d]pyridazin-4(5H)-one (120 mg, 0.338 mmol, Example 2—Step 6) in 1,2-dimethoxyethane (4 mL) and water (1 mL) was added N-[2-fluoro-5-(4,4,5,5-tetramethyl-1,3,2-dioxaborolan-2-yl)phenyl]acetamide (113 mg, 0.406 mmol, Step 1), $K_2CO_3$ (117 mg, 0.846 mmol) and tetrakis(triphenylphosphine)palladium(0) (39.1 mg, 0.034 mmol). The resulting mixture was stirred at 80° C. under $N_2$ overnight. The mixture was diluted with water and extracted with ethyl acetate. The organic phase was washed with brine and concentrated under reduced pressure to give a residue that was purified by preparative HPLC (method B) to supply the titled compound (70 mg, yield 50%). LCMS (ESI+) m/z 427 (M+H)$^+$, retention time 3.325 minutes; $^1$H NMR (400 MHz, CDCl$_3$) δ ppm 9.15 (d, J=6.62 Hz, 1H), 7.89 (br, s, 1H), 7.37-7.55 (m, 3H), 7.34 (d, J=8.38 Hz, 2H), 7.23-7.27 (m, 1H), 5.46 (s, 2H), 2.73 (s, 3H), 2.31 (s, 3H).

Example 9

7-(2,5-dimethoxyphenyl)-5-[4-methoxy-3-(trifluoromethyl)benzyl]-3-methyl[1,2]oxazolo[4,5-d]pyridazin-4(5H)-one The titled compound was prepared using the procedures described for Example 5 substituting (2,5-dimethoxyphenyl) boronic acid for (2,4-dimethoxyphenyl)boronic acid in Step 1 and 4-(bromomethyl)-1-methoxy-2-(trifluoromethyl)benzene for 4-(bromomethyl)pyridine in Step 2. $^1$H NMR (400 MHz, CD$_3$OD): δ7.71-7.68 (m, 2H), 7.17-7.11 (m, 3H), 6.99 (s, 2H), 5.43 (s, 2H), 3.88 (s, 3H), 3.80 (s, 3H), 3.77 (s, 3H), 2.63 (s, 3H); m/z 476.0 (M+H)$^+$ Example 10

5-[2-(4-chlorophenyl)ethyl]-7-(2,5-dimethoxyphenyl)-3-methyl[1,2]oxazolo[4,5-d]pyridazin-4(5H)-one Step 1: 7-(2,5-dimethoxyphenyl)-3-methyl[1,2]oxazolo[4,5-d]pyridazin-4(5H)-one Under argon, 7-bromo-3-methyl[1,2]oxazolo[4,5-d]pyridazin-4(5H)-one (100 mg, 0.435 mmol, Example 2—Step 5) was suspended in toluene and methanol (3 mL, 1:1). 2 M Aqueous sodium bicarbonate (0.326 mL, 0.652 mmol) and (2,5-dimethoxyphenyl)boronic acid (79 mg, 0.435 mmol) were added followed by tetrakis(triphenylphosphine)palladium(0) (50.2 mg, 0.043 mmol). The reaction mixture was heated with stirring in a Biotage® microwave reactor at 120° C. for 30 minutes. The reaction mixture was then partitioned between water and ethyl acetate. The aqueous phase was extracted twice more with ethyl acetate. The combined organic fractions were dried over MgSO$_4$ and then concentrated under reduced pressure. The residue was purified by flash chromatography on a Teledyne Isco CombiFlash® Companion® apparatus using a RediSep® silica gel cartridge (4 g) eluted with 10% methanol/dichloromethane. MS (ESI+) m/z 288.1 (M+H)$^+$.

Step 2: 5-[2-(4-chlorophenyl)ethyl]-7-(2,5-dimethoxyphenyl)-3-methyl[1,2]oxazolo[4,5-d]pyridazin-4(5H)-one 7-(2,5-Dimethoxyphenyl)-3-methyl[1,2]oxazolo[4,5-d]pyridazin-4(5H)-one (50 mg, 0.174 mmol) was dissolved in N,N-dimethylformamide (5 mL), and the resultant solution was cooled to 0° C. 1-(2-Bromoethyl)-4-chlorobenzene (57.3 mg, 0.261 mmol) and potassium carbonate (60.1 mg, 0.435 mmol) were added. The reaction mixture was allowed to warm to room temperature and was stirred overnight. The reaction mixture was partitioned between ethyl acetate and water. The aqueous phase was extracted twice more with ethyl acetate. The combined organic fractions were washed with brine, dried over MgSO$_4$, and concentrated under reduced pressure. The residue was purified by flash chromatography on a Teledyne Isco CombiFlash® Companion® apparatus using a RediSep® silica gel cartridge (4 g) eluted with 10% methanol/dichloromethane. The solid was triturated with a little ethyl acetate/heptane (1:1), and the precipitate was collected by vacuum filtration. The solid was dried in a vacuum oven to give the titled compound. $^1$H NMR (600 MHz, DMSO-d$_6$) δ ppm 7.36-7.31 (m, 2H), 7.26-7.21 (m, 2H), 7.18-7.09 (m, 2H), 6.75 (d, J=3.1 Hz, 1H), 4.43 (t, J=7.1 Hz, 2H), 3.73 (d, J=12.8 Hz, 6H), 3.32 (s, OH), 3.08 (t, J=7.1 Hz, 2H), 2.60 (s, 3H); MS (ESI+) m/z 426.1 (M+H)$^+$.

Example 11

7-[2-amino-5-(trifluoromethyl)phenyl]-5-[1-(4-chlorophenyl)ethyl]-3-methyl[1,2]oxazolo[4,5-d]pyridazin-4(5H)-one 7-Bromo-5-[1-(4-chlorophenyl)ethyl]-3-methyl[1,2]oxazolo[4,5-d]pyridazin-4(5H)-one (80 mg, 0.217 mmol, Example 39—Step 5) in ethanol/toluene (1:1, 2 mL) was combined with 2 M aqueous sodium carbonate (0.163 mL, 0.326 mmol) and 2-(4,4,5,5-tetramethyl-1,3,2-dioxaborolan-2-yl)-4-(trifluoromethyl)aniline (62.3 mg, 0.217 mmol). Then tetrakis(triphenylphosphine)palladium(0) (25.08 mg, 0.022 mmol) was added, and the mixture was heated in a CEM microwave reactor for 30 minutes at 130° C. under an argon atmosphere. The reaction mixture was partitioned between water and ethyl acetate. The organic fraction was then washed with brine, dried over MgSO$_4$, and concentrated under reduced pressure. The residue was purified by flash chromatography on a Teledyne Isco CombiFlash® Rf apparatus using a silica gel cartridge (4 g) eluted with ethyl acetate/cyclohexane. A second flash chromatography on a Teledyne Isco CombiFlash® Rf apparatus using a silica gel cartridge (4 g, m) eluted with 30% ethyl acetate/cyclohexane provided the titled compound which was dried overnight in a vacuum oven. $^1$H NMR (600 MHz, DMSO-d$_6$) δ ppm 7.53 (d, J=8.7 Hz, 1H), 7.41-7.31 (m, 4H), 6.83-6.74 (m, 2H), 6.30 (q, J=7.1 Hz, 1H), 6.17 (s, 2H), 3.35-3.29 (m, 1H), 2.59 (s, 3H), 1.68 (d, J=7.0 Hz, 3H), 1.40 (s, 2H); MS (ESI+) m/z 449.1 (M+H)$^+$.

Example 12

5-[1-(4-chlorophenyl)ethyl]-7-(1H-indol-6-yl)-3-methyl[1,2]oxazolo[4,5-d]pyridazin-4(5H)-one 7-Bromo-5-[1-(4-chlorophenyl)ethyl]-3-methyl[1,2]oxazolo[4,5-d]pyridazin-4(5H)-one (60 mg, 0.163 mmol, Example 39—Step 5) in 1,2-dimethoxyethane/water (4:1, 5 mL) was combined with potassium carbonate (56.2 mg, 0.407 mmol) and (1H-indol-6-yl)boronic acid (31.4 mg, 0.195 mmol). Then tetrakis(triphenylphosphine)palladium (0) (18.81 mg, 0.016 mmol) was added, and the mixture was heated for 4 hours at 80° C. under an argon atmosphere. The reaction mixture was partitioned between water and ethyl acetate. The organic fraction was then washed with brine, dried over MgSO$_4$, and concentrated under reduced pressure. The residue was purified by flash chromatography on a Teledyne Isco CombiFlash® Rf apparatus using a silica gel cartridge (4 g) eluted with 30% ethyl acetate/cyclohexane. The residue was triturated with a little ethyl acetate/diisopropyl ether. The solid was collected by vacuum filtration and dried overnight in a vacuum oven to give the titled compound. $^1$H NMR (600 MHz, DMSO-d$_6$) δ ppm 11.45 (s, 1H), 7.77 (dd, J=7.4, 0.9 Hz, 1H), 7.60 (dt, J=8.1, 1.0 Hz, 1H), 7.45 (t, J=2.8 Hz, 1H), 7.41 (s, 4H), 7.32-7.25 (m, 1H), 6.66 (ddd, J=3.0, 2.1, 0.9 Hz, 1H), 6.44 (q, J=7.0 Hz, 1H), 2.64 (s, 3H), 1.85 (d, J=7.0 Hz, 3H); MS (ESI+) m/z 405.1 (M+H)$^+$.

Example 13

5-(4-chlorobenzyl)-7-(2,5-dimethoxyphenyl)-3-(propan-2-yl)[1,2]oxazolo[4,5-d]pyridazin-4(5H)-one To a solution of 7-bromo-5-(4-chlorobenzyl)-3-(propan-2-yl)[1,2]oxazolo[4,5-d]pyridazin-4(5H)-one (280 mg, 0.73 mmol, Example 98—Step 6) in N,N-dimethylformamide (2 mL) and water (0.5 mL) was added (2,5-dimethoxyphenyl) boronic acid (134 mg, 0.73 mmol), K$_2$CO$_3$ (202 mg, 1.47 mmol) and tetrakis(triphenylphosphine)palladium(0) (30 mg, 0.037 mmol). After stirring at 80° C. overnight under nitrogen, the mixture was diluted with water and extracted with ethyl acetate. The organic phase was washed with brine and concentrated under reduced pressure to give a residue that was purified by preparative HPLC (method C) to give the titled compound (72 mg, yield 22%). $^1$H NMR (400 MHz, CDCl$_3$) δ ppm 7.46 (d, J=8.4 Hz, 2H), 7.31 (d, J=8.4 Hz, 2H), 7.07-6.97 (m, 3H), 5.42 (s, 2H), 3.82 (d, J=1.8 Hz, 6H), 3.59-3.48 (m, 1H), 1.47 (d, J=7.1 Hz, 6H); LCMS (method B) (ESI+) m/z 439.1 (M+H)$^+$, retention time 3.031 minutes.

Example 14

7-(2-aminophenyl)-5-[1-(4-chlorophenyl)ethyl]-3-methyl[1,2]oxazolo[4,5-d]pyridazin-4(5H)-one The titled compound was obtained using the reaction conditions described for Example 6 substituting 2-(4,4,5,5-tetramethyl-1,3,2-dioxaborolan-2-yl)aniline for methyl (4-chloro-2-(4,4,5,5-tetramethyl-1,3,2-dioxaborolan-2-yl) phenyl)carbamate. The reaction mixture was partitioned between ethyl acetate and water. The organic fraction was washed with brine, dried over MgSO$_4$, and concentrated under reduced pressure. The residue was purified by flash chromatography on a Teledyne Isco CombiFlash® Rf apparatus using a silica gel cartridge (4 g) eluted with 40% ethyl acetate/cyclohexane. A second flash chromatography on a Teledyne Isco CombiFlash® Rf apparatus using a silica gel cartridge (4 g) eluted with 2% methanol/dichloromethane. The residue was triturated with a little ethyl acetate/diisopropyl ether (1:1). The residue was dried overnight in a vacuum oven to give the titled compound. $^1$H NMR (600 MHz, DMSO-d$_6$) δ ppm 7.67 (dd, J=7.9, 1.5 Hz, 1H), 7.44-7.37 (m, 4H), 7.18 (ddd, J=8.6, 7.1, 1.6 Hz, 1H), 6.80 (dd, J=8.3, 1.2 Hz, 1H), 6.69 (ddd, J=8.1, 7.1, 1.2 Hz, 1H), 6.38 (q, J=7.0 Hz, 1H), 5.84 (s, 2H), 5.76 (s, 1H), 2.62 (s, 3H), 1.75 (d, J=7.0 Hz, 3H).

Example 15

N-(3-{5-[4-methoxy-3-(trifluoromethyl)benzyl]-3-methyl-4-oxo-4,5-dihydro[1,2]oxazolo[4,5-d]pyridazin-7-yl}phenyl)acetamide The titled compound was prepared using the procedures described for Example 5 substituting (3-acetamidophenyl) boronic acid for (2,4-dimethoxyphenyl)boronic acid in Step 1 and 4-(bromomethyl)-1-methoxy-2-(trifluoromethyl)benzene for 4-(bromomethyl)pyridine in Step 2. Yield 46%.

1H NMR (400 MHz, DMSO): δ 10.19 (br, 1H), 8.31 (s, 1H), 7.77-7.40 (m, 5H), 7.23 (s, 1H), 5.41 (s, 2H), 3.84 (s, 3H), 2.59 (s, 3H), 2.06 (s, 3H). +) m/z 453.1 (M+H)$^+$,

Example 16

5-[1-(4-chlorophenyl)ethyl]-7-(5-hydroxy-2-methylphenyl)-3-methyl[1,2]oxazolo[4,5-d]pyridazin-4 (5H)-one The titled compound was obtained using the reaction conditions described for Example 6 substituting (5-hydroxy-2-methylphenyl)boronic acid for methyl (4-chloro-2-(4,4,5,5-tetramethyl-1,3,2-dioxaborolan-2-yl)phenyl)carbamate. The reaction mixture was partitioned between ethyl acetate and water. The organic fraction was washed with brine, dried over MgSO$_4$, and concentrated under reduced pressure. The residue was purified by flash chromatography on a Teledyne Isco CombiFlash® Rf apparatus using a silica gel cartridge (4 g) eluted with 40% ethyl acetate/cyclohexane. The residue was triturated with a little ethyl acetate/diisopropyl ether (1:1). The solid was collected by vacuum filtration and was dried overnight in a vacuum oven to give the titled compound. $^1$H NMR (600 MHz, DMSO-$^1$H NMR (600 MHz, DMSO-d$_6$) δ ppm 9.59 (s, 1H), 7.44-7.34 (m, 4H), 7.19-7.14 (m, 1H), 6.98 (d, J=2.6 Hz, 1H), 6.84 (dd, J=8.3, 2.6 Hz, 1H), 6.35 (q, J=7.0 Hz, 1H), 2.60 (s, 3H), 2.11 (s, 3H), 1.73 (d, J=7.1 Hz, 3H); MS (ESI+) m/z 396.1 (M+H)$^+$.

Example 17

N-(2-fluoro-5-{5-[2-fluoro-5-(trifluoromethyl)benzyl]-3-methyl-4-oxo-4,5-dihydro[1,2]oxazolo[4,5-d] pyridazin-7-yl}phenyl)acetamide The titled compound was prepared using the procedures described for Example 5 substituting (3-acetamido-4-fluorophenyl)boronic acid for (2,4-dimethoxyphenyl)boronic acid in Step 1 and 2-(bromomethyl)-1-fluoro-4-(trifluoromethyl)benzene for 4-(bromomethyl)pyridine in Step 2. Yield 22%.

$^1$H NMR (400 MHz, CD$_3$OD): δ 8.21-8.19 (m, 1H), 8.00-7.99 (d, J=5.2 Hz, 1H), 7.73-7.71 (m, 1H), 7.62 (br, 1H), 7.45-7.41 (t, J=9.2 Hz, 1H), 7.24-7.20 (t, J=8.8 Hz, 1H), 5.09-5.05 (m, 2H), 2.66 (s, 3H), 1.95 (s, 3H). m/z 479.2

Example 18

N-(3-{5-[1-(4-chlorophenyl)ethyl]-3-methyl-4-oxo-4,5-dihydro[1,2]oxazolo[4,5-d]pyridazin-7-yl}-4-methylphenyl)acetamide The titled compound was obtained using the reaction conditions described for Example 6 substituting N-(4-methyl-3-(4,4,5,5-tetramethyl-1,3,2-dioxaborolan-2-yl)phenyl)acetamide for methyl (4-chloro-2-(4,4,5,5-tetramethyl-1,3,2-dioxaborolan-2-yl)phenyl)carbamate. The reaction mixture was partitioned between ethyl acetate and water. The organic fraction was washed with brine, dried over MgSO$_4$, and concentrated under reduced pressure. The residue was purified by flash chromatography on a Teledyne Isco CombiFlash® Rf apparatus using a silica gel cartridge (4 g) eluted with 60% ethyl acetate/cyclohexane. A second flash chromatography on a Teledyne Isco CombiFlash® Rf apparatus using a silica gel cartridge (4 g) eluted with 3% methanol/dichloromethane. The residue was triturated with a little ethyl acetate/diisopropyl ether (1:1). The residue was dried overnight in a vacuum oven to give the titled compound. $^1$H NMR (500 MHz, DMSO-$d_6$) δ ppm 10.07 (s, 1H), 7.84 (d, J=2.2 Hz, 1H), 7.62 (dd, J=8.4, 2.3 Hz, 1H), 7.39 (s, 4H), 7.30 (d, J=8.5 Hz, 1H), 6.35 (q, J=7.0 Hz, 1H), 2.61 (s, 2H), 2.39 (s, 1H), 2.16 (s, 3H), 2.04 (s, 3H), 1.99 (s, 1H), 1.73 (d, J=7.0 Hz, 3H), 1.30 (s, 2H); MS (ESI+) m/z 437.1 (M+H)$^+$.

Example 19

7-(4-fluorophenyl)-3-methyl-5-[4-(trifluoromethyl)benzyl][1,2]oxazolo[4,5-d]pyridazin-4(5H)-one Step 1: (Z)-ethyl 3-aminobut-2-enoate

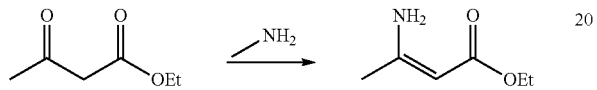

Aqueous methane amine (250 ml, 922 mmol) was added dropwise to an aqueous NaOH solution (2M) (300 ml) to give methane amine gas. The gas was bubbled through ethyl 3-oxobutanoate (60 g, 461 mmol). The mixture was stirred at room temperature overnight. MTBE was added. The organic layer was separated and washed with water to pH=8, dried over Na$_2$SO$_4$, concentrated under reduced pressure to get (Z)-ethyl 3-aminobut-2-enoate (45 g, 348 mmol, 76% yield).

Step 2: 2-chloro-1-(4-fluorophenyl)-2-oxoethyl acetate

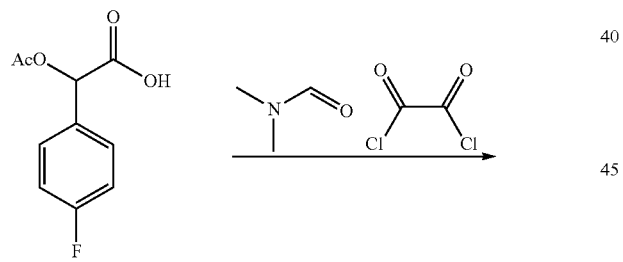

To an ice cooled solution of Oxalyl chloride (49.5 ml, 566 mmol) and DMF (18.25 ml, 236 mmol) in DCM (1600 ml) was added 2-acetoxy-2-(4-fluorophenyl)acetic acid (100 g, 471 mmol) in DCM (1600 ml). The mixture was stirred at 0° C. for 1 hour. The solvent was removed under reduced pressure to get 2-chloro-1-(4-fluorophenyl)-2-oxoethyl acetate (97 g, 421 mmol, 89% yield), which was directly used to the next step.

Step 3: (Z)-ethyl 2-(2-acetoxy-2-(4-fluorophenyl)acetyl)-3-(methylamino)but-2-enoate

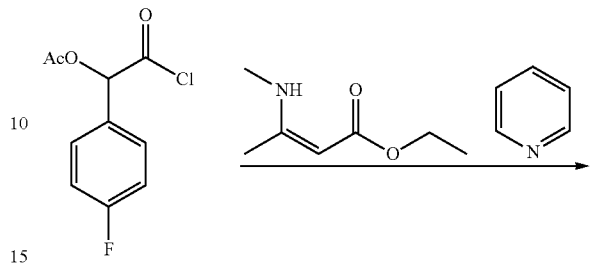

To a solution of (Z)-ethyl 3-(methylamino)but-2-enoate (50 g, 349 mmol) in THF (1200 ml) and pyridine (28.2 ml, 349 mmol) 2-chloro-1-(4-fluorophenyl)-2-oxoethyl acetate (97 g, 419 mmol) in THF (1200 ml) was added at 0° C. The mixture was stirred at room temperature overnight. Water and EtOAc were added. The mixture was extracted with EtOAc. The organic layer was concentrated and purified by pre-TLC to get (Z)-ethyl 2-(2-acetoxy-2-(4-fluorophenyl)acetyl)-3-(methylamino)but-2-enoate (90 g, 267 mmol, 76% yield), which was directly used to the next step.

Step 4: 5-(4-fluorobenzoyl)-3-methylisoxazole-4-carboxylate

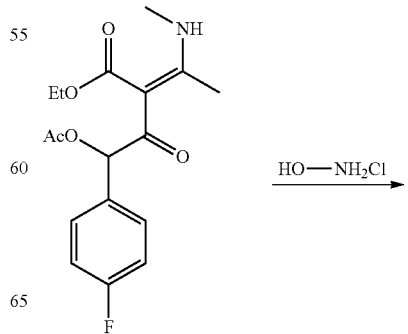

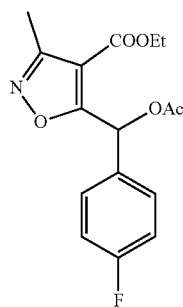

To a solution of (Z)-ethyl 2-(2-acetoxy-2-(4-fluorophenyl)acetyl)-3-(methylamino)but-2-enoate (90 g, 267 mmol) in acetic acid (800 ml) hydroxylamine hydrochloride (22.25 g, 320 mmol) was added. The mixture was refluxed for 30 min. The solvent was removed under reduced pressure. Then MTBE was added. The solution was washed with water, Na₂CO₃ and water, then dried and concentrated to get ethyl 5-(acetoxy(4-fluorophenyl)methyl)-3-methylisoxazole-4-carboxylate (90 g, 280 mmol, 105% yield) which was directly used to the next step.

Step 5: 5-(4-fluorobenzoyl)-3-methylisoxazole-4-carboxylate

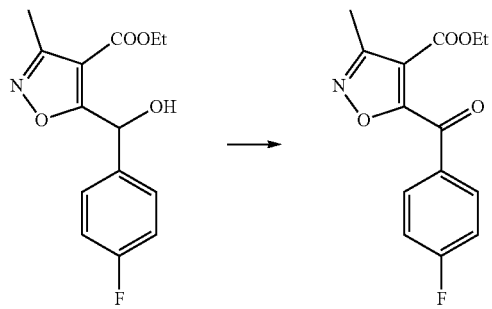 [SMILES: CCOC(=O)c1c(C)noc1C(O)c1ccc(F)cc1 ; CCOC(=O)c1c(C)noc1C(=O)c1ccc(F)cc1]

To a solution of ethyl 5-((4-fluorophenyl)(hydroxy)methyl)-3-methylisoxazole-4-carboxylate (40 g, 143 mmol) in Jones' reagent (80 ml, 143 mmol) (26.73 g chromium trioxide and 23 mL concentrated H₂SO₄ was diluted to 100 ml with water to get Jones' reagent.) The mixture was stirred at room temperature for 4 hours. The precipitated salts were filtered off and washed with acetone and the acetone layer was stirred with Na₂SO₃ for 2 hours. The solution was filtered and the acetone was removed under reduced pressure. The solid residue was washed with ethanol and dried to get ethyl 5-(4-fluorobenzoyl)-3-methylisoxazole-4-carboxylate (34.5 g, 124 mmol, 87% yield).

Step 6: 7-(4-fluorophenyl)-3-methylisoxazolo[4,5-d]pyridazin-4(5H)-one (23 g, 94 mmol, 75% yield)

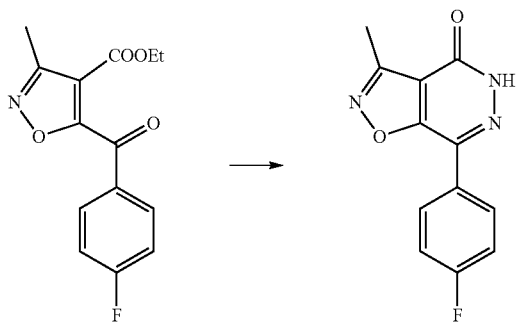 [SMILES: CCOC(=O)c1c(C)noc1C(=O)c1ccc(F)cc1 ; Cc1noc2c(-c3ccc(F)cc3)n[nH]c(=O)c12]

To a solution of ethyl 5-(4-fluorobenzoyl)-3-methylisoxazole-4-carboxylate (34.5 g, 124 mmol) in ethanol (400 ml) hydrazine hydrate (12.44 g, 249 mmol) was added. The mixture was stirred at room temperature for 4 hours. The white solid was collected and washed with ethanol give 7-(4-fluorophenyl)-3-methylisoxazolo[4,5-d]pyridazin-4(5H)-one (23 g, 94 mmol, 75% yield).

Step 7: 7-(4-fluorophenyl)-3-methyl-5-(4-(trifluoromethyl)benzyl)isoxazolo[4,5-d]pyridazin-4(5H)-one To a solution of 7-(4-fluorophenyl)-3-methyl[1,2]oxazolo[4,5-d]pyridazin-4(5H)-one (100 mg, 0.408 mmol) in N,N-dimethylformamide (2 mL), NaH (14.68 mg, 0.612 mmol) was added. The mixture was stirred at room temperature for 15 minutes, and then 1-(bromomethyl)-4-(trifluoromethyl)benzene (117 mg, 0.489 mmol) was added. The mixture was stirred at room temperature overnight. 60% of the starting material was remaining. The mixture was quenched with water. The solid precipitate was collected and washed with water and methanol, then dried to give 7-(4-fluorophenyl)-3-methyl-5-(4-(trifluoromethyl)benzyl)isoxazolo[4,5-d]pyridazin-4(5H)-one (36 mg, yield 21.9%) as a solid.
¹H NMR (400 MHz, DMSO-d₆) δ ppm 8.09 (m, 2H), 7.62 (dd, J=8.4, 2.3 Hz, 2H), 7.59 (m, 2H), 7.44 (m, 2H), 5.52 (s, 2H), 2.60 (s, 3H); MS (ESI+) m/z 404.0 (M+H)⁺.

Example 20

5-(2-fluorobenzyl)-3,7-dimethyl[1,2]oxazolo[4,5-d]pyridazin-4(5H)-one

A 100 mg/mL slurry of NaH in N,N-dimethylformamide was prepared fresh from solid NaH. In a 4 mL vial equipped with a stirrer was added 3,7-dimethyl[1,2]oxazolo[4,5-d]pyridazin-4(5H)-one (12.40 mg, 0.08 mmol) dissolved in 300 μL of N,N-dimethylformamide. At room temperature without nitrogen, 27.03 μL (2.70 mg, 1.5 equivalents, 0.11 mmol) of sodium hydride was added. Bubbles appeared, and the reaction was allowed to react for 30 minutes with stirring at room temperature. To this mixture, 130 μL of a solution of 1-(bromomethyl)-2-fluorobenzene from a 0.6 mmol pre-weighed vial (1 equivalent, 15.1 mg, 0.08 mmol) in N,N-dimethylformamide (1 mL), was added. The reaction was then stirred for 6 hours at room temperature. The reaction was quenched with water (100 μL), and the reaction mixture was purified directly by preparative liquid chromatography (Method C, 0.5-8.5 minutes linear gradient 45-75% A). ¹H NMR (400 MHz, DMSO-d₆/D₂O) δ ppm 7.39-7.33 (m, 1H), 7.27-7.20 (m, 2H), 7.20-7.13 (m, 1H), 5.36 (s, 2H), 2.57 (s, 3H), 2.49 (s, 3H); MS (APCI⁺) m/z 274.1 (M+H)⁺.

Example 21

5-[1-(4-chlorophenyl)ethyl]-7-(2,5-dimethoxyphenyl)-3-methyl[1,2]oxazolo[4,5-d]pyridazin-4(5H)-one 7-Bromo-5-[1-(4-chlorophenyl)ethyl]-3-methyl[1,2]oxazolo[4,5-d]pyridazin-4(5H)-one (60 mg, 0.163 mmol, Example 39—Step 5) in ethanol/toluene (1:1, 3 mL) was combined with sodium carbonate (25.9 mg, 0.244 mmol) and (2,5-dimethoxyphenyl)boronic acid (29.6 mg, 0.163 mmol). Then tetrakis(triphenylphosphine)palladium(0) (18.81 mg, 0.016 mmol) was added, and the mixture was heated in a CEM® microwave reactor for 30 minutes at 130°

C. under an argon atmosphere. The reaction mixture was partitioned between water and ethyl acetate. The organic fraction was then washed with brine, dried over MgSO$_4$, and concentrated under reduced pressure. The residue was stirred with ethyl acetate, and the precipitate was collected and dried in a vacuum oven overnight. The material was purified by flash chromatography on a Teledyne Isco CombiFlash® Rf apparatus using a silica gel cartridge (4 g) eluted with 20% ethyl acetate/cyclohexane. The residue was dried in a vacuum oven overnight to give the titled compound. $^1$H NMR (600 MHz, DMSO-d$_6$) δ ppm 7.42 (s, 4H), 7.20-7.11 (m, 2H), 6.99-6.93 (m, 1H), 6.32 (q, J=7.0 Hz, 1H), 3.77-3.66 (m, 7H), 3.64 (s, 1H), 2.59 (s, 3H), 1.73 (d, J=7.0 Hz, 3H).

Example 22

5-[1-(4-chlorophenyl)ethyl]-7-(5-fluoropyridin-3-yl)-3-methyl[1,2]oxazolo[4,5-d]pyridazin-4(5H)-one The titled compound was prepared using the procedure described in Example 4 substituting (5-fluoropyridin-3-yl)boronic acid (23 mg, 0.16 mmol) for (2,6-difluoropyridin-4-yl)boronic acid. Purification was achieved by preparative liquid chromatography (Method C, 0.5-8.5 minutes linear gradient 45-75% A). $^1$H NMR (400 MHz, DMSO-d$_6$/D$_2$O, Temperature=90° C.) δ ppm 9.13-9.04 (m, 1H), 8.69 (d, J=2.6 Hz, 1H), 8.20-8.14 (m, 1H), 7.49-7.42 (m, 2H), 7.40-7.35 (m, 2H), 6.33 (q, J=7.0 Hz, 1H), 2.62 (s, 3H), 1.83 (d, J=7.0 Hz, 3H); MS (APCI$^+$) m/z 385 (M+H)$^+$.

Example 23

5-(4-chlorobenzyl)-7-(3-fluorophenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added (3-fluorophenyl)boronic acid (47.2 mg, 0.338 mmol), K$_2$CO$_3$ (0.097 g, 0.705 mmol) and tetrakis(triphenylphosphine)palladium(0) (0.033 g, 0.028 mmol). The resulting mixture was stirred at 80° C. overnight under N$_2$. After cooling down to room temperature, the reaction mixture was concentrated under reduced pressure to give a residue that was washed with a mixture of CH$_3$OH and H$_2$O to give the titled compound. Yield 37%

1H NMR (CDCl3, 400 MHz): δ 7.97 (d, J=7.94 Hz, 1H), 7.86 (dd, J=11.69, 1.98 Hz, 1H), 7.38-7.55 (m, 3H), 7.32 (d, J=8.38 Hz, 2H), 7.20 (td, J=8.27, 1.98 Hz, 1H), 5.44 (s, 2H), 2.71 (s, 3H); m/z 369.8.

Example 24

N-(3-{5-[1-(4-chlorophenyl)ethyl]-3-methyl-4-oxo-4,5-dihydro[1,2]oxazolo[4,5-d]pyridazin-7-yl}phenyl)methanesulfonamide The titled compound was prepared using the procedure described in Example 4 substituting (3-(methylsulfonamido)phenyl)boronic acid (34 mg, 0.16 mmol) for (2,6-difluoropyridin-4-yl)boronic acid. Purification was achieved by preparative liquid chromatography (Method C, 0.5-8.5 minutes linear gradient 45-75% A). $^1$H NMR (400 MHz, DMSO-d$_6$/D$_2$O, Temperature=90° C.) δ ppm 8.02 (t, J=2.0 Hz, 1H), 7.82 (dt, J=7.9, 1.3 Hz, 1H), 7.55 (t, J=8.0 Hz, 1H), 7.47-7.43 (m, 2H), 7.40-7.35 (m, 3H), 6.35 (q, J=7.0 Hz, 1H), 3.04 (s, 3H), 2.62 (s, 3H), 1.82 (d, J=7.0 Hz, 3H); MS (APCI+) m/z 459 (M+H)+.

Example 25

5-[2-fluoro-5-(trifluoromethyl)benzyl]-3,7-dimethyl[1,2]oxazolo[4,5-d]pyridazin-4(5H)-one The titled compound was prepared using the procedure described in Example 20 substituting 2-(bromomethyl)-1-fluoro-4-(trifluoromethyl)benzene for 1-(bromomethyl)-2-fluorobenzene. Purification was achieved by preparative liquid chromatography (Method C, 0.5-8.5 minutes linear gradient 60-100% A). $^1$H NMR (400 MHz, DMSO-d$_6$/D$_2$O) δ ppm 7.81-7.75 (m, 1H), 7.71 (dd, J=6.7, 2.4 Hz, 1H), 7.47 (t, J=9.2 Hz, 1H), 5.42 (s, 2H), 2.57 (s, 3H), 2.49 (s, 3H); MS (APCI$^+$) m/z 342.0 (M+H)$^+$.

Example 26

7-(2-methoxyphenyl)-3-methyl-5-(pyridin-4-ylmethyl)[1,2]oxazolo[4,5-d]pyridazin-4(5H)-one The titled compound was prepared using the procedures described for Example 5 substituting (2-methoxyphenyl)boronic acid for (2,4-dimethoxyphenyl)boronic acid in Step 1. Yield 19%.

$^1$H NMR (400 MHz, CDCl$_3$): δ 8.77-8.75 (m, 2H), 7.94-7.93 (m, 2H), 7.55-7.53 (m, 1H), 7.48-7.45 (m, 1H), 7.21-7.19 (m, 1H), 7.11-7.09 (m, 1H), 5.73 (s, 2H), 3.84 (s, 3H), 2.64 (s, 3H). m/z 348.4.

Example 27

N-{3-[5-(4-chlorobenzyl)-3-(methoxymethyl)-4-oxo-4,5-dihydro[1,2]oxazolo[4,5-d]pyridazin-7-yl]phenyl}acetamide Step 1: methyl 2-(methoxymethyl)-4-oxo-4,5-dihydrofuran-3-carboxylate The reaction was run in duplicate and combined for purification. To a solution of methyl 4-methoxy-3-oxobutanoate (10 g, 68.4 mmol) in toluene (150 mL) was added magnesium ethoxide (12.67 g, 89 mmol) at room temperature. The mixture was stirred at 110° C. for 4 hours. The reaction was cooled to 0° C. and solid was removed from the solution. 2-Chloroacetyl chloride (14.00 ml, 137 mmol) was added dropwise, and the mixture was stirred at room temperature overnight. The duplicate reaction mixtures were combined. The mixture was diluted by the addition of water and extracted with ethyl acetate (200 mL×3). The organic phase was dried over Na$_2$SO$_4$ and concentrated under reduced pressure. The residue was purified by column chromatography on silica gel and eluted with EtOAc/PE to give the titled compound (10 g, yield 39%). $^1$H NMR (400 MHz, CDCl$_3$) δ ppm 4.59 (s, 2H), 4.52 (s, 2H), 3.84-3.81 (m, 3H), 3.45 (s, 3H).

Step 2: methyl 5-(hydroxymethyl)-3-(methoxymethyl)-1,2-oxazole-4-carboxylate

To a solution of methyl 2-(methoxymethyl)-4-oxo-4,5-dihydrofuran-3-carboxylate (9 g, 48.3 mmol, Step 1) in anhydrous ethanol (5 mL) was added sodium acetate (5.95 g, 72.5 mmol) and NH$_2$OH*HCl (4.03 g, 58.0 mmol). The mixture was heated to reflux for 1 hour. The solvent was removed under reduced pressure. The residue was diluted with water and extracted with ethyl acetate (200 mL×3). The organic phase was washed with brine, dried over $Na_2SO_4$, and concentrated under reduced pressure to give a residue that was purified by column chromatography on silica gel (EtOAc/PE, 1: 20-5) to give the titled compound (2.3 g, yield 23%). $^1$H NMR (400 MHz, $CDCl_3$) δ ppm 4.92 (s, 2H), 4.69 (s, 2H), 3.91 (s, 3H), 3.44 (s, 3H).

Step 3: methyl 5-formyl-3-(methoxymethyl)-1,2-oxazole-4-carboxylate

The reaction was run in triplicate and combined for purification. To a solution of methyl 5-(hydroxymethyl)-3-(methoxymethyl)-1,2-oxazole-4-carboxylate (0.5 g, 2.48 mmol, Step 2) in anhydrous dichloromethane (10 mL) was added Dess-Martin periodinane (2.108 g, 4.97 mmol). The mixture was stirred at room temperature for overnight. All three reaction mixtures were combined. The mixture was diluted by the addition of water and extracted with dichloromethane (50 mL×3). The organic phase was dried over $Na_2SO_4$, filtered and concentrated under reduced pressure to give a residue that was purified by column chromatography on silica gel (EtOAc/PE, 1:20~5) to give the titled compound (0.78 g, yield 55%). $^1$H NMR (400 MHz, $CDCl_3$) δ ppm 10.34 (s, 1H), 4.79 (s, 2H), 4.00 (s, 3H), 3.48 (s, 3H).

Step 4: 3-(methoxymethyl)[1,2]oxazolo[4,5-d]pyridazin-4(5H)-one

To a solution of methyl 5-formyl-3-(methoxymethyl)-1,2-oxazole-4-carboxylate (1.03 g, 5.17 mmol, Step 3) in anhydrous ethanol (20 mL) was added hydrazine (0.812 mL, 25.9 mmol). The mixture was stirred at room temperature for overnight. The solvent was removed under reduced pressure to give a residue that was diluted with water and extracted with dichloromethane (50 mL×3). The organic phase was dried over $Na_2SO_4$ and concentrated under reduced pressure to give the titled compound (1 g, yield 96%). $^1$H NMR (400 MHz, $CDCl_3$) δ ppm 8.36 (s, 1H), 4.93 (s, 1H), 3.55 (s, 1H).

Step 5: 7-bromo-3-(methoxymethyl)[1,2]oxazolo[4,5-d]pyridazin-4(5H)-one

To a solution of 3-(methoxymethyl)[1,2]oxazolo[4,5-d]pyridazin-4(5H)-one (1 g, 5.52 mmol, Step 4) in $CH_3OH$ (20 mL) was added LiOH (0.66 g, 27.6 mmol) and $Br_2$ (0.853 mL, 16.56 mmol) at 0° C. The mixture was stirred at the reflux temperature for overnight. After cooling to room temperature, the solvent was removed under reduced pressure to give a residue that was diluted by the addition of water and extracted with ethyl acetate (50 mL×3). The organic phase was dried over $Na_2SO_4$ and concentrated under reduced pressure to give the titled compound (0.85 g, yield 59%). $^1$H NMR (400 MHz, methanol-$d_4$) δ ppm 4.86 (s, 2H), 3.49 (s, 3H).

Step 6: 7-bromo-5-(4-chlorobenzyl)-3-(methoxymethyl)[1,2]oxazolo[4,5-d]pyridazin-4(5H)-one To a solution of 7-bromo-3-(methoxymethyl)[1,2]oxazolo[4,5-d]pyridazin-4(5H)-one (0.27 g, 1.05 mmol, Step 5) in N,N-dimethylformamide (10 mL) was added $K_2CO_3$ (0.29 g, 2.11 mmol) and 1-chloro-4-(chloromethyl) benzene (0.25 g, 1.58 mmol) at 0° C. The mixture was stirred at 50° C. for 4 hours. The mixture was diluted with water and extracted with ethyl acetate (50 mL×3). The combined organic phase was washed with brine and concentrated under reduced pressure. The residue was purified by column chromatography on silica gel to give the titled compound (0.36 g, yield 89%). $^1$H NMR (400 MHz, $CDCl_3$) δ ppm 7.44-7.38 (m, 2H), 7.35-7.30 (m, 3H), 5.33 (s, 2H), 4.89 (s, 2H), 3.53 (s, 3H).

Step 7: N-{3-[5-(4-chlorobenzyl)-3-(methoxymethyl)-4-oxo-4,5-dihydro[1,2]oxazolo[4,5-d]pyridazin-7-yl]phenyl}acetamide To a solution of 7-bromo-5-(4-chlorobenzyl)-3-(methoxymethyl)[1,2]oxazolo[4,5-d]pyridazin-4(5H)-one (0.18 g, 0.46 mmol, Step 6) in 1,4-dioxane (15 mL) and water (5 mL) was added (3-acetamidophenyl)boronic acid (0.084 g, 0.468 mmol), $K_2CO_3$ (0.16 g, 1.17 mmol) and tetrakis(triphenylphosphine)palladium(0) (0.054 g, 0.047 mmol). After stirring at 80° C. overnight, the mixture was diluted with water and extracted with ethyl acetate (50 mL×3). The organic phase was washed with brine and concentrated under reduced pressure to supply a residue that was purified by preparative HPLC (method B) to give the titled compound (0.079 g, yield 38%). $^1$H NMR (400 MHz, $CDCl_3$) δ ppm 8.21 (s, 1H), 7.91 (d, J=7.5 Hz, 1H), 7.78 (d, J=7.5 Hz, 1H), 7.56-7.43 (m, 3H), 7.33 (d, J=8.4 Hz, 2H), 5.45 (s, 2H), 4.97 (s, 2H), 3.56 (s, 3H), 2.26 (s, 3H).

Example 28

5-[4-chloro-3-(trifluoromethyl)benzyl]-7-(4-fluorophenyl)-3-methyl[1,2]oxazolo[4,5-d]pyridazin-4(5H)-one To a solution of 7-(4-fluorophenyl)-3-methyl[1,2]oxazolo[4,5-d]pyridazin-4(5H)-one (Example 19, 100 mg, 0.408 mmol) in N,N-dimethylformamide (2 mL) was added NaH (14.68 mg, 0.612 mmol). The mixture was stirred at room temperature for 15 minutes, and then 4-(bromomethyl)-1-chloro-2-(trifluoromethyl)benzene (134 mg, 0.489 mmol) was added. The solid was collected by filtration and washed with water and methanol to give the titled compound. $^1$H NMR (400 MHz, DMSO-$d_6$) δ ppm 8.09-8.06 (m, 2H), 7.93 (s, 1H), 7.68-7.65 (m, 2H), 7.42-7.33 (m, 2H), 5.51 (s, 2H), 2.59 (s, 3H); MS ($APCI^+$) m/z 438.0 $(M+H)^+$.

Example 29

N-(2-fluoro-5-{3-methyl-4-oxo-5-[4-(trifluoromethyl)benzyl]-4,5-dihydro[1,2]oxazolo[4,5-d]pyridazin-7-yl}phenyl)acetamide The titled compound was prepared using the procedures described for Example 5 substituting (3-acetamido-4-fluorophenyl)boronic acid for (2,4-dimethoxyphenyl)boronic acid in Step 1 and 1-(bromomethyl)-4-(trifluoromethyl)benzene for 4-(bromomethyl)pyridine in Step 2. Yield 14%.
$^1$H NMR (400 MHz, $CD_3OD$): δ 8.02 (s, 1H), 8.01-7.99 (d, J=6.8 Hz, 1H), 7.59-7.57 (t, J=8.0 Hz, 2H), 7.46-7.41 (m, 3H), 5.15-5.11 (m, 1H), 4.94-4.91 (m, 1H), 2.66 (s, 3H), 1.98 (s, 3H). m/z 461.2.

Example 30

5-(4-fluorobenzyl)-3,7-dimethyl[1,2]oxazolo[4,5-d]pyridazin-4(5H)-one

The titled compound was prepared using the procedure described in Example 20 substituting 1-(bromomethyl)-4- fluorobenzene for 1-(bromomethyl)-2-fluorobenzene. Purification was achieved by preparative liquid chromatography (Method C, 0.5-8.5 minutes linear gradient 45-75% A). $^1$H NMR (400 MHz, DMSO-$d_6$/$D_2$O) δ ppm 7.39-7.34 (m, 2H), 7.20-7.13 (m, 2H), 5.29 (s, 2H), 2.57 (s, 3H), 2.50 (s, 3H); MS (APCI$^+$) m/z 274.1 (M+H)$^+$.

Example 31

5-[(1S)-1-(4-chlorophenyl)ethyl]-3,7-dimethyl[1,2]oxazolo[4,5-d]pyridazin-4(5H)-one The individual enantiomers of the mixture of Example 114 were separated by preparative chiral chromatography (WHELK-O® 1 (S,S), 30×250 mm column, 5 m, concentration of 75 mg/mL in CH$_3$OH/CH$_2$Cl$_2$ (8:2), flow rate 75 mL/minute; 20% CH$_3$OH in CO$_2$ at 100 psi=6.89 bar) to afford the title compound as the first-eluting enantiomer with a retention time of 4.6 minutes. Stereocenter arbitrarily assigned. 1H NMR (300 MHz, CDCl$_3$) δ ppm 7.41-7.35 (m, 2H), 7.31-7.26 (m, 2H), 6.33 (q, J=7.1, 7.1, 7.1 Hz, 1H), 2.66 (s, 3H), 2.56 (s, 3H), 1.77 (d, J=7.1 Hz, 3H); MS (DCI/NH$_3$) m/z 304 (M+H)$^+$, 321 (M+NH$_4$)+.

Example 32

7-(2,4-dimethoxyphenyl)-5-[4-methoxy-3-(trifluoromethyl)benzyl]-3-methyl[1,2]oxazolo[4,5-d]pyridazin-4(5H)-one The titled compound was prepared using the procedures described for Example 5 substituting 4-(bromomethyl)-1-methoxy-2-(trifluoromethyl)benzene for 4-(bromomethyl)pyridine in Step 2. Yield 19%.
$^1$H NMR (400 MHz, CD$^3$OD): δ 7.70-7.66 (m, 2H), 7.37-7.35 (d, J=8.4 Hz, 1H), 7.16-7.14 (d, J=8.8 Hz, 1H), 6.71-6.66 (m, 2H), 5.41 (s, 2H), 3.93 (s, 6H), 3.81 (s, 3H), 2.63 (s, 3H). m/z 475.4.

Example 33

N-(3-{5-[1-(4-chlorophenyl)ethyl]-3-methyl-4-oxo-4,5-dihydro[1,2]oxazolo[4,5-d]pyridazin-7-yl}-2-methoxyphenyl)acetamide Step 1: N-(2-methoxy-3-(4,4,5,5-tetramethyl-1,3,2-dioxaborolan-2-yl)phenyl)acetamide A mixture of 2-methoxy-3-(4,4,5,5-tetramethyl-1,3,2-dioxaborolan-2-yl)aniline (13 g, 52.2 mmol) and acetic anhydride (50 mL, 530 mmol) in acetic acid (10 mL) was stirred at room temperature for 16 hours. The mixture was concentrated, and the residue was triturated with diethyl ether. The solid was collected by filtration, washed with diethyl ether, and dried to give the titled compound. $^1$H NMR (300 MHz, DMSO-$d_6$) δ ppm 9.23 (s, 1H), 8.10 (d, J=7.8 Hz, 1H), 7.28 (d, J=6.6 Hz, 1H), 7.04 (t, J=7.5 Hz, 1H), 3.73 (s, 3H), 2.12 (s, 3H), 1.30 (s, 12H); MS (ESI+) m/z 292 (M+H)$^+$.
Step 2: Under argon, 7-bromo-5-[1-(4-chlorophenyl)ethyl]-3-methyl[1,2]oxazolo[4,5-d]pyridazin-4(5H)-one (70 mg, 0.190 mmol, Example 39—Step 5) was suspended in toluene and ethanol (4 mL, 1:1). 2 M Aqueous sodium bicarbonate (0.142 mL, 0.285 mmol) and N-(2-methoxy-3-(4,4,5,5-tetramethyl-1,3,2-dioxaborolan-2-yl)phenyl)acetamide (55.3 mg, 0.190 mmol, Step 1) were added followed by tetrakis(triphenylphosphine)palladium(0) (21.94 mg, 0.019 mmol). The reaction mixture was heated with stirring in a Biotage® microwave reactor at 130° C. for 30 minutes. The reaction mixture was then partitioned between water and ethyl acetate. The organic fraction was washed with brine, dried over MgSO$_4$ and then concentrated under reduced pressure. The residue was purified by flash chromatography on a Teledyne Isco CombiFlash® Rf apparatus using a silica gel cartridge (4 g) eluted with 3-5% methanol/dichloromethane. A second flash chromatography on a Teledyne Isco CombiFlash® Rf apparatus using a silica gel cartridge (4 g) eluted with 3-5% methanol/dichloromethane was performed. The residue was stirred overnight with diisopropyl ether, and the resultant precipitate was collected and dried in a vacuum oven overnight to give the titled compound. $^1$H NMR (500 MHz, DMSO-$d_6$) δ ppm 9.60 (s, 1H), 8.13-8.07 (m, 1H), 7.40 (s, 4H), 7.29-7.24 (m, 2H), 6.35 (q, J=7.0 Hz, 1H), 3.42 (s, 3H), 2.60 (s, 3H), 2.14 (s, 3H), 1.75 (d, J=7.0 Hz, 3H).

Example 34

N-(3-{5-[(1R)-1-(4-chlorophenyl)ethyl]-3-methyl-4-oxo-4,5-dihydro[1,2]oxazolo[4,5-d]pyridazin-7-yl}phenyl)acetamide Example 78 (500 mg, 1.064 mmol) was separated by chiral super critical fluid chromatography (method A) to give recovered racemic material (50.6 mg, yield 11.2%), the enantiomer of the titled compound (162.9 mg, yield 36.2%, Example 72) and the titled compound (208 mg, yield 46.2%). $^1$H NMR (400 MHz, methanol-$d_4$) δ ppm 68.39 (s, 1H), 7.77 (d, J=0.0 Hz, 1H), 7.60 (d, J=7.6 Hz, 1H), 7.41-7.36 (m, 3H), 7.25 (d, J=8.4 Hz, 2H), 6.32 (q, J=6.8 Hz, 1H), 2.55 (s, 3H), 2.09 (s, 3H), 1.80 (d, J=7.2 Hz, 3H); LCMS (method C) (ESI+) m/z 423 (M+H)$^+$, retention time 3.366 minutes.

Example 35

N-[4-methyl-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide Step 1: (R)-7-bromo-3-methyl-5-(1-(4-(trifluoromethyl)phenyl)ethyl)isoxazolo[4,5-d]pyridazin-4(5H)-one Into a 50-ml 3-neck bottom flask, was placed (S)-1-(4-(trifluoromethyl)phenyl)ethanol (455 mg, 2.391 mmol), 7-bromo-3-methylisoxazolo[4,5-d]pyridazin-4(5H)-one (500 mg, 2.174 mmol), and triphenylphosphine (684 mg, 2.61 mmol) in tetrahydrofuran (15 ml). The solution was cooled to 0° C. (E)-diisopropyl diazene-1,2-dicarboxylate (0.507 ml, 2.61 mmol) was added dropwise to the reaction mixture. The mixture was stirred for 3 h at room temperature. The solution was concentrated under vacuum and purified by HPLC-TLC, to give (R)-7-bromo-3-methyl-5-(1-(4-(trifluoromethyl)phenyl)ethyl)-isoxazolo[4,5-d]pyridazin-4(5H)-one (800 mg, 1.989 mmol, 92% yield).

Step 2: 7-(5-amino-2-methylphenyl)-3-methyl-5-{(1R)-1-[4-(trifluoromethyl)phenyl]ethyl}[1,2]oxazolo[4,5-d]pyridazin-4(5H)-one 7-Bromo-3-methyl-5-{(1R)-1-[4-(trifluoromethyl)phenyl]ethyl}[1,2]oxazolo[4,5-d]pyridazin-4(5H)-one (Example 35, 100 mg, 0.249 mmol), 4-methyl-3-(4,4,5,5-tetramethyl-1,3,2-dioxaborolan-2-yl)aniline (63.8 mg, 0.274 mmol), sodium carbonate (79 mg, 0.746 mmol), and [1,1'-bis(diphenylphosphino)ferrocene]dichloropalladium(II) (18.19 mg, 0.025 mmol, PdCl₂(dppf)) were combined with 1,4-dioxane (3 mL) and water (0.3 mL) in a 5 mL sealed tube. The reaction mixture was irradiated at 100° C. for 60 minutes in a microwave reactor. The reaction mixture was then concentrated, and the residue was purified by silica gel column chromatography eluted with EtOAc/PE (1:3) to give 7-(5-amino-2-methylphenyl)-3-methyl-5-{(1R)-1-[4-(trifluoromethyl)phenyl]ethyl}[1,2]oxazolo[4,5-d]pyridazin-4 (5H)-one.

Step 3: N-[4-methyl-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide 7-(5-Amino-2-methylphenyl)-3-methyl-5-{(1R)-1-[4-(trifluoromethyl)phenyl]ethyl}[1,2]oxazolo[4,5-d]pyridazin-4(5H)-one (100 mg, 0.233 mmol) and triethylamine (23.62 mg, 0.233 mmol) were combined in dichloromethane (10 mL). Acetyl chloride (18.32 mg, 0.233 mmol) was added dropwise, and the reaction mixture was stirred at ambient temperature for 1 hour. The reaction mixture was concentrated under reduced pressure, and the residue was purified by silica gel column chromatography eluted with EtOAc/PE (4:1) to give the title compound (11 mg, 8.1% yield). ¹H NMR (400 MHz, CD₃OD) δ ppm 1.88 (d, 3H), 2.15 (s, 3H), 2.22 (s, 3H), 2.68 (s, 3H), 6.52 (q, 1H), 7.33 (d, 1H), 7.65 (m, 5H), 7.82 (s, 1H); MS (ESI+) m/z 471.2 (M+H)⁺.

Example 36

5-(4-chlorobenzyl)-7-(2,5-dimethoxyphenyl)-3-ethyl[1,2]oxazolo[4,5-d]pyridazin-4(5H)-one To a solution of 7-bromo-5-(4-chlorobenzyl)-3-ethyl[1,2]oxazolo[4,5-d]pyridazin-4(5H)-one (221 mg, 0.60 mmol, Example 129—Step 6) in 1,4-dioxane (5 mL) and water (2 mL) was added (2,5-dimethoxyphenyl)boronic acid (109 mg, 0.6 mmol), K₂CO₃ (63.6 mg, 0.6 mmol) and tetrakis(triphenylphosphine)palladium(0) (69.3 mg, 0.6 mmol) at room temperature under nitrogen. After stirring at 80° C. overnight, the mixture was diluted with water and extracted with ethyl acetate (20 mL×3). The organic phase was washed with brine and concentrated in vacuum. The residue was purified by preparative HPLC (method B) to give the titled compound (54.4 mg, yield 21%). ¹H NMR (400 MHz, CDCl₃) δ ppm 7.40-7.36 (m, 2H), 7.25-7.21 (m, 2H), 6.99-6.95 (m, 1H), 6.93 (s, 1H), 6.92-6.90 (m, 1H), 5.34 (s, 2H), 3.74 (d, J=3.1 Hz, 6H), 3.02 (q, J=7.5 Hz, 2H), 1.36 (t, J=7.5 Hz, 3H); LCMS (method B) (ESI+) m/z 425.9 (M+H)⁺, retention time 3.324 minutes.

Example 37

7-(2,4-dimethoxyphenyl)-5-[4-fluoro-3-(trifluoromethyl)benzyl]-3-methyl[1,2]oxazolo[4,5-d]pyridazin-4(5H)-one The titled compound was prepared using the procedures described for Example 5 substituting 4-(bromomethyl)-1-fluoro-2-(trifluoromethyl)benzene for 4-(bromomethyl)pyridine in Step 2. Yield 21%.

¹H NMR (400 MHz, CD₃OD): δ 7.85-7.69 (m, 2H), 7.41-7.22 (m, 2H), 6.74-6.62 (m, 2H), 5.47 (s, 2H), 3.88 (s, 3H), 3.81 (s, 3H), 2.63 (s, 3H). m/z 463.4.

Example 38

3-{5-[1-(4-chlorophenyl)ethyl]-3-methyl-4-oxo-4,5-dihydro[1,2]oxazolo[4,5-d]pyridazin-7-yl})-4-methoxy-N,N-dimethylbenzamide Sodium hydride (10.94 mg, 0.456 mmol, 18.23 mg of 60% dispersion in oil) was added to a solution of 3-{5-[1-(4-chlorophenyl)ethyl]-3-methyl-4-oxo-4,5-dihydro[1,2]oxazolo[4,5-d]pyridazin-7-yl}-4-methoxybenzamide (50 mg, 0.114 mmol, Example 59) dissolved in N,N-dimethylformamide (1 mL). After 30 minutes, iodomethane (0.021 mL, 48.5 mg, 0.342 mmol) was added, and the reaction mixture was stirred for 3 hours. The reaction mixture was then partitioned between ethyl acetate and water. The aqueous phase was extracted twice with ethyl acetate. The combined organic fractions were washed with brine, dried over MgSO₄ and concentrated. The residue was purified by flash chromatography on a Teledyne Isco CombiFlash® apparatus using a RediSep® silica gel cartridge (4 g) eluted with 0-10% methanol/dichloromethane. The residue was dried in a vacuum oven to give the titled compound (25 mg, yield 47%). ¹H NMR (600 MHz, DMSO-d₆) δ ppm 7.66 (dd, J=8.6, 2.2 Hz, 2H), 7.50 (d, J=2.2 Hz, 2H), 7.44-7.36 (m, 9H), 7.29 (d, J=8.6 Hz, 2H), 6.31 (q, J=7.0 Hz, 2H), 4.00-3.93 (m, OH), 3.84 (s, 7H), 3.33 (s, 1H), 2.99 (s, 14H), 2.95 (s, 1H), 2.59 (s, 7H), 1.73 (d, J=7.0 Hz, 7H), 1.28 (s, 1H), 1.26 (s, 3H), 1.23 (s, 1H), 1.09 (d, J=6.2 Hz, 3H).

Example 39

N-(3-{5-[1-(4-chlorophenyl)ethy]-3-methyl-4-oxo-4,5-dihydro[1,2]oxazolo[4,5-d]pyridazin-7-yl}-4-methoxyphenyl)acetamide Step 1: 3-bromo-4-methoxyaniline To a solution of 2-bromo-1-methoxy-4-nitrobenzene (5.0 g, 21.55 mmol) in ethanol (40 mL) and H₂O (20 mL) was added Zn (7.04 g, 108 mmol) and NH₄Cl (5.76 g, 108 mmol). The resulting mixture was stirred at 80° C. for 3 hours. Then the hot reaction mixture was filtered, and the filtrate was concentrated. The aqueous phase was extracted with dichloromethane (100 mL×3). The organic layer was dried over Na₂SO₄, filtered and concentrated to give the titled compound which was used without further purification.

Step 2: N-(3-bromo-4-methoxyphenyl)acetamide

To a solution of 3-bromo-4-methoxyaniline (3.03 g, 15.00 mmol, Step1) in dichloromethane (50 mL) was added triethylamine (3.14 mL, 22.49 mmol) and acetic anhydride (1.698 mL, 18.00 mmol). The resulting mixture was stirred at 25° C. for 3 hours. The mixture was poured into H₂O and extracted with dichloromethane (100 mL×3). The organic layer was dried over Na₂SO₄, filtered and concentrated. The residue was purified by column chromatography on silica gel and eluted with EtOAc/PE to give the titled compound (3.3 g, yield 90%). ¹H NMR (400 MHz, CDCl₃) δ ppm 7.67 (d, J=2.2 Hz, 1H), 7.42 (dd, J=2.2, 8.8 Hz, 2H), 6.83 (d, J=8.8 Hz, 1H), 3.89-3.82 (m, 3H), 2.20-2.10 (m, 3H).

Step 3: N-[4-methoxy-3-(4,4,5,5-tetramethyl-1,3,2-dioxaborolan-2-yl)phenyl]acetamide To a solution of N-(3-bromo-4-methoxyphenyl)acetamide (2 g, 8.19 mmol) in dioxane (40 mL) was added 4,4,4',4', 5,5,5',5'-octamethyl-2,2'-bi(1,3,2-dioxaborolane) (2.08 g, 8.19 mmol), potassium acetate (0.77 mL, 8.19 mmol), and [1,1'-bis(diphenylphosphino)ferrocene]dichloropalladium (II) (6.00 g, 8.19 mmol, PdCl$_2$(dppf)). The mixture was refluxed for 3 hours under N$_2$. After cooling down to room temperature, the mixture was concentrated. The residue was purified by column chromatography on silica gel and eluted with EtOAc/PE to give the titled compound (1.3 g, yield 54%). $^1$H NMR (400 MHz, CDCl$_3$) δ ppm 7.79 (dd, J=2.6, 8.8 Hz, 1H), 7.48 (d, J=2.6 Hz, 1H), 7.32 (br. s., 1H), 6.83 (s, 1H), 3.79 (s, 3H), 2.11 (s, 3H), 1.33 (s, 12H).

Step 4: 1-(1-bromoethyl)-4-chlorobenzene

A solution of 1-(4-chlorophenyl)ethanol (3.5 g, 22.35 mmol) in dry tetrahydrofuran (150 mL) was treated dropwise with PBr$_3$ (0.927 mL, 9.83 mmol). The mixture was heated at reflux for 1 hour, then cooled, and washed twice with water. The organic fraction was dried and concentrated. The residue was purified by column chromatography on silica gel eluted with petroleum ether to give the titled compound (6 g, purity 55%, yield 67.3%). LCMS (method A) (ESI+) m/z 221(M+H)$^+$, retention time 1.405 minutes; $^1$H NMR (400 MHz, CDCl$_3$) δ ppm 7.40-7.35 (m, 2H), 7.34-7.29 (m, 2H), 5.17 (q, J=6.9 Hz, 1H), 2.03 (d, J=6.6 Hz, 3H).

Step 5: 7-bromo-5-[1-(4-chlorophenyl)ethyl]-3-methyl[1,2]oxazolo[4,5-d]pyridazin-4(5H)-one To a solution of 7-bromo-3-methyl[1,2]oxazolo[4,5-d]pyridazin-4(5H)-one (3 g, 13.04 mmol, Example 2—Step 5) in N,N-dimethylformamide (60 mL) was added potassium carbonate (3.61 g, 26.1 mmol), and then 1-(1-bromoethyl)-4-chlorobenzene (6 g, purity 55%, 15.03 mmol, Step 1) was added in one portion. The mixture was stirred at room temperature for 4 hours. The reaction mixture was diluted with water and extracted with ethyl acetate. The organic phase was washed with brine and concentrated under reduced pressure. The residue was washed with methanol, and the solid cake was air dried to give the titled compound (2.2 g, purity 90%, yield 41.2%). $^1$H NMR (400 MHz CDCl$_3$) δ ppm 7.31 (d, J=8.4 Hz, 2H), 7.24 (d, J=8.8 Hz, 2H), 6.25-6.19 (m, 1H), 2.58 (s, 3H), 1.72 (d, J=7.2 Hz, 3H).

Step 6: N-(3-{5-[1-(4-chlorophenyl)ethyl]-3-methyl-4-oxo-4,5-dihydro[1,2]-oxazolo[4,5-d]pyridazin-7-yl}-4-methoxyphenyl)acetamide To a stirred solution of 7-bromo-5-[1-(4-chlorophenyl)ethyl]-3-methyl[1,2]oxazolo[4,5-d]pyridazin-4(5H)-one (1 g, 2.7 mmol, Step 5) in 1,2-dimethoxyethane (10 mL) and H$_2$O (2.5 mL) was added N-[4-methoxy-3-(4,4,5,5-tetramethyl-1,3,2-dioxaborolan-2-yl)phenyl]acetamide (0.66 g, 2.27 mmol, Step 3), K$_2$CO$_3$ (1.12 g, 8.14 mmol) and tetrakis(tripehenylphosphine)palladium(0) (0.26 g, 0.228 mmol). Then the mixture was stirred at 80° C. under nitrogen overnight. The mixture was concentrated to give a residue that was diluted with water and extracted with ethyl acetate. The organic layers were dried and concentrated under reduced pressure. The residue was purified by preparatory HPLC (method B) to give the titled compound (0.5 g, yield 40%). $^1$H NMR (400 MHz, CDCl$_3$) δ ppm 7.63 (dd, J=2.4, 9.0 Hz, 1H), 7.56 (d, J=2.2 Hz, 1H), 7.45 (d, J=8.4 Hz, 2H), 7.32-7.22 (m, 3H), 7.01 (d, J=8.8 Hz, 1H), 6.39 (q, J=7.1 Hz, 1H), 3.83 (s, 3H), 3.49 (s, 1H), 2.67 (s, 3H), 2.20 (s, 3H), 1.82 (d, J=7.1 Hz, 3H); LCMS (method C) (ESI+) m/z 453.2 (M+H)$^+$, retention time 3.251 minutes.

Example 40

N-(3-{5-[(1R)-1-(4-chlorophenyl)ethyl]-3-methyl-4-oxo-4,5-dihydro[1,2]oxazolo[4,5-d]pyridazin-7-yl}-4-methoxyphenyl)acetamide The enantiomers of N-(3-{5-[1-(4-chlorophenyl)ethyl]-3-methyl-4-oxo-4,5-dihydro[1,2]oxazolo[4,5-d]pyridazin-7-yl}-4-methoxyphenyl)acetamide (0.4 g, 0.883 mmol, Example 39) were separated by chiral super critical chromatograph (method B) to give N-(3-{5-[(1S)-1-(4-chlorophenyl)ethyl]-3-methyl-4-oxo-4,5-dihydro[1,2]oxazolo[4,5-d]pyridazin-7-yl}-4-methoxyphenyl)acetamide (0.09 g, yield 23%, Example 117) and the titled compound (0.08 g, yield 20%). $^1$H NMR (400 MHz, CDCl$_3$) δ ppm 7.56 (dd, J=2.6, 8.8 Hz, 1H), 7.48 (d, J=2.6 Hz, 1H), 7.38 (d, J=8.4 Hz, 2H), 7.23 (d, J=8.8 Hz, 2H), 7.07 (br. s., 1H), 6.95 (d, J=8.8 Hz, 1H), 6.32 (q, J=6.8 Hz, 1H), 3.76 (s, 3H), 2.61 (s, 3H), 2.13 (s, 3H), 1.75 (d, J=7.1 Hz, 3H); LCMS (method C) (ESI+) m/z 453.2 (M+H)$^+$, retention time 3.241 minutes.

Example 41

N-(3-{5-[4-fluoro-3-(trifluoromethyl)benzyl]-3-methyl-4-oxo-4,5-dihydro[1,2]oxazolo[4,5-d]pyridazin-7-yl}phenyl)acetamide The titled compound was prepared using the procedures described for Example 5 substituting (3-acetamidophenyl)boronic acid for (2,4-dimethoxyphenyl)boronic acid in Step 1 and 4-(bromomethyl)-1-fluoro-2-(trifluoromethyl)benzene for 4-(bromomethyl)pyridine in Step 2. Yield 21%.
$^1$H NMR (400 MHz, CD$_3$OD): δ 7.85-7.69 (m, 2H), 7.41-7.22 (m, 2H), 6.74-6.62 (m, 2H), 5.47 (s, 2H), 3.88 (s, 3H), 3.81 (s, 3H), 2.63 (s, 3H). m/z 463.4.

Example 42

5-(4-chlorobenzyl)-7-(3,4-difluorophenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added (3,4-difluorophenyl)boronic acid (53.4 mg, 0.338 mmol), K$_2$CO$_3$ (0.097 g, 0.705 mmol) and tetrakis(triphenylphosphine)palladium(0) (0.033 g, 0.028 mmol). The resulting mixture was stirred at 80° C. overnight under N$_2$. After cooling down to room temperature, the reaction mixture was concentrated under reduced pressure to give a residue that was washed with a mixture of CH$_3$OH and H$_2$O to give the titled compound. Yield 53%.
$^1$H NMR (CDCl$_3$, 400 MHz): δ 7.94-8.08 (m, 2H), 7.46 (d, J=8.38 Hz, 2H), 7.31-7.40 (m, 3H), 5.45 (s, 2H), 2.74 (s, 3H). m/z 387.8.

Example 43

5-[4-fluoro-3-(trifluoromethyl)benzyl]-3,7-dimethyl[1,2]oxazolo[4,5-d]pyridazin-4(5H)-one The titled compound was prepared using the procedure described in Example 20 substituting 4-(bromomethyl)-1-fluoro-2-(trifluoromethyl)benzene for 1-(bromomethyl)-2- fluorobenzene. Purification was achieved by preparative liquid chromatography (Method C, 0.5-8.5 minutes linear gradient 60-100% A). $^1$H NMR (400 MHz, DMSO-$d_6$/$D_2$O) δ ppm 7.76 (dd, J=7.1, 2.2 Hz, 1H), 7.66 (ddd, J=7.8, 4.9, 2.3 Hz, 1H), 7.47 (dd, J=10.7, 8.6 Hz, 1H), 5.37 (s, 2H), 2.57 (s, 3H), 2.51 (s, 3H); MS (APCI$^+$) m/z 342.1 (M+H)$^+$.

Example 44

3,7-dimethyl-5-(pyridin-4-ylmethyl)[1,2]oxazolo[4,5-d]pyridazin-4(5H)-one

The titled compound was prepared using the procedure described in Example 20 substituting 4-(bromomethyl)pyridine for 1-(bromomethyl)-2-fluorobenzene. Purification was achieved by preparative liquid chromatography (Method C, 0.5-8.5 minutes linear gradient 10-40% A). $^1$H NMR (400 MHz, DMSO-$d_6$/$D_2$O) δ ppm 8.75-8.71 (m, 2H), 7.74-7.70 (m, 2H), 5.55 (s, 2H), 2.57 (s, 3H), 2.52 (s, 3H); MS (APCI$^+$) m/z 257.1 (M+H)$^+$.

Example 45

N-{3-[5-(4-chlorobenzyl)-3-methyl-4-oxo-4,5-dihydro[1,2]oxazolo[4,5-d]pyridazin-7-yl]-4-methoxyphenyl}acetamide Step 1: 3-bromo-4-methoxyaniline To a solution of 2-bromo-1-methoxy-4-nitrobenzene (5 g, 21.55 mmol) in ethanol (40 mL) and $H_2O$ (20 mL) was added zinc (7.04 g, 108 mmol) and $NH_4Cl$ (5.76 g, 108 mmol). The resulting mixture was stirred at 80° C. for 3 hours. Then the hot reaction mixture was filtered, and the filtrate was concentrated. The aqueous phase was extracted with ethyl acetate. The organic layer was dried over $Na_2SO_4$ and concentrated to give the titled compound (3.3 g, yield 76%) that was used for the next step without further purification. $^1$H NMR (400 MHz, methanol-$d_4$) δ ppm 7.01 (s, 1H), 6.88-6.86 (d, J=8.0 Hz, 1H), 6.75-6.72 (d, J=12.0 Hz, 1H), 3.81 (s, 3H).

Step 2: N-(3-bromo-4-methoxyphenyl)acetamide

To a solution of 3-bromo-4-methoxyaniline (3.1 g, 15.3 mmol, Step 1) in dichloromethane (30 mL) was added acetic anhydride (1.74 mL, 18.4 mmol) and triethylamine (3.2 mL, 23.0 mmol). The resulting mixture was stirred at room temperature for 3 hours. The solvent was removed to give the titled compound (3.6 g, yield 96%) that was used for the next step without further purification. $^1$H NMR (400 MHz, methanol-$d_4$) δ ppm 7.81-7.80 (s, 1H), 7.43-7.40 (d, J=12.0 Hz, 1H), 6.97-6.95 (d, J=8.0 Hz, 1H), 3.83 (s, 3H), 2.08 (s, 3H).

Step 3: N-[4-methoxy-3-(4,4,5,5-tetramethyl-1,3,2-dioxaborolan-2-yl)phenyl]acetamide To a solution of N-(3-bromo-4-methoxyphenyl)acetamide (2 g, 8.19 mmol, Step 2) in 1,4-dioxane (40 mL) was added 4,4,4',4',5,5,5',5'-octamethyl-2,2'-bi-1,3,2-dioxaborolane (3.12 g, 12.29 mmol), potassium acetate (2.41 g, 24.58 mmol) and [1,1'-bis(diphenylphosphino)ferrocene]dichloropalladium(II) (0.60 g, 0.82 mmol, Pd(dppf)Cl$_2$). The resulting mixture was stirred at 110° C. for 3 hours under $N_2$. After cooling down to room temperature, the mixture was concentrated to give a residue that was purified by column chromatography on silica gel and eluted with EtOAc/PE to give the titled compound (800 mg, yield 33%). $^1$H NMR (400 MHz, methanol-$d_4$) δ ppm 7.67-7.63 (d, J=16.0 Hz, 1H), 7.42-7.40 (d, J=8.0 Hz, 1H), 6.92-6.84 (m, 1H), 3.78 (s, 3H), 2.08 (s, 3H), 1.33 (s, 3H).

Step 4: N-{3-[5-(4-chlorobenzyl)-3-methyl-4-oxo-4,5-dihydro[1,2]oxazolo[4,5-d]pyridazin-7-yl]-4-methoxyphenyl}acetamide To a solution of N-[4-methoxy-3-(4,4,5,5-tetramethyl-1,3,2-dioxaborolan-2-yl)phenyl]acetamide (750 mg, 2.58 mmol, Step 3) in 1,2-dimethoxyethane (10 mL) and $H_2O$ (2.5 mL) was added 7-bromo-5-(4-chlorobenzyl)-3-methyl[1,2]oxazolo[4,5-d]pyridazin-4(5H)-one (1.09 g, 3.09 mmol, Example 2—Step 6), $K_2CO_3$ (1.07 g, 7.73 mmol) and tetrakis(triphenylphosphine)palladium(0) (298 mg, 0.258 mmol). The resulting mixture was stirred at 80° C. overnight under $N_2$. After cooling down to room temperature, the mixture was concentrated to give a residue that was washed with methanol and dried to obtain the titled compound (281 mg, yield 24%). $^1$H NMR (400 MHz, DMSO-$d_6$) δ ppm 9.97 (s, 1H), 7.71-7.66 (m, 2H), 7.41-7.38 (m, 4H), 7.17-7.15 (d, J=8.0 Hz, 1H), 5.36 (s, 2H), 3.73 (s, 3H), 2.57 (s, 3H), 2.00 (s, 3H); LCMS (method D) (ESI+) m/z 439 (M+H)$^+$, retention time 2.46 minutes.

Example 46

5-[2-fluoro-5-(trifluoromethyl)benzyl]-7-(2-methoxyphenyl)-3-methyl[1,2]oxazolo[4,5-d]pyridazin-4(5H)-one The titled compound was prepared using the procedures described for Example 5 substituting (2-methoxyphenyl)boronic acid for (2,4-dimethoxyphenyl)boronic acid in Step 1 and 2-(bromomethyl)-1-fluoro-4-(trifluoromethyl)benzene for 4-(bromomethyl)pyridine in Step 2. Yield 15%
$^1$H NMR (400 MHz, CD$_3$OD): δ 7.76-7.73 (m, 2H), 7.53-7.51 (m, 1H), 7.40-7.34 (m, 1H), 7.19-7.17 (m, 1H), 7.10-7.08 (m, 1H), 5.58 (s, 2H), 3.82 (s, 3H), 2.64 (s, 3H). m/z 433.4.

Example 47

5-(4-chlorobenzyl)-3-cyclopropyl-7-(2,5-dimethoxyphenyl)[1,2]oxazolo[4,5-d]pyridazin-4(5H)-one To a solution of 7-bromo-5-(4-chlorobenzyl)-3-cyclopropyl[1,2]oxazolo[4,5-d]pyridazin-4(5H)-one (280 mg, 0.73 mmol, Example 51—Step 6) in N,N-dimethylformamide (2 mL) and water (0.5 mL) was added (2,5-dimethoxyphenyl)boronic acid (161 mg, 0.88 mmol), $K_2CO_3$ (254 mg, 1.83 mmol) and tetrakis(triphenylphosphine)palladium(0) (85 mg, 0.074 mmol). After stirring at 80° C. overnight under nitrogen, the mixture was diluted with water and extracted with ethyl acetate. The organic phase was washed with brine and then concentrated under reduced pressure to give a residue that was purified by preparative HPLC (method C) to give the titled compound (33 mg, yield 10%). $^1$H NMR (400 MHz, CDCl$_3$) δ ppm 7.43-7.36 (m, 1H), 7.17-7.09 (m, 1H), 6.97 (d, J=2.2 Hz, 1H), 5.38 (s, 2H), 3.72 (d, J=11.0 Hz, 6H), 2.46-2.38 (m, 1H), 1.20-1.13 (m, 4H); LCMS (method B) (ESI+) m/z 438.1 (M+H)$^+$, retention time 3.365 minutes.

Example 48

7-(2,4-dimethoxyphenyl)-5-[2-fluoro-5-(trifluoromethyl)benzyl]-3-methyl[1,2]oxazolo[4,5-d]pyridazin-4(5H)-one The titled compound was prepared using the procedures described for Example 5 substituting 2-(bromomethyl)-1-fluoro-4-(trifluoromethyl)benzene for 4-(bromomethyl)pyridine in Step 2. Yield 16%

1H NMR (400 MHz, CD$_3$OD): δ 7.77-7.64 (m, 2H), 7.38-7.28 (m, 2H), 6.72-6.61 (m, 2H), 5.56 (s, 2H), 3.87 (s, 3H), 3.82-3.77 (m, 3H), 2.63 (s, 3H). m/z 463.4.

Example 49

N-[3-{5-[1-(4-chlorophenyl)ethyl]-3-methyl-4-oxo-4,5-dihydro[1,2]oxazolo[4,5-d]pyridazin-7-yl}-4-(trifluoromethoxy)phenyl]acetamide

Step 1: N-(3-(4,4,5,5-tetramethyl-1,3,2-dioxaborolan-2-yl)-4-(trifluoromethoxy)phenyl)acetamide 3-(4,4,5,5-Tetramethyl-1,3,2-dioxaborolan-2-yl)-4-(trifluoromethoxy)aniline (19.0 g, 62.7 mmol), triethylamine (19.03 g, 188 mmol), and dichloromethane (200 mL) were combined under an atmosphere of nitrogen. Then the mixture was cooled to 0° C. and acetyl chloride (5.91 g, 75 mmol) was added dropwise. The resultant mixture was allowed to warm to ambient temperature with continued stirring overnight. The reaction mixture was concentrated under reduced pressure, and the residue was purified by column chromatography on silica gel eluted with 25% ethyl acetate/hexane to give a mixture of the titled compound and (5-acetamido-2-(trifluoromethoxy)phenyl)boronic acid.

Step 2: N-[3-{5-[1-(4-chlorophenyl)ethyl]-3-methyl-4-oxo-4,5-dihydro[1,2]oxazolo[4,5-d]pyridazin-7-yl}-4-(trifluoromethoxy)phenyl]acetamide Under argon, 7-bromo-5-[1-(4-chlorophenyl)ethyl]-3-methyl[1,2]oxazolo[4,5-d]pyridazin-4(5H)-one (70 mg, 0.190 mmol, Example 39—Step 5) was suspended in toluene and ethanol (4 mL, 1:1). 2 M Aqueous sodium bicarbonate (0.142 mL, 0.285 mmol) and N-(3-(4,4,5,5-tetramethyl-1,3,2-dioxaborolan-2-yl)-4-(trifluoromethoxy)phenyl)acetamide (65.5 mg, 0.190 mmol, Step 1) were added followed by tetrakis(triphenylphosphine)palladium(0) (21.94 mg, 0.019 mmol). The reaction mixture was heated with stirring in a Biotage® microwave reactor at 130° C. for 30 minutes. The reaction mixture was then partitioned between water and ethyl acetate. The organic fraction was washed with brine, dried over MgSO$_4$ and then concentrated under reduced pressure. The residue was purified by flash chromatography on a Teledyne Isco CombiFlash® Rf apparatus using a silica gel cartridge (4 g) eluted with 3-5% methanol/dichloromethane. The residue was dried in a vacuum oven overnight to give the titled compound (37 mg, yield 38%). $^1$H NMR (600 MHz, DMSO-d$_6$) δ ppm 10.39 (s, 1H), 8.06 (d, J=2.6 Hz, 1H), 7.87 (dd, J=9.1, 2.7 Hz, 1H), 7.57 (dd, J=9.1, 1.5 Hz, 1H), 7.43-7.35 (m, 3H), 6.33 (q, J=7.0 Hz, 1H), 2.60 (s, 2H), 2.09 (s, 3H), 1.73 (d, J=7.0 Hz, 3H), 1.29 (s, 1H), 1.08-1.01 (m, 1H).

Example 50

5-[4-methoxy-3-(trifluoromethyl)benzyl]-3,7-dimethyl[1,2]oxazolo[4,5-d]pyridazin-4(5H)-one The titled compound was prepared using the procedure described in Example 20 substituting 4-(bromomethyl)-1-methoxy-2-(trifluoromethyl)benzene for 1-(bromomethyl)-2-fluorobenzene. Purification was achieved by preparative liquid chromatography (Method C, 0.5-8.5 minutes linear gradient 50-80% A). $^1$H NMR (400 MHz, DMSO-d$_6$/D$_2$O) δ ppm 7.64-7.56 (m, 2H), 7.23 (d, J=8.6 Hz, 1H), 5.29 (s, 2H), 3.86 (s, 3H), 2.57 (s, 3H), 2.50 (s, 3H); MS (APCI$^+$) m/z 354.0 (M+H)$^+$.

Example 51

N-{3-[5-(4-chlorobenzyl)-3-cyclopropyl-4-oxo-4,5-dihydro[1,2]oxazolo[4,5-d]pyridazin-7-yl]phenyl}acetamide

Step 1: methyl 2-cyclopropyl-4-oxo-4,5-dihydrofuran-3-carboxylate

To a solution of magnesium ethanolate (19.32 g, 169 mmol) in toluene (80 mL) was slowly added methyl 3-cyclopropyl-3-oxopropanoate 1 (20 g, 141 mmol) at 0° C. After stirring for 1 hour, acetonitrile (80 mL) was added followed by the addition of 2-chloroacetyl chloride (15.89 g, 141 mmol) at 0° C. The mixture was allowed to warm to room temperature and left to stir for 2 hours. A diluted solution of sulfuric acid (1 mL acid in 30 mL ice/water) was added, followed by extraction with tert-butyl methyl ether. The combined organic fractions were dried over Na$_2$SO$_4$ and filtered. To the filtrate was added a solution of triethylamine (49 mL, 338 mmol) in tert-butyl methyl ether (150 mL). The reaction mixture was stirred at room temperature overnight. The mixture was diluted with water (200 mL), and extracted with dichloromethane. The organic phase was concentrated under reduced pressure to supply a residue that was purified by chromatography on silica gel and eluted with EtOAc/PE to give the titled compound (24 g, yield 94%). $^1$H NMR (400 MHz, CDCl$_3$) δ ppm 4.50 (s, 1H), 4.33 (q, J=7.2 Hz, 2H), 3.18-3.08 (m, 1H), 1.40-1.32 (m, 5H), 1.29-1.22 (m, 2H).

Step 2: methyl 3-cyclopropyl-5-(hydroxymethyl)-1,2-oxazole-4-carboxylate

To a solution of methyl 2-cyclopropyl-4-oxo-4,5-dihydrofuran-3-carboxylate (24 g, 122 mmol, Step 1) in anhydrous ethanol (200 mL) was added sodium acetate (15.05 g, 183 mmol) and NH$_2$OH*HCl (10.20 g, 147 mmol). The mixture was heated to reflux for 1 hour. The mixture was concentrated under reduced pressure to give a residue that was diluted with water and extracted with ethyl acetate. The organic phase was washed with brine, dried over Na$_2$SO$_4$, and concentrated under reduced pressure. The residue was purified by chromatography on silica gel (EtOAc/PE, 1:20-5) to give the titled compound (3.9 g, yield 15%). $^1$H NMR (400 MHz, CDCl$_3$) δ ppm 4.85 (s, 2H), 4.39 (q, J=7.2 Hz, 2H), 2.36-2.23 (m, 1H), 1.40 (t, J=7.1 Hz, 3H), 1.03 (br. s., 4H).

Step 3: methyl 3-cyclopropyl-5-formyl-1,2-oxazole-4-carboxylate

To a solution of methyl 3-cyclopropyl-5-(hydroxymethyl)-1,2-oxazole-4-carboxylate (3.9 g, 18.46 mmol, Step 2) in anhydrous toluene (30 mL) was added MnO$_2$ (4.82 g, 55.4 mmol). The mixture was heated to reflux for 4 hours. The volatiles were removed under reduced pressure to give a residue that was purified by column chromatography on silica gel (EtOAc/PE, 1:20-5) to give the titled compound (3.7 g, yield 96%) that was used directly in the next step. LCMS (ESI+) m/z 196.1 (M+H)$^+$, retention time 0.581 minute.

Step 4: 3-cyclopropyl[1,2]oxazolo[4,5-d]pyridazin-4 (5H)-one

To a solution of methyl 3-cyclopropyl-5-formyl-1,2-oxazole-4-carboxylate (3.7 g, 17.6 mmol, Step 3) in anhydrous ethanol (50 mL) was added hydrazine hydrate (2.78 ml, 88 mmol) at 0° C. The resulting mixture was stirred at room temperature for 2 hours. The solid was collected by filtration and dried to give the titled compound (3.0 g, yield 96%). $^1$H NMR (400 MHz, CDCl$_3$) δ ppm 10.81 (br. s., 1H), 8.23 (s, 1H), 2.48-2.37 (m, 1H), 1.31-1.22 (m, 2H), 1.20-1.10 (m, 2H).

Step 5: 7-bromo-3-cyclopropyl[1,2]oxazolo[4,5-d]pyridazin-4(5H)-one

To a solution of 3-cyclopropyl[1,2]oxazolo[4,5-d]pyridazin-4(5H)-one (4.7 g, 26.5 mmol, Step 4) and LiOH*H$_2$O (3.18 g, 133 mmol) in CH$_3$OH (50 mL) was added Br$_2$ (4.10 mL, 80 mmol) at 0° C. The resulting mixture was stirred at 70° C. for 12 hours. The mixture was concentrated under reduced pressure to give a residue that was poured into H$_2$O (50 mL). The resulting mixture was extracted with ethyl acetate. The combined organic layers were dried over Na$_2$SO$_4$ and concentrated to give a residue that was purified by column chromatography on silica gel (EtOAc/PE, 1: 20-5) to give the titled compound (1.3 g, yield 19%). $^1$H NMR (400 MHz, CDCl$_3$) δ ppm 10.65 (br. s., 1H), 2.47-2.33 (m, 1H), 1.29-1.22 (m, 2H), 1.20-1.11 (m, 2H).

Step 6: 7-bromo-5-(4-chlorobenzyl)-3-cyclopropyl [1,2]oxazolo[4,5-d]pyridazin-4(5H)-one To a solution of 7-bromo-3-cyclopropyl[1,2]oxazolo[4,5-d]pyridazin-4(5H)-one (300 mg, 1.17 mmol, Step 5) in N,N-dimethylformamide (5 mL) was added K$_2$CO$_3$ (648 mg, 4.69 mmol) and 1-chloro-4-(chloromethyl)benzene (283 mg, 1.75 mmol). After stirring at 50° C. for 2 hours, the mixture was diluted with water and extracted with ethyl acetate. The combined organic phase was washed with brine and concentrated under reduced pressure to give the titled compound (270 mg, yield 60%). $^1$H NMR (400 MHz, CDCl$_3$) δ ppm 8.17 (s, 1H), 7.36-7.29 (m, 2H), 7.27-7.20 (m, 2H), 5.27 (d, J=13.7 Hz, 2H), 2.46-2.36 (m, 1H), 1.22-1.17 (m, 2H), 1.15-1.09 (m, 2H).

Step 7: N-{3-[5-(4-chlorobenzyl)-3-cyclopropyl-4-oxo-4,5-dihydro[1,2]oxazolo-[4,5-d]pyridazin-7-yl] phenyl}acetamide To a solution of 7-bromo-5-(4-chlorobenzyl)-3-cyclopropyl[1,2]oxazolo[4,5-d]pyridazin-4(5H)-one (270 mg, 0.7 mmol, Step 6) in N,N-dimethylformamide (2 mL) and water (0.5 mL) was added (3-acetamidophenyl)boronic acid (152 mg, 0.85 mmol), K$_2$CO$_3$ (245 mg, 1.77 mmol) and tetrakis (triphenylphosphine)palladium(0) (82 mg, 0.071 mmol). After stirring at 80° C. overnight under nitrogen, the mixture was diluted with water and extracted with ethyl acetate. The organic phase was washed with brine and concentrated under reduced pressure to give a residue that was purified by preparative HPLC (method C) to give the titled compound (87 mg, yield 28%). $^1$H NMR (400 MHz, DMSO-d$_6$) δ ppm 10.19 (s, 1H), 8.28 (s, 1H), 7.77 (d, J=8.4 Hz, 1H), 7.67 (d, J=7.9 Hz, 1H), 7.47 (t, J=8.2 Hz, 1H), 5.42 (s, 2H), 2.09-2.04 (m, 3H), 1.22-1.14 (m, 4H); LCMS (method B) (ESI+) m/z 435.1 (M+H)$^+$, retention time 3.568 minutes.

Example 52

5-(4-chlorobenzyl)-7-(2,5-dimethoxyphenyl)-3-propyl[1,2]oxazolo[4,5-d]pyridazin-4(5H)-one To a solution of 7-bromo-5-(4-chlorobenzyl)-3-propyl[1, 2]oxazolo[4,5-d]pyridazin-4(5H)-one (180 mg, 0.454 mmol, Example 91—Step 6) in N,N-dimethylformamide (2 mL) and water (0.5 mL) was added (2,5-dimethoxyphenyl) boronic acid (99 mg, 0.545 mmol), K$_2$CO$_3$ (157 mg, 1.134 mmol) and tetrakis(triphenylphosphine)palladium(0) (52.4 mg, 0.045 mmol). After stirring at 80° C. overnight under nitrogen, the mixture was diluted with water and extracted with ethyl acetate (50 mL×3). The organic phase was washed with brine and concentrated under reduced pressure. The residue was purified by preparative HPLC (method B) to give the titled compound (68 mg, yield 33%). $^1$H NMR (400 MHz, CDCl$_3$) δ ppm 7.38 (d, J=8.4 Hz, 2H), 7.24 (d, J=8.4 Hz, 2H), 7.02-6.89 (m, 3H), 5.34 (s, 2H), 3.74 (d, J=4.0 Hz, 6H), 2.96 (t, J=7.5 Hz, 2H), 1.82 (sxt, J=7.4 Hz, 2H), 1.02-0.92 (m, 3H); LCMS (method B) (ESI+) m/z 440.2 (M+H)$^+$, retention time 3.327 minutes.

Example 53

3-{5-[1-(4-chlorophenyl)ethyl]-3-methyl-4-oxo-4,5-dihydro[1,2]oxazolo[4,5-d]pyridazin-7-yl}benzenesulfonamide The titled compound was prepared using the procedure described in Example 4 substituting (3-sulfamoylphenyl) boronic acid (32 mg, 0.16 mmol) for (2,6-difluoropyridin-4-yl)boronic acid. Purification was achieved by preparative liquid chromatography (Method C, 0.5-8.5 minutes linear gradient 40-70% A). (46 mg, yield 40%).

$^1$H NMR (400 MHz, DMSO-d$_6$/D$_2$O, Temperature=90° C.) δ ppm 8.52 (t, J=1.8 Hz, 1H), 8.28-8.21 (m, 1H), 8.04-7.97 (m, 1H), 7.79 (t, J=7.9 Hz, 1H), 7.47-7.43 (m, 2H), 7.40-7.35 (m, 2H), 6.35 (q, J=7.0 Hz, 1H), 2.63 (s, 3H), 1.84 (d, J=7.0 Hz, 3H); MS (APCI+) m/z 445 (M+H)$^+$.

Example 54

5-[4-fluoro-3-(trifluoromethyl)benzyl]-7-(2-methoxyphenyl)-3-methyl[1,2]oxazolo[4,5-d]pyridazin-4(5H)-one The titled compound was prepared using the procedures described for Example 5 substituting (2-methoxyphenyl) boronic acid for (2,4-dimethoxyphenyl)boronic acid in Step 1 and 4-(bromomethyl)-1-fluoro-2-(trifluoromethyl)benzene for 4-(bromomethyl)pyridine in Step 2. Yield 13%

$^1$H NMR (400 MHz, CD$_3$OD): δ 7.82-77 (m, 2H), 7.55-7.52 (m, 1H), 7.44-7.42 (m, 1H), 7.19-7.18 (m, 1H), 7.10-7.09 (m, 2H), 5.49 (s, 2H), 3.82 (s, 3H), 2.64 (s, 3H).

Example 55

N-(3-{5-[1-(4-chlorophenyl)ethyl]-3-methyl-4-oxo-4,5-dihydro[1,2]oxazolo[4,5-d]pyridazin-7-yl}-4-methoxyphenyl)methanesulfonamide Under argon, 7-bromo-5-[1-(4-chlorophenyl)ethyl]-3-methyl[1,2]oxazolo[4,5-d]pyridazin-4(5H)-one (80 mg, 0.217 mmol, Example 39—Step 5) was suspended in toluene and methanol (2.4 mL, 1:1). 2 M Aqueous sodium bicarbonate (0.163 mL, 0.326 mmol) and N-(4-methoxy-3-(4,4,5,5-tetramethyl-1,3,2-dioxaborolan-2-yl)phenyl)methanesulfonamide (71.0 mg, 0.217 mmol) were added followed by tetrakis(triphenylphosphine)palladium(0) (25.08 mg, 0.022 mmol). The reaction mixture was heated with stirring in a Biotage® microwave reactor at 130° C. for 30 minutes. The reaction mixture was then partitioned between water and ethyl acetate. The aqueous phase was extracted twice more with ethyl acetate. The combined organic fractions were washed with brine, dried over $MgSO_4$ and then concentrated under reduced pressure. The residue was purified by flash chromatography on a Teledyne Isco Combi-Flash® apparatus using a RediSep® silica gel cartridge (4 g) eluted with 0-10% methanol/dichloromethane. The residue was stirred with a little diisopropyl ether, and the resultant precipitate was collected and dried in a vacuum oven to give the titled compound (49 mg, yield 46%).

$^1$H NMR (600 MHz, DMSO-$d_6$) δ ppm 9.66 (s, 1H), 7.44-7.37 (m, 5H), 7.40-7.33 (m, 1H), 7.29-7.22 (m, 1H), 6.33 (q, J=7.0 Hz, 1H), 3.78 (s, 3H), 2.97 (s, 3H), 2.58 (s, 3H), 1.73 (d, J=7.1 Hz, 3H); MS (ESI+) m/z 489.2 (M+H)$^+$.

Example 56

5-(4-chlorobenzyl)-3-methyl-7-(thiophen-2-yl)[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added thiophen-2-ylboronic acid (43.2 mg, 0.338 mmol), $K_2CO_3$ (0.097 g, 0.705 mmol) and tetrakis(triphenylphosphine)palladium(0) (0.033 g, 0.028 mmol). The resulting mixture was stirred at 80° C. overnight under $N_2$. After cooling down to room temperature, the reaction mixture was concentrated under reduced pressure to give a residue that was washed with a mixture of $CH_3OH$ and $H_2O$ to give the titled compound (31 mg, yield 31%). $^1$H NMR (CDCl$_3$, 400 MHz): δ 8.00 (d, J=3.1 Hz, 1H), 7.50 (d, J=4.9 Hz, 1H), 7.45 (d, J=8.4 Hz, 2H), 7.31 (d, J=8.4 Hz, 2H), 7.19 (dd, J=4.0, 4.9 Hz, 1H), 5.39 (s, 2H), 2.71 (s, 3H). m/z 357.8.

Example 57

N-(3-{3-methyl-4-oxo-5-[4-(trifluoromethyl)benzyl]-4,5-dihydro[1,2]oxazolo[4,5-d]pyridazin-7-yl}phenyl)acetamide The titled compound was prepared using the procedures described for Example 5 substituting (3-acetamidophenyl)boronic acid for (2,4-dimethoxyphenyl)boronic acid in Step 1 and 1-(bromomethyl)-4-(trifluoromethyl)benzene for 4-(bromomethyl)pyridine in Step 2. Yield 37%

$^1$H NMR (400 MHz, DMSO): δ 10.18 (br, 1H), 8.28 (s, 1H), 7.80-7.78 (d, J=7.6 Hz, 1H), 7.77-7.60 (m, 3H), 7.59-7.57 (d, J=7.6 Hz, 2H), 7.48-7.44 (t, J=7.6 Hz, 1H), 5.50 (s, 2H), 2.59 (s, 3H), 2.06 (s, 3H). m/z 443.2.

Example 58

5-[(1R)-1-(4-chlorophenyl)ethyl]-3,7-dimethyl[1,2]oxazolo[4,5-d]pyridazin-4(5H)-one The individual enantiomers of the mixture of Example 114 were separated by preparative chiral chromatography (WHELK-O® 1 (S,S), 30×250 mm column, 5 m, concentration of 75 mg/mL in $CH_3OH/CH_2Cl_2$ (8:2), flow rate 75 mL/minute; 20% $CH_3OH$ in $CO_2$ at 100 psi) 6.89 bar) to afford the title compound as the second-eluting enantiomer with a retention time of 8.6 minutes. Stereocenter arbitrarily assigned. $^1$H NMR (300 MHz, CDCl$_3$) δ ppm 7.41-7.35 (m, 2H), 7.31-7.26 (m, 2H), 6.33 (q, J=7.1, 7.1, 7.1 Hz, 1H), 2.66 (s, 3H), 2.56 (s, 3H), 1.77 (d, J=7.1 Hz, 3H); MS (DCI/NH$_3$) m/z 304 (M+H)$^+$, 321 (M+NH$_4$)+.

Example 59

3-{5-[1-(4-chlorophenyl)ethyl]-3-methyl-4-oxo-4,5-dihydro[1,2]oxazolo[4,5-d]pyridazin-7-yl})-4-methoxybenzamide Under argon, 7-bromo-5-[1-(4-chlorophenyl)ethyl]-3-methyl[1,2]oxazolo[4,5-d]pyridazin-4(5H)-one (400 mg, 1.085 mmol, Example 39—Step 5) was suspended in toluene and methanol (12 mL, 1:1). 2 M Aqueous sodium bicarbonate (0.814 mL, 1.628 mmol) and 4-methoxy-3-(4,4,5,5-tetramethyl-1,3,2-dioxaborolan-2-yl)benzamide (301 mg, 1.085 mmol) were added followed by tetrakis(triphenylphosphine)palladium(0) (125 mg, 0.109 mmol). The reaction mixture was heated with stirring in a Biotage® microwave reactor at 130° C. for 30 minutes. The reaction mixture was then partitioned between water and ethyl acetate. The aqueous phase was extracted twice more with ethyl acetate. The combined organic fractions were washed with brine, dried over $MgSO_4$ and then concentrated under reduced pressure. The residue was purified by flash chromatography on a Teledyne Isco CombiFlash® apparatus using a RediSep® silica gel cartridge (4 g) eluted with 0-10% methanol/dichloromethane. The residue was purified with a second flash chromatography on a Teledyne Isco CombiFlash® apparatus using an Agilent silica gel cartridge (8 g) eluted with 0-8% methanol/dichloromethane to give the titled compound (380 mg, yield 80%).

$^1$H NMR (600 MHz, DMSO-$d_6$) δ ppm 8.12-8.07 (m, 1H), 8.03-7.94 (m, 2H), 7.41 (s, 4H), 7.38 (s, 1H), 7.31 (d, J=8.8 Hz, 1H), 6.32 (q, J=7.0 Hz, 1H), 3.90 (s, OH), 3.85 (s, 3H), 2.59 (s, 3H), 1.75 (d, J=7.1 Hz, 3H); MS (ESI+) m/z 439.1 (M+H)$^+$.

Example 60

5-[2-(4-chlorophenyl)ethyl]-3,7-dimethyl[1,2]oxazolo[4,5-d]pyridazin-4(5H)-one 3,7-Dimethyl[1,2]oxazolo[4,5-d]pyridazin-4(5H)-one (100 mg, 0.606 mmol) was dissolved in N,N-dimethylformamide (3 mL) and treated at room temperature with sodium hydride (17.44 mg, 0.727 mmol, 29.1 mg as a 60% dispersion in oil) under an argon atmosphere. After 30 minutes, 1-(2-bromoethyl)-4-chlorobenzene (133 mg, 0.088 mL, 0.606 mmol) was added, and the mixture was stirred for an additional 5 hours at ambient temperature. The reaction mixture was partitioned between ethyl acetate and water. The aqueous phase was extracted twice more with ethyl acetate. The combined organic fractions were washed with brine, dried over MgSO₄, and concentrated under reduced pressure. The residue was treated with ethyl acetate/diisopropyl ether (1:4), and the precipitate was collected and dried in a vacuum oven to give the titled compound. ¹HNMR (600 MHz, DMSO-d₆) δ ppm 7.36-7.31 (m, 2H), 7.27-7.21 (m, 2H), 4.34-4.28 (m, 2H), 3.01 (dd, J=8.3, 6.7 Hz, 2H), 2.56 (s, 3H), 2.48 (s, 3H); MS (ESI+) m/z 304.1 (M+H)⁺.

Example 61

N-(2-fluoro-5-{5-[4-fluoro-3-(trifluoromethyl)benzyl]-3-methyl-4-oxo-4,5-dihydro[1,2]oxazolo[4,5-d]pyridazin-7-yl}phenyl)acetamide The titled compound was prepared using the procedures described for Example 5 substituting (3-acetamido-4-fluorophenyl)boronic acid for (2,4-dimethoxyphenyl)boronic acid in Step 1 and 4-(bromomethyl)-1-fluoro-2-(trifluoromethyl)benzene for 4-(bromomethyl)pyridine in Step 2. Yield 17%
¹H NMR (400 MHz, CD₃OD): δ 8.23-8.21 (m, 1H), 7.98-7.96 (d, J=7.9 Hz, 1H), 7.58-7.54 (m, 2H), 7.47-7.42 (t, J=8.8 Hz, 1H), 7.27-7.23 (t, J=8.8 Hz, 1H), 5.00-4.97 (m, 2H), 2.67 (s, 3H), 1.96 (s, 3H). m/z 479.1.

Example 62

N-(2-fluoro-5-{5-[4-methoxy-3-(trifluoromethyl)benzyl]-3-methyl-4-oxo-4,5-dihydro[1,2]oxazolo[4,5-d]pyridazin-7-yl}phenyl)acetamide The titled compound was prepared using the procedures described for Example 5 substituting (3-acetamido-4-fluorophenyl)boronic acid for (2,4-dimethoxyphenyl)boronic acid in Step 1 and 4-(bromomethyl)-1-methoxy-2-(trifluoromethyl)benzene for 4-(bromomethyl)pyridine in Step 2. Yield 15%
¹H NMR (400 MHz, CD₃OD): δ 8.19 (s, 1H), 7.92-7.90 (d, J=7.2 Hz, 1H), 7.46-7.41 (m, 3H), 7.09-7.07 (d, J=8.8 Hz, 1H), 5.03-5.01 (m, 1H), 4.75-4.72 (m, 1H), 3.86 (s, 3H), 2.66 (s, 3H), 1.94 (s, 3H). m/z 491.2.

Example 63

5-[1-(4-chlorophenyl)ethyl]-7-(5-fluoro-2-methoxyphenyl)-3-methyl[1,2]oxazolo[4,5-d]pyridazin-4(5H)-one 7-Bromo-5-[1-(4-chlorophenyl)ethyl]-3-methyl[1,2]oxazolo[4,5-d]pyridazin-4(5H)-one (80 mg, 0.217 mmol, Example 39—Step 5) was combined with potassium carbonate (75.0 mg, 0.543 mmol) and (5-fluoro-2-methoxyphenyl)boronic acid (36.9 mg, 0.217 mmol) in 1,2-dimethoxyethane and water (5 mL, 4:1). Then tetrakis (triphenylphosphine)palladium(0) (25.08 mg, 0.022 mmol) was added, and the mixture was heated for 4 hours at 80° C. under an argon atmosphere. The reaction mixture was partitioned between water and ethyl acetate. The organic fraction was then washed with brine, dried over MgSO₄, and concentrated under reduced pressure. The residue was purified by flash chromatography on a Teledyne Isco Combi-Flash® Rf apparatus using a silica gel cartridge (8 g) eluted with 20% ethyl acetate/cyclohexane The residue was dried in a vacuum oven overnight to give the titled compound (19 mg, yield 28%).
¹H NMR (500 MHz, DMSO-d₆) δ ppm 7.47-7.38 (m, 1H), 7.41 (s, 3H), 7.33-7.23 (m, 2H), 6.30 (q, J=7.0 Hz, 1H), 3.79 (s, 3H), 3.73 (s, OH), 2.59 (s, 3H), 1.73 (d, J=7.0 Hz, 3H); MS (ESI+) m/z 414.2 (M+H)⁺.

Example 64

N-(4-methoxy-3-{3-methyl-4-oxo-5-[4-(trifluoromethyl)benzyl]-4,5-dihydro[1,2]oxazolo[4,5-d]pyridazin-7-yl}phenyl)acetamide

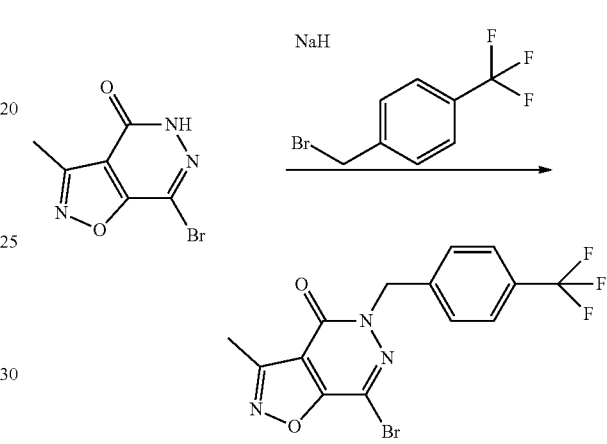

Step 2: 7-(5-amino-2-methoxyphenyl)-3-methyl-5-[4-(trifluoromethyl)benzyl]-[1,2]oxazolo[4,5-d]pyridazin-4(5H)-one 7-Bromo-3-methyl-5-[4-(trifluoromethyl)benzyl][1,2]oxazolo[4,5-d]pyridazin-4(5H)-one (Example 64, 120 mg, 0.309 mmol), 4-methoxy-3-(4,4,5,5-tetramethyl-1,3,2-dioxaborolan-2-yl)aniline (77 mg, 0.309 mmol), sodium carbonate (32.8 mg, 0.309 mmol), and [1,1'-bis(diphenylphosphino)ferrocene]dichloropalladium(II) (226 mg, 0.309 mmol, PdCl₂(dppf)) were combined with 1,4-dioxane (3 mL) and water (0.3 mL) in a 10-mL sealed tube. The reaction mixture was irradiated in a microwave reactor for 60 minutes at 100° C. The reaction mixture was then concentrated under reduced pressure, and the residue was purified by silica gel column chromatography eluted with EtOAc/PE (1:2) to give the titled compound.

Step 3: N-(4-methoxy-3-{3-methyl-4-oxo-5-[4-(trifluoromethyl)benzyl]-4,5-dihydro[1,2]oxazolo[4,5-d]pyridazin-7-yl}phenyl)acetamide 7-(5-Amino-2-methoxyphenyl)-3-methyl-5-[4-(trifluoromethyl)benzyl][1,2]oxazolo[4,5-d]pyridazin-4(5H)-one (60 mg, 0.139 mmol) and triethylamine (14.11 mg, 0.139 mmol) were combined in dichloromethane (5 mL). Then acetyl chloride (10.94 mg, 0.139 mmol) was added, and the resultant reaction mixture was stirred at ambient temperature for 1 hour. The mixture was concentrated under reduced pressure, and the residue was purified by reverse phase (C18) column chromatography eluted with methanol/water (9:1) to give the titled compound. ¹H NMR (300 MHz, CD$_3$OD) δ ppm 2.15 (s, 3H), 2.67 (s, 3H), 3.85 (s, 3H), 5.57 (s, 2H), 7.18 (d, 1H), 7.69 (m, 6H); MS (ESI+) m/z 473.2 (M+H)$^+$.

Example 65

2-amino-6-{5-[1-(4-chlorophenyl)ethyl]-3-methyl-4-oxo-4,5-dihydro[1,2]oxazxazolo[4,5-d]pyridazin-7-yl}benzamide Step 1: 2-amino-6-(4,4,5,5-tetramethyl-1,3,2-dioxaborolan-2-yl)benzonitrile To a degassed suspension of 2-amino-6-chlorobenzonitrile (0.25 g, 1.638 mmol), bis(pinacolato)diboron (0.416 g, 1.638 mmol), and potassium acetate (0.241 g, 2.458 mmol) in dioxane (5.0 mL), tricyclohexylphosphine (0.032 g, 0.115 mmol) and tris(dibenzylideneacetone)dipalladium(0) (0.045 g, 0.049 mmol, Pd$_2$(dba)$_3$) were added. The mixture was purged with nitrogen for 5 minutes and then heated at 120° C. for 2 hours. The mixture was filtered through diatomaceous earth, and the cake was washed with ethyl acetate. The filtrate and wash were combined and concentrated. The residue was purified by silica gel chromatography eluted with 5-40% ethyl acetate/hexane to give the titled compound. $^1$H NMR (400 MHz, CDCl$_3$) δ ppm 1.37 (s, 12H) 4.44 (s, 2H) 6.83 (d, J=8.24 Hz, 1H) 7.18 (d, J=7.16 Hz, 1H) 7.27-7.39 (m, 1H).

Step 2: 2-amino-6-{5-[1-(4-chlorophenyl)ethyl]-3-methyl-4-oxo-4,5-dihydro[1,2]oxazolo[4,5-d]pyridazin-7-yl}benzamide 7-Bromo-5-[1-(4-chlorophenyl)ethyl]-3-methyl[1,2]oxazolo[4,5-d]pyridazin-4(5H)-one (60 mg, 0.163 mmol, Example 39—Step 5) was combined with potassium carbonate (56.2 mg, 0.407 mmol) and 2-amino-6-(4,4,5,5-tetramethyl-1,3,2-dioxaborolan-2-yl)benzonitrile (47.7 mg, 0.195 mmol, Step 1) in 1,2-dimethoxyethane and water (5 mL, 4:1). Then tetrakis(triphenylphosphine)palladium(0) (18.81 mg, 0.016 mmol) was added, and the mixture was heated for 4 hours at 80° C. under an argon atmosphere. The reaction mixture was partitioned between water and ethyl acetate. The organic fraction was then washed with brine, dried over MgSO$_4$, and concentrated under reduced pressure. The residue was purified by flash chromatography using a Teledyne Isco CombiFlash® Rf apparatus with a 4 g silica gel cartridge eluted with 30% ethyl acetate/cyclohexane. The product containing fractions were combined and concentrated. The residue was stirred with a small amount of ethyl acetate/diisopropyl ether (1:1). The resultant solid was collected by vacuum filtration and was dried in a vacuum oven overnight to give the titled compound (12 mg, yield 17%).
$^1$H NMR (500 MHz, DMSO-d$_6$) δ ppm 7.51 (s, 1H), 7.43-7.35 (m, 4H), 7.24 (t, J=7.8 Hz, 1H), 7.17 (s, 1H), 6.92 (ddd, J=17.3, 7.8, 1.0 Hz, 2H), 6.22 (q, J=7.0 Hz, 1H), 5.42 (s, 2H), 3.31 (s, 1H), 2.58 (s, 3H), 1.72 (d, J=7.1 Hz, 3H); MS (ESI+) m/z 424.1 (M+H)$^+$.

Example 66

7-(4-fluorophenyl)-5-[4-methoxy-3-(trifluoromethyl)benzyl]-3-methyl[1,2]oxazolo[4,5-d]pyridazin-4(5H)-one To a solution of 7-(4-fluorophenyl)-3-methyl[1,2]oxazolo[4,5-d]pyridazin-4(5H)-one (Example 19, 100 mg, 0.408 mmol) in N,N-dimethylformamide (2 mL) was added NaH (14.68 mg, 0.612 mmol). The mixture was stirred at room temperature for 15 minutes, and then 4-(bromomethyl)-1-methoxy-2-(trifluoromethyl)benzene (132 mg, 0.489 mmol) was added. The mixture was stirred at room temperature overnight. The solid was collected by filtration and washed with water and methanol to give the titled compound (98 mg, yield 55%).
$^1$H NMR (400 MHz, DMSO-d$_6$) δ ppm 8.51 (m, 2H), 8.09-8.05 (m, 2H), 7.45-7.40 (m, 2H), 7.31-7.30 (m, 2H), 5.47 (s, 2H), 2.59 (s, 3H); MS (APCI$^+$) m/z 434.0 (M+H)$^+$.

Example 67

5-(4-chlorobenzyl)-7-(2-methoxyphenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added (2-methoxyphenyl)boronic acid (51.4 mg, 0.338 mmol), K$_2$CO$_3$ (0.097 g, 0.705 mmol) and tetrakis(triphenylphosphine)palladium(0) (0.033 g, 0.028 mmol). The resulting mixture was stirred at 80° C. overnight under N$_2$. After cooling down to room temperature, the reaction mixture was concentrated under reduced pressure to give a residue that was washed with a mixture of CH$_3$OH and H$_2$O to give the titled compound. Yield 54%
1H NMR (CDCl3, 400 MHz): δ 7.48-7.56 (m, 1H), 7.37-7.47 (m, 3H), 7.31 (d, J=8.38 Hz, 2H), 7.00-7.15 (m, 2H), 5.40 (s, 2H), 3.84 (s, 3H), 2.68 (s, 3H). m/z 381.8.

Example 68

5-[(1S)-1-(4-chlorophenyl)ethyl]-3-cyclopropyl-7-(2,5-dimethoxyphenyl)[1,2]oxazolo[4,5-d]pyridazin-4(5H)-one 5-[1-(4-chlorophenyl)ethyl]-3-cyclopropyl-7-(2,5-dimethoxyphenyl)[1,2]oxazolo[4,5-d]pyridazin-4(5H)-one was synthesized in analogy to Example 1. The enantiomers were separated by supercritical fluid chromatography to give the titled compound The mobile phase was comprised of supercritical CO$_2$ supplied by a bulk tank of 99.5% bone-dry non-certified CO$_2$ pressurized to 1200 psi (82.7 bar) with a modifier of methanol (0.1 N NH$_4$OH) at a flow rate of 70 g/minute. UV detection was set to collect at a wavelength of 220 nm, the column was heated to 35° C., and the back-pressure regulator was set to maintain 100 bar. The sample was dissolved in methanol at a concentration of about 50 mg/mL, and the injection volume was 1 mL. The mobile phase was held isocratically at 40% methanol (0.1 N NH$_4$OH):CO2. The instrument was fitted with a Chiralpak® AS-H 5 µm, 30 mm×250 mm column. $^1$H NMR (400 MHz, DMSO-d$_6$) δ ppm 7.39 (s, 3H), 7.17-7.08 (m, 2H), 6.92 (d, J=2.6 Hz, 1H), 6.30 (q, J=6.9 Hz, 1H), 3.71 (d, J=7.1 Hz, 6H), 2.46-2.39 (m, 1H), 1.71 (d, J=7.1 Hz, 3H), 1.14 (d, J=7.5 Hz, 4H).

Example 69

5-[4-chloro-3-(trifluoromethyl)benzyl]-3,7-dimethyl[1,2]oxazolo[4,5-d]pyridazin-4(5H)-one The titled compound was prepared using the procedure described in Example 20 substituting 4-(bromomethyl)-1-chloro-2-(trifluoromethyl)benzene for 1-(bromomethyl)-2- fluorobenzene. Purification was achieved by preparative liquid chromatography (Method C, 0.5-8.5 minutes linear gradient 60-100% A). $^1$H NMR (400 MHz, DMSO-$d_6$/$D_2O$) δ ppm 7.83 (d, J=2.1 Hz, 1H), 7.69 (d, J=8.3 Hz, 1H), 7.58 (dd, J=8.4, 2.1 Hz, 1H), 5.38 (s, 2H), 2.57 (s, 3H), 2.51 (s, 3H); MS (APCI$^+$) m/z 358.0 (M+H)$^+$.

Example 70

N-{3-[5-(4-chlorobenzyl)-3-methyl-4-oxo-4,5-dihydro[1,2]oxazolo[4,5-d]pyridazin-7-yl]phenyl}acetamide To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added (3-acetamidophenyl)boronic acid (60.5 mg, 0.338 mmol), $K_2CO_3$ (0.097 g, 0.705 mmol) and tetrakis(triphenylphosphine)palladium(0) (0.033 g, 0.028 mmol). The resulting mixture was stirred at 80° C. overnight under $N_2$. After cooling down to room temperature, the reaction mixture was concentrated under reduced pressure to give a residue that was washed with a mixture of $CH_3OH$ and $H_2O$ to give the titled compound. Yield 56%

$^1$H NMR (CDCl$_3$, 400 MHz): δ 8.11 (s, 1H), 7.83 (d, J=7.94 Hz, 1H), 7.72 (d, J=7.94 Hz, 1H), 7.31-7.49 (m, 3H), 7.25 (d, J=8.38 Hz, 3H), 5.37 (s, 2H), 2.64 (s, 3H), 2.17 (s, 3H). m/z 408.8.

Example 71

5-(4-chlorobenzyl)-7-(2,5-dimethoxyphenyl)-3-(methoxymethyl)[1,2]oxazolo[4,5-d]pyridazin-4(5H)-one To a solution of 7-bromo-5-(4-chlorobenzyl)-3-(methoxymethyl)[1,2]oxazolo[4,5-d]pyridazin-4(5H)-one (0.18 g, 0.468 mmol, Example 27—Step 6) in 1,4-dioxane (15 mL) and water (5 mL) was added (2,5-dimethoxyphenyl)boronic acid (0.085 g, 0.46 mmol), $K_2CO_3$ (0.16 g, 1.17 mmol) and tetrakis(triphenylphosphine)palladium(0) (0.054 g, 0.047 mmol). After stirring at 80° C. overnight, the mixture was diluted with water and extracted with ethyl acetate (50 mL×3). The organic phase was washed with brine and concentrated under reduced pressure to furnish a residue that was purified by preparative HPLC (method B) to give the titled compound (40.6 mg, yield 19%). $^1$H NMR (400 MHz, CDCl$_3$) δ ppm 7.46 (d, J=7.9 Hz, 2H), 7.32 (d, J=8.4 Hz, 2H), 7.09-6.98 (m, 3H), 5.42 (s, 2H), 4.94 (s, 2H), 3.82 (d, J=6.6 Hz, 7H), 3.56 (s, 3H).

Example 72

N-(3-{5-[(1S)-1-(4-chlorophenyl)ethyl]-3-methyl-4-oxo-4,5-dihydro[1,2]oxazolo[4,5-d]pyridazin-7-yl}phenyl)acetamide Example 78 (500 mg, 1.064 mmol) was separated by chiral super critical fluid chromatography (method A) to give recovered racemic material (50.6 mg, yield 11.2%), the titled compound (162.9 mg, yield 36.2%) and the enantiomer (208 mg, yield 46.2%, Example 34). $^1$H NMR (400 MHz, methanol-$d_4$) δ ppm 8.37 (s, 1H), 7.75 (d, J=7.2 Hz, 1H), 7.59 (d, J=8.0 Hz, 1H), 7.40-7.33 (m, 3H), 7.24 (d, J=8.0 Hz, 2H), 6.30 (q, J=6.8 Hz, 1H), 2.54 (s, 3H), 2.08 (s, 3H), 1.79 (d, J=7.2 Hz, 3H); LCMS (method C) (ESI+) m/z 423 (M+H)$^+$, retention time 3.364 minutes.

Example 73

3-{5-[1-(4-chlorophenyl)ethyl]-3-methyl-4-oxo-4,5-dihydro[1,2]oxazolo[4,5-d]pyridazin-7-yl})-4-methoxybenzoic acid 7-Bromo-5-[1-(4-chlorophenyl)ethyl]-3-methyl[1,2]oxazolo[4,5-d]pyridazin-4(5H)-one (80 mg, 0.217 mmol, Example 39—Step 5) in ethanol/toluene (1:1, 2.4 mL) was combined with 2 M aqueous sodium carbonate (0.163 mL, 0.326 mmol) and 4-methoxy-3-(4,4,5,5-tetramethyl-1,3,2-dioxaborolan-2-yl)benzoic acid (60.4 mg, 0.217 mmol). Then tetrakis(triphenylphosphine)palladium(0) (25.08 mg, 0.022 mmol) was added, and the mixture was heated in a Biotage® microwave reactor for 30 minutes at 130° C. under an argon atmosphere. The reaction mixture was partitioned between water and ethyl acetate. The aqueous phase was extracted twice more with ethyl acetate. The combined organic fractions were then washed with brine, dried over MgSO$_4$, and concentrated under reduced pressure. The residue was purified by flash chromatography on a Teledyne Isco CombiFlash® apparatus using a silica gel cartridge (4 g) eluted with 10% methanol/dichloromethane. The residue was stirred in a small amount of diisopropyl ether, and the precipitate was collected to give the titled compound (19 mg, yield 20%). $^1$H NMR (600 MHz, DMSO-$d_6$) δ ppm 12.94 (s, 1H), 8.13 (dd, J=8.7, 2.2 Hz, 1H), 8.03 (d, J=2.2 Hz, 1H), 7.41 (s, 4H), 6.33 (q, J=7.0 Hz, 1H), 3.87 (s, 3H), 2.59 (s, 3H), 1.74 (d, J=7.1 Hz, 3H); MS (ESI+) m/z 440.1 (M+H)$^+$.

Example 74

7-(4-fluorophenyl)-3-methyl-5-(pyridin-4-ylmethyl)[1,2]oxazolo[4,5-d]pyridazin-4(5H)-one To a solution of 7-(4-fluorophenyl)-3-methyl[1,2]oxazolo[4,5-d]pyridazin-4(5H)-one (Example 19, 100 mg, 0.408 mmol) in N,N-dimethylformamide (2 mL) was added NaH (14.68 mg, 0.612 mmol). The mixture was stirred at room temperature for 15 minutes, and then 4-(bromomethyl)pyridine hydrobromide (124 mg, 0.489 mmol) was added. The solid was collected by filtration and washed with water and methanol to give the titled compound (18 mg, yield 13%). $^1$H NMR (400 MHz, DMSO-$d_6$) δ ppm 8.09-8.06 (m, 2H), 7.68-7.65 (m, 2H), 7.45-7.41 (m, 2H), 7.22 (m, 1H), 5.41 (s, 2H), 3.84 (s, 3H), 2.59 (s, 3H); MS (APCI$^+$) m/z 434.0 (M+H)$^+$.

Example 75

5-[(R)-(4-chlorophenyl)(phenyl)methyl]-3,7-diethyl[1,2]oxazolo[4,5-d]pyridazin-4(5H)-one The racemic parent structure could be prepared as described in Example 114—Step 2 substituting 3,7-diethyl[1,2]oxazolo[4,5-d]pyridazin-4(5H)-one for 3,7-dimethyl-[1,2]oxazolo[4,5-d]pyridazin-4(5H)-one and 1-[bromo(phenyl)methyl]-4-chlorobenzene for 1-(1-bromoethyl)-4-chlorobenzene. The individual enantiomers of the mixture were separated by preparative chiral chromatography (Chiralpak® AD-H, 21×250 mm column, 5 m, concentration of 15 mg/mL in CH$_3$OH, flow rate 70 mL/minute CH$_3$OH, 20% CH$_3$OH/CO$_2$, 150 psi=10.34 bar) to afford the titled compound as the second-eluting enantiomer (relative to Example 89) with a retention time of 2.122 minutes, 94% ee. Stereocenter arbitrarily assigned. MS (ESI+) m/z 394 (M+H)+.

Example 76

5-(4-chlorobenzyl)-3-methyl-7-(2-methylphenyl)[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added o-tolylboronic acid (46.0 mg, 0.338 mmol), $K_2CO_3$ (0.097 g, 0.705 mmol) and tetrakis(triphenylphosphine)palladium(0) (0.033 g, 0.028 mmol). The resulting mixture was stirred at 80° C. overnight under $N_2$. After cooling down to room temperature, the reaction mixture was concentrated under reduced pressure to give a residue that was washed with a mixture of $CH_3OH$ and $H_2O$ to give the titled compound. Yield 35%
$^1$H NMR (DMSO, 400 MHz): δ 7.52 (d, J=7.50 Hz, 1H), 7.33-7.48 (m, 7H), 5.39 (s, 2H), 2.60 (s, 3H), 2.23 (s, 3H). m/z 365.8.

Example 77

7-(2-amino-3,5-difluorophenyl)-5-[1-(4-chlorophenyl)ethyl]-3-methyl[1,2]oxazolo[4,5-d]pyridazin-4(5H)-one The titled compound was obtained using the reaction conditions described for Example 6 substituting 2,4-difluoro-6-(4,4,5,5-tetramethyl-1,3,2-dioxaborolan-2-yl)aniline for methyl (4-chloro-2-(4,4,5,5-tetramethyl-1,3,2-dioxaborolan-2-yl)phenyl)carbamate. The reaction mixture was partitioned between ethyl acetate and water. The organic fraction was washed with brine, dried over $MgSO_4$, and concentrated under reduced pressure. The residue was purified by flash chromatography on a Teledyne Isco CombiFlash® Rf apparatus using a silica gel cartridge (4 g) eluted with 25% ethyl acetate/cyclohexane. The residue was triturated with a little ethyl acetate/diisopropyl ether (1:1), and the solid was dried overnight in a vacuum oven to give the titled compound (35 mg, yield 52%). $^1$H NMR (600 MHz, DMSO-$d_6$) δ ppm 7.44-7.31 (m, 6H), 6.37 (q, J=7.0 Hz, 1H), 5.68 (s, 2H), 2.62 (s, 3H), 1.75 (d, J=7.0 Hz, 3H); MS (ESI+) m/z 417.1 (M+H)+.

Example 78

N-(3-{5-[1-(4-chlorophenyl)ethyl]-3-methyl-4-oxo-4,5-dihydro[1,2]oxazolo[4,5-d]pyridazin-7-yl}phenyl)acetamide The reactions were conducted in parallel (different scale) but combined for purification.
The first batch: To a solution of 7-bromo-5-[1-(4-chlorophenyl)ethyl]-3-methyl[1,2]oxazolo[4,5-d]pyridazin-4(5H)-one (40 mg, 0.109 mmol, Example 39—Step 5) and (3-acetamidophenyl)boronic acid (38.8 mg, 0.217 mmol) in 1,2-dimethoxyethane:water (1.25 mL, 4:1), were added potassium carbonate (37.5 mg, 0.271 mmol) and tetrakis(triphenylphosphine)palladium(0) (12.54 mg, 10.85 µmol). Then the reaction mixture was stirred at 100° C. under a nitrogen atmosphere overnight. Then the reaction mixture was concentrated under reduced pressure, and the aqueous mixture was extracted with ethyl acetate. The organic phase was dried and concentrated. The residue was purified by preparative thin layer chromatography on silica gel and eluted with EtOAc/PE to give crude titled compound.
The second batch: To a solution of 7-bromo-5-[1-(4-chlorophenyl)ethyl]-3-methyl[1,2]oxazolo[4,5-d]pyridazin-4(5H)-one (180 mg, 0.488 mmol, Example 39—Step 5) and (3-acetamidophenyl)boronic acid (175 mg, 0.977 mmol) in 1,2-dimethoxyethane:water (5 mL, 4:1), were added potassium carbonate (169 mg, 1.221 mmol) and tetrakis(triphenylphosphine)palladium(0) (56.4 mg, 0.049 mmol). Then the reaction mixture was stirred at 90° C. under a nitrogen atmosphere overnight. The reaction mixture was concentrated under reduced pressure, and the residue was purified by preparative thin layer chromatography on silica gel and eluted with EtOAc/PE to give crude titled compound.
The third batch: To a solution of 7-bromo-5-[1-(4-chlorophenyl)ethyl]-3-methyl[1,2]oxazolo[4,5-d]pyridazin-4(5H)-one (500 mg, 1.221 mmol, Example 39—Step 5) and (3-acetamidophenyl)boronic acid (328 mg, 1.831 mmol) in 1,2-dimethoxyethane:water (20 mL, 4:1), were added potassium carbonate (422 mg, 3.05 mmol) and tetrakis(triphenylphosphine)palladium(0) (141 mg, 0.122 mmol). Then the reaction mixture was stirred at 90° C. under nitrogen overnight. Then the reaction mixture was concentrated under reduced pressure, and the residue was purified by column chromatography on silica gel (EtOAc/PE=1:5-1:2) to give crude titled compound.
The fourth batch: To a solution of 7-bromo-5-[1-(4-chlorophenyl)ethyl]-3-methyl[1,2]oxazolo[4,5-d]pyridazin-4(5H)-one (1.7 g, 4.15 mmol, Example 39—Step 5) and (3-acetamidophenyl)boronic acid (1.114 g, 6.23 mmol) in 1,2-dimethoxyethane:water (50 mL, 4:1), were added potassium carbonate (1.434 g, 10.38 mmol) and tetrakis(triphenylphosphine)palladium(0) (0.480 g, 0.415 mmol). Then the reaction mixture was stirred at 90° C. under nitrogen overnight. The reaction mixture was concentrated under reduced pressure, and the residue was purified by column chromatography on silica gel (EtOAc/PE=1:5~1:2) to give crude titled compound.
The above crude products in four batches were combined, and then further purified by preparative high performance liquid chromatography (method A) to give the titled compound (500 mg, yield 17.9%). $^1$H NMR (400 MHz $CDCl_3$) δ ppm 8.18 (s, 1H), 7.83 (d, J=7.6 Hz, 1H), 7.67 (d, J=8.0 Hz, 1H), 7.45-7.39 (m, 3H), 7.25-7.23 (m, 3H), 6.36 (q, J=7.2 Hz, 1H), 2.64 (s, 3H), 2.19 (s, 3H), 1.82 (d, J=7.2 Hz, 3H); LCMS (method B) (ESI+) m/z 423 (M+H)+, retention time 3.038 minutes.

Example 79

5-[1-(4-chlorophenyl)ethyl]-7-[2-methoxy-5-(trifluoromethyl)phenyl]-3-methyl[1,2]oxazolo[4,5-d]pyridazin-4(5H)-one 7-Bromo-5-[1-(4-chlorophenyl)ethyl]-3-methyl[1,2]oxazolo[4,5-d]pyridazin-4(5H)-one (80 mg, 0.217 mmol, Example 39—Step 5) in ethanol/toluene (1:1, 2 mL) was combined with 2 M aqueous sodium carbonate (0.163 mL, 0.326 mmol) and ((2-methoxy-5-(trifluoromethyl)phenyl)boronic acid (47.7 mg, 0.217 mmol). Then tetrakis(triphenylphosphine)palladium(0) (25.08 mg, 0.022 mmol) was added, and the mixture was heated in a CEM microwave reactor for 30 minutes at 130° C. under an argon atmosphere. The reaction mixture was partitioned between water and ethyl acetate. The organic fraction was then washed with brine, dried over $MgSO_4$, and concentrated under reduced pressure. The residue was purified by flash chromatography on a Teledyne Isco CombiFlash® Rf apparatus using a silica gel cartridge (4 g) eluted with 20% ethyl acetate/cyclohexane. The titled compound was obtained after drying overnight in a vacuum oven (16 mg, yield 16%). $^1$H NMR (600 MHz, DMSO-$d_6$) δ ppm 7.53 (d, J=8.7 Hz, 1H), 7.41—$^1$H NMR (600 MHz, DMSO-$d_6$) δ ppm 7.95 (ddd, J=8.8, 2.5, 0.8 Hz, 1H), 7.74 (d, J=2.6 Hz, 1H), 7.45 (d, J=8.7 Hz, 1H), 7.41 (s, 3H), 6.31 (q, J=7.0 Hz, 1H), 3.89 (s, 3H), 2.59 (s, 3H), 1.73 (d, J=7.1 Hz, 3H), 1.40 (s, 3H), 1.09 (s, 2H); MS (ESI+) m/z 464.1 (M+H)$^+$.

Example 80

5-(4-chlorobenzyl)-7-(2,5-dimethoxyphenyl)-3-phenyl[1,2]oxazolo[4,5-d]pyridazin-4(5H)-one To a solution of 7-bromo-5-(4-chlorobenzyl)-3-phenyl[1,2]oxazolo[4,5-d]pyridazin-4(5H)-one (120 mg, 0.288 mmol, Example 107—Step 6) in 1,2-dimethoxyethane (4 mL) and water (1 mL) was added (2,5-dimethoxyphenyl)boronic acid (62.9 mg, 0.346 mmol), $K_2CO_3$ (100 mg, 0.720 mmol) and tetrakis(triphenylphosphine)palladium(0) (33.3 mg, 0.029 mmol). The mixture was stirred at 80° C. under $N_2$ overnight. The mixture was diluted with water and extracted with ethyl acetate. The organic phase was washed with brine and concentrated under reduced pressure. The residue was washed with methanol and dried to give the titled compound (113 mg, yield 83%). $^1$H NMR (400 MHz, DMSO-$d_6$) δ ppm 8.24 (d, J=7.06 Hz, 2H), 7.49-7.65 (m, 3H), 7.41 (s, 4H) 7.08-7.24 (m, 2H), 7.04 (d, J=2.65 Hz, 1H), 5.43 (s, 2H), 3.75 (d, J=2.21 Hz, 6H); LCMS (method E) (ESI+) m/z 474.1 (M+H)$^+$, retention time 3.241 minutes.

Example 81

7-(2,5-dimethoxyphenyl)-5-[4-fluoro-3-(trifluoromethyl)benzyl]-3-methyl[1,2]oxazolo[4,5-d]pyridazin-4(5H)-one The titled compound was prepared using the procedures described for Example 5 substituting (2,5-dimethoxyphenyl)boronic acid for (2,4-dimethoxyphenyl)boronic acid in Step 1 and 4-(bromomethyl)-1-fluoro-2-(trifluoromethyl)benzene for 4-(bromomethyl)pyridine in Step 2. Yield 35%.

$^1$H NMR (CDCl$_3$, 400 MHz): δ 7.93 (br. s, 2H), 7.37-7.49 (m, 3H), 7.31 (d, J=8.38 Hz, 3H), 5.44 (s, 2H), 2.71 (s, 3H), 2.47 (s, 3H). m/z 365.8.

Example 82

3-{5-[(1S)-1-(4-chlorophenyl)ethyl]-3-methyl-4-oxo-4,5-dihydro[1,2]oxazolo[4,5-d]pyridazin-7-yl}-4-methoxy-N-methylbenzamide Step 1: 7-bromo-5-[(1S)-1-(4-chlorophenyl)ethyl]-3-methyl[1,2]oxazolo[4,5-d]pyridazin-4(5H)-(one)

7-bromo-5-[(1S)-1-(4-chlorophenyl)ethyl]-3-methyl[1,2]oxazolo[4,5-d]pyridazin-4(5H)-(one) was separated by SFC chiral chromatography (3.58 g, column: Whelk-O1 (S,S) (Regis Technologies), Liquid phase: 5-50% MeOH:CO2 10 min @ 3 ml/min, 150 bar to give 7-bromo-5-[(1S)-1-(4-chlorophenyl)ethyl]-3-methyl[1,2]oxazolo[4,5-d]pyridazin-4(5H)-(one) (1554 mg Rotation value [α]=+144.9° in MeOH (c=3.33 mg/1 ml, Peak A: RT=2.466 min, 99.6% ee) and (R)-7-bromo-5-(1-(4-chlorophenyl)ethyl)-3-methyl-isoxazolo[4,5-d]pyridazin-4(5H)-one (1454 mg, rotation value [α]=−129.7° in MeOH (c=3.92 mg/1, Peak B: RT=4.149 min, 96.7% ee).

Step 2: 3-{5-[(1S)-1-(4-chlorophenyl)ethyl]-3-methyl-4-oxo-4,5-dihydro[1,2]oxazolo[4,5-d]pyridazin-7-yl}-4-methoxy-N-(methylbenzamide)

Under argon, 7-bromo-5-[(1S)-1-(4-chlorophenyl)ethyl]-3-methyl[1,2]oxazolo[4,5-d]pyridazin-4(5H)-one (300 mg, 0.81 mmol) was suspended in toluene and ethanol (6 ml, 1:1). 2 M Aqueous sodium bicarbonate (0.6 ml, 1.22 mmol) and 4-methoxy-N-methyl-3-(4,4,5,5-tetramethyl-1,3,2-dioxaborolan-2-yl)benzamide (237 mg, 0.81 mmol, Example 119—Step 1) were added followed by tetrakis(triphenylphosphine)palladium(0) (94 mg, 0.08 mmol). The reaction mixture was heated under stirring in a CEM microwave reactor at 130° C. for 30 minutes. The reaction mixture was then partitioned between water and ethyl acetate. The organic fraction was washed with brine, dried over MgSO$_4$ and then concentrated under reduced pressure. The residue was purified by flash chromatography on a Teledyne Isco CombiFlash® Rf apparatus using a silica gel cartridge (12 g) eluted with 50% ethyl acetate/heptane. The residue was stirred with diisopropyl ether, and the solid was collected by vacuum filtration and dried in a vacuum oven overnight. A second flash chromatography was performed on the material in the mother liquor on a Teledyne Isco CombiFlash® Rf apparatus using a silica gel cartridge (4 g, 15 μm) eluted with 50% ethyl acetate/heptane was performed. The residue was stirred with diisopropyl ether and collected by vacuum filtration. The two solid batches were combined and dried in a vacuum oven overnight to give the titled compound (40 mg, yield 11%). $^1$H NMR (600 MHz, DMSO-$d_6$) δ ppm 8.46 (q, J=4.6 Hz, 1H), 8.05 (dd, J=8.7, 2.2 Hz, 1H), 7.95 (d, J=2.2 Hz, 1H), 7.41 (s, 4H), 7.32 (d, J=8.8 Hz, 1H), 6.33 (q, J=7.0 Hz, 1H), 3.60 (p, J=6.1 Hz, 0H), 2.79 (d, J=4.5 Hz, 3H), 2.59 (s, 2H), 1.75 (d, J=7.0 Hz, 4H), 1.04 (d, J=6.0 Hz, 3H); MS (ESI+) m/z 453.0 (M+H)+; [α]=+20° (c=1 mg/mL, CH$_3$OH)

Example 83

5-(4-chlorobenzyl)-7-(4-fluorophenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (100 mg, 0.282 mmol, Example 2—Step 6) in 1,2-dimethoxyethane (4 mL) and water (1 mL) was added 4-fluorophenylboronic acid (47 mg, 0.338 mmol), potassium carbonate (97 mg, 0.705 mmol) and tetrakis(triphenylphosphine)palladium(0) (33 mg, 0.028 mmol). The resulting mixture was stirred at 80° C. overnight under $N_2$. After cooling to room temperature, the reaction mixture was concentrated under reduced pressure to get a residue that was washed with a mixture of methanol and water to give the titled compound, 68 mg (65%). $^1$H NMR (400 MHz, CDCl$_3$) δ ppm 8.16-8.13 (m, 2H), 7.44-7.42 (m, 2H), 7.32-7.30 (m, 2H), 7.24-7.20 (m, 2H), 5.43 (s, 2H), 2.71 (s, 3H); LCMS (method F) (ESI+) m/z 369.8 (M+H)$^+$.

Example 84

5-(3-chloro-4-fluorobenzyl)-3,7-dimethyl[1,2]oxazolo[4,5-d]pyridazin-4(5H)-one

The titled compound was prepared using the procedure described in Example 20 substituting 4-(bromomethyl)-2- chloro-1-fluorobenzene for 1-(bromomethyl)-2-fluorobenzene. Purification was achieved by preparative liquid chromatography (Method C, 0.5-8.5 minutes linear gradient 50-80% A). $^1$H NMR (400 MHz, DMSO-$d_6$/$D_2O$) δ ppm 7.52 (dd, J=7.1, 2.1 Hz, 1H), 7.37 (t, J=8.9 Hz, 1H), 7.32 (ddd, J=8.5, 4.9, 2.1 Hz, 1H), 5.29 (s, 2H), 2.57 (s, 3H), 2.51 (s, 3H); MS (APCI$^+$) m/z 308.0 (M+H)$^+$.

Example 85

N-(3-{5-[2-fluoro-5-(trifluoromethyl)benzyl]-3-methyl-4-oxo-4,5-dihydro[1,2]oxazolo[4,5-d]pyridazin-7-yl}phenyl)acetamide The titled compound was prepared using the procedures described for Example 5 substituting (3-acetamidophenyl)boronic acid for (2,4-dimethoxyphenyl)boronic acid in Step 1 and 2-(bromomethyl)-1-fluoro-4-(trifluoromethyl)benzene for 4-(bromomethyl)pyridine in Step 2. Yield 36%.

$^1$H NMR (400 MHz, DMSO): δ 10.18 (br, 1H), 8.29 (s, 1H), 7.84-7.76 (m, 3H), 7.64-7.62 (d, J=7.6 Hz, 1H), 7.51-7.44 (m, 2H), 5.53 (s, 2H), 2.60 (s, 3H), 2.06 (s, 3H). m/z 461.2.

Example 86

7-(2-aminopyridin-3-yl)-5-[1-(4-chlorophenyl)ethyl]-3-methyl[1,2]oxazolo[4,5-d]pyridazin-4(5H)-one 7-Bromo-5-[1-(4-chlorophenyl)ethyl]-3-methyl[1,2]oxazolo[4,5-d]pyridazin-4(5H)-one (60 mg, 0.163 mmol, Example 39—Step 5) was combined with potassium carbonate (56.2 mg, 0.407 mmol) and 3-(4,4,5,5-tetramethyl-1,3,2-dioxaborolan-2-yl)pyridin-2-amine (43.0 mg, 0.195 mmol) in 1,2-dimethoxyethane and water (5 mL, 4:1). Then tetrakis(triphenylphosphine)palladium(0) (18.81 mg, 0.016 mmol) was added, and the mixture was heated for 4 hours at 80° C. under an argon atmosphere. The reaction mixture was partitioned between water and ethyl acetate. The organic fraction was then washed with brine, dried over MgSO$_4$, and concentrated under reduced pressure. The residue was purified by flash chromatography using a Teledyne Isco CombiFlash® Rf apparatus with a 4 g silica gel cartridge eluted with 40% ethyl acetate/cyclohexane. The product containing fractions were combined and concentrated. The residue was stirred with a small amount of ethyl acetate/diisopropyl ether (1:1), and the solid was dried in a vacuum oven overnight to give the titled compound (22 mg, yield 35%). $^1$H NMR (600 MHz, DMSO-$d_6$) δ ppm 8.13-8.05 (m, 2H), 7.44-7.37 (m, 4H), 6.76 (dd, J=7.7, 4.8 Hz, 1H), 6.65 (s, 2H), 6.37 (q, J=7.0 Hz, 1H), 3.36-3.31 (m, 0H), 2.62 (s, 3H), 1.76 (d, J=7.0 Hz, 3H), 1.04 (d, J=6.1 Hz, 0H); MS (ESI+) m/z 382.0 (M+H)$^+$.

Example 87

5-(4-chlorobenzyl)-7-(2,4-dimethoxyphenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added (2,4-dimethoxyphenyl)boronic acid (61.5 mg, 0.338 mmol), K$_2$CO$_3$ (0.097 g, 0.705 mmol) and tetrakis(triphenylphosphine)palladium(0) (0.033 g, 0.028 mmol). The resulting mixture was stirred at 80° C. overnight under N$_2$. After cooling down to room temperature, the reaction mixture was concentrated under reduced pressure to give a residue that was washed with a mixture of CH$_3$OH and H$_2$O to give the titled compound. Yield 28%.

$^1$H NMR (CDCl$_3$, 400 MHz): δ 7.37 (d, J=8.38 Hz, 2H), 7.21-7.32 (m, 3H), 6.50-6.58 (m, 2H), 5.32 (s, 2H), 3.81 (s, 3H), 3.76 (s, 3H), 2.61 (s, 3H). m/z 411.8.

Example 88

5-(5-chloro-2-fluorobenzyl)-3,7-dimethyl[1,2]oxazolo[4,5-d]pyridazin-4(5H)-one

The titled compound was prepared using the procedure described in Example 20 substituting 2-(bromomethyl)-4-chloro-1-fluorobenzene for 1-(bromomethyl)-2-fluorobenzene. Purification was achieved by preparative liquid chromatography (Method C, 0.5-8.5 minutes linear gradient 50-80% A). $^1$H NMR (400 MHz, DMSO-$d_6$/$D_2O$) δ ppm 7.42 (ddd, J=8.8, 4.5, 2.8 Hz, 1H), 7.33-7.25 (m, 2H), 5.34 (s, 2H), 2.57 (s, 3H), 2.50 (s, 3H). MS (APCI$^+$) m/z 308.0 (M+H)$^+$.

Example 89

5-[(S)-(4-chlorophenyl)(phenyl)methyl]-3,7-diethyl[1,2]oxazolo[4,5-d]pyridazin-4(5H)-one The racemic parent structure could be prepared as described in Example 114—Step 2 substituting 3,7-diethyl[1,2]oxazolo[4,5-d]pyridazin-4(5H)-one for 3,7-dimethyl[1,2]oxazolo[4,5-d]pyridazin-4(5H)-one and 1-[bromo(phenyl)methyl]-4-chlorobenzene for 1-(1-bromoethyl)-4-chlorobenzene. The individual enantiomers of the mixture were separated by preparative chiral chromatography (Chiralpak® AD-H, 21×250 mm column, 5 m, concentration of 15 mg/mL in CH$_3$OH, flow rate 70 mL/minute CH$_3$OH, 20% CH$_3$OH/CO$_2$, 150 psi=10.34 bar) to afford the titled compound as the first-eluting enantiomer (relative to Example 75) with a retention time of 1.837 minutes, 99% ee. Stereocenter arbitrarily assigned. MS (ESI$^+$) m/z 394 (M+H)$^+$.

Example 90

5-(4-chlorobenzyl)-7-(3,5-difluorophenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added (3,5-difluorophenyl)boronic acid (53.4 mg, 0.338 mmol), K$_2$CO$_3$ (0.097 g, 0.705 mmol) and tetrakis(triphenylphosphine)palladium(0) (0.033 g, 0.028 mmol). The resulting mixture was stirred at 80° C. overnight under N$_2$. After cooling down to room temperature, the reaction mixture was concentrated under reduced pressure to give a residue that was washed with a mixture of CH$_3$OH and H$_2$O to give the titled compound. Yield 21%.

$^1$H NMR (DMSO, 400 MHz): δ 7.72 (d, J=6.62 Hz, 2H) 7.32-7.55 (m, 5H) 5.45 (s, 2H) 2.61 (s, 3H). m/z 387.8.

Example 91

N-{3-[5-(4-chlorobenzyl)-4-oxo-3-propyl-4,5-dihydro[1,2]oxazolo[4,5-d]pyridazin-7-yl]phenyl}acetamide Step 1: methyl 4-oxo-2-propyl-4,5-dihydrofuran-3-carboxylate To a solution of magnesium ethanolate (8.68 g, 76 mmol) in toluene (50 mL) cooled in an ice bath was added ethyl 3-oxohexanoate (12 g, 76 mmol) dropwise. The mixture was stirred at room temperature for 1 hour. Anhydrous acetonitrile (5 mL) was added to the mixture at −10 OC, followed by the slow addition of 2-chloroacetyl chloride (10.28 g, 91 mmol). The mixture was allowed to warm to room temperature and left to stir for 2 hours. A diluted solution of sulfuric acid (0.8 mL acid in 28 mL ice/water) was added followed by extraction with tert-butyl methyl ether. The combined organic fractions were dried over $Na_2SO_4$ and filtered. The filtrate was cooled to 0° C. A solution of triethylamine (23.33 g, 231 mmol) in tert-butyl methyl ether (50 mL) was added. The reaction mixture was left to stir at room temperature overnight. The mixture was diluted with water and extracted with dichloromethane (200 mL×3). The organic phase was concentrated under reduced pressure. The residue was purified by column chromatography on silica gel and eluted with EtOAc/PE to give the titled compound (9.3 g, yield 62%).

Step 2: methyl 5-(hydroxymethyl)-3-propyl-1,2-oxazole-4-carboxylate

To a solution of methyl 4-oxo-2-propyl-4,5-dihydrofuran-3-carboxylate (9.21 g, 46.5 mmol, Step 1 in anhydrous ethanol (100 mL) was added sodium acetate (5.72 g, 69.7 mmol) and $NH_2OH*HCl$ (3.87 g, 55.8 mmol). The mixture was heated to reflux for 1 hour. The solvent was removed under reduced pressure to give a residue that was diluted with water and extracted with ethyl acetate (200 mL×3). The organic phase was washed with brine, dried over $Na_2SO_4$, and concentrated under reduced pressure. The residue was purified by column chromatography on silica gel (EtOAc/PE, 1:20-5) to give the titled compound (4.25 g, yield 42%).

Step 3: methyl 5-formyl-3-propyl-1,2-oxazole-4-carboxylate

To a solution of methyl 5-(hydroxymethyl)-3-propyl-1,2-oxazole-4-carboxylate (4.25 g, 19.93 mmol, Step 2) in anhydrous toluene (100 mL) was added $MnO_2$ (5.20 g, 59.8 mmol). The mixture was heated to reflux for 6 hours. The reaction mixture was concentrated under reduced pressure. The residue was purified by column chromatography on silica gel (EtOAc/PE, 1: 20-5) to give the titled compound (3.6 g, yield 86%).

Step 4: 3-propyl[1,2]oxazolo[4,5-d]pyridazin-4(5H)-one

To a solution of methyl 5-formyl-3-propyl-1,2-oxazole-4-carboxylate (3.6 g, 17.04 mmol, Step 3) in anhydrous ethanol (50 mL) was added hydrazine hydrate (2.67 mL, 85 mmol) 0° C. The resulting mixture was stirred at room temperature for 2 hours. The solid was collected by filtration and dried to give the titled compound (2.8 g, yield 92%). $^1H$ NMR (400 MHz, $CDCl_3$) δ ppm 8.41-8.08 (m, 1H), 6.41-6.30 (m, 1H), 3.13-2.76 (m, 2H), 2.07-1.65 (m, 2H), 1.13-0.91 (m, 3H).

Step 5: 7-bromo-3-propyl[1,2]oxazolo[4,5-d]pyridazin-4(5H)-one

To a solution of 3-propyl[1,2]oxazolo[4,5-d]pyridazin-4 (5H)-one (2.8 g, 15.63 mmol, Step 4) and $LiOH*H_2O$ (3.28 g, 78 mmol) in methanol (50 mL) was added $Br_2$ (2.41 mL, 46.9 mmol) at 0° C. The resulting mixture was stirred at 70° C. for 12 hours. The volatiles were removed under reduced pressure. The residue was poured into $H_2O$ and extracted with ethyl acetate (100 mL×3). The combined organic layers were dried over $Na_2SO_4$ and concentrated in vacuum. The residue was purified by column chromatography on silica gel (EtOAc/PE, 1: 20-5) to give the titled compound (1.5 g, yield 37%). $^1H$ NMR (400 MHz, $CDCl_3$) δ ppm 10.85 (br. s., 1H), 2.96 (t, J=7.7 Hz, 2H), 1.82 (sxt, J=7.4 Hz, 2H), 1.02-0.87 (m, 3H).

Step 6: 7-bromo-5-(4-chlorobenzyl)-3-propyl[1,2]oxazolo[4,5-d]pyridazin-4(5H)-one To a solution of: 7-bromo-3-propyl[1,2]oxazolo[4,5-d]pyridazin-4(5H)-one (400 mg, 1.550 mmol, Step 5) in N,N-dimethylformamide (10 mL) was added $K_2CO_3$ (857 mg, 6.20 mmol) and 1-chloro-4-(chloromethyl)benzene (374 mg, 2.325 mmol). After stirring at 50° C. for 2 hours, the mixture was diluted with water and extracted with ethyl acetate (50 mL×3). The combined organic phase was washed with brine and concentrated under reduced pressure to give the titled compound (400 mg, yield 67%) which was used directly for the next step.

Step 7: N-{3-[5-(4-chlorobenzyl)-4-oxo-3-propyl-4,5-dihydro[1,2]oxazolo[4,5-d]pyridazin-7-yl]phenyl}acetamide To a solution of 7-bromo-5-(4-chlorobenzyl)-3-propyl[1,2]oxazolo[4,5-d]pyridazin-4(5H)-one (180 mg, 0.454 mmol, Step 6) in N,N-dimethylformamide (2 mL) and water (0.5 mL) was added (3-acetamidophenyl)boronic acid (97 mg, 0.545 mmol), $K_2CO_3$ (157 mg, 1.134 mmol) and tetrakis (triphenylphosphine)palladium(0) (52.4 mg, 0.045 mmol). After stirring at 80° C. overnight under nitrogen, the mixture was diluted with water and extracted with ethyl acetate (50 mL×3). The organic phase was washed with brine and concentrated under reduced pressure. The residue was purified by preparative HPLC (method C) to give the titled compound (61 mg, yield 29%). $^1H$ NMR (400 MHz, $CDCl_3$) δ ppm 8.11 (s, 1H), 7.83 (d, J=7.9 Hz, 1H), 7.71 (d, J=7.5 Hz, 1H), 7.48-7.35 (m, 3H), 7.33-7.22 (m, 3H), 5.37 (s, 2H), 3.07-2.90 (m, 2H), 2.17 (s, 3H), 1.82 (sxt, J=7.4 Hz, 2H), 1.06-0.91 (m, 3H); LCMS (method B) (ESI+) m/z 437.1 (M+H)+, retention time 3.319 minutes.

Example 92

5-(4-chloro-2-fluorobenzyl)-3,7-dimethyl[1,2]oxazolo[4,5-d]pyridazin-4(5H)-one The titled compound was prepared using the procedure described in Example 20 substituting 1-(bromomethyl)-4-chloro-2-fluorobenzene for 1-(bromomethyl)-2-fluorobenzene. Purification was achieved by preparative liquid chromatography (Method C, 0.5-8.5 minutes linear gradient 50-80% A). $^1H$ NMR (400 MHz, DMSO-$d_6$/$D_2O$) δ ppm 7.43 (dd, J=10.0, 2.0 Hz, 1H), 7.30 (t, J=8.1 Hz, 1H), 7.25 (dd, J=8.4, 2.0 Hz, 1H), 5.33 (s, 2H), 2.57 (s, 3H), 2.49 (s, 3H); MS (APCI+) m/z 308.0 (M+H)+.

Example 93

7-(2,5-dimethoxyphenyl)-3-methyl-5-(pyridin-4-ylmethyl)[1,2]oxazolo[4,5-d]pyridazin-4(5H)-one The titled compound was prepared using the procedures described for Example 5 substituting (2,5-dimethoxyphenyl)boronic acid for (2,4-dimethoxyphenyl)boronic acid in Step 1. Yield 14%.

¹H NMR (400 MHz, CD₃OD): δ8.78 (s, 2H), 7.97-7.96 (m, 2H), 7.12 (s, 2H), 7.05 (s, 1H), 5.74 (s, 2H), 3.79 (s, 6H), 2.64 (s, 3H). m/z 379.0.

Example 94

N-{2-fluoro-5-[3-methyl-4-oxo-5-(pyridin-4-ylmethyl)-4,5-dihydro[1,2]oxazolo[4,5-d]pyridazin-7-yl]phenyl}acetamide The titled compound was prepared using the procedures described for Example 5 substituting (3-acetamido-4-fluorophenyl)boronic acid for (2,4-dimethoxyphenyl)boronic acid in Step 1. Yield 16%.
¹H NMR (400 MHz, DMSO): δ 9.92 (br, 1H), 8.76 (s, 2H), 8.64-8.62 (d, J=6.8 Hz, 1H), 7.79-7.77 (m, 3H), 7.49-7.44 (m, 1H), 5.66 (s, 2H), 2.60 (s, 3H), 2.11 (s, 3H). m/z 394.2.

Example 95

7-(2,5-dimethoxyphenyl)-3-methyl-5-[4-(trifluoromethyl)benzyl][1,2]oxazolo[4,5-d]pyridazin-4(5H)-one The titled compound was prepared using the procedures described for Example 5 substituting (2,5-dimethoxyphenyl)boronic acid for (2,4-dimethoxyphenyl)boronic acid in Step 1 and 1-(bromomethyl)-4-(trifluoromethyl)benzene for 4-(bromomethyl)pyridine in Step 2. Yield 26%.
1H NMR (400 MHz, CD₃OD): δ7.66-7.64 (d, J=8.0 Hz, 2H), 7.60-7.58 (d, J=8.4 Hz, 2H), 7.10 (s, 2H), 7.00 (s, 1H), 5.52 (s, 2H), 3.78 (s, 3H), 3.77 (s, 3H), 2.63 (s, 3H). m/z 446.0.

Example 96

N-{3-[5-(4-chlorobenzyl)-4-oxo-3-(propan-2-yl)-4,5-dihydro[1,2]oxazolo[4,5-d]pyridazin-7-yl]phenyl}acetamide Step 1: methyl 4-oxo-2-(propan-2-yl)-4,5-dihydrofuran-3-carboxylate To a solution of magnesium ethanolate (23.81 g, 208 mmol) in toluene (150 mL) chilled in an ice bath was added ethyl 4-methyl-3-oxopentanoate (25 g, 173 mmol) dropwise. The mixture was stirred at room temperature for 1 hour. Anhydrous acetonitrile (150 mL) was added to the mixture at −10° C. followed by the slow addition of 2-chloroacetyl chloride (19.59 g, 173 mmol). The mixture was allowed to warm to room temperature and left to stir for 2 hours. A diluted solution of sulfuric acid was added followed by extraction with tert-butyl methyl ether. The combined organic phase was dried over Na₂SO₄ and filtered. The filtrate was cooled to 0° C. A solution of triethylamine (48.3 ml, 347 mmol) in tert-butyl methyl ether (100 mL) was added. The reaction mixture was stirred at room temperature overnight. The mixture was diluted with water and extracted with dichloromethane. The organic phase was concentrated under reduced pressure to supply a residue that was purified by chromatography on silica gel and eluted with EtOAc/PE to give the titled compound (28 g, yield 88%). ¹H NMR (400 MHz, CDCl₃) δ ppm 4.56 (s, 2H), 4.27 (q, J=7.1 Hz, 2H), 3.86 (td, J=7.0, 13.8 Hz, 1H), 1.31 (t, J=7.3 Hz, 3H), 1.24 (d, J=7.1 Hz, 6H).

Step 2: methyl 5-(hydroxymethyl)-3-(propan-2-yl)-1,2-oxazole-4-carboxylate

To a solution of methyl 4-oxo-2-(propan-2-yl)-4,5-dihydrofuran-3-carboxylate (28 g, 141 mmol, Step 1) in anhydrous ethanol (150 mL) was added sodium acetate (17.38 g, 212 mmol) and NH₂OH*HCl (11.78 g, 170 mmol). The mixture was heated to reflux for 1 hour. The solvent was removed under reduced pressure to give a residue that was diluted with water and extracted with ethyl acetate. The organic phase was washed with brine, dried over Na₂SO₄, and concentrated in vacuum. The residue was purified by column chromatography on silica gel (EtOAc/PE, 1:20-5) to give the titled compound (19 g, yield 63%) which was used directly in the next step.

Step 3: methyl 5-formyl-3-(propan-2-yl)-1,2-oxazole-4-carboxylate

A mixture of methyl 5-(hydroxymethyl)-3-(propan-2-yl)-1,2-oxazole-4-carboxylate (4.25 g, 19.93 mmol, Step 2) and MnO₂ (23.24 g, 267 mmol) in anhydrous toluene (100 mL) was heated to reflux for 6 hours. The volatiles were removed under reduced pressure. The residue was purified by column chromatography on silica gel (EtOAc/PE, 1:20-5) to give the titled compound (10 g, yield 53%). ¹H NMR (400 MHz, CDCl₃) δ ppm 10.36 (s, 1H), 4.47 (q, J=7.1 Hz, 2H), 3.59-3.49 (m, 1H), 1.45 (t, J=7.3 Hz, 3H), 1.40 (d, J=6.6 Hz, 6H).

Step 4: 3-(propan-2-yl)[1,2]oxazolo[4,5-d]pyridazin-4(5H)-one

To a solution of methyl 5-formyl-3-(propan-2-yl)-1,2-oxazole-4-carboxylate (10 g, 47.3 mmol, Step 3) in anhydrous ethanol (100 mL) was added hydrazine hydrate (7.43 mL, 237 mmol) at 0° C. The resulting mixture was stirred at room temperature for 2 hours. The solid was collected by filtration and dried to give the titled compound (4.1 g, yield 48%) which was used directly in the next step. ¹H NMR (400 MHz, CDCl₃) δ ppm 11.48 (br. s., 1H), 8.34 (s, 1H), 3.53 (td, J=6.8, 13.7 Hz, 1H), 1.48 (d, J=7.1 Hz, 6H).

Step 5: 7-bromo-3-(propan-2-yl)[1,2]oxazolo[4,5-d]pyridazin-4(5H)-one

To a solution of 3-(propan-2-yl)[1,2]oxazolo[4,5-d]pyridazin-4(5H)-one (4.7 g, 26.2 mmol, Step 4) and LiOH*H₂O (3.14 g, 131 mmol) in CH₃OH (50 mL) was added Br₂ (4.05 mL, 79 mmol) at 0° C. The resulting mixture was stirred at 70° C. for 12 hours. The solvent was removed under reduced pressure to give a residue that was poured into H₂O and extracted with ethyl acetate. The combined organic layer was dried over Na₂SO₄ and concentrated in vacuum. The residue was purified by column chromatography on silica gel (EtOAc/PE, 1:20-5) to give the titled compound (1.3 g, yield 19%). ¹H NMR (400 MHz, CDCl₃) δ ppm 11.06 (br. s., 1H), 3.44 (td, J=7.0, 13.8 Hz, 1H), 1.41 (d, J=7.1 Hz, 6H).

Step 6: 7-bromo-5-(4-chlorobenzyl)-3-(propan-2-yl)[1,2]oxazolo[4,5-d]pyridazin-4(5H)-one To a solution of 7-bromo-3-(propan-2-yl)[1,2]oxazolo[4,5-d]pyridazin-4(5H)-one (600 mg, 2.3 mmol, Step 5) in N,N-dimethylformamide (10 mL) was added K₂CO₃ (640 mg, 4.6 mmol) and 1-chloro-4-(chloromethyl)benzene (650 mg, 4.1 mmol). After stirring at 50° C. for 2 hours, the mixture was diluted with water and extracted with ethyl acetate. The combined organic phase was washed with brine and concentrated in vacuum. The residue was purified by column chromatography on silica gel (EtOAc/PE, 1:20-5) to give the titled compound (560 mg, yield 59%). $^1$H NMR (400 MHz, CDCl$_3$) δ ppm 7.42-7.36 (m, 2H), 7.33-7.28 (m, 2H), 5.32 (s, 2H), 3.48 (td, J=6.7, 13.9 Hz, 1H), 1.49-1.39 (m, 6H).

Step 7: N-{3-[5-(4-chlorobenzyl)-4-oxo-3-(propan-2-yl)-4,5-dihydro[1,2]oxazolo[4,5-d]pyridazin-7-yl]phenyl}acetamide To a solution of 7-bromo-5-(4-chlorobenzyl)-3-(propan-2-yl)[1,2]oxazolo[4,5-d]pyridazin-4(5H)-one (280 mg, 0.73 mmol, Step 6) in N,N-dimethylformamide (2 mL) and water (0.5 mL) was added (3-acetamidophenyl)boronic acid (132 mg, 0.735 mmol), K$_2$CO$_3$ (202 mg, 1.47 mmol) and tetrakis(triphenylphosphine)palladium(O) (30 mg, 0.037 mmol). After stirring at 80° C. overnight under nitrogen, the mixture was diluted with water and extracted with ethyl acetate. The organic phase was washed with brine and concentrated under reduced pressure to give a residue that was purified by preparative HPLC (method C) to give the titled compound (45 mg, yield 14%). $^1$H NMR (400 MHz, CDCl$_3$) δ ppm 8.11 (s, 1H), 7.82 (d, J=7.9 Hz, 1H), 7.70 (d, J=7.9 Hz, 1H), 7.45-7.36 (m, 3H), 7.25 (d, J=8.4 Hz, 2H), 5.38 (s, 2H), 3.51 (td, J=7.0, 13.8 Hz, 1H), 2.17 (s, 3H), 1.41 (d, J=7.1 Hz, 6H); LCMS (method B) (ESI+) m/z 436.1 (M+H)+, retention time 3.407 minutes.

Example 97

7-(2-amino-5-fluorophenyl)-5-[1-(4-chlorophenyl)ethyl]-3-methyl[1,2]oxazolo[4,5-d]pyridazin-4(5H)-one The titled compound was obtained using the reaction conditions described for Example 6 substituting 4-fluoro-2-(4,4,5,5-tetramethyl-1,3,2-dioxaborolan-2-yl)aniline for methyl (4-chloro-2-(4,4,5,5-tetramethyl-1,3,2-dioxaborolan-2-yl)phenyl)carbamate. The reaction mixture was partitioned between ethyl acetate and water. The organic fraction was washed with brine, dried over MgSO$_4$, and concentrated under reduced pressure. The residue was purified by column chromatography on silica gel eluted with 40% ethyl acetate/cyclohexane. The residue was triturated with a little ethyl acetate/diisopropyl ether (1:1), and the solid was dried overnight in a vacuum oven to give the titled compound (19 mg, yield 29%). $^1$H NMR (600 MHz, DMSO-d$_6$) δ ppm 7.48 (dd, J=10.2, 3.0 Hz, 1H), 7.44-7.37 (m, 4H), 7.10 (ddd, J=9.0, 8.1, 3.0 Hz, 1H), 6.82 (dd, J=9.0, 5.1 Hz, 1H), 6.37 (q, J=7.0 Hz, 1H), 5.74 (s, 2H), 2.62 (s, 3H), 1.74 (d, J=7.0 Hz, 3H); MS (ESI+) m/z 399.0 (M+H)$^+$.

Example 98

5-[1-(4-chlorophenyl)ethyl]-7-[2-methoxy-5-(pyrrolidin-1-ylcarbonyl)phenyl]-3-methyl[1,2]oxazolo[4,5-d]pyridazin-4(5H)-one 3-{5-[1-(4-Chlorophenyl)ethyl]-3-methyl-4-oxo-4,5-dihydro[1,2]oxazolo[4,5-d]pyridazin-7-yl}-4-methoxybenzamide (100 mg, 0.228 mmol, Example 59), potassium carbonate (44.6 mg, 0.322 mmol), tetrabutylammonium hydrogensulfate (8.51 mg, 0.025 mmol) and pulverized sodium hydroxide (44.5 mg, 1.112 mmol) were combined in dried toluene (4 mL). 1,4-Dibromobutane (59.0 mg, 0.033 mL, 0.273 mmol) dissolved in toluene was added dropwise to the stirred mixture. The resultant mixture was heated to reflux or 2.5 hours. After cooling to room temperature, the reaction mixture was partitioned between ethyl acetate and water. The aqueous phase was extracted twice more with ethyl acetate. The combined organic fractions were washed with brine, dried over MgSO$_4$, and concentrated under reduced pressure. The residue was purified by flash chromatography using a Teledyne Isco CombiFlash® Rf apparatus with a 4 g RediSep® silica gel cartridge eluted with 8% methanol/dichloromethane. The residue was triturated with ethyl acetate/diisopropyl ether to give a precipitate that collected and dried under vacuum to give the titled compound (40 mg, yield 36%). $^1$H NMR (600 MHz, DMSO-d$_6$) δ ppm 7.78 (dd, J=8.6, 2.3 Hz, 1H), 7.60 (d, J=2.2 Hz, 1H), 7.44-7.37 (m, 4H), 7.28 (d, J=8.7 Hz, 1H), 6.32 (q, J=7.0 Hz, 1H), 3.85 (s, 3H), 3.46 (dt, J=8.6, 6.3 Hz, 4H), 2.59 (s, 3H), 1.85 (dp, J=25.5, 6.7 Hz, 3H), 1.73 (d, J=7.0 Hz, 3H); MS (ESI+) m/z 493.2 (M+H)$^+$.

Example 99

5-(4-chlorobenzyl)-7-(3,4-dimethoxyphenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added (3,4-dimethoxyphenyl)boronic acid (61.5 mg, 0.338 mmol), K$_2$CO$_3$ (0.097 g, 0.705 mmol) and tetrakis(triphenylphosphine)palladium(0) (0.033 g, 0.028 mmol). The resulting mixture was stirred at 80° C. overnight under N$_2$. After cooling down to room temperature, the reaction mixture was concentrated under reduced pressure to give a residue that was washed with a mixture of CH$_3$OH and H$_2$O to give the titled compound. Yield 73%.

$^1$H NMR (DMSO, 400 MHz): δ 7.66 (dd, J=8.38, 2.21 Hz, 1H), 7.52 (d, J=2.21 Hz, 1H), 7.42 (s, 4H), 7.15 (d, J=8.82 Hz, 1H), 5.41 (s, 2H), 3.82 (d, J=3.09 Hz, 6H), 2.60 (s, 3H). m/z 411.8.

Example 100

5-[1-(4-chlorophenyl)ethyl]-7-(2-hydroxyphenyl)-3-methyl[1,2]oxazolo[4,5-d]pyridazin-4(5H)-one The titled compound was obtained using the reaction conditions described for Example 6 substituting (2-hydroxyphenyl)boronic acid for methyl (4-chloro-2-(4,4,5,5-tetramethyl-1,3,2-dioxaborolan-2-yl)phenyl)carbamate. The reaction mixture was partitioned between ethyl acetate and water. The organic fraction was washed with brine, dried over MgSO$_4$, and concentrated under reduced pressure. The residue was purified by column chromatography on silica gel eluted with 30% ethyl acetate/cyclohexane. The residue was triturated with a little ethyl acetate/diisopropyl ether (1:1), and the solid was dried overnight in a vacuum oven to give the titled compound (21 mg, yield 34%). $^1$H NMR (600 MHz, DMSO-d$_6$) δ ppm 10.14 (s, 1H), 7.41 (s, 4H), 7.45-7.35 (m, 2H), 7.02-6.94 (m, 2H), 6.32 (q, J=7.0 Hz, 1H), 2.59 (s, 3H), 1.74 (d, J=7.0 Hz, 3H); MS (ESI+) m/z 382.1 (M+H)$^+$.

Example 101

7-(2-methoxyphenyl)-5-[4-methoxy-3-(trifluoromethyl)benzyl]-3-methyl[1,2]oxazolo[4,5-d]pyridazin-4(5H)-one The titled compound was prepared using the procedures described for Example 5 substituting (2-methoxyphenyl) boronic acid for (2,4-dimethoxyphenyl)boronic acid in Step 1 and 4-(bromomethyl)-1-methoxy-2-(trifluoromethyl)benzene for 4-(bromomethyl)pyridine in Step 2. Yield 15%.

$^1$H NMR (400 MHz, CD$_3$OD): δ 7.70-7.66 (m, 2H), 7.55-7.54 (m, 1H), 7.44-7.42 (m, 1H), 7.19-7.16 (m, 2H), 7.13-7.10 (m, 1H), 5.42 (s, 2H), 3.88 (s, 3H), 3.82 (s, 3H), 2.63 (s, 3H). m/z 445.3.

Example 102

5-(4-chlorobenzyl)-7-(2,5-dimethoxyphenyl)-3-methyl[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added (2,5-dimethoxyphenyl)boronic acid (61.5 mg, 0.338 mmol), K$_2$CO$_3$ (0.097 g, 0.705 mmol) and tetrakis(triphenylphosphine)palladium(0) (0.033 g, 0.028 mmol). The resulting mixture was stirred at 80° C. overnight under N$_2$. After cooling down to room temperature, the reaction mixture was concentrated under reduced pressure to give a residue that was washed with a mixture of CH$_3$OH and H$_2$O to give the titled compound. Yield 55%.

1H NMR (DMSO, 400 MHz): δ 7.34-7.45 (m, 4H), 7.09-7.20 (m, 2H), 6.98 (d, J=2.65 Hz, 1H), 5.37 (s, 2H), 3.74 (s, 3H), 3.71 (s, 3H), 2.57 (s, 3H). m/z 411.8.

Example 103

N-[4-methoxy-3-(3-methyl-4-oxo-5-{(1)-1-[4-(trifluoromethyl)phenyl]ethyl}-4,5-dihydro[1,2]oxazolo[4,5-d]pyridazin-7-yl)phenyl]acetamide Step 1: 7-(5-amino-2-methoxyphenyl)-3-methyl-5-{(1S)-1-[4-(trifluoromethyl)phenyl]ethyl}[1,2]oxazolo[4,5-d]pyridazin-4(5H)-one 7-Bromo-3-methyl-5-{(1S)-1-[4-(trifluoromethyl)phenyl]ethyl}[1,2]oxazolo[4,5-d]pyridazin-4(5H)-one (Example 35, 100 mg, 0.249 mmol), 4-methoxy-3-(4,4,5,5-tetramethyl-1,3,2-dioxaborolan-2-yl)aniline (68.1 mg, 0.274 mmol), sodium carbonate (79 mg, 0.746 mmol), and [1,1'-bis(diphenylphosphino)ferrocene]dichloropalladium(II) (18.19 mg, 0.025 mmol, PdCl$_2$(dppf)) were combined with 1,4-dioxane (3 mL) and water (0.3 mL) in a 5 mL sealed tube. The reaction mixture was irradiated at 100° C. for 60 minutes in a microwave reactor. The reaction mixture was then concentrated, and the residue was purified by silica gel column chromatography eluted with EtOAc/PE (1:4) to give the titled compound.

Step 2: N-[4-methoxy-3-(3-methyl-4-oxo-5-{(1S)-1-[4-(trifluoromethyl)phenyl]ethyl}-4,5-dihydro[1,2]oxazolo[4,5-d]pyridazin-7-yl)phenyl]acetamide 7-(5-Amino-2-methoxyphenyl)-3-methyl-5-{(1S)-1-[4-(trifluoromethyl)phenyl]ethyl}[1,2]oxazolo[4,5-d]pyridazin-4(5H)-one (50 mg, 0.113 mmol, Step 1) and triethylamine (14.80 mg, 0.146 mmol) were combined in dichloromethane (10 mL). Acetyl chloride (9.71 mg, 0.124 mmol) was added, and the reaction mixture was stirred at ambient temperature for 1 hour. The reaction mixture was concentrated under reduced pressure, and the residue was purified by silica gel column chromatography eluted with EtOAc/PE (4:1) to give the titled compound (10 mg, yield 15%). $^1$H NMR (400 MHz, CD$_3$OD) δ ppm 1.89 (d, 3H), 2.15 (s, 3H), 2.65 (s, 3H), 3.84 (s, 3H), 6.47 (q, 1H), 7.17 (d, 1H), 7.69 (m, 5H), 7.76 (s, 1H); $^{19}$F NMR (376 MHz, CD$_3$OD)$^6$F ppm −63.81 (s, 3F); MS (ESI+) m/z 509.3 (M+Na)$^+$.

Example 104

N-{3-[5-(4-chlorobenzyl)-4-oxo-3-phenyl-4,5-dihydro[1,2]oxazolo[4,5-d]pyridazin-7-yl]phenyl}acetamide Step 1: ethyl 4-oxo-2-phenyl-4,5-dihydrofuran-3-carboxylate To an ice bath chilled solution of magnesium ethanolate (14.29 g, 125 mmol) in toluene (30 mL) was added ethyl 3-oxo-3-phenylpropanoate (20 g, 104 mmol) dropwise. The mixture was stirred at room temperature for 1 hour. Anhydrous acetonitrile (30 mL) was added, and the mixture was cooled to −10° C. followed by the slowly addition of 2-chloroacetyl chloride (11.75 g, 104 mmol). The mixture was then allowed to warm to room temperature and left to stir for two hours. A dilute solution of sulfuric acid (6 mL acid in 190 mL ice/water) was added, and the mixture was extracted with tert-butyl methyl ether. The combined organic fractions were dried over Na$_2$SO$_4$ and filtered. The filtrate was then cooled to 0° C., and a solution of triethylamine (14.50 ml, 104 mmol) in tert-butyl methyl ether (24 mL) was added. The reaction mixture was stirred at room temperature overnight. The reaction mixture was diluted with water and extracted with dichloromethane. The organic phase was dried over Na$_2$SO$_4$ and concentrated under reduced pressure to give a residue that was purified by chromatography on silica gel and eluted with EtOAc/PE to supply the titled compound (7.1 g, yield 29%). $^1$H NMR (400 MHz, CDCl$_3$) δ ppm 7.89 (d, J=7.94 Hz, 2H), 7.55-7.65 (m, 1H), 7.44-7.55 (m, 2H), 4.76 (s, 2H), 4.32 (q, J=7.06 Hz, 2H), 4.03-4.23 (m, 1H), 1.30 (t, J=7.06 Hz, 3H).

Step 2: ethyl 5-(hydroxymethyl)-3-phenyl-1,2-oxazole-4-carboxylate

To a solution of ethyl 4-oxo-2-phenyl-4,5-dihydrofuran-3-carboxylate (7 g, 30.1 mmol, Step 1) in anhydrous ethanol (100 mL) was added sodium acetate (2.473 g, 30.1 mmol) and hydroxylamine hydrochloride (2.095 g, 30.1 mmol). The mixture was heated to reflux for 3 hours. The volatiles were removed under reduced pressure to give a residue that was diluted with water and extracted with ethyl acetate. The organic phase was washed with brine, dried over Na$_2$SO$_4$, and concentrated under reduced pressure. The resultant residue was purified by chromatography on silica gel and eluted with EtOAc/PE to give the titled compound (5.4 g, yield 72%). $^1$H NMR (400 MHz, CDCl$_3$) δ ppm 7.55-7.65 (m, 2H), 7.33-7.54 (m, 3H), 4.96 (d, J=7.06 Hz, 2H), 4.26 (q, J=7.06 Hz, 2H), 3.90 (t, J=7.28 Hz, 1H), 1.18 (t, J=7.06 Hz, 3H).

Step 3: ethyl 5-formyl-3-phenyl-1,2-oxazole-4-carboxylate

To a solution of ethyl 5-(hydroxymethyl)-3-phenyl-1,2-oxazole-4-carboxylate (5.4 g, 21.84 mmol, Step 2) in anhydrous toluene (20 mL) was added $MnO_2$ (5.70 g, 65.5 mmol). The mixture was refluxed under $N_2$ overnight. The solids were removed by filtration, and the filtrate was concentrated under reduced pressure. The resultant residue was purified by chromatography on silica gel eluted with EtOAc/PE (1:30) to give the titled compound (3 g, yield 56%). $^1$H NMR (400 MHz, $CDCl_3$) δ ppm 10.30 (s, 1H), 7.61 (d, J=7.06 Hz, 2H), 7.34-7.52 (m, 3H), 4.31 (q, J=7.20 Hz, 2H), 1.23 (t, J=7.28 Hz, 3H).

Step 4: 3-phenyl[1,2]oxazolo[4,5-d]pyridazin-4(5H)-one

To an ice-bath cooled solution of ethyl 5-formyl-3-phenyl-1,2-oxazole-4-carboxylate (3 g, 12.23 mmol, Step 3) in ethanol (30 mL) was added hydrazine hydrate (6.12 g, 122 mmol) dropwise. The mixture was stirred for 2 hours in an ice-bath. The precipitate was collected by filtration and then dried to give the titled compound (2.1 g, yield 81%). $^1$H NMR (400 MHz, DMSO-$d_6$) δ ppm 8.78 (s, 1H), 8.33 (d, J=7.94 Hz, 2H), 7.53-7.62 (m, 3H).

Step 5: 7-bromo-3-phenyl[1,2]oxazolo[4,5-d]pyridazin-4(5H)-one

To a solution of 3-phenyl[1,2]oxazolo[4,5-d]pyridazin-4(5H)-one (2.1 g, 7.19 mmol, Step 4) in a mixture solvent of ethyl acetate (5 mL) and methanol (20 mL) was added lithium hydroxide hydrate (0.413 g, 9.85 mmol) and bromine (1.574 g, 9.85 mmol) and the mixture was heated to 70° C. After stirring for 3 minutes, bromine (1.574 g, 9.85 mmol) was added, followed by the addition of lithium hydroxide hydrate (0.413 g, 9.85 mmol). The mixture was heated to reflux overnight. The volatiles were removed under reduced pressure to give a residue that was diluted with water and extracted with ethyl acetate. The organic phase was dried over $Na_2SO_4$ and concentrated under reduced pressure to give the titled compound (2.3 g, yield 80%) which was used for next step without further purification. $^1$H NMR (400 MHz, DMSO-$d_6$) δ ppm 8.24-8.47 (m, 2H), 7.46-7.64 (m, 3H).

Step 6: 7-bromo-5-(4-chlorobenzyl)-3-phenyl[1,2]oxazolo[4,5-d]pyridazin-4(5H)-one To a solution of 7-bromo-3-phenyl[1,2]oxazolo[4,5-d]pyridazin-4(5H)-one (180 mg, 0.616 mmol, Step 5) in N,N-dimethylformamide (4 mL) was added potassium carbonate (85 mg, 0.616 mmol). Then 1-chloro-4-(chloromethyl)benzene (99 mg, 0.616 mmol) was added in one portion. The resulting mixture was stirred at room temperature for 4 hours. The reaction mixture was diluted with water and extracted with ethyl acetate. The organic fraction was washed with brine and concentrated under reduced pressure. The residue was washed with methanol and dried to give the titled compound (220 mg, yield 86%). $^1$H NMR (400 MHz, DMSO-$d_6$) δ ppm 8.21 (d, J=6.62 Hz, 2H), 7.50-7.66 (m, 3H), 7.29-7.46 (m, 4H), 5.36 (s, 2H).

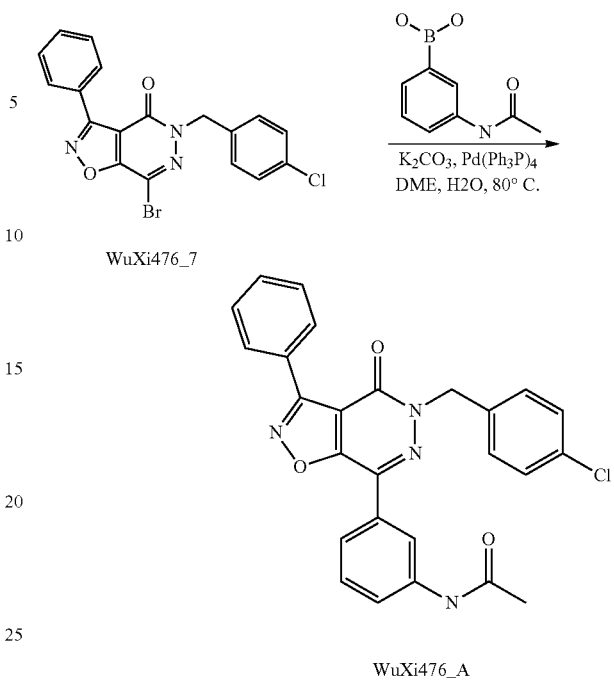

WuXi476_7

WuXi476_A

Step 7: N-{3-[5-(4-chlorobenzyl)-4-oxo-3-phenyl-4,5-dihydro[1,2]oxazolo[4,5-d]pyridazin-7-yl]phenyl}acetamide To a solution of 7-bromo-5-(4-chlorobenzyl)-3-phenyl[1,2]oxazolo[4,5-d]pyridazin-4(5H)-one (130 mg, 0.312 mmol, Step 6) in 1,2-dimethoxyethane (4 mL) and water (1 mL) was added (3-acetamidophenyl)boronic acid (67.0 mg, 0.374 mmol), $K_2CO_3$ (108 mg, 0.780 mmol) and tetrakis(triphenylphosphine)palladium(0) (36 mg, 0.031 mmol). After stirring at 80° C. overnight, the mixture was diluted with water and extracted with ethyl acetate. The organic phase was washed with brine and concentrated under reduced pressure. The residue was washed with methanol and dried to give the titled compound. $^1$H NMR (400 MHz, DMSO-$d_6$) δ ppm 10.22 (s, 1H), 8.36 (s, 1H), 8.26 (d, J=7.94 Hz, 2H), 7.71-7.85 (m, 2H), 7.56-7.63 (m, 3H), 7.48-7.56 (m, 1H), 7.38-7.46 (m, 4H), 5.47 (s, 2H) 2.08 (s, 3H); LCMS (method B) (ESI+) m/z 470.9 (M+H)$^+$, retention time 3.456 minutes.

Example 105

N-[4-methoxy-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide

Step 1: 7-(5-amino-2-methoxyphenyl)-3-methyl-5-{(1R)-1-[4-(trifluoromethyl)phenyl]ethyl}[1,2]oxazolo[4,5-d]pyridazin-4(5H)-one 7-Bromo-3-methyl-5-{(1R)-1-[4-(trifluoromethyl)phenyl]ethyl}[1,2]oxazolo[4,5-d]pyridazin-4(5H)-one (Example 35, 100 mg, 0.249 mmol), 4-methoxy-3-(4,4,5,5-tetramethyl-1,3,2-dioxaborolan-2-yl)aniline (68.1 mg, 0.274 mmol), sodium carbonate (79 mg, 0.746 mmol), and [1,1'-bis(diphenylphosphino)ferrocene]dichloropalladium(II) (18.19 mg, 0.025 mmol, $PdCl_2$(dppf)) were combined with 1,4-dioxane (3 mL) and water (0.3 mL) in a 5 mL sealed tube. The reaction mixture was irradiated at 100° C. for 60 minutes in a microwave reactor. The reaction mixture was then concentrated, and the residue was purified by silica gel column chromatography eluted with EtOAc/PE (1:3) to give the titled compound.

Step 2: N-[4-methoxy-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide 7-(5-Amino-2-methoxyphenyl)-3-methyl-5-{(1R)-1-[4-(trifluoromethyl)phenyl]ethyl}[1,2]oxazolo[4,5-d]pyridazin-4(5H)-one (50 mg, 0.113 mmol, Step 1) and triethylamine (22.77 mg, 0.225 mmol) were combined in dichloromethane (10 mL). Acetyl chloride (9.71 mg, 0.124 mmol) was added, and the reaction mixture was stirred at ambient temperature for 1 hour. The reaction mixture was concentrated under reduced pressure, and the residue was purified by silica gel column chromatography eluted with EtOAc/PE (4:1) to give the titled compound (17 mg, yield 25%). $^1$H NMR (400 MHz, CD$_3$OD) δ ppm 1.89 (d, 3H), 2.15 (s, 3H), 2.65 (s, 3H), 3.84 (s, 3H), 6.47 (q, 1H), 7.17 (d, 1H), 7.69 (m, 5H), 7.76 (s, 1H); MS (ESI+) m/z 487.2 (M+H)$^+$.

Example 106

3-{5-[1-(4-chlorophenyl)ethyl]-3-methyl-4-oxo-4,5-dihydro[1,2]oxazolo[4,5-d]pyridazin-7-yl}benzamide The titled compound was prepared using the procedure described in Example 4 substituting (3-carbamoylphenyl)boronic acid (26 mg, 0.16 mmol) for (2,6-difluoropyridin-4-yl)boronic acid. Purification was achieved by preparative liquid chromatography (Method C, 0.5-8.5 minutes linear gradient 40-70% A). $^1$H NMR (400 MHz, DMSO-d$_6$/D$_2$O, Temperature=90° C.) δ ppm 8.51 (t, J=1.8 Hz, 1H), 8.21-8.15 (m, 1H), 8.02-7.97 (m, 1H), 7.67 (t, J=7.9 Hz, 1H), 7.47-7.42 (m, 2H), 7.40-7.35 (m, 2H), 6.34 (q, J=7.0 Hz, 1H), 2.62 (s, 3H), 1.84 (d, J=7.0 Hz, 3H); MS (APCI+) m/z 409 (M+H)$^+$.

Example 107

N-(4-methyl-3-{3-methyl-4-oxo-5-[4-(trifluoromethyl)benzyl]-4,5-dihydro[1,2]oxazolo[4,5-d]pyridazin-7-yl}phenyl)acetamide

Step 1: 7-(5-amino-2-methylphenyl)-3-methyl-5-[4-(trifluoromethyl)-benzyl][1,2]oxazolo[4,5-d]pyridazin-4(5H)-one 7-Bromo-3-methyl-5-[4-(trifluoromethyl)benzyl][1,2]oxazolo[4,5-d]pyridazin-4(5H)-one (Example 64, 120 mg, 0.309 mmol), 4-methyl-3-(4,4,5,5-tetramethyl-1,3,2-dioxaborolan-2-yl)aniline (22.62 mg, 0.031 mmol), sodium carbonate (82 mg, 0.773 mmol), and [1,1'-bis(diphenylphosphino)ferrocene]dichloropalladium(II) (226 mg, 0.309 mmol, PdCl$_2$(dppf)) were combined with 1,4-dioxane (2 mL) and water (0.2 mL) in a 5-mL sealed tube. The reaction mixture was irradiated in a microwave reactor for 45 minutes at 100° C. The reaction mixture was then concentrated under reduced pressure, and the residue was purified by silica gel column chromatography eluted with EtOAc/PE (1:4) to give the titled compound.

Step 2: N-(4-methyl-3-{3-methyl-4-oxo-5-[4-(trifluoromethyl)benzyl]-4,5-dihydro[1,2]oxazolo[4,5-d]pyridazin-7-yl}phenyl)acetamide 7-(5-Amino-2-methylphenyl)-3-methyl-5-[4-(trifluoromethyl)benzyl][1,2]oxazolo[4,5-d]pyridazin-4(5H)-one (60 mg, 0.145 mmol, Step 1) and triethylamine (14.65 mg, 0.145 mmol) were combined in dichloromethane (5 mL). Then acetyl chloride (11.73 mg, 0.145 mmol) was added, and the resultant reaction mixture was stirred at ambient temperature for 1 hour. The mixture was concentrated under reduced pressure, and the residue was purified by reverse phase (C18) column chromatography eluted with methanol/water (9:1) to give the titled compound (30 mg, yield 46%). $^1$H NMR (400 MHz, DMSO-d$_6$) δ ppm 2.04 (s, 3H), 2.17 (s, 3H), 2.61 (s, 3H), 5.51 (s, 2H), 7.31 (d, 1H), 7.57 (m, 3H), 7.72 (d, 2H), 7.82 (s, 1H), 10.09 (brs, 1H); MS (ESI−) m/z −454.9 (M−H)$^-$.

Example 108

3,7-dimethyl-5-(3-methylbutyl)[1,2]oxazolo[4,5-d]pyridazin-4(5H)-one

The titled compound was prepared using the procedure described in Example 20 substituting 1-bromo-3-methylbutane for 1-(bromomethyl)-2-fluorobenzene. Purification was achieved by preparative liquid chromatography (Method C, 0.5-8.5 minutes linear gradient 50-80% A). $^1$H NMR (400 MHz, DMSO-d$_6$/D$_2$O) δ ppm 4.16-4.08 (m, 2H), 2.57 (s, 3H), 2.50 (s, 3H), 1.63-1.55 (m, 3H), 0.92 (d, J=6.1 Hz, 6H); MS (APCI$^-$) m/z 236.1 (M+H)$^+$.

Example 109

5-[1-(4-chlorophenyl)ethyl]-3-methyl-7-(pyridin-3-yl)[1,2]oxazolo[4,5-d]pyridazin-4(5H)-one The titled compound was prepared using the procedure described in Example 4 substituting pyridin-3-ylboronic acid (20 mg, 0.16 mmol) for (2,6-difluoropyridin-4-yl)boronic acid. Purification was achieved by preparative liquid chromatography (Method C, 0.5-8.5 minutes linear gradient 35-65% A). $^1$H NMR (400 MHz, DMSO-d$_6$/D$_2$O, Temperature=90° C.) δ ppm 9.18 (d, J=2.2 Hz, 1H), 8.71 (dd, J=4.9, 1.6 Hz, 1H), 8.39 (dt, J=8.0, 2.0 Hz, 1H), 7.68-7.57 (m, 1H), 7.50-7.32 (m, 4H), 6.34 (q, J=7.0 Hz, 1H), 2.62 (s, 3H), 1.83 (d, J=7.0 Hz, 3H); MS (APCI$^+$) m/z 367 (M+H)$^+$.

Example 110

N-{3-[3-methyl-4-oxo-5-(pyridin-4-ylmethyl)-4,5-dihydro[1,2]oxazolo[4,5-d]pyridazin-7-yl]phenyl}acetamide The titled compound was prepared using the procedures described for Example 5 substituting (3-acetamidophenyl)boronic acid for (2,4-dimethoxyphenyl)boronic acid in Step 1. Yield 59%.

$^1$H NMR (400 MHz, CD$_3$OD): δ 8.76 (s, 2H), 8.48 (s, 1H), 7.96-7.94 (d, J=6.4 Hz, 2H), 7.88-7.86 (d, J=8.0 Hz, 1H), 7.64-7.62 (d, J=8.0 Hz, 1H), 7.50-7.46 (t, J=8.0 Hz, 1H), 5.76 (s, 2H), 2.67 (s, 3H), 2.16 (s, 3H). m/z 376.2.

Example 111

3-{5-[(1R)-1-(4-chlorophenyl)ethyl]-3-methyl-4-oxo-4,5-dihydro[1,2]oxazolo[4,5-d]pyridazin-7-yl}-4-methoxy-N-methylbenzamide Under argon, 7-bromo-5-[(1R)-1-(4-chlorophenyl)ethyl]-3-methyl[1,2]-oxazolo[4,5-d]pyridazin-4(5H)-one (Example 82, 300 mg, 0.814 mmol) was suspended in toluene and ethanol (12 mL, 1:1). 2 M Aqueous sodium bicarbonate (0.610 mL, 1.221 mmol) and 4-methoxy-N-methyl-3-(4,4,5,5-tetramethyl-1,3,2-dioxaborolan-2-yl)benzamide (261 mg, 0.895 mmol, Example 119—Step 1) were added followed by tetrakis(triphenylphosphine)palladium(0) (94 mg, 0.081 mmol). The reaction mixture was heated with stirring in a Biotage® microwave reactor at 130° C. for 30 minutes. The reaction mixture was then partitioned between water and ethyl acetate. The organic fraction was washed with brine, dried over MgSO$_4$ and then concentrated under reduced pressure. The residue was purified by flash chromatography on a Teledyne Isco CombiFlash® Rf apparatus using a silica gel cartridge (4 g) eluted with 3-5% methanol/dichloromethane. A second flash chromatography on a Teledyne Isco CombiFlash® Rf apparatus using a silica gel cartridge (4 g, 15 μm) eluted with 50% ethyl acetate/heptane was performed. The residue was stirred with diisopropyl ether and collected by vacuum filtration. The precipitate was dissolved in ethyl acetate and concentrated. The residue was stirred again with diisopropyl ether, and the precipitate was collected by vacuum filtration. The precipitate was dried in a vacuum oven overnight to give the titled compound (117 mg, yield 32%). $^1$H NMR (600 MHz, DMSO-d$_6$) δ ppm 8.46 (q, J=4.5 Hz, 1H), 8.05 (dd, J=8.7, 2.3 Hz, 1H), 7.95 (d, J=2.3 Hz, 1H), 7.41 (s, 4H), 7.32 (d, J=8.8 Hz, 1H), 6.33 (q, J=7.0 Hz, 1H), 3.85 (s, 3H), 3.32 (s, 1H), 2.79 (d, J=4.5 Hz, 3H), 2.59 (s, 3H), 1.75 (d, J=7.1 Hz, 3H), 1.04 (d, J=6.1 Hz, 1H).

Example 112

N-[6-fluoro-2-methyl-3-(3-methyl-4-oxo-5-{(1R)-1-[4-(trifluoromethyl)-phenyl]ethyl}-4,5-dihydro[1,2]oxazolo[4,5-d]pyridazin-7-yl)phenyl]acetamide 7-Bromo-3-methyl-5-{(1R)-1-[4-(trifluoromethyl)phenyl]ethyl}[1,2]oxazolo-[4,5-d]pyridazin-4(5H)-one (Example 35, 100 mg, 0.249 mmol), N-(6-fluoro-2-methyl-3-(4,4,5,5-tetramethyl-1,3,2-dioxaborolan-2-yl)phenyl)acetamide (80 mg, 0.274 mmol), sodium carbonate (79 mg, 0.746 mmol), and [1,1'-bis(diphenyl-phosphino)ferrocene]dichloropalladium(II) (18.19 mg, 0.025 mmol, PdCl$_2$(dppf)) were combined with 1,4-dioxane (5 mL) and water (0.5 mL) under a nitrogen atmosphere. The reaction mixture was stirred at 100° C. for 3 hours. The reaction mixture was then concentrated, and the residue was purified by silica gel column chromatography eluted with EtOAc/PE (1:3) to give the titled compound (25 mg, yield 17%).

$^1$H NMR (400 MHz, CD$_3$OD) δ ppm 1.87 (d, 3H), 2.15 (s, 3H), 2.21 (s, 3H), 2.68 (s, 3H), 6.52 (q, 1H), 7.23 (t, 1H), 7.54 (m, 1H), 7.64 (m, 4H); MS (ESI+) m/z 489.2 (M+H)$^+$.

Example 113

5-[1-(4-chlorophenyl)ethyl]-3-methyl-7-(pyrimidin-5-yl)[1,2]oxazolo[4,5-d]pyridazin-4(5H)-one The titled compound was obtained using the reaction conditions described for Example 6 substituting pyrimidin-5-ylboronic acid for methyl (4-chloro-2-(4,4,5,5-tetramethyl-1,3,2-dioxaborolan-2-yl)phenyl)carbamate. The reaction mixture was partitioned between ethyl acetate and water. The organic fraction was washed with brine, dried over MgSO$_4$, and concentrated under reduced pressure. The residue was purified by column chromatography on silica gel eluted with 30% ethyl acetate/cyclohexane. The residue was triturated with a little ethyl acetate/diisopropyl ether (1:1), and the solid was collected by vacuum filtration. The filtrate was concentrated, and the residue was treated overnight with ethyl acetate/diisopropyl ether (1:9). The combined solids were dried overnight in a vacuum oven to give the titled compound. $^1$H NMR (600 MHz, DMSO-d$_6$) δ ppm 9.40 (s, 2H), 9.36 (s, 1H), 7.53-7.48 (m, 2H), 7.44-7.37 (m, 2H), 6.34 (q, J=7.0 Hz, 1H), 3.34 (s, OH), 2.62 (s, 3H), 1.82 (d, J=7.0 Hz, 3H); MS (ESI+) m/z 368.2 (M+H)$^+$.

Example 114

5-[1-(4-chlorophenyl)ethyl]-3,7-dimethyl[1,2]oxazolo[4,5-d]pyridazin-4(5H)-one

Step 1: 1-(1-bromoethyl)-4-chlorobenzene

To a solution of 1-(4-chlorophenyl)ethanol (3.132 g, 20.00 mmol) in anhydrous CH$_2$Cl$_2$ (30 mL) was added pyridine (4.84 mL, 60.0 mmol), and the solution chilled to −20° C., followed by the slow addition of 1.0 M PBr$_3$ (20.00 mL, 20.00 mmol). The reaction was stirred at ambient temperature for 36 hours. The reaction was quenched by the addition of 150 mL of ice, and the mixture was stirred for 30 minutes. The mixture was then diluted with water (200 mL) containing citric acid (2 g) and then extracted four times with diethyl ether. The combined organic extracts were washed with brine, dried over MgSO$_4$, filtered and concentrated to give the titled compound (2.635 g, 60% yield). $^1$H NMR (300 MHz, CDCl$_3$) δ ppm 7.48-7.34 (m, 4H), 5.24 (q, J=6.9, 6.9, 6.9 Hz, 1H), 2.09 (dd, J=6.9, 0.4 Hz, 3H).

Step 2: 5-[1-(4-chlorophenyl)ethyl]-3,7-dimethyl[1,2]oxazolo[4,5-d]pyridazin-4(5H)-one Anhydrous potassium carbonate (1.657 g, 11.99 mmol) was added to a solution of 3,7-dimethyl[1,2]oxazolo[4,5-d]pyridazin-4(5H)-one (1.32 g, 7.99 mmol) in N,N-dimethylformamide (50 ml) followed by the dropwise addition of a solution of 1-(1-bromoethyl)-4-chlorobenzene (1.930 g, 8.79 mmol, Step 1) in N,N-dimethylformamide (1.5 mL). The reaction mixture was heated at 56° C. for 2 hours, then cooled to ambient temperature and poured into an aqueous brine/ammonium chloride solution. The mixture was extracted with ethyl acetate (3×). The combined organic extracts were washed with brine, dried (MgSO$_4$), filtered and concentrated under reduced pressure. The residue was purified by silica gel chromatography, eluting with a gradient of 10-40% ethyl acetate in heptane to give 2.43 g (100%) of the titled compound. $^1$H NMR (300 MHz, CDCl$_3$) δ ppm 7.43-7.37 (m, 2H), 7.30 (d, J=9.8 Hz, 2H), 6.36 (q, J=7.1, 7.1, 7.1 Hz, 1H), 2.68 (s, 3H), 2.58 (s, 3H), 1.79 (d, J=7.1 Hz, 3H); MS (DCI/NH$_3$) m/z 304 (M+H)$^+$, 321 (M+NH$_4$)+.

Example 115

5-[1-(4-chlorophenyl)ethyl]-7-(1-ethyl-1H-pyrazol-5-yl)-3-methyl[1,2]oxazolo[4,5-d]pyridazin-4(5H)-one The titled compound was obtained using the reaction conditions described for Example 6 substituting (1-ethyl- 1H-pyrazol-5-yl)boronic acid for methyl (4-chloro-2-(4,4,5,5-tetramethyl-1,3,2-dioxaborolan-2-yl)phenyl)carbamate. The reaction mixture was partitioned between ethyl acetate and water. The organic fraction was washed with brine, dried over MgSO$_4$, and concentrated under reduced pressure. The residue was purified by flash chromatography using a Teledyne Isco CombiFlash® Rf apparatus with a 4 g silica gel cartridge eluted with 35% ethyl acetate/cyclohexane. The residue was dried under vacuum to give the titled compound. $^1$H NMR (600 MHz, DMSO-d$_6$) δ ppm 7.66 (d, J=2.0 Hz, 6H), 7.40 (q, J=8.8 Hz, 34H), 7.00 (d, J=2.0 Hz, 6H), 6.39 (q, J=7.0 Hz, 9H), 4.33 (ddq, J=34.6, 13.6, 7.0 Hz, 22H), 1.77 (d, J=7.0 Hz, 30H), 1.26-1.17 (m, 37H).

Example 116

5-[1-(4-chlorophenyl)ethyl]-3-methyl-7-(1H-pyrrolo[3,2-b]pyridin-6-yl)[1,2]oxazolo[4,5-d]pyridazin-4(5H)-one The titled compound was obtained using the reaction conditions described for Example 6 substituting 6-(4,4,5,5-tetramethyl-1,3,2-dioxaborolan-2-yl)-1H-pyrrolo[3,2-b]pyridine for methyl (4-chloro-2-(4,4,5,5-tetramethyl-1,3,2-dioxaborolan-2-yl)phenyl)carbamate. The reaction mixture was partitioned between ethyl acetate and water. The organic fraction was washed with brine, dried over MgSO$_4$, and concentrated under reduced pressure. The residue was purified by flash chromatography using a Teledyne Isco CombiFlash® Rf apparatus with a 4 g silica gel cartridge eluted with ethyl acetate/cyclohexane. The residue was triturated with 60% ethyl acetate/diisopropyl ether (1:1). The collected solid was dried under vacuum to give the titled compound (13 mg, yield 20%). $^1$H NMR (600 MHz, DMSO-d$_6$) δ ppm 11.61 (s, 1H), 9.00 (d, J=2.0 Hz, 1H), 8.44 (dd, J=2.0, 0.9 Hz, 1H), 7.84 (dd, J=3.2, 1.5 Hz, 1H), 7.51-7.45 (m, 2H), 7.46-7.39 (m, 2H), 6.67 (d, J=3.1 Hz, 1H), 6.37 (q, J=7.0 Hz, 1H), 2.63 (s, 3H), 1.84 (d, J=7.0 Hz, 3H), 1.04 (d, J=6.1 Hz, 1H).

Example 117

N-(3-{5-[(1S)-1-(4-chlorophenyl)ethyl]-3-methyl-4-oxo-4,5-dihydro[1,2]oxazolo[4,5-d]pyridazin-7-yl}-4-methoxyphenyl)acetamide The enantiomers of N-(3-{5-[l1-(4-chlorophenyl)ethyl]-3-methyl-4-oxo-4,5-dihydro[1,2]oxazolo[4,5-d]pyridazin-7-yl}-4-methoxyphenyl)acetamide (0.4 g, 0.883 mmol, Example 39) were separated by chiral super critical chromatograph (method B) to give the titled compound (0.09 g, yield 23%) and N-(3-{5-[(1R)-1-(4-chlorophenyl)ethyl]-3-methyl-4-oxo-4,5-dihydro[1,2]oxazolo[4,5-d]pyridazin-7-yl}-4-methoxyphenyl)acetamide (0.08 g, yield 20%, Example 40). $^1$H NMR (400 MHz, CDCl$_3$) δ ppm 7.63 (dd, J=2.4, 9.0 Hz, 1H), 7.56 (d, J=2.6 Hz, 1H), 7.44 (d, J=8.4 Hz, 2H), 7.35-7.23 (m, 3H), 7.01 (d, J=8.8 Hz, 1H), 6.39 (q, J=7.1 Hz, 1H), 3.82 (s, 3H), 2.67 (s, 3H), 2.19 (s, 3H), 1.82 (d, J=7.1 Hz, 3H); LCMS (method C) (ESI+) m/z 453.1 (M+H)$^+$, retention time 3.240 minutes.

Example 118

7-(2-methoxyphenyl)-3-methyl-5-[4-(trifluoromethyl)benzyl][1,2]oxazolo[4,5-d]pyridazin-4(5H)-one The titled compound was prepared using the procedures described for Example 5 substituting (2-methoxyphenyl) boronic acid for (2,4-dimethoxyphenyl)-boronic acid in Step 1 and 1-(bromomethyl)-4-(trifluoromethyl)benzene for 4-(bromomethyl)pyridine in Step 2. Yield 22%.
$^1$H NMR (400 MHz, CD$_3$OD): δ 7.66-7.65 (m, 2H), 7.61-7.59 (m, 2H), 7.58-7.52 (m, 1H), 7.46-7.43 (m, 1H), 7.19-7.17 (m, 1H), 7.12-7.10 (m, 1H), 5.53 (s, 2H), 3.83 (s, 3H), 2.62 (s, 3H). m/z 415.4.

Example 119

3-{5-[1-(4-chlorophenyl)ethyl]-3-methyl-4-oxo-4,5-dihydro[1,2]oxazolo[4,5-d]pyridazin-7-yl}-4-methoxy-N-methylbenzamide Step 1: 4-methoxy-N-methyl-3-(4,4,5,5-tetramethyl-1,3,2-dioxaborolan-2-yl)benzamide 3-Bromo-4-methoxy-N-methylbenzamide (1.00 g, 4.10 mmol), 4,4,4',4',5,5,5',5'-octamethyl-2,2'-bi(1,3,2-dioxaborolane) 1.457 g (5.74 mmol), potassium carbonate (1.005 g, 10.24 mmol, and [1,1'-bis(diphenylphosphino)ferro-cene]dichloropalladium(II) dichloromethane complex (167 mg, 0.205 mmol) were combined in dioxane (10 mL) and heated to 90° C. for 7 hours. The reaction mixture was then concentrated under reduced pressure. The residue was combined with ethyl acetate (25 mL), and remaining residue was removed by filtration. Ethyl acetate was distilled off, and the residue was purified by flash chromatography on a Teledyne Isco CombiFlash® apparatus using a RediSep® silica gel cartridge (40 g) eluted with 10% methanol/dichloromethane. Impurities remained, and a second flash chromatography on a Teledyne Isco CombiFlash® apparatus using a RediSep® silica gel cartridge (40 g) eluted with ethyl acetate was performed to give the titled compound.

Step 2: 3-{5-[1-(4-chlorophenyl)ethyl]-3-methyl-4-oxo-4,5-dihydro[1,2]oxazolo[4,5-d]pyridazin-7-yl}-4-methoxy-N-methylbenzamide 7-Bromo-5-[1-(4-chlorophenyl)ethyl]-3-methyl[1,2]oxazolo[4,5-d]pyridazin-4(5H)-one (80 mg, 0.217 mmol, Example 39—Step 5) in ethanol/toluene (1:1, 2 mL) was combined with 2 M aqueous sodium carbonate (0.163 mL, 0.326 mmol) and 4-methoxy-N-methyl-3-(4,4,5,5-tetramethyl-1,3,2-dioxaborolan-2-yl)benzamide (63.2 mg, 0.217 mmol, Step 1). Then tetrakis(triphenylphosphine)palladium (0) (25.08 mg, 0.022 mmol) was added, and the mixture was heated in a CEM microwave reactor for 30 minutes at 130° C. under an argon atmosphere. The reaction mixture was partitioned between water and dichloromethane. The organic fraction was then washed with brine, dried over MgSO$_4$, and concentrated under reduced pressure. The residue was purified by flash chromatography on a Teledyne Isco CombiFlash® Rf apparatus using a silica gel cartridge (4 g) eluted with 4% methanol/dichloromethane. Impurities remained, and a second flash chromatography on a Teledyne Isco CombiFlash® Rf apparatus using a silica gel cartridge (4 g) eluted with ethyl acetate was performed. The titled compound was obtained after drying overnight in a vacuum oven (22 mg, yield 22%). $^1$H NMR (600 MHz, DMSO-d$_6$) δ ppm 8.46 (q, J=4.5 Hz, 1H), 8.05 (dd, J=8.7, 2.3 Hz, 1H), 7.95 (d, J=2.3 Hz, 1H), 7.41 (s, 4H), 7.32 (d, J=8.8 Hz, 1H), 6.33 (q, J=7.0 Hz, 1H), 3.85 (s, 3H), 2.79 (d, J=4.5 Hz, 3H), 2.59 (s, 3H), 1.75 (d, J=7.1 Hz, 3H); MS (ESI+) m/z 453.2 (M+H)$^+$.

Example 120

5-(4-chlorobenzyl)-3-methyl-7-(pyridin-3-yl)[1,2]oxazolo[4,5-d]pyridazin-4(5H)-one To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxyethane (4 mL) and water (1 mL) was added pyridin-3-ylboronic acid (41.5 mg, 0.338 mmol), $K_2CO_3$ (0.097 g, 0.705 mmol) and tetrakis(triphenylphosphine)palladium(0) (0.033 g, 0.028 mmol). The resulting mixture was stirred at 80° C. overnight under $N_2$. After cooling down to room temperature, the reaction mixture was concentrated under reduced pressure to give a residue that was washed with a mixture of $CH_3OH$ and $H_2O$ to give the titled compound. Yield 48%.

$^1$H NMR (DMSO, 400 MHz): δ 9.18 (d, J=1.76 Hz, 1H), 8.69-8.75 (m, 1H), 8.38 (d, J=7.94 Hz, 1H), 7.63 (dd, J=7.94, 4.85 Hz, 1H), 7.37-7.46 (m, 4H), 5.44 (s, 2H), 2.61 (s, 3H). m/z 352.8.

Example 121

3,7-dimethyl-5-[3-(trifluoromethyl)benzyl][1,2]oxazolo[4,5-d]pyridazin-4(5H)-one The titled compound was prepared using the procedure described in Example 20 substituting 1-(bromomethyl)-3-(trifluoromethyl)benzene for 1-(bromomethyl)-2-fluorobenzene. Purification was achieved by preparative liquid chromatography (Method C, 0.5-8.5 minutes linear gradient 60-100% A). $^1$H NMR (400 MHz, DMSO-$d_6$/$D_2O$) δ ppm 7.70-7.65 (m, 2H), 7.58 (dd, J=5.0, 1.8 Hz, 2H), 5.40 (s, 2H), 2.57 (s, 3H), 2.51 (s, 3H); MS (APCI$^+$) m/z 324.1 (M+H)$^+$.

Example 122

5-(4-chlorobenzyl)-3-methyl-7-phenyl[1,2]oxazolo[4,5-d]pyridazin-4(5H)-one

To a solution of 7-bromo-5-(4-chlorobenzyl)-3-methyl[1,2]oxazolo[4,5-d]pyridazin-4(5H)-one (0.1 g, 0.282 mmol, Example 2—Step 6) in 1,2-dimethoxy-ethane (4 mL) and water (1 mL) was added phenylboronic acid (41.2 mg, 0.338 mmol), $K_2CO_3$ (0.097 g, 0.705 mmol) and tetrakis(triphenylphosphine)palladium(0) (0.033 g, 0.028 mmol). The resulting mixture was stirred at 80° C. overnight under $N_2$. After cooling down to room temperature, the reaction mixture was concentrated under reduced pressure to give a residue that was washed with a mixture of $CH_3OH$ and $H_2O$ to give the titled compound. Yield 47%.

$^1$H NMR (CDCl$_3$, 400 MHz): δ 8.14 (d, J=6.62 Hz, 2H), 7.38-7.60 (m, 5H), 7.32 (d, J=8.38 Hz, 2H), 5.44 (s, 2H), 2.72 (s, 3H). m/z 351.8.

Example 123

5-(2,4-difluorobenzyl)-3,7-dimethyl[1,2]oxazolo[4,5-d]pyridazin-4(5H)-one 1-(bromomethyl)-2,4-difluorobenzene The titled compound was prepared using the procedure described in Example 20 substituting 1-(bromomethyl)-2,4-difluorobenzene for 1-(bromomethyl)-2-fluorobenzene. Purification was achieved by preparative liquid chromatography (Method C, 0.5-8.5 minutes linear gradient 45-75% A). $^1$H NMR (400 MHz, DMSO-$d_6$/$D_2O$) δ ppm 7.35 (td, J=8.7, 6.6 Hz, 1H), 7.23 (ddd, J=10.5, 9.4, 2.6 Hz, 1H), 7.08-7.01 (m, 1H), 5.32 (s, 2H), 2.57 (s, 3H), 2.49 (s, 3H); MS (APCI$^+$) m/z 292.0 (M+H)$^+$.

Example 124

3,7-dimethyl-5-[4-(trifluoromethyl)benzyl][1,2]oxazolo[4,5-d]pyridazin-4(5H)-one The titled compound was prepared using the procedure described in Example 20 substituting 1-(bromomethyl)-4-(trifluoromethyl)benzene for 1-(bromomethyl)-2-fluorobenzene. Purification was achieved by preparative liquid chromatography (Method C, 0.5-8.5 minutes linear gradient 60-100% A). $^1$H NMR (400 MHz, DMSO-$d_6$/$D_2O$) δ ppm 7.71 (d, J=8.2 Hz, 2H), 7.51 (d, J=8.0 Hz, 2H), 5.40 (s, 2H), 2.57 (s, 3H), 2.51 (s, 3H); MS (APC$^+$) m/z 324.0 (M+H)$^+$.

Example 125

7-(2,5-dimethoxyphenyl)-3-methyl-5-{(1R)-1-[4-(trifluoromethyl)phenyl]ethyl}[1,2]oxazolo[4,5-d]pyridazin-4(5H)-one 7-Bromo-3-methyl-5-{(1R)-1-[4-(trifluoromethyl)phenyl]ethyl}[1,2]oxazolo[4,5-d]pyridazin-4(5H)-one (Example 35, 100 mg, 0.249 mmol), 2-(2,5-dimethoxyphenyl)-4,4,5,5-tetramethyl-1,3,2-dioxaborolane (72.2 mg, 0.274 mmol), sodium carbonate (79 mg, 0.746 mmol), and [1,1'-bis(diphenylphosphino)ferrocene]dichloropalladium(II) (18.19 mg, 0.025 mmol, PdCl$_2$(dppf)) were combined with 1,4-dioxane (5 mL) and water (0.5 mL) under a nitrogen atmosphere. The reaction mixture was stirred at 100° C. for 3 hours. The reaction mixture was then concentrated under reduced pressure, and the residue was purified by silica gel column chromatography eluted with EtOAc/PE (1:3) to give the titled compound (10 mg, yield 9%).

$^1$H NMR (400 MHz, CD$_3$OD) δ ppm 1.88 (d, 3H), 2.65 (s, 3H), 3.78 (s, 6H), 6.48 (q, 1H), 6.96 (s, 1H), 7.12 (m, 2H), 7.66 (m, 4H); $^{19}$F NMR (282 MHz, CDCl$_3$)$^6$F ppm −63.23 (s, 3F); MS (ESI+) m/z 460.2 (M+H)$^+$.

Example 126

7-(3-aminophenyl)-5-[1-(4-chlorophenyl)ethyl]-3-methyl[1,2]oxazolo[4,5-d]pyridazin-4(5H)-one The titled compound was prepared using the procedure described in Example 4 substituting (3-aminophenyl)boronic acid (22 mg, 0.16 mmol) for (2,6-difluoropyridin-4-yl)boronic acid. Purification was achieved by preparative liquid chromatography (Method C, 0.5-8.5 minutes linear gradient 35-65% A). (12 mg, yield 17%).

$^1$H NMR (400 MHz, DMSO-$d_6$/$D_2O$, Temperature=90° C.) δ ppm 7.47-7.36 (m, 4H), 7.34-7.30 (m, 1H), 7.25-7.19 (m, 2H), 6.80-6.74, (m, 1H), 6.38-6.27 (m, 1H), 2.61 (s, 3H), 1.81 (d, J=7.0 Hz, 3H); MS (APCI+) m/z 381 (M+H)$^+$.

Example 127

7-(2,4-dimethoxyphenyl)-3-methyl-5-[4-(trifluoromethyl)benzyl][1,2]oxazolo[4,5-d]pyridazin-4(5H)-one The titled compound was prepared using the procedures described for Example 5 substituting 1-(bromomethyl)-4-(trifluoromethyl)benzene for 4-(bromomethyl)pyridine in Step 2. Yield 9%.

¹H NMR (400 MHz, CD$_3$OD): δ7.66-7.64 (d, J=8.4 Hz, 2H), 7.60-7.58 (d, J=8.4 Hz, 2H), 7.38-7.36 (d, J=8.4 Hz, 1H), 6.67-6.65 (m, 2H), 5.52 (s, 2H), 3.87 (s, 3H), 3.81 (s, 3H), 2.63 (s, 3H). m/z 446.0.

Example 128

5-[(1R)-1-(4-chlorophenyl)ethyl]-3-cyclopropyl-7-(2,5-dimethoxyphenyl)-[1,2]oxazolo[4,5-d]pyridazin-4(5H)-one 5-[1-(4-chlorophenyl)ethyl]-3-cyclopropyl-7-(2,5-dimethoxyphenyl)-[1,2]oxazolo[4,5-d]pyridazin-4(5H)-one was synthesized in analogy to example 1. The enantiomers were separated by supercritical fluid chromatography to give the titled compound. The mobile phase was comprised of supercritical CO$_2$ supplied by a bulk tank of 99.5% bone-dry non-certified CO$_2$ pressurized to 1200 psi (82.7 bar) with a modifier of methanol (0.1 N NH$_4$OH) at a flow rate of 70 g/minute. UV detection was set to collect at a wavelength of 220 nm, the column was heated to 35° C., and the back-pressure regulator was set to maintain 100 bar. The sample was dissolved in methanol at a concentration of about 50 mg/mL, and the injection volume was 1 mL. The mobile phase was held isocratically at 40% methanol (0.1 N NH$_4$OH):CO2. The instrument was fitted with a Chiralpak® AS-H 5 μm, 30 mm×250 mm column. ¹H NMR (400 MHz, DMSO-d$_6$) δ ppm 7.39 (s, 3H), 7.17-7.08 (m, 2H), 6.92 (d, J=2.6 Hz, 1H), 6.30 (q, J=6.9 Hz, 1H), 3.71 (d, J=7.1 Hz, 6H), 2.46-2.39 (m, 1H), 1.71 (d, J=7.1 Hz, 3H), 1.14 (d, J=7.5 Hz, 4H).

Example 129

N-{3-[5-(4-chlorobenzyl)-3-ethyl-4-oxo-4,5-dihydro[1,2]oxazolo[4,5-d]pyridazin-7-yl]phenyl}acetamide Step 1: ethyl 2-ethyl-4-oxo-4,5-dihydrofuran-3-carboxylate To an ice bath cooled solution of magnesium ethanolate (17.58 g, 154 mmol) in toluene (100 mL) was added ethyl 3-oxopentanoate (20 g, 154 mmol) dropwise. The mixture was stirred at room temperature for 1 hour. Anhydrous acetonitrile (100 mL) was added to the mixture at −10° C. followed by the slow addition of 2-chloroacetyl chloride (20.83 g, 184 mmol). The mixture was allowed to warm to room temperature and left to stir for 2 hours. A dilute solution of sulfuric acid (8 mL acid in 280 mL ice/water) was added, followed by extraction with tert-butyl methyl ether. The combined organic fractions were dried over Na$_2$SO$_4$ and filtered. The filtrate was cooled to 0° C. A solution of triethylamine (107 mL, 768 mmol) in tert-butyl methyl ether (100 mL) was added. The reaction mixture was left to stir at room temperature overnight. The mixture was diluted with water, and extracted with dichloromethane. The organic phase was concentrated under reduced pressure to give a residue that was purified by column chromatography on silica gel and eluted with EtOAc/PE to give the titled compound (15 g, yield 57.4%). ¹H NMR (400 MHz, CDCl$_3$) δ ppm 4.53 (s, 2H), 4.25-4.18 (m, 2H), 2.95 (q, J=7.5 Hz, 2H), 1.28-1.17 (m, 6H).

Step 2: ethyl 3-ethyl-5-(hydroxymethyl)-1,2-oxazole-4-carboxylate

To a solution of ethyl 2-ethyl-4-oxo-4,5-dihydrofuran-3-carboxylate (8.0 g, 40 mmol, Step 1) in anhydrous ethanol (50 mL) was added sodium acetate (3.6 g, 40 mmol) and hydroxylamine (2.8 g, 40 mmol). The mixture was heated to reflux for 1 hour and then concentrated. The residue was diluted with water and extracted with ethyl acetate. The organic phase was washed with brine, dried over Na$_2$SO$_4$, and concentrated under reduced pressure. The residue which was purified by column chromatography on silica gel and eluted with EtOAc/PE to give the titled compound (6.1 g, yield 94%). ¹H NMR (400 MHz, CDCl$_3$) δ ppm 4.85 (s, 2H), 4.32 (q, J=7.1 Hz, 2H), 4.11-4.03 (m, 1H), 2.88-2.80 (m, 2H), 1.38-1.32 (m, 3H), 1.25 (t, J=7.5 Hz, 3H).

Step 3: ethyl 3-ethyl-5-formyl-1,2-oxazole-4-carboxylate

To a solution of ethyl 3-ethyl-5-(hydroxymethyl)-1,2-oxazole-4-carboxylate (6.0 g, 30 mmol, step 2) in anhydrous toluene (200 mL) was added manganese(IV) oxide (7.9 g, 90 mmol). The mixture was heated to reflux for 6 hours. The manganese salts were removed by filtration, and the filtrate was concentrated under reduced pressure. The residue was purified by column chromatography on silica gel and eluted with EtOAc/PE to give the titled compound (3.3 g, yield 56%). ¹H NMR (400 MHz, CDCl$_3$) δ ppm 10.33 (s, 1H), 4.45-4.30 (m, 2H), 3.55 (s, 1H), 3.02-2.82 (m, 2H), 1.48-1.19 (m, 6H).

Step 4: 3-ethyl[1,2]oxazolo[4,5-d]pyridazin-4(5H)-one

To a solution of ethyl 3-ethyl-5-formyl-1,2-oxazole-4-carboxylate (3.02 g, 15.3 mmol, Step 3) in ethanol (60 mL) chilled in an ice-bath was added hydrazine hydrate (3.72 mL, 119 mmol) dropwise. The resulting mixture was stirred for 2 hours. The mixture was filtered through diatomaceous earth, and the filtrate was diluted with ethyl acetate (200 mL) and water (50 mL). The solid was collected by filtration and dried to give the titled compound (2.1 g, yield 83%). ¹H NMR (400 MHz, methanol-d$_4$) δ ppm 11.80 (br. s., 1H), 8.30-8.27 (m, 1H), 3.09-3.00 (m, 2H), 1.43-1.34 (m, 3H).

Step 5: 7-bromo-3-ethyl[1,2]oxazolo[4,5-d]pyridazin-4(5H)-one

To a solution of 3-ethyl[1,2]oxazolo[4,5-d]pyridazin-4(5H)-one (2.0 g, 12 mmol, Step 4) in methanol (120 mL) chilled in an ice-water bath was added lithium hydroxide hydrate (1.43 g, 60 mmol) and Br$_2$ (0.012 g, 72 mmol) dropwise. The mixture was heated to reflux overnight. The mixture was diluted with water and extracted with ethyl acetate. The organic phase was washed with brine, dried over Na$_2$SO$_4$, and concentrated under reduced pressure. The residue was purified by column chromatography on silica gel and eluted with EtOAc/PE to give the titled compound (1.65 g, yield 70%). ¹H NMR (400 MHz, CDCl$_3$) δ ppm 3.03 (q, J=7.6 Hz, 2H), 1.39 (t, J=7.7 Hz, 3H).

Step 6: 7-bromo-5-(4-chlorobenzyl)-3-ethyl[1,2]oxazolo[4,5-d]pyridazin-4(5H)-one To a solution of 7-bromo-3-ethyl[1,2]oxazolo[4,5-d]pyridazin-4(5H)-one (0.20 g, 0.83 mmol, Step 5) in N,N-dimethylformamide (3 mL) was added K$_2$CO$_3$ (0.57 g, 4.15 mmol) at room temperature. 1-Chloro-4-(chloromethyl)benzene (0.17 g, 1.07 mmol) was added in one portion. The mixture was heated to 80° C. for 2 hours. The reaction mixture was concentrated, diluted with water (20 mL), and extracted with ethyl acetate (50 mL×3). The combined organic layers were dried over $Na_2SO_4$, filtered and concentrated in vacuum to give the titled compound (0.45 g, yield 99%). $^1$H NMR (400 MHz, $CDCl_3$) δ ppm 7.42-7.38 (m, 2H), 7.34-7.29 (m, 2H), 5.32 (s, 2H), 3.09-3.02 (m, 2H), 1.40 (t, J=7.5 Hz, 3H).

Step 7: N-{3-[5-(4-chlorobenzyl)-3-ethyl-4-oxo-4,5-dihydro[1,2]oxazolo[4,5-d]pyridazin-7-yl]phenyl}acetamide To a solution of 7-bromo-5-(4-chlorobenzyl)-3-ethyl[1,2]oxazolo[4,5-d]pyridazin-4(5H)-one (216 mg, 0.586 mmol, Step 6) in 1,4-dioxane (5 mL) and water (2 mL) was added (3-acetamidophenyl)boronic acid (105 mg, 0.58 mmol), $K_2CO_3$ (62.1 mg, 0.58 mmol) and tetrakis(triphenylphosphine)palladium(O) (67.7 mg, 0.059 mmol) at room temperature under nitrogen. After stirring at 80° C. overnight, the mixture was diluted with water, and extracted with ethyl acetate (20 mL×3). The organic phase was washed with brine and concentrated in vacuum. The residue was purified by preparative HPLC (method B) to give the titled compound (82.5 mg, yield 33%). $^1$H NMR (400 MHz, $CDCl_3$) δ ppm 8.11 (s, 1H), 7.82 (d, J=7.9 Hz, 1H), 7.71 (d, J=7.9 Hz, 1H), 7.44-7.41 (m, 1H), 7.40-7.38 (m, 1H), 7.38-7.36 (m, 1H), 7.31 (br. s., 1H), 7.25-7.22 (m, 1H), 7.19 (s, 1H), 5.37 (s, 2H), 3.05 (q, J=7.6 Hz, 2H), 2.17 (s, 3H), 1.37 (t, J=7.5 Hz, 3H); LCMS (method B) (ESI+) m/z 422.9 $(M+H)^+$, retention time 3.138 minutes Example 130

7-(2,5-dimethoxyphenyl)-5-[2-fluoro-5-(trifluoromethyl)benzyl]-3-methyl[1,2]oxazolo[4,5-d]pyridazin-4(5H)-one The titled compound was prepared using the procedures described for Example 5 substituting (2,5-dimethoxyphenyl)boronic acid for (2,4-dimethoxyphenyl)boronic acid in Step 1 and 2-(bromomethyl)-1-fluoro-4-(trifluoromethyl)benzene for 4-(bromomethyl)pyridine in Step 2. Yield 46%.

$^1$H NMR (400 MHz, $CD_3OD$): δ7.77-7.68 (m, 2H), 7.36-7.31 (m, 1H), 7.09 (s, 2H), 6.94 (s, 2H), 5.57 (s, 2H), 3.77 (s, 3H), 3.76 (s, 3H), 2.63 (s, 3H). m/z 464.0.

Example 131

3-{5-[1-(4-chlorophenyl)ethyl]-3-methyl-4-oxo-4,5-dihydro[1,2]oxazolo[4,5-d]pyridazin-7-yl})-N-ethyl-4-methoxybenzamide Sodium hydride (3.28 mg, 0.137 mmol, 5.47 mg of 60% dispersion in oil) was added to a solution of 3-{5-[1-(4-chlorophenyl)ethyl]-3-methyl-4-oxo-4,5-dihydro[1,2]oxazolo[4,5-d]pyridazin-7-yl}-4-methoxybenzamide (50 mg, 0.114 mmol, Example 59) dissolved in N,N-dimethylformamide (1 mL). After 30 minutes, iodoethane (10.99 µL, 21.32 mg, 0.137 mmol) was added, and the reaction mixture was stirred at ambient temperature overnight. The reaction mixture was then partitioned between ethyl acetate and water. The aqueous phase was extracted twice with ethyl acetate. The combined organic fractions were washed with brine, dried over $MgSO_4$ and concentrated. The residue was purified by flash chromatography on a Teledyne Isco CombiFlash® apparatus using a RediSep® silica gel cartridge (4 g) eluted with 0-10% methanol/dichloromethane. The residue was treated with ethyl acetate, and the precipitate was collected by vacuum filtration and dried in a vacuum oven to give the titled compound (5 mg, yield 9%).

$^1$H NMR (600 MHz, DMSO-$d_6$) δ ppm 8.48 (t, J=5.5 Hz, 2H), 8.06 (dd, J=8.8, 2.2 Hz, 2H), 7.94 (d, J=2.3 Hz, 1H), 7.41 (s, 5H), 7.31 (d, J=8.8 Hz, 2H), 6.33 (q, J=7.0 Hz, 2H), 2.59 (s, 3H), 1.75 (d, J=7.0 Hz, 5H), 1.13 (t, J=7.2 Hz, 5H).

Determination of Biological Activity

Abbreviations: EGTA for ethylene glycol-bis(2-aminoethylether)-N,N,N',N'-tetraacetic acid; GABA for γ-aminobutyric acid; GTPgS for guanosine 5'-O-[gamma-thio]triphosphate; and Tris for tris(hydroxymethyl)aminomethane.

Preparation of Rat Brain Membranes for Native Receptor Assays

Membranes from rat brain cortex were prepared as described in detail by Olpe et al. and stored at concentrations of 1.66 mg/mL protein at −80° C. until required. (Olpe, H.-R, et al. Eur J Pharmacol 1990; 187: 27-38).

[$^{35}$S]GTPgS Binding Assay

The composition of the assay mixtures [in a final volume of 200 µL in 96-well U-bottom plates (Greiner) was as follows: 50 mM Tris-HCl buffer, pH 7.7, 10 mM $MgCl_2$, 0.2 mM EGTA, 2 mM $CaCl_2$, 100 mM NaCl, 20 µM guanosine 5'-diphosphate (Sigma), 0.3 nM [$^{35}$S]GTPgS (1250 Ci/mmol (PerkinElmer)), and the test compounds at increasing concentrations (from 10 nM up to 10 µM), 10 µg of rat cortical membranes, and a concentration of 1 µM GABA, that has been observed in previous experiments to correspond to the $EC_{25}$, a concentration that gives 25% of the maximal response of GABA. The samples were incubated at room temperature for 60 minutes on a shaker. The incubation was stopped by rapid vacuum filtration over glass-fiber filter plates (UniFilter-96 well, GF/B membrane plates, PerkinElmer) using a 96-well plate harvester (TOMTEK© Harvester). The UniFilter plate was washed five times with ice-cold wash buffer (50 mM Tris-HCl buffer, pH 7.7, 10 mM $MgCl_2$, and 100 mM NaCl. After filtration the plate was dried for 90 minutes at 55° C. The plates were closed on the bottom with black sealing membranes, and liquid scintillation cocktail (35 µL, Betaplate Scint, PerkinElmer) was added to each well. After sealing the top of the plate, an additional incubation step of 90 minutes at room temperature followed before measuring the plate. The amount of membrane-bound [$^{35}$S]GTPgS was measured using a 96-well plate reader (Microbeta®, PerkinElmer). Nonspecific binding was measured in the presence of unlabeled 10 µM of GTPgS (Millipore) and without GABA. Basal binding was measured in the absence of 1 µM GABA, and maximal binding was measured in the presence of GABA using 1 mM GABA concentrations.

Data analysis. The concentration-response curves of compounds of the present disclosure in the presence of $EC_{25}$ of GABA-B receptor agonist were generated using the GraphPad Prism® program (GraphPad Software, San Diego, Calif.). Data was normalized using basal binding as 0% and maximal binding as 100%. The curves were fitted by nonlinear regression allowing determination of $EC_{50}$ values from sigmoidal dose-response curves. Each curve was performed using triplicate sample per date point and 10 concentrations.

| Example | GTPgS Binding EC$_{50}$ (μM) |
|---|---|
| 1 | 0.051 |
| 2 | >10 |
| 3 | >10 |
| 4 | 1.66 |
| 6 | 1.96 |
| 7 | 0.6 |
| 8 | 2.11 |
| 10 | 1.06 |
| 11 | >10 |
| 12 | 0.347 |
| 13 | 3.54 |
| 14 | 2.13 |
| 16 | 0.222 |
| 18 | 0.389 |
| 19 | 1.58 |
| 21 | 0.229 |
| 22 | 2.69 |
| 23 | >10 |
| 24 | 1.85 |
| 27 | 3.2 |
| 28 | 3.47 |
| 31 | 1.81 |
| 33 | >10 |
| 34 | 4.81 |
| 35 | 0.562 |
| 36 | 0.895 |
| 37 | 3.67 |
| 38 | 0.643 |
| 39 | 0.105 |
| 40 | >10 |
| 41 | 4.67 |
| 42 | 9.64 |
| 45 | 0.376 |
| 46 | 2.29 |
| 47 | 0.578 |
| 48 | 1.55 |
| 49 | 0.283 |
| 51 | 1.5 |
| 52 | >10 |
| 53 | 0.62 |
| 54 | 1.2 |
| 55 | 0.08 |
| 56 | 0.982 |
| 57 | 3.33 |
| 58 | >10 |
| 59 | 0.017 |
| 60 | >10 |
| 61 | >10 |
| 63 | 0.491 |
| 64 | 0.644 |
| 65 | 1.85 |
| 66 | 2.79 |
| 67 | 2.13 |
| 68 | 0.048 |
| 70 | 0.935 |
| 71 | 2.21 |
| 72 | 7.7 |
| 73 | 0.039 |
| 74 | 3.41 |
| 75 | 1.76 |
| 76 | 1.93 |
| 77 | 2.48 |
| 78 | 6.35 |
| 79 | 0.511 |
| 82 | 0.023 |
| 83 | 3.09 |
| 85 | 2.62 |
| 86 | 2.76 |
| 87 | 1.03 |
| 89 | 1.39 |
| 91 | 2.12 |
| 95 | 1.74 |
| 96 | 2.59 |
| 97 | 1.85 |
| 98 | 0.45 |
| 100 | 0.667 |
| 101 | 3.71 |
| 102 | 0.846 |

-continued

| Example | GTPgS Binding EC$_{50}$ (μM) |
|---|---|
| 103 | 0.439 |
| 105 | 0.033 |
| 106 | 0.847 |
| 107 | 1.47 |
| 109 | 1.21 |
| 111 | >10 |
| 112 | 3.63 |
| 113 | 3.84 |
| 114 | 3.8 |
| 115 | 4.12 |
| 116 | 0.855 |
| 117 | 0.043 |
| 118 | 2.93 |
| 119 | 0.056 |
| 120 | 6.82 |
| 122 | 3.8 |
| 125 | 0.582 |
| 126 | 0.501 |
| 127 | 1.56 |
| 128 | >10 |
| 129 | 2.11 |
| 131 | 0.453 |

It is understood that the foregoing detailed description and accompanying examples are merely illustrative and are not to be taken as limitations upon the scope of the invention, which is defined solely by the appended claims and their equivalents. Various changes and modifications to the described embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

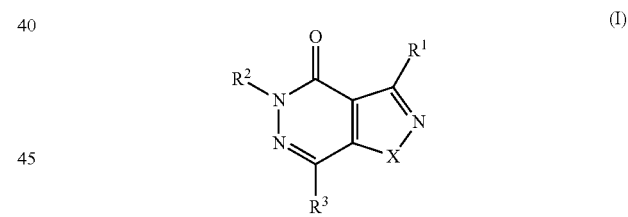

or a pharmaceutically acceptable salt thereof, wherein:
X is O or S;
R$^1$ is selected from the group consisting of C$_1$-C$_6$alkyl, C$_2$-C$_6$alkenyl, C$_2$-C$_6$alkynyl, C$_3$-C$_6$cycloalkyl, and phenyl; wherein,
  C$_1$-C$_6$alkyl, C$_2$-C$_6$alkenyl, and C$_2$-C$_6$alkynyl are unsubstituted, partly or completely fluorinated and/ or substituted with one or more substituents independently selected from the group consisting of C$_1$-C$_6$alkoxy, fluoroC$_1$-C$_6$alkoxy, hydroxy, and oxo;
  C$_3$-C$_6$cycloalkyl is optionally substituted with one or more substituents independently selected from the group consisting of C$_1$-C$_6$alkyl, C$_1$-C$_6$alkoxy, fluorine, fluoroC$_1$-C$_6$alkyl, fluoroC$_1$-C$_6$alkoxy, hydroxy, and oxo;
  phenyl is optionally substituted with one or more substituents selected from the group consisting of C$_1$-C$_6$alkyl, C$_1$-C$_6$alkoxy, fluoroC$_1$-C$_6$alkyl, fluoroC$_1$-C$_6$alkoxy, and halo;

$R^2$ is selected from the group consisting of 4-chlorophenylmethyl, 3-(trifluoromethyl)phenylmethyl, 4-(trifluoromethyl)phenylmethyl, 4-methoxy-3-(trifluoromethyl)phenylmethyl, 2-fluoro-5-(trifluoromethyl)phenylmethyl, 5-chloro-2-fluorophenylmethyl, 4-chloro-2-fluorophenylmethyl, 4-chlorophenylphenylmethyl, 2,4-difluorophenylmethyl, 4-fluoro-3-(trifluoromethyl)phenylmethyl, 4-chloro-3-(trifluoromethyl)phenylmethyl, 2-fluorophenylmethyl, 4-fluorophenylmethyl, 1-(4-chlorophenyl)ethyl, 2-(4-chlorophenyl)ethyl, 1-(4-(trifluoromethyl)phenyl)ethyl, and 4-pyridylmethyl;

$R^3$ is selected from the group consisting of $C_1$-$C_6$alkyl, $C_3$-$C_6$cycloalkyl, phenyl, phenyl$C_1$-$C_6$alkyl, bicyclic aryl, bicyclic aryl$C_1$-$C_6$alkyl, monocyclic heteroaryl$C_1$-$C_6$alkyl, monocyclic heteroaryl, and bicyclic heteroaryl; wherein
  $C_1$-$C_6$alkyl is unsubstituted, partly or completely fluorinated and/or substituted with one or more substituents independently selected from the group consisting of $C_1$-$C_6$alkoxy, fluoro$C_1$-$C_6$alkoxy, hydroxy, and oxo;
  $C_3$-$C_6$cycloalkyl is optionally substituted with one or more substituents independently selected from the group consisting of $C_1$-$C_6$alkyl, $C_1$-$C_6$alkoxy, fluoro$C_1$-$C_6$alkoxy, fluorine, hydroxy, and oxo; and
  phenyl, phenyl of phenyl$C_1$-$C_6$alkyl, bicyclic aryl, bicyclic aryl of bicyclic aryl$C_1$-$C_6$alkyl, monocyclic heteroaryl of monocyclic heteroaryl$C_1$-$C_6$alkyl, monocyclic heteroaryl and bicyclic heteroaryl are optionally substituted with 1, 2, 3 or 4 substituents $R^{Ar}$, which are independently selected from the group consisting of $C_1$-$C_6$alkyl, $C_2$-$C_6$alkenyl, $C_2$-$C_6$alkynyl, halogen, cyano, —$OR^{1a}$, —$OC(O)R^{1a}$, —$OC(O)N(R^d)(R^{3a})$, —$SR^{1a}$, —$S(O)_2R^{2a}$, —$S(O)_2N(R^d)(R^{3a})$, —$C(O)R^{1a}$, —$C(O)OR^{1a}$, —$C(O)N(R^d)(R^{3a})$, —$N(R^d)(R^{3a})$, —$N(R^c)C(O)R^{1a}$, —$N(R^c)S(O)_2R^{2a}$, —$N(R^c)C(O)O(R^{1a})$, —$N(R^c)C(O)N(R^d)(R^{3a})$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^d)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^d)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^d)(R^{3a})$, —$(CR^{4a}R^{5a})_m$—$N(R^d)(R^{3a})$, —$(CR^{4a}R^{5a})_m$—$N(R^c)C(O)R^{1a}$, —$(CR^{4a}R^{5a})_m$—$N(R^c)S(O)_2R^{2a}$, —$(CR^{4a}R^{5a})_m$—$N(R)C(O)O(R^{1a})$, —$(CR^{4a}R^{5a})_m$—$N(R)C(O)N(R^d)(R^{3a})$, cyano$C_1$-$C_6$-alkyl, and fluoro$C_1$-$C_6$-alkyl;

m is 1, 2, 3, or 4;
  $R^c$ and $R^d$, at each occurrence, are each independently hydrogen, $C_1$-$C_6$alkyl, or fluoro$C_1$-$C_6$-alkyl;
  $R^{1a}$ and $R^{3a}$, at each occurrence, are each independently hydrogen, $C_1$-$C_6$alkyl, or fluoro$C_1$-$C_6$-alkyl; or
  $R^d$ and $R^{3a}$, if present as a group $N(R^d)(R^{3a})$, may together with the nitrogen atom of $N(R^d)(R^{3a})$ also form an N-bound saturated 3 to 8 membered heterocycle, which in addition to the nitrogen atom may have 1 or 2 further heteroatoms as ring members, which are selected from the group consisting of O, S and N;
  $R^c$ and $R^{1a}$, if present as a group —$N(R^c)C(O)R^{1a}$, may together with the atoms of said moiety form an N-bound saturated 3 to 8 membered heterocycle, which has an oxo group in 2-position and which in addition to the nitrogen atom may have 1 or 2 further heteroatoms as ring members, which are selected from the group consisting of O, S and N;
  $R^{2a}$, at each occurrence, is independently $C_1$-$C_6$alkyl, or fluoro$C_1$-$C_6$-alkyl; and
  $R^{4a}$ and $R^{5a}$, at each occurrence, are each independently hydrogen, fluorine, $C_1$-$C_6$alkyl, or fluoro$C_1$-$C_6$-alkyl.

2. The compound or pharmaceutically acceptable salt of claim 1, wherein
  $R^1$ is selected from the group consisting of $C_1$-$C_6$alkyl, $C_2$-$C_6$alkenyl, $C_2$-$C_6$alkynyl and $C_3$-$C_6$cycloalkyl; wherein,
  $C_1$-$C_6$alkyl, $C_2$-$C_6$alkenyl, and $C_2$-$C_6$alkynyl are unsubstituted, partly or completely fluorinated and/or substituted with one or two substituents independently selected from the group consisting of $C_1$-$C_6$alkoxy, hydroxy, and oxo; and
  $C_3$-$C_6$cycloalkyl is unsubstituted or substituted with 1, 2, 3, 4 or 5 substituents independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo.

3. The compound or pharmaceutically acceptable salt of claim 1, wherein $R^1$ is phenyl optionally substituted with 1, 2, 3 or 4 substituents selected from the group consisting of $C_1$-$C_6$alkyl, $C_1$-$C_6$alkoxy, fluoro$C_1$-$C_6$alkyl, fluoro$C_1$-$C_6$alkoxy, and halo.

4. The compound or pharmaceutically acceptable salt of claim 1, wherein $R^1$ is selected from the group consisting of methyl; ethyl; isopropyl; n-propyl; cyclopropyl; methoxymethyl; and phenyl, which is unsubstituted or substituted by halo.

5. The compound or pharmaceutically acceptable salt of claim 1, wherein $R^3$ is selected from the group consisting of $C_1$-$C_6$alkyl and $C_3$-$C_6$cycloalkyl; wherein
  $C_1$-$C_6$alkyl is unsubstituted, partly or completely fluorinated and/or substituted with one or two substituents independently selected from the group consisting of $C_1$-$C_6$alkoxy, hydroxy, and oxo; and
  $C_3$-$C_6$cycloalkyl is unsubstituted or substituted with 1, 2, 3, 4 or 5 substituents independently selected from the group consisting of $C_1$-$C_6$alkyl, $C_1$-$C_6$alkoxy, fluorine, fluoro$C_1$-$C_6$alkyl, fluoro$C_1$-$C_6$alkoxy, hydroxy, and oxo.

6. The compound or pharmaceutically acceptable salt of claim 1, wherein
  $R^3$ is selected from the group consisting of phenyl, phenyl$C_1$-$C_6$alkyl, bicyclic aryl, bicyclic aryl$C_1$-$C_6$alkyl, monocyclic heteroaryl$C_1$-$C_6$alkyl, monocyclic heteroaryl, and bicyclic heteroaryl; wherein
  the phenyl, the phenyl of phenyl$C_1$-$C_6$alkyl, the bicyclic aryl, the bicyclic aryl of bicyclic aryl$C_1$-$C_6$alkyl, the monocyclic heteroaryl of monocyclic heteroaryl$C_1$-$C_6$alkyl, the monocyclic heteroaryl and the bicyclic heteroaryl are optionally substituted with 1, 2, 3 or 4 substituents $R^{Ar}$.

7. The compound or pharmaceutically acceptable salt of claim 1, wherein
  $R^{Ar}$, independently of its occurrence, is selected from the group consisting of $C_1$-$C_6$alkyl, halogen, —$OR^{1a}$, —$S(O)_2N(R^d)(R^{3a})$, —$C(O)R^{1a}$, —$C(O)OR^{1a}$, —$C(O)N(R^d)(R^{3a})$, —$N(R^d)(R^{3a})$, —$N(R^c)C(O)R^{1a}$, —$N(R^c)S(O)_2R^{2a}$ and fluoro$C_1$-$C_6$-alkyl; wherein
  $R^c$ and $R^d$, at each occurrence, are each independently hydrogen, $C_1$-$C_6$alkyl, or fluoro$C_1$-$C_6$-alkyl;

$R^{1a}$ and $R^{3a}$, at each occurrence, are each independently hydrogen, $C_1$-$C_6$alkyl, or fluoro$C_1$-$C_6$-alkyl; or $R^d$ and $R^{3a}$, if present as a group $N(R^d)R^{3a}$, may together with the nitrogen atom of said moiety form an N-bound pyrrolidin, N-bound piperidin or N-bound azepan radical; and $R^{2a}$, at each occurrence, is independently $C_1$-$C_6$alkyl, or fluoro$C_1$-$C_6$-alkyl.

8. The compound or pharmaceutically acceptable salt of claim 1, wherein $R^3$ is selected from the group consisting of methyl, ethyl, phenyl, 3-fluorophenyl, 4-fluorophenyl, 2-aminophenyl, 3-aminophenyl, 2-hydroxyphenyl, 2-methylphenyl, 2-methoxyphenyl, 4-methoxyphenyl, 3-carbamoylphenyl, 3-(acetylamino)phenyl, 3-(methyl sulfonylamino)phenyl, 3-(aminosulfonyl)phenyl, 3,4-difluorophenyl, 3,5-difluorophenyl, 2,4-bis(methoxy)phenyl, 3,4-bis(methoxy)phenyl, 2,5-bis(methoxy)phenyl, 2-methoxy-5-fluorophenyl, 2-amino-5-fluorophenyl, 2-methoxy-5-carboxyphenyl, 2-methoxy-5-(trifluoro-methyl)phenyl, 2-methoxy-5-(acetylamino)phenyl, 2-methoxy-3-(acetylamino)phenyl, 2-(trifluoromethoxy)-5-(acetylamino)phenyl, 2-methoxy-5-(methyl sulfonylamino)phenyl, 4-fluoro-3-(acetylamino)phenyl, 2-methyl-5-(acetylamino)phenyl, 2-methyl-5-hydroxyphenyl, 2-methoxy-5-(aminocarbonyl)phenyl, 3-amino-2-(aminocarbonyl)phenyl, 2-methoxy-5-(N-methylaminocarbonyl)phenyl, 2-methoxy-5-(N-ethylaminocarbonyl)phenyl, 2-methoxy-5-(N,N-dimethylaminocarbonyl)phenyl, 2-methoxy-5-(pyrrolidin-1-ylcarbonyl)phenyl, 2-methoxy-5-(pyrrolidin-2-on-1-yl)phenyl, 3-methoxy-5-(N,N-dimethylaminocarbonyl)phenyl, 2-amino-5-chlorophenyl, 2-amino-5-(trifluoromethyl)phenyl, 2-amino-3,5-difluorophenyl, 2-methyl-3-(acetylamino)-4-fluorophenyl, 3-pyridyl, 5-pyrimidinyl, 2-fluoro-3-pyridyl, 2-amino-4-pyridyl, 5-fluoro-3-pyridyl, 2-chloro-3-pyridyl, indol-5-yl, 2,6-difluoropyridin-4-yl, 2-thienyl, 1-ethylpyrazol-5-yl, and 1H-pyrrolo[2,3-b]pyridine-6-yl.

9. The compound or pharmaceutically acceptable salt of claim 1, wherein X is O.

10. A compound selected from the group consisting of:
N-(3-{5-[(1S)-1-(4-chlorophenyl)ethyl]-3-cyclopropyl-4-oxo-4,5-dihydro[1,2]oxazolo[4,5-d]pyridazin-7-yl}-4-methoxyphenyl)acetamide;
5-(4-chlorobenzyl)-7-(4-methoxyphenyl)-3-methyl[1,2]oxazolo[4,5-d]pyridazin-4(5H)-one;
N-(3-{5-[(1R)-1-(4-chlorophenyl)ethyl]-3-cyclopropyl-4-oxo-4,5-dihydro[1,2]oxazolo[4,5-d]pyridazin-7-yl}-4-methoxyphenyl)acetamide;
5-[1-(4-chlorophenyl)ethyl]-7-(2,6-difluoropyridin-4-yl)-3-methyl[1,2]oxazolo[4,5-d]pyridazin-4(5H)-one;
7-(2,4-dimethoxyphenyl)-3-methyl-5-(pyridin-4-ylmethyl)[1,2]oxazolo[4,5-d]pyridazin-4(5H)-one;
7-(2-amino-5-chlorophenyl)-5-[1-(4-chlorophenyl)ethyl]-3-methyl[1,2]oxazolo[4,5-d]pyridazin-4(5H)-one;
5-[1-(4-chlorophenyl)ethyl]-7-(2-chloropyridin-3-yl)-3-methyl[1,2]oxazolo[4,5-d]pyridazin-4(5H)-one;
N-{5-[5-(4-chlorobenzyl)-3-methyl-4-oxo-4,5-dihydro[1,2]oxazolo[4,5-d]pyridazin-7-yl]-2-fluorophenyl)}acetamide;
7-(2,5-dimethoxyphenyl)-5-[4-methoxy-3-(trifluoromethyl)benzyl]-3-methyl[1,2]oxazolo[4,5-d]pyridazin-4(5H)-one;
5-[2-(4-chlorophenyl)ethyl]-7-(2,5-dimethoxyphenyl)-3-methyl[1,2]oxazolo[4,5-d]pyridazin-4(5H)-one;
7-[2-amino-5-(trifluoromethyl)phenyl]-5-[1-(4-chlorophenyl)ethyl]-3-methyl[1,2]oxazolo[4,5-d]pyridazin-4(5H)-one;
5-[1-(4-chlorophenyl)ethyl]-7-(1H-indol-6-yl)-3-methyl[1,2]oxazolo[4,5-d]pyridazin-4(5H)-one;
5-(4-chlorobenzyl)-7-(2,5-dimethoxyphenyl)-3-(propan-2-yl)[1,2]oxazolo[4,5-d]pyridazin-4(5H)-one;
7-(2-aminophenyl)-5-[1-(4-chlorophenyl)ethyl]-3-methyl[1,2]oxazolo[4,5-d]pyridazin-4(5H)-one;
N-(3-{5-[4-methoxy-3-(trifluoromethyl)benzyl]-3-methyl-4-oxo-4,5-dihydro[1,2]oxazolo[4,5-d]pyridazin-7-yl}phenyl)acetamide;
5-[1-(4-chlorophenyl)ethyl]-7-(5-hydroxy-2-methylphenyl)-3-methyl[1,2]oxazolo[4,5-d]pyridazin-4(5H)-one;
N-(2-fluoro-5-{5-[2-fluoro-5-(trifluoromethyl)benzyl]-3-methyl-4-oxo-4,5-dihydro[1,2]oxazolo[4,5-d]pyridazin-7-yl}phenyl)acetamide;
N-(3-{5-[1-(4-chlorophenyl)ethyl]-3-methyl-4-oxo-4,5-dihydro[1,2]oxazolo[4,5-d]pyridazin-7-yl}-4-methylphenyl)acetamide;
7-(4-fluorophenyl)-3-methyl-5-[4-(trifluoromethyl)benzyl][1,2]oxazolo[4,5-d]pyridazin-4(5H)-one;
5-(2-fluorobenzyl)-3,7-dimethyl[1,2]oxazolo[4,5-d]pyridazin-4(5H)-one;
5-[1-(4-chlorophenyl)ethyl]-7-(2,5-dimethoxyphenyl)-3-methyl[1,2]oxazolo[4,5-d]pyridazin-4(5H)-one;
5-[1-(4-chlorophenyl)ethyl]-7-(5-fluoropyridin-3-yl)-3-methyl[1,2]oxazolo[4,5-d]pyridazin-4(5H)-one;
5-(4-chlorobenzyl)-7-(3-fluorophenyl)-3-methyl[1,2]oxazolo[4,5-d]pyridazin-4(5H)-one;
N-(3-{5-[1-(4-chlorophenyl)ethyl]-3-methyl-4-oxo-4,5-dihydro[1,2]oxazolo[4,5-d]pyridazin-7-yl}phenyl)methanesulfonamide;
5-[2-fluoro-5-(trifluoromethyl)benzyl]-3,7-dimethyl[1,2]oxazolo[4,5-d]pyridazin-4(5H)-one;
7-(2-methoxyphenyl)-3-methyl-5-(pyridin-4-ylmethyl)[1,2]oxazolo[4,5-d]pyridazin-4(5H)-one;
N-{3-[5-(4-chlorobenzyl)-3-(methoxymethyl)-4-oxo-4,5-dihydro[1,2]oxazolo[4,5-d]pyridazin-7-yl]phenyl}acetamide;
5-[4-chloro-3-(trifluoromethyl)benzyl]-7-(4-fluorophenyl)-3-methyl[1,2]oxazolo[4,5-d]pyridazin-4(5H)-one;
N-(2-fluoro-5-{3-methyl-4-oxo-5-[4-(trifluoromethyl)benzyl]-4,5-dihydro[1,2]oxazolo[4,5-d]pyridazin-7-yl}phenyl)acetamide;
5-(4-fluorobenzyl)-3,7-dimethyl[1,2]oxazolo[4,5-d]pyridazin-4(5H)-one;
5-[(1S)-1-(4-chlorophenyl)ethyl]-3,7-dimethyl[1,2]oxazolo[4,5-d]pyridazin-4(5H)-one;
7-(2,4-dimethoxyphenyl)-5-[4-methoxy-3-(trifluoromethyl)benzyl]-3-methyl[1,2]oxazolo[4,5-d]pyridazin-4(5H)-one;
N-(3-{5-[1-(4-chlorophenyl)ethyl]-3-methyl-4-oxo-4,5-dihydro[1,2]oxazolo[4,5-d]pyridazin-7-yl}-2-methoxyphenyl)acetamide;
N-(3-{5-[(1R)-1-(4-chlorophenyl)ethyl]-3-methyl-4-oxo-4,5-dihydro[1,2]oxazolo[4,5-d]pyridazin-7-yl}phenyl)acetamide;
N-[4-methyl-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide;
5-(4-chlorobenzyl)-7-(2,5-dimethoxyphenyl)-3-ethyl[1,2]oxazolo[4,5-d]pyridazin-4(5H)-one;
7-(2,4-dimethoxyphenyl)-5-[4-fluoro-3-(trifluoromethyl)benzyl]-3-methyl[1,2]oxazolo[4,5-d]pyridazin-4(5H)-one;

3-{5-[1-(4-chlorophenyl)ethyl]-3-methyl-4-oxo-4,5-dihydro[1,2]oxazolo[4,5-d]pyridazin-7-yl}-4-methoxy-N,N-dimethylbenzamide;
N-(3-{5-[1-(4-chlorophenyl)ethyl]-3-methyl-4-oxo-4,5-dihydro[1,2]oxazolo[4,5-d]pyridazin-7-yl}-4-methoxyphenyl)acetamide;
N-(3-{5-[(1R)-1-(4-chlorophenyl)ethyl]-3-methyl-4-oxo-4,5-dihydro[1,2]oxazolo[4,5-d]pyridazin-7-yl}-4-methoxyphenyl)acetamide;
N-(3-{5-[4-fluoro-3-(trifluoromethyl)benzyl]-3-methyl-4-oxo-4,5-dihydro[1,2]oxazolo[4,5-d]pyridazin-7-yl}phenyl)acetamide;
5-(4-chlorobenzyl)-7-(3,4-difluorophenyl)-3-methyl[1,2]oxazolo[4,5-d]pyridazin-4(5H)-one;
5-[4-fluoro-3-(trifluoromethyl)benzyl]-3,7-dimethyl[1,2]oxazolo[4,5-d]pyridazin-4(5H)-one;
3,7-dimethyl-5-(pyridin-4-ylmethyl)[1,2]oxazolo[4,5-d]pyridazin-4(5H)-one;
N-{3-[5-(4-chlorobenzyl)-3-methyl-4-oxo-4,5-dihydro[1,2]oxazolo[4,5-d]pyridazin-7-yl]-4-methoxyphenyl}acetamide;
5-[2-fluoro-5-(trifluoromethyl)benzyl]-7-(2-methoxyphenyl)-3-methyl[1,2]oxazolo[4,5-d]pyridazin-4(5H)-one;
5-(4-chlorobenzyl)-3-cyclopropyl-7-(2,5-dimethoxyphenyl)[1,2]oxazolo[4,5-d]pyridazin-4(5H)-one;
7-(2,4-dimethoxyphenyl)-5-[2-fluoro-5-(trifluoromethyl)benzyl]-3-methyl[1,2]oxazolo[4,5-d]pyridazin-4(5H)-one;
N-[3-{5-[1-(4-chlorophenyl)ethyl]-3-methyl-4-oxo-4,5-dihydro[1,2]oxazolo[4,5-d]pyridazin-7-yl}-4-(trifluoromethoxy)phenyl]acetamide;
5-[4-methoxy-3-(trifluoromethyl)benzyl]-3,7-dimethyl[1,2]oxazolo[4,5-d]pyridazin-4(5H)-one;
N-{3-[5-(4-chlorobenzyl)-3-cyclopropyl-4-oxo-4,5-dihydro[1,2]oxazolo[4,5-d]pyridazin-7-yl]phenyl}acetamide;
5-(4-chlorobenzyl)-7-(2,5-dimethoxyphenyl)-3-propyl[1,2]oxazolo[4,5-d]pyridazin-4(5H)-one;
3-{5-[1-(4-chlorophenyl)ethyl]-3-methyl-4-oxo-4,5-dihydro[1,2]oxazolo[4,5-d]pyridazin-7-yl}benzenesulfonamide;
5-[4-fluoro-3-(trifluoromethyl)benzyl]-7-(2-methoxyphenyl)-3-methyl[1,2]oxazolo[4,5-d]pyridazin-4(5H)-one;
N-(3-{5-[1-(4-chlorophenyl)ethyl]-3-methyl-4-oxo-4,5-dihydro[1,2]oxazolo[4,5-d]pyridazin-7-yl}-4-methoxyphenyl)methanesulfonamide;
5-(4-chlorobenzyl)-3-methyl-7-(thiophen-2-yl)[1,2]oxazolo[4,5-d]pyridazin-4(5H)-one;
N-(3-{3-methyl-4-oxo-5-[4-(trifluoromethyl)benzyl]-4,5-dihydro[1,2]oxazolo[4,5-d]pyridazin-7-yl}phenyl)acetamide;
5-[(1R)-1-(4-chlorophenyl)ethyl]-3,7-dimethyl[1,2]oxazolo[4,5-d]pyridazin-4(5H)-one;
3-{5-[1-(4-chlorophenyl)ethyl]-3-methyl-4-oxo-4,5-dihydro[1,2]oxazolo[4,5-d]pyridazin-7-yl}-4-methoxybenzamide;
5-[2-(4-chlorophenyl)ethyl]-3,7-dimethyl[1,2]oxazolo[4,5-d]pyridazin-4(5H)-one;
N-(2-fluoro-5-{5-[4-fluoro-3-(trifluoromethyl)benzyl]-3-methyl-4-oxo-4,5-dihydro[1,2]oxazolo[4,5-d]pyridazin-7-yl}phenyl)acetamide;
N-(2-fluoro-5-{5-[4-methoxy-3-(trifluoromethyl)benzyl]-3-methyl-4-oxo-4,5-dihydro[1,2]oxazolo[4,5-d]pyridazin-7-yl}phenyl)acetamide;
5-[1-(4-chlorophenyl)ethyl]-7-(5-fluoro-2-methoxyphenyl)-3-methyl[1,2]oxazolo[4,5-d]pyridazin-4(5H)-one;
N-(4-methoxy-3-{3-methyl-4-oxo-5-[4-(trifluoromethyl)benzyl]-4,5-dihydro[1,2]oxazolo[4,5-d]pyridazin-7-yl}phenyl)acetamide;
2-amino-6-{5-[1-(4-chlorophenyl)ethyl]-3-methyl-4-oxo-4,5-dihydro[1,2]oxazolo[4,5-d]pyridazin-7-yl}benzamide;
7-(4-fluorophenyl)-5-[4-methoxy-3-(trifluoromethyl)benzyl]-3-methyl[1,2]oxazolo[4,5-d]pyridazin-4(5H)-one;
5-(4-chlorobenzyl)-7-(2-methoxyphenyl)-3-methyl[1,2]oxazolo[4,5-d]pyridazin-4(5H)-one;
5-[(1S)-1-(4-chlorophenyl)ethyl]-3-cyclopropyl-7-(2,5-dimethoxyphenyl)[1,2]oxazolo[4,5-d]pyridazin-4(5H)-one;
5-[4-chloro-3-(trifluoromethyl)benzyl]-3,7-dimethyl[1,2]oxazolo[4,5-d]pyridazin-4(5H)-one;
N-{3-[5-(4-chlorobenzyl)-3-methyl-4-oxo-4,5-dihydro[1,2]oxazolo[4,5-d]pyridazin-7-yl]phenyl}acetamide;
5-(4-chlorobenzyl)-7-(2,5-dimethoxyphenyl)-3-(methoxymethyl)[1,2]oxazolo[4,5-d]pyridazin-4(5H)-one;
N-(3-{5-[(1S)-1-(4-chlorophenyl)ethyl]-3-methyl-4-oxo-4,5-dihydro[1,2]oxazolo[4,5-d]pyridazin-7-yl}phenyl)acetamide;
3-{5-[1-(4-chlorophenyl)ethyl]-3-methyl-4-oxo-4,5-dihydro[1,2]oxazolo[4,5-d]pyridazin-7-yl}-4-methoxybenzoic acid;
7-(4-fluorophenyl)-3-methyl-5-(pyridin-4-ylmethyl)[1,2]oxazolo[4,5-d]pyridazin-4(5H)-one;
5-[(R)-(4-chlorophenyl)(phenyl)methyl]-3,7-diethyl[1,2]oxazolo[4,5-d]pyridazin-4(5H)-one;
5-(4-chlorobenzyl)-3-methyl-7-(2-methylphenyl)[1,2]oxazolo[4,5-d]pyridazin-4(5H)-one;
7-(2-amino-3,5-difluorophenyl)-5-[1-(4-chlorophenyl)ethyl]-3-methyl[1,2]oxazolo[4,5-d]pyridazin-4(5H)-one;
N-(3-{5-[1-(4-chlorophenyl)ethyl]-3-methyl-4-oxo-4,5-dihydro[1,2]oxazolo[4,5-d]pyridazin-7-yl}phenyl)acetamide;
5-[1-(4-chlorophenyl)ethyl]-7-[2-methoxy-5-(trifluoromethyl)phenyl]-3-methyl[1,2]oxazolo[4,5-d]pyridazin-4(5H)-one;
5-(4-chlorobenzyl)-7-(2,5-dimethoxyphenyl)-3-phenyl[1,2]oxazolo[4,5-d]pyridazin-4(5H)-one;
7-(2,5-dimethoxyphenyl)-5-[4-fluoro-3-(trifluoromethyl)benzyl]-3-methyl[1,2]oxazolo[4,5-d]pyridazin-4(5H)-one;
3-{5-[(1S)-1-(4-chlorophenyl)ethyl]-3-methyl-4-oxo-4,5-dihydro[1,2]oxazolo[4,5-d]pyridazin-7-yl}-4-methoxy-N-methylbenzamide;
5-(4-chlorobenzyl)-7-(4-fluorophenyl)-3-methyl[1,2]oxazolo[4,5-d]pyridazin-4(5H)-one;
5-(3-chloro-4-fluorobenzyl)-3,7-dimethyl[1,2]oxazolo[4,5-d]pyridazin-4(5H)-one;
N-(3-{5-[2-fluoro-5-(trifluoromethyl)benzyl]-3-methyl-4-oxo-4,5-dihydro[1,2]oxazolo[4,5-d]pyridazin-7-yl}phenyl)acetamide;
7-(2-aminopyridin-3-yl)-5-[1-(4-chlorophenyl)ethyl]-3-methyl[1,2]oxazolo[4,5-d]pyridazin-4(5H)-one;
5-(4-chlorobenzyl)-7-(2,4-dimethoxyphenyl)-3-methyl[1,2]oxazolo[4,5-d]pyridazin-4(5H)-one;
5-(5-chloro-2-fluorobenzyl)-3,7-dimethyl[1,2]oxazolo[4,5-d]pyridazin-4(5H)-one;
5-[(S)-(4-chlorophenyl)(phenyl)methyl]-3,7-diethyl[1,2]oxazolo[4,5-d]pyridazin-4(5H)-one;
5-(4-chlorobenzyl)-7-(3,5-difluorophenyl)-3-methyl[1,2]oxazolo[4,5-d]pyridazin-4(5H)-one;

N-{3-[5-(4-chlorobenzyl)-4-oxo-3-propyl-4,5-dihydro[1,2]oxazolo[4,5-d]pyridazin-7-yl]phenyl}acetamide;
5-(4-chloro-2-fluorobenzyl)-3,7-dimethyl[1,2]oxazolo[4,5-d]pyridazin-4(5H)-one;
7-(2,5-dimethoxyphenyl)-3-methyl-5-(pyridin-4-ylmethyl)[1,2]oxazolo[4,5-d]pyridazin-4(5H)-one;
N-{2-fluoro-5-[3-methyl-4-oxo-5-(pyridin-4-ylmethyl)-4,5-dihydro[1,2]oxazolo[4,5-d]pyridazin-7-yl]phenyl}acetamide;
7-(2,5-dimethoxyphenyl)-3-methyl-5-[4-(trifluoromethyl)benzyl][1,2]oxazolo[4,5-d]pyridazin-4(5H)-one;
N-{3-[5-(4-chlorobenzyl)-4-oxo-3-(propan-2-yl)-4,5-dihydro[1,2]oxazolo[4,5-d]pyridazin-7-yl]phenyl}acetamide;
7-(2-amino-5-fluorophenyl)-5-[1-(4-chlorophenyl)ethyl]-3-methyl[1,2]oxazolo[4,5-d]pyridazin-4(5H)-one;
5-[1-(4-chlorophenyl)ethyl]-7-[2-methoxy-5-(pyrrolidin-1-ylcarbonyl)phenyl]-3-methyl[1,2]oxazolo[4,5-d]pyridazin-4(5H)-one;
5-(4-chlorobenzyl)-7-(3,4-dimethoxyphenyl)-3-methyl[1,2]oxazolo[4,5-d]pyridazin-4(5H)-one;
5-[1-(4-chlorophenyl)ethyl]-7-(2-hydroxyphenyl)-3-methyl[1,2]oxazolo[4,5-d]pyridazin-4(5H)-one;
7-(2-methoxyphenyl)-5-[4-methoxy-3-(trifluoromethyl)benzyl]-3-methyl[1,2]oxazolo[4,5-d]pyridazin-4(5H)-one;
5-(4-chlorobenzyl)-7-(2,5-dimethoxyphenyl)-3-methyl[1,2]oxazolo[4,5-d]pyridazin-4(5H)-one;
N-[4-methoxy-3-(3-methyl-4-oxo-5-{(1S)-1-[4-(trifluoromethyl)phenyl]ethyl}-4,5-dihydro[1,2]oxazolo[4,5-d]pyridazin-7-yl)phenyl]acetamide;
N-{3-[5-(4-chlorobenzyl)-4-oxo-3-phenyl-4,5-dihydro[1,2]oxazolo[4,5-d]pyridazin-7-yl]phenyl}acetamide;
N-[4-methoxy-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide;
3-{5-[1-(4-chlorophenyl)ethyl]-3-methyl-4-oxo-4,5-dihydro[1,2]oxazolo[4,5-d]pyridazin-7-yl}benzamide;
N-(4-methyl-3-{3-methyl-4-oxo-5-[4-(trifluoromethyl)benzyl]-4,5-dihydro[1,2]oxazolo[4,5-d]pyridazin-7-yl}phenyl)acetamide;
3,7-dimethyl-5-(3-methylbutyl)[1,2]oxazolo[4,5-d]pyridazin-4(5H)-one;
5-[1-(4-chlorophenyl)ethyl]-3-methyl-7-(pyridin-3-yl)[1,2]oxazolo[4,5-d]pyridazin-4(5H)-one;
N-{3-[3-methyl-4-oxo-5-(pyridin-4-ylmethyl)-4,5-dihydro[1,2]oxazolo[4,5-d]pyridazin-7-yl]phenyl}acetamide;
3-{5-[(1R)-1-(4-chlorophenyl)ethyl]-3-methyl-4-oxo-4,5-dihydro[1,2]oxazolo[4,5-d]pyridazin-7-yl}-4-methoxy-N-methylbenzamide;
N-[6-fluoro-2-methyl-3-(3-methyl-4-oxo-5-{(1R)-1-[4-(trifluoromethyl)phenyl]ethyl})-4,5-dihydro[1,2]oxazolo[4,5-d]pyridazin-7-yl)phenyl]acetamide;
5-[1-(4-chlorophenyl)ethyl]-3-methyl-7-(pyrimidin-5-yl)[1,2]oxazolo[4,5-d]pyridazin-4(5H)-one;
5-[1-(4-chlorophenyl)ethyl]-3,7-dimethyl[1,2]oxazolo[4,5-d]pyridazin-4(5H)-one;
5-[1-(4-chlorophenyl)ethyl]-7-(1-ethyl-1H-pyrazol-5-yl)-3-methyl[1,2]oxazolo[4,5-d]pyridazin-4(5H)-one;
5-[1-(4-chlorophenyl)ethyl]-3-methyl-7-(1H-pyrrolo[3,2-b]pyridin-6-yl)[1,2]oxazolo[4,5-d]pyridazin-4(5H)-one;
N-(3-{5-[(1S)-1-(4-chlorophenyl)ethyl]-3-methyl-4-oxo-4,5-dihydro[1,2]oxazolo[4,5-d]pyridazin-7-yl}-4-methoxyphenyl)acetamide;
7-(2-methoxyphenyl)-3-methyl-5-[4-(trifluoromethyl)benzyl][1,2]oxazolo[4,5-d]pyridazin-4(5H)-one;
3-{5-[1-(4-chlorophenyl)ethyl]-3-methyl-4-oxo-4,5-dihydro[1,2]oxazolo[4,5-d]pyridazin-7-yl}-4-methoxy-N-methylbenzamide;
5-(4-chlorobenzyl)-3-methyl-7-(pyridin-3-yl)[1,2]oxazolo[4,5-d]pyridazin-4(5H)-one;
3,7-dimethyl-5-[3-(trifluoromethyl)benzyl][1,2]oxazolo[4,5-d]pyridazin-4(5H)-one;
5-(4-chlorobenzyl)-3-methyl-7-phenyl[1,2]oxazolo[4,5-d]pyridazin-4(5H)-one;
5-(2,4-difluorobenzyl)-3,7-dimethyl[1,2]oxazolo[4,5-d]pyridazin-4(5H)-one;
3,7-dimethyl-5-[4-(trifluoromethyl)benzyl][1,2]oxazolo[4,5-d]pyridazin-4(5H)-one;
7-(2,5-dimethoxyphenyl)-3-methyl-5-{(1R)-1-[4-(trifluoromethyl)phenyl]ethyl}[1,2]oxazolo[4,5-d]pyridazin-4(5H)-one;
7-(3-aminophenyl)-5-[1-(4-chlorophenyl)ethyl]-3-methyl[1,2]oxazolo[4,5-d]pyridazin-4(5H)-one;
7-(2,4-dimethoxyphenyl)-3-methyl-5-[4-(trifluoromethyl)benzyl][1,2]oxazolo[4,5-d]pyridazin-4(5H)-one;
5-[(1R)-1-(4-chlorophenyl)ethyl]-3-cyclopropyl-7-(2,5-dimethoxyphenyl)[1,2]oxazolo[4,5-d]pyridazin-4(5H)-one;
N-{3-[5-(4-chlorobenzyl)-3-ethyl-4-oxo-4,5-dihydro[1,2]oxazolo[4,5-d]pyridazin-7-yl]phenyl}acetamide;
7-(2,5-dimethoxyphenyl)-5-[2-fluoro-5-(trifluoromethyl)benzyl]-3-methyl[1,2]oxazolo[4,5-d]pyridazin-4(5H)-one; and
3-{5-[1-(4-chlorophenyl)ethyl]-3-methyl-4-oxo-4,5-dihydro[1,2]oxazolo[4,5-d]pyridazin-7-yl}-N-ethyl-4-methoxybenzamide;
or a pharmaceutically acceptable salt thereof.

11. The compound of claim 10, wherein the compound is selected from the group consisting of
N-(3-{5-[(1S)-1-(4-chlorophenyl)ethyl]-3-cyclopropyl-4-oxo-4,5-dihydro[1,2]oxazolo[4,5-d]pyridazin-7-yl}-4-methoxyphenyl)acetamide;
5-[1-(4-chlorophenyl)ethyl]-7-(2,6-difluoropyridin-4-yl)-3-methyl[1,2]oxazolo[4,5-d]pyridazin-4(5H)-one;
7-(2-amino-5-chlorophenyl)-5-[1-(4-chlorophenyl)ethyl]-3-methyl[1,2]oxazolo[4,5-d]pyridazin-4(5H)-one;
5-[1-(4-chlorophenyl)ethyl]-7-(2-chloropyridin-3-yl)-3-methyl[1,2]oxazolo[4,5-d]pyridazin-4(5H)-one;
N-{5-[5-(4-chlorobenzyl)-3-methyl-4-oxo-4,5-dihydro[1,2]oxazolo[4,5-d]pyridazin-7-yl]-2-fluorophenyl}acetamide;
5-[2-(4-chlorophenyl)ethyl]-7-(2,5-dimethoxyphenyl)-3-methyl[1,2]oxazolo[4,5-d]pyridazin-4(5H)-one;
5-[1-(4-chlorophenyl)ethyl]-7-(1H-indol-6-yl)-3-methyl[1,2]oxazolo[4,5-d]pyridazin-4(5H)-one;
5-(4-chlorobenzyl)-7-(2,5-dimethoxyphenyl)-3-(propan-2-yl)[1,2]oxazolo[4,5-d]pyridazin-4(5H)-one;
7-(2-aminophenyl)-5-[1-(4-chlorophenyl)ethyl]-3-methyl[1,2]oxazolo[4,5-d]pyridazin-4(5H)-one;
5-[1-(4-chlorophenyl)ethyl]-7-(5-hydroxy-2-methylphenyl)-3-methyl[1,2]oxazolo[4,5-d]pyridazin-4(5H)-one;
N-(3-{5-[1-(4-chlorophenyl)ethyl]-3-methyl-4-oxo-4,5-dihydro[1,2]oxazolo[4,5-d]pyridazin-7-yl]-4-methylphenyl)acetamide;
7-(4-fluorophenyl)-3-methyl-5-[4-(trifluoromethyl)benzyl][1,2]oxazolo[4,5-d]pyridazin-4(5H)-one;
5-(2-fluorobenzyl)-3,7-dimethyl[1,2]oxazolo[4,5-d]pyridazin-4(5H)-one; 20

5-[1-(4-chlorophenyl)ethyl]-7-(2,5-dimethoxyphenyl)-3-methyl[1,2]oxazolo[4,5-d]pyridazin-4(5H)-one;

5-[1-(4-chlorophenyl)ethyl]-7-(5-fluoropyridin-3-yl)-3-methyl[1,2]oxazolo[4,5-d]pyridazin-4(5H)-one;

N-(3-{5-[1-(4-chlorophenyl)ethyl]-3-methyl-4-oxo-4,5-dihydro[1,2]oxazolo[4,5-d]pyridazin-7-yl}phenyl)methanesulfonamide;

N-{3-[5-(4-chlorobenzyl)-3-(methoxymethyl)-4-oxo-4,5-dihydro[1,2]oxazolo[4,5-d]pyridazin-7-yl]phenyl}acetamide;

5-[4-chloro-3-(trifluoromethyl)benzyl]-7-(4-fluorophenyl)-3-methyl[1,2]oxazolo[4,5-d]pyridazin-4(5H)-one;

5-[(1S)-1-(4-chlorophenyl)ethyl]-3,7-dimethyl[1,2]oxazolo[4,5-d]pyridazin-4(5H)-one;

N-(3-{5-[(1R)-1-(4-chlorophenyl)ethyl]-3-methyl-4-oxo-4,5-dihydro[1,2]oxazolo[4,5-d]pyridazin-7-yl}phenyl)acetamide;

N-[4-methyl-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide;

5-(4-chlorobenzyl)-7-(2,5-dimethoxyphenyl)-3-ethyl[1,2]oxazolo[4,5-d]pyridazin-4(5H)-one;

7-(2,4-dimethoxyphenyl)-5-[4-fluoro-3-(trifluoromethyl)benzyl]-3-methyl[1,2]oxazolo[4,5-d]pyridazin-4(5H)-one;

3-{5-[1-(4-chlorophenyl)ethyl]-3-methyl-4-oxo-4,5-dihydro[1,2]oxazolo[4,5-d]pyridazin-7-yl}-4-methoxy-N,N-dimethylbenzamide;

N-(3-{5-[1-(4-chlorophenyl)ethyl]-3-methyl-4-oxo-4,5-dihydro[1,2]oxazolo[4,5-d]pyridazin-7-yl}-4-methoxyphenyl)acetamide;

N-(3-{5-[4-fluoro-3-(trifluoromethyl)benzyl]-3-methyl-4-oxo-4,5-dihydro[1,2]oxazolo[4,5-d]pyridazin-7-yl}phenyl)acetamide;

5-(4-chlorobenzyl)-7-(3,4-difluorophenyl)-3-methyl[1,2]oxazolo[4,5-d]pyridazin-4(5H)-one;

N-{3-[5-(4-chlorobenzyl)-3-methyl-4-oxo-4,5-dihydro[1,2]oxazolo[4,5-d]pyridazin-7-yl]-4-methoxyphenyl}acetamide;

5-[2-fluoro-5-(trifluoromethyl)benzyl]-7-(2-methoxyphenyl)-3-methyl[1,2]oxazolo[4,5-d]pyridazin-4(5H)-one;

5-(4-chlorobenzyl)-3-cyclopropyl-7-(2,5-dimethoxyphenyl)[1,2]oxazolo[4,5-d]pyridazin-4(5H)-one;

7-(2,4-dimethoxyphenyl)-5-[2-fluoro-5-(trifluoromethyl)benzyl]-3-methyl[1,2]oxazolo[4,5-d]pyridazin-4(5H)-one;

N-[3-{5-[1-(4-chlorophenyl)ethyl]-3-methyl-4-oxo-4,5-dihydro[1,2]oxazolo[4,5-d]pyridazin-7-yl}-4-(trifluoromethoxy)phenyl]acetamide;

N-{3-[5-(4-chlorobenzyl)-3-cyclopropyl-4-oxo-4,5-dihydro[1,2]oxazolo[4,5-d]pyridazin-7-yl]phenyl}acetamide;

3-{5-[1-(4-chlorophenyl)ethyl]-3-methyl-4-oxo-4,5-dihydro[1,2]oxazolo[4,5-d]pyridazin-7-yl}benzenesulfonamide;

5-[4-fluoro-3-(trifluoromethyl)benzyl]-7-(2-methoxyphenyl)-3-methyl[1,2]oxazolo[4,5-d]pyridazin-4(5H)-one;

N-(3-{5-[1-(4-chlorophenyl)ethyl]-3-methyl-4-oxo-4,5-dihydro[1,2]oxazolo[4,5-d]pyridazin-7-yl}-4-methoxyphenyl)methanesulfonamide;

5-(4-chlorobenzyl)-3-methyl-7-(thiophen-2-yl)[1,2]oxazolo[4,5-d]pyridazin-4(5H)-one;

N-(3-{3-methyl-4-oxo-5-[4-(trifluoromethyl)benzyl]-4,5-dihydro[1,2]oxazolo[4,5-d]pyridazin-7-yl}phenyl)acetamide;

3-{5-[1-(4-chlorophenyl)ethyl]-3-methyl-4-oxo-4,5-dihydro[1,2]oxazolo[4,5-d]pyridazin-7-yl}-4-methoxybenzamide;

5-[1-(4-chlorophenyl)ethyl]-7-(5-fluoro-2-methoxyphenyl)-3-methyl[1,2]oxazolo[4,5-d]pyridazin-4(5H)-one;

N-(4-methoxy-3-{3-methyl-4-oxo-5-[4-(trifluoromethyl)benzyl]-4,5-dihydro[1,2]oxazolo[4,5-d]pyridazin-7-yl}phenyl)acetamide;

2-amino-6-{5-[1-(4-chlorophenyl)ethyl]-3-methyl-4-oxo-4,5-dihydro[1,2]oxazolo[4,5-d]pyridazin-7-yl}benzamide;

7-(4-fluorophenyl)-5-[4-methoxy-3-(trifluoromethyl)benzyl]-3-methyl[1,2]oxazolo[4,5-d]pyridazin-4(5H)-one;

5-(4-chlorobenzyl)-7-(2-methoxyphenyl)-3-methyl[1,2]oxazolo[4,5-d]pyridazin-4(5H)-one;

5-[(1S)-1-(4-chlorophenyl)ethyl]-3-cyclopropyl-7-(2,5-dimethoxyphenyl)[1,2]oxazolo[4,5-d]pyridazin-4(5H)-one;

N-{3-[5-(4-chlorobenzyl)-3-methyl-4-oxo-4,5-dihydro[1,2]oxazolo[4,5-d]pyridazin-7-yl]phenyl}acetamide;

5-(4-chlorobenzyl)-7-(2,5-dimethoxyphenyl)-3-(methoxymethyl)[1,2]oxazolo[4,5-d]pyridazin-4(5H)-one;

N-(3-{5-[(1S)-1-(4-chlorophenyl)ethyl]-3-methyl-4-oxo-4,5-dihydro[1,2]oxazolo[4,5-d]pyridazin-7-yl}phenyl)acetamide;

3-{5-[1-(4-chlorophenyl)ethyl]-3-methyl-4-oxo-4,5-dihydro[1,2]oxazolo[4,5-d]pyridazin-7-yl}-4-methoxybenzoic acid;

7-(4-fluorophenyl)-3-methyl-5-(pyridin-4-ylmethyl)[1,2]oxazolo[4,5-d]pyridazin-4(5H)-one;

5-[(R)-(4-chlorophenyl)(phenyl)methyl]-3,7-diethyl[1,2]oxazolo[4,5-d]pyridazin-4(5H)-one;

5-(4-chlorobenzyl)-3-methyl-7-(2-methylphenyl)[1,2]oxazolo[4,5-d]pyridazin-4(5H)-one;

7-(2-amino-3,5-difluorophenyl)-5-[1-(4-chlorophenyl)ethyl]-3-methyl[1,2]oxazolo[4,5-d]pyridazin-4(5H)-one;

N-(3-{5-[1-(4-chlorophenyl)ethyl]-3-methyl-4-oxo-4,5-dihydro[1,2]oxazolo[4,5-d]pyridazin-7-yl}phenyl)acetamide;

5-[1-(4-chlorophenyl)ethyl]-7-[2-methoxy-5-(trifluoromethyl)phenyl]-3-methyl[1,2]oxazolo[4,5-d]pyridazin-4(5H)-one;

3-{5-[(1S)-1-(4-chlorophenyl)ethyl]-3-methyl-4-oxo-4,5-dihydro[1,2]oxazolo[4,5-d]pyridazin-7-yl}-4-methoxy-N-methylbenzamide;

5-(4-chlorobenzyl)-7-(4-fluorophenyl)-3-methyl[1,2]oxazolo[4,5-d]pyridazin-4(5H)-one;

N-(3-{5-[2-fluoro-5-(trifluoromethyl)benzyl]-3-methyl-4-oxo-4,5-dihydro[1,2]oxazolo[4,5-d]pyridazin-7-yl}phenyl)acetamide;

7-(2-aminopyridin-3-yl)-5-[1-(4-chlorophenyl)ethyl]-3-methyl[1,2]oxazolo[4,5-d]pyridazin-4(5H)-one;

5-(4-chlorobenzyl)-7-(2,4-dimethoxyphenyl)-3-methyl[1,2]oxazolo[4,5-d]pyridazin-4(5H)-one;

5-[(S)-(4-chlorophenyl)(phenyl)methyl]-3,7-diethyl[1,2]oxazolo[4,5-d]pyridazin-4(5H)-one;

N-{3-[5-(4-chlorobenzyl)-4-oxo-3-propyl-4,5-dihydro[1,2]oxazolo[4,5-d]pyridazin-7-yl]phenyl}acetamide;

7-(2,5-dimethoxyphenyl)-3-methyl-5-[4-(trifluoromethyl)benzyl][1,2]oxazolo[4,5-d]pyridazin-4(5H)-one;

N-{3-[5-(4-chlorobenzyl)-4-oxo-3-(propan-2-yl)-4,5-dihydro[1,2]oxazolo[4,5-d]pyridazin-7-yl]phenyl}acetamide;

7-(2-amino-5-fluorophenyl)-5-[1-(4-chlorophenyl)ethyl]-3-methyl[1,2]oxazolo[4,5-d]pyridazin-4(5H)-one;

5-[1-(4-chlorophenyl)ethyl]-7-[2-methoxy-5-(pyrrolidin-1-ylcarbonyl)phenyl]-3-methyl[1,2]oxazolo[4,5-d]pyridazin-4(5H)-one;

5-[1-(4-chlorophenyl)ethyl]-7-(2-hydroxyphenyl)-3-methyl[1,2]oxazolo[4,5-d]pyridazin-4(5H)-one;

7-(2-methoxyphenyl)-5-[4-methoxy-3-(trifluoromethyl)benzyl]-3-methyl[1,2]oxazolo[4,5-d]pyridazin-4(5H)-one;

5-(4-chlorobenzyl)-7-(2,5-dimethoxyphenyl)-3-methyl[1,2]oxazolo[4,5-d]pyridazin-4(5H)-one;

N-[4-methoxy-3-(3-methyl-4-oxo-5-{(1S)-1-[4-(trifluoromethyl)phenyl]ethyl}-4,5-dihydro[1,2]oxazolo[4,5-d]pyridazin-7-yl)phenyl]acetamide;

N-[4-methoxy-3-(3-methyl-4-oxo-5-{(1R)-1-[4-(trifluoromethyl)phenyl]ethyl}-4,5-dihydro[1,2]oxazolo[4,5-d]pyridazin-7-yl)phenyl]acetamide;

3-{5-[1-(4-chlorophenyl)ethyl]-3-methyl-4-oxo-4,5-dihydro[1,2]oxazolo[4,5-d]pyridazin-7-yl}benzamide;

N-(4-methyl-3-{3-methyl-4-oxo-5-[4-(trifluoromethyl)benzyl]-4,5-dihydro[1,2]oxazolo[4,5-d]pyridazin-7-yl}phenyl)acetamide;

5-[1-(4-chlorophenyl)ethyl]-3-methyl-7-(pyridin-3-yl)[1,2]oxazolo[4,5-d]pyridazin-4(5H)-one;

N-[6-fluoro-2-methyl-3-(3-methyl-4-oxo-5-{(1R)-1-[4-(trifluoromethyl)phenyl]ethyl})-4,5-dihydro[1,2]oxazolo[4,5-d]pyridazin-7-yl)phenyl]acetamide;

5-[1-(4-chlorophenyl)ethyl]-3-methyl-7-(pyrimidin-5-yl)[1,2]oxazolo[4,5-d]pyridazin-4(5H)-one;

5-[1-(4-chlorophenyl)ethyl]-3,7-dimethyl[1,2]oxazolo[4,5-d]pyridazin-4(5H)-one;

5-[1-(4-chlorophenyl)ethyl]-7-(1-ethyl-1H-pyrazol-5-yl)-3-methyl[1,2]oxazolo[4,5-d]pyridazin-4(5H)-one;

5-[1-(4-chlorophenyl)ethyl]-3-methyl-7-(1H-pyrrolo[3,2-b]pyridin-6-yl)[1,2]oxazolo[4,5-d]pyridazin-4(5H)-one;

N-(3-{5-[(1S)-1-(4-chlorophenyl)ethyl]-3-methyl-4-oxo-4,5-dihydro[1,2]oxazolo[4,5-d]pyridazin-7-yl}-4-methoxyphenyl)acetamide;

7-(2-methoxyphenyl)-3-methyl-5-[4-(trifluoromethyl)benzyl][1,2]oxazolo[4,5-d]pyridazin-4(5H)-one;

3-{5-[1-(4-chlorophenyl)ethyl]-3-methyl-4-oxo-4,5-dihydro[1,2]oxazolo[4,5-d]pyridazin-7-yl}-4-methoxy-N-methylbenzamide;

5-(4-chlorobenzyl)-3-methyl-7-(pyridin-3-yl)[1,2]oxazolo[4,5-d]pyridazin-4(5H)-one;

5-(4-chlorobenzyl)-3-methyl-7-phenyl[1,2]oxazolo[4,5-d]pyridazin-4(5H)-one;

7-(2,5-dimethoxyphenyl)-3-methyl-5-{(1R)-1-[4-(trifluoromethyl)phenyl]ethyl}[1,2]oxazolo[4,5-d]pyridazin-4(5H)-one;

7-(3-aminophenyl)-5-[1-(4-chlorophenyl)ethyl]-3-methyl[1,2]oxazolo[4,5-d]pyridazin-4(5H)-one;

7-(2,4-dimethoxyphenyl)-3-methyl-5-[4-(trifluoromethyl)benzyl][1,2]oxazolo[4,5-d]pyridazin-4(5H)-one;

N-{3-[5-(4-chlorobenzyl)-3-ethyl-4-oxo-4,5-dihydro[1,2]oxazolo[4,5-d]pyridazin-7-yl]phenyl)}acetamide; and 3-{5-[1-(4-chlorophenyl)ethyl]-3-methyl-4-oxo-4,5-dihydro[1,2]oxazolo[4,5-d]pyridazin-7-yl}-N-ethyl-4-methoxybenzamide;

or a pharmaceutically acceptable salt thereof.

12. The compound of claim 10, wherein the compound is N-(3-{5-[(1S)-1-(4-chlorophenyl)ethyl]-3-methyl-4-oxo-4,5-dihydro[1,2]oxazolo[4,5-d]pyridazin-7-yl}-4-methoxyphenyl)acetamide, or a pharmaceutically acceptable salt thereof.

13. The compound of claim 10, wherein the compound is 3-{5-[(1S)-1-(4-chlorophenyl)ethyl]-3-methyl-4-oxo-4,5-dihydro[1,2]oxazolo[4,5-d]pyridazin-7-yl}-4-methoxy-N-methylbenzamide, or a pharmaceutically acceptable salt thereof.

14. The compound of claim 10, wherein the compound is 3-{5-[1-(4-chlorophenyl)ethyl]-3-methyl-4-oxo-4,5-dihydro[1,2]oxazolo[4,5-d]pyridazin-7-yl}-4-methoxy-N-methylbenzamide, or a pharmaceutically acceptable salt thereof.

15. The compound of claim 10, wherein the compound is 3-{5-[1-(4-chlorophenyl)ethyl]-3-methyl-4-oxo-4,5-dihydro[1,2]oxazolo[4,5-d]pyridazin-7-yl}-4-methoxybenzamide, or a pharmaceutically acceptable salt thereof.

16. The compound of claim 10, wherein the compound is 5-[(1S)-1-(4-chlorophenyl)ethyl]-3-cyclopropyl-7-(2,5-dimethoxyphenyl)[1,2]oxazolo[4,5-d]pyridazin-4(5H)-one, or a pharmaceutically acceptable salt thereof.

* * * * *